(12) United States Patent
Lyssikatos et al.

(10) Patent No.: US 8,648,087 B2
(45) Date of Patent: Feb. 11, 2014

(54) N4-PHENYL-QUINAZOLINE-4-AMINE DERIVATIVES AND RELATED COMPOUNDS AS ERBB TYPE I RECEPTOR TYROSINE KINASE INHIBITORS FOR THE TREATMENT OF HYPERPROLIFERATIVE DISEASES

(75) Inventors: Joseph P. Lyssikatos, Piedmont, CA (US); Julie Marie Greschuk, Erie, CO (US); Fredrik P. Marmsäter, Boulder, CO (US); Qian Zhao, Superior, CO (US); D. David Hennings, Loveland, CO (US); Weidong Liu, Superior, CO (US)

(73) Assignee: Array Biopharma, Inc., Boulder, CO (US)

( * ) Notice: Subject to any disclaimer, the term of this patent is extended or adjusted under 35 U.S.C. 154(b) by 1606 days.

(21) Appl. No.: 12/085,048

(22) PCT Filed: Nov. 15, 2006

(86) PCT No.: PCT/US2006/044431
§ 371 (c)(1),
(2), (4) Date: May 15, 2008

(87) PCT Pub. No.: WO2007/059257
PCT Pub. Date: May 24, 2007

(65) Prior Publication Data
US 2011/0034689 A1    Feb. 10, 2011

Related U.S. Application Data

(60) Provisional application No. 60/736,289, filed on Nov. 15, 2005, provisional application No. 60/817,019, filed on Jun. 28, 2006.

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC .................. 514/266.1; 544/283; 544/284

(58) Field of Classification Search
USPC ........................ 544/283; 514/266.1
See application file for complete search history.

(56) References Cited

U.S. PATENT DOCUMENTS

| | | |
|---|---|---|
| 3,890,319 A | 6/1975 | Danielewicz et al. |
| 4,029,792 A | 6/1977 | Danielewicz et al. |
| 5,112,817 A | 5/1992 | Fukazawa et al. |
| 5,204,348 A | 4/1993 | Fukazawa et al. |
| 5,405,843 A | 4/1995 | Fukazawa et al. |
| 5,502,187 A | 3/1996 | Ayer et al. |
| 5,821,246 A | 10/1998 | Brown et al. |
| 5,866,572 A | 2/1999 | Barker et al. |
| 5,955,464 A | 9/1999 | Barker |
| 6,017,922 A | 1/2000 | Stogniew et al. |
| 6,127,374 A | 10/2000 | Bridges |
| 6,169,091 B1 | 1/2001 | Cockerill et al. |
| 6,184,225 B1 | 2/2001 | Thomas et al. |
| 6,225,318 B1 | 5/2001 | Sobolov-Jaynes et al. |
| 6,258,952 B1 | 7/2001 | Stogniew et al. |
| 6,344,455 B1 | 2/2002 | Bridges et al. |
| 6,344,459 B1 | 2/2002 | Bridges et al. |
| 6,391,874 B1 | 5/2002 | Cockerill et al. |
| 6,399,602 B1 | 6/2002 | Barker et al. |
| 6,465,472 B1 | 10/2002 | Upasani et al. |
| 6,469,004 B1 | 10/2002 | Barrett et al. |
| 6,492,383 B1 | 12/2002 | Munchhof et al. |
| 6,562,818 B1 | 5/2003 | Bridges |
| 6,602,863 B1 | 8/2003 | Bridges et al. |
| 6,756,006 B1 | 6/2004 | Levijoki |
| 6,828,320 B2 | 12/2004 | Cockerill et al. |
| 6,890,924 B2 | 5/2005 | Kath et al. |
| 6,897,214 B2 | 5/2005 | Barker et al. |
| 6,924,285 B2 | 8/2005 | Himmelsbach et al. |
| 6,964,961 B2 | 11/2005 | Luzzio et al. |
| 7,081,461 B1 | 7/2006 | Mortlock et al. |
| 7,119,084 B2 | 10/2006 | Himmelsbach et al. |
| 7,157,466 B2 | 1/2007 | McClure et al. |
| 7,332,493 B2 | 2/2008 | Kath et al. |
| 7,488,823 B2 | 2/2009 | Wallace et al. |
| 7,501,427 B2 | 3/2009 | Wallace et al. |
| 7,585,869 B2 | 9/2009 | Bhattacharya et al. |
| 7,585,975 B2 | 9/2009 | Wallace et al. |

(Continued)

FOREIGN PATENT DOCUMENTS

| | | | |
|---|---|---|---|
| JP | 5-268177 A | 10/1993 | |
| JP | 2002544196 A | 12/2002 | |

(Continued)

OTHER PUBLICATIONS

Pinedo et al.*

(Continued)

*Primary Examiner* — Paul V. Ward
(74) *Attorney, Agent, or Firm* — McDermott Will & Emery LLP

(57) ABSTRACT

This invention provides compounds of Formula I

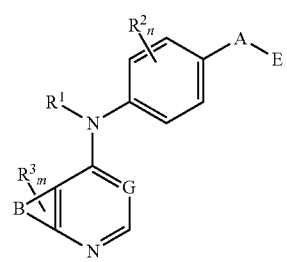

wherein B, G, A, E, $R^1$, $R^2$, $R^3$, m and n are as defined herein, which are useful as type I receptor tyrosine kinase inhibitors, and methods of use thereof in the treatment of hyperproliferative disorders in mammals.

37 Claims, No Drawings

(56) References Cited

U.S. PATENT DOCUMENTS

| | | |
|---|---|---|
| 7,652,006 B2 | 1/2010 | Upasani et al. |
| 7,777,032 B2 | 8/2010 | Wallace et al. |
| 7,786,131 B2 | 8/2010 | Bridges et al. |
| 7,910,731 B2 | 3/2011 | Himmelsbach et al. |
| 8,003,658 B2 | 8/2011 | Ham et al. |
| 2004/0158065 A1 | 8/2004 | Barth et al. |
| 2005/0059678 A1 | 3/2005 | Wissner et al. |
| 2005/0101618 A1 | 5/2005 | Connell et al. |
| 2005/0119288 A1 | 6/2005 | Bhattacharya et al. |
| 2006/0025430 A1 | 2/2006 | Mishani et al. |
| 2007/0082921 A1 | 4/2007 | Hennequin et al. |
| 2007/0088044 A1 | 4/2007 | Hennequin et al. |
| 2009/0012290 A1 | 1/2009 | Wallace et al. |
| 2009/0048279 A1 | 2/2009 | Wallace et al. |

FOREIGN PATENT DOCUMENTS

| | | |
|---|---|---|
| JP | 2004-517059 A | 6/2004 |
| JP | 2004527486 A | 9/2004 |
| JP | 2005-515176 | 5/2005 |
| JP | 2007502786 A | 2/2007 |
| WO | WO 96/09294 | 3/1996 |
| WO | WO 99/09019 | 2/1999 |
| WO | WO-02/36570 A1 | 5/2002 |
| WO | WO-02083622 | 10/2002 |
| WO | WO-2005/007083 | 1/2005 |
| WO | WO 2005/016346 A1 | 2/2005 |
| WO | WO 2005/026151 A1 | 3/2005 |
| WO | WO 2005/026152 A1 | 3/2005 |

OTHER PUBLICATIONS

McMahon et al.*

Canadian Office Action issued in Canadian Patent Application No. 2,632,194 dated Feb. 16, 2010.

English translation of Chinese Office Action issued in Chinese Patent Application No. CN 200680050689.2 dated Jan. 26, 2011.

English translation of Korean Notice of Preliminary Rejection issued in Korean Patent Application No. KR 10-2008-7014416 dated Nov. 29, 2010.

English translation of Russian Office Action issued in Russian Patent Application No. 2008118417 dated Oct. 19, 2010.

English translation of Russian Office Action issued in Russian Patent Application No. 2008118417 dated May 28, 2010.

English translation of Ukrainian Office Action issued in Ukrainian Patent Application No. 2008 08026 dated Dec. 22, 2010.

S. R. Vippagunta et al., "Crystalline solids," Advanced Drug Delivery Reviews 48 (2001) pp. 3-26.

D.W. Rusnak et al., "The Characterization of Novel, Dual ErbB-2/EGFR, Tyrosine Kinase Inhibitors: Potential Therapy for Cancer," Cancer Research 61, pp. 7196-7203, Oct. 1, 2001.

D.W. Rusnak et al., "The Effects of the Novel, Reversible Epidermal Growth Factor Receptor/ErbB-2 Tytosince Kinase Inhibitor, GW2016, on Growth of Human Normal and Tumor-derived Cell Lines in Vitro and in Vivo," Molecular Cancer Thereapeutics, vol. 1, pp. 85-94, Dec. 2001.

Shi et al., "QSAR analysis of tyrosine kinase inhibitor using modified ant colony optimization and multiple linear regression," European Journal of Medicinal Chemistry 42 (2007), pp. 81-86.

K. Koch, Ph.D., Arry-380: A Selective, Oral HER2 Inhibitor for the Treatment of Solid Tumors, Apr. 3, 2011.

English translation of Chinese Office Action issued in Chinese Patent Application No. CN 200680050689.2 Aug. 4, 2010.

Notification Concerning Transmittal of International Preliminary Report on Patentability (Chapter I of the Patent Cooperation Treaty) issued in PCT/US2006/044431, date of mailing May 29, 2008.

European Search Report issued in European Patent Application No. EP 09157031 dated Jun. 24, 2009.

Japanese Office Action issued in Japanese Patent Application No. 2010-198848 dated Nov. 27, 2012.

English translation of Japanese Office Action issued in Japanese Patent Application No. 2008-541330 dated Jun. 15, 2012.

D.W. Fry et al., "Specific, irreversible inactivation of the epidermal growth factor receptor and erbB2, by a new class of tyrosine kinase inhibitor," Proc. Natl. Acad. Sci. USA; vol. 95, pp. 12022-12027, Sep. 1998; Pharmacoogy.

* cited by examiner

N4-PHENYL-QUINAZOLINE-4-AMINE DERIVATIVES AND RELATED COMPOUNDS AS ERBB TYPE I RECEPTOR TYROSINE KINASE INHIBITORS FOR THE TREATMENT OF HYPERPROLIFERATIVE DISEASES

CROSS REFERENCE TO RELATED APPLICATIONS

This application claims priority to U.S. Provisional application No. 60/736,289, filed Nov. 15, 2005, and U.S. Provisional application No. 60/817,019, filed Jun. 28, 2006, each of which is incorporated herein by reference in its entirety.

BACKGROUND OF THE INVENTION

1. Field of the Invention

This invention relates to novel inhibitors of type I receptor tyrosine kinases and related kinases, pharmaceutical compositions containing the inhibitors, and methods for preparing these inhibitors. The inhibitors are useful for the treatment of hyperproliferative diseases, such as cancer and inflammation, in mammals and especially in humans.

2. Description of the State of the Art

The type I receptor tyrosine kinase family consists of four closely related receptors: EGFR (ErbB1 or HER1), ErbB2 (HER2), ErbB3 (HER), and ErbB4 (HER4) (Reviewed in Riese and Stem, *Bioessays* (1998) 20:41-48; Olayioye et al., *EMBO Journal* (2000) 19:3159-3167; and Schlessinger, *Cell* (2002) 110:669-672). These are single pass transmembrane glycoprotein receptors containing an extracellular ligand binding region and an intracellular signaling domain. In addition, all receptors contain an intracellular active tyrosine kinase domain with the exception of ErbB3, whose kinase domain does not exhibit enzymatic activity. These receptors transmit extracellular signals through the cytosol to the nucleus upon activation. The activation process is initiated by ligand binding to the extacellular domain of the receptor by one of a number of different hormones. Upon ligand binding, homo- or heterodimerization is induced, which results in the activation of the tyrosine kinase domains and phosphorylation of tyrosines on the intracellular signaling domains. Since no known ligand for ErbB2 has been described and ErbB3 lacks an active kinase domain, these receptors must heterodimerize to elicit a response. The phosphotyrosines then recruit the necessary cofactors to initiate several different signaling cascades including the ras/raf/MEK/MAPK and PI3K/AKT pathways. The precise signal elicited will depend on what ligands are present, since the intracellular signaling domains differ as to what pathways are activated. These signaling pathways lead to both cell proliferation and cell survival through inhibition of apoptosis.

Several investigators have demonstrated the role of EGFR and ErbB2 in development of cancer (reviewed in Salomon, et al., *Crit. Rev. Oncol. Hematol.* (1995) 19:183-232; Klapper, et al., *Adv. Cancer Res.* (2000) 77:25-79; and Hynes and Stern, *Biochim. Biophys. Acta* (1994) 1198:165-184). Squamous carcinomas of the head, neck and lung express high levels of EGFR. Also, constitutively active EGFR has been found in gliomas, breast cancer and lung cancer. ErbB2 overexpression occurs in approximately 30% of all breast cancer. It has also been implicated in other human cancers including colon, ovary, bladder, stomach, esophagus, lung, uterus and prostate. ErbB2 overexpression has also been correlated with poor prognosis in human cancer, including metastasis and early relapse.

The type I tyrosine kinase receptor family has been an active area of anti-cancer research (Reviewed in Mendelsohn and Baselga, *Oncogene* (2000) 19:6550-6565; and Normanno et al., *Endocrine-Related Cancer* (2003) 10:1-21). For example, U.S. Pat. No. 6,828,320 discloses certain substituted quinolines and quinazolines as protein tyrosine kinase inhibitors.

Several inhibitors of the EGFR and the ErbB2 signaling pathway have demonstrated clinical efficacy in cancer treatment. HERCEPTIN®, a humanized version of anti-ErbB2 monoclonal antibody, was approved for use in breast cancer in the United States in 1998. IRESSA® and TARCEVA® are small molecule inhibitors of EGFR that are commercially available. In addition, several other antibodies and small molecules that target the interruption of the type I tyrosine kinase receptor signaling pathways are in clinical and preclinical development. For example, ERBITUX®, a human-murine chimeric monoclonal antibody against EGFR, is available for the treatment of irinotecan-refractory colorectal cancer.

SUMMARY OF THE INVENTION

This invention provides compounds that inhibit type I receptor tyrosine kinases. Such compounds have utility as therapeutic agents for diseases that can be treated by the inhibition of type I receptor tyrosine kinases. They may also act as inhibitors of serine, threonine, and dual specificity kinases inhibitors. In general, the invention relates to compounds of Formula I

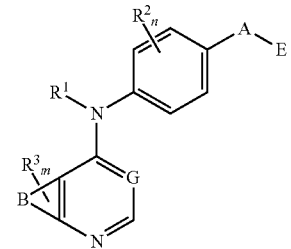

and solvates, metabolites, and pharmaceutically acceptable salts and prodrugs thereof, wherein B, G, A, E, $R^1$, $R^2$, $R^3$, m and n are as defined herein, wherein when said compound of Formula I is represented by the formula

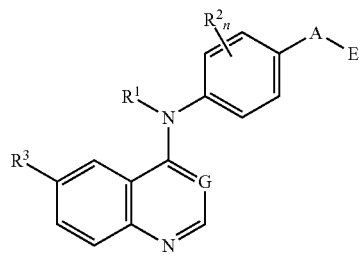

and $R^3$ is other than Q or Z wherein Q and Z are as defined herein, then E is not a benzofuranyl, indolyl, quinazolinyl, quinolinyl, or isoquinolinyl ring.

In a further aspect, the present invention provides a method of treating diseases or medical conditions mediated by type I receptor tyrosine kinases which comprises administering to a warm-blooded animal an effective amount of a compound of Formula I, or a metabolite, solvate, or pharmaceutically acceptable salt or prodrug thereof.

In a further aspect, the present invention provides a method of inhibiting the production of type I receptor kinases which comprises administering to a warm-blooded animal an effective amount of a compound of Formula I, or a metabolite, solvate, or pharmaceutically acceptable salt or prodrug thereof.

In a further aspect, the present invention provides a method of providing type I receptor kinase inhibitory effect comprising administering to a warm-blooded animal an effective amount of a compound of Formula I, or a metabolite, solvate, or pharmaceutically acceptable salt or prodrug thereof.

In a further aspect, the present invention provides treating or preventing a type I receptor kinase mediated condition, comprising administering an amount of a compound effective to treat or prevent said type I receptor kinase-mediated condition or a pharmaceutical composition comprising said compound, to a human or animal in need thereof, wherein said compound is a compound of Formula I, or a pharmaceutically-acceptable salt or in vivo cleavable prodrug thereof. The type I receptor kinase mediated conditions that can be treated according to the methods of this invention include, but are not limited to, hyperproliferative disorders, such as cancer of the head and neck, lung, breast, colon, ovary, bladder, stomach, kidney, skin, pancreas, leukemias, lymphomas, esophagus, uterus or prostate, among other kinds of hyperproliferative disorders.

The compounds of Formula I may be used advantageously in combination with other known therapeutic agents.

The invention also relates to pharmaceutical compositions comprising an effective amount of an agent selected from compounds of Formula I or a pharmaceutically acceptable prodrug, pharmaceutically active metabolite, or a pharmaceutically acceptable salt or prodrug thereof.

This invention also provides compound of Formula I for use as medicaments in the treatment or prevention of a type I receptor kinase-mediated condition.

An additional aspect of the invention is the use of a compound of Formula I in the preparation of a medicament for the treatment or prevention of a type I receptor kinase-mediated condition.

This invention further provides kits for the treatment or prevention of a type I receptor kinase-mediated condition, said kit comprising a compound of Formula I, or a solvate, metabolite, or pharmaceutically acceptable salt or prodrug thereof, a container, and optionally a package insert or label indicating a treatment. The kits may further comprise a second compound or formulation comprising a second pharmaceutical agent useful for treating said disease or disorder.

This invention further includes methods of preparing, methods of separating, and methods of purifying of the compounds of this invention.

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, cyclopropyl, cyclobutyl, cyclopentyl, cyclohexyl, cycloheptyl, and cyclooctyl.

The term "alkyl" includes saturated linear or branched-chain monovalent hydrocarbon radicals of one to six carbon atoms (e.g., $C_1$-$C_6$ alkyl), wherein the alkyl radical may be optionally substituted independently with one or more substituents described below.

The term "alkenyl" as used herein refers to linear or branched-chain monovalent hydrocarbon radical of two to twelve carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—$CH=CH_2$), alkyl (—$CH_2CH=CH_2$), 1-cyclopent-1-enyl, 1-cyclopent-2-enyl, 1-cyclopent-3-enyl, 5-hexenyl, 1-cyclohex-1-enyl, 1-cyclohex-2-enyl, and 1-cyclohex-3-enyl.

The term "alkynyl" as used herein refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡CH) and propynyl (propargyl, —CH$_2$≡CH).

The terms "cycloalkyl," "carbocyclyl," and "carbocycle" as used herein are interchangeable and refer to a monovalent non-aromatic, saturated or partially unsaturated cyclic hydrocarbon radical having from three to ten carbon atoms. Examples of monocyclic carbocyclic radicals include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. The cycloalkyl may be optionally substituted independently in one or more substitutable positions with various groups. The term "cycloalkyl" also includes polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocyclyl ring or an aryl or heteroaryl ring. Bicyclic carbocycles having 7 to 12 atoms can be arranged, for example, as a bicyclo[4,5], [5,5], [5,6] or [6,6] system, or as bridged systems such as bicyclo[2.2.1]heptane, bicyclo[2.2.2]octane and bicyclo[3.2.2]nonane.

The term "heteroalkyl" as used herein refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The term "heteroalkenyl" as used herein refers to linear or branched-chain monovalent hydrocarbon radical of two to twelve carbon atoms, containing at least one double bond, e.g., ethenyl, propenyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkenyl radical may be optionally substituted independently with one or more substituents described herein, and includes radicals having "cis" and "trans" orientations, or alternatively, "E" and "Z" orientations.

The term "heteroalkynyl" as used herein refers to a linear or branched monovalent hydrocarbon radical of two to twelve carbon atoms containing at least one triple bond. Examples include, but are not limited to, ethynyl, propynyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkynyl radical may be optionally substituted independently with one or more substituents described herein.

The terms "heterocycle" and "heterocyclyl" as used herein are used interchangeably and refer to a saturated or partially unsaturated carbocyclic radical of 3 to 8 ring atoms in which at least one ring atom is a heteroatom independently selected from nitrogen, oxygen and sulfur, the remaining ring atoms being C, where one or more ring atoms may be optionally substituted independently with one or more substituents described below. The radical may be a carbon radical or heteroatom radical. The term "heterocyclyl" includes heterocycloalkoxy. "Heterocyclyl" also includes radicals wherein the heterocyclyl radicals are fused with a saturated, partially unsaturated, or fully unsaturated (i.e., aromatic) carbocyclic or heterocyclic ring. Examples of heterocyclyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocyclyl radical may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo (═O) moieties are isoindoline-1,3-dionyl and 1,1-dioxo-thiomorpholinyl. The heterocyclyl groups herein are unsubstituted or, as specified, substituted in one or more substitutable positions with various groups.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Further examples of carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridinzinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "arylalkyl" as used herein means an alkyl moiety (as defined above) substituted with one or more aryl moiety (also as defined above). Examples of arylalkyl radicals include aryl-C$_{1-3}$-alkyls such as, but not limited to, benzyl, phenylethyl, and the like.

The term "heteroarylalkyl" as used herein means an alkyl moiety (as defined above) substituted with a heteroaryl moiety (also as defined above). Examples of heteroarylalkyl radicals include 5- or 6-membered heteroaryl-C$_{1-3}$-alkyls such as, but not limited to, oxazolylmethyl, pyridylethyl and the like.

The term "heterocyclylalkyl" as used herein means an alkyl moiety (as defined above) substituted with a heterocyclyl moiety (also defined above). Examples of heterocyclylalkyl radicals include 5- or 6-membered heterocyclyl-C$_{1-3}$-alkyls such as, but not limited to, tetrahydropyranylmethyl.

The term "cycloalkylalkyl" as used herein means an alkyl moiety (as defined above) substituted with a cycloalkyl moiety (also defined above). Examples of heterocyclyl radicals include 5- or 6-membered cycloalkyl-$C_{1-3}$-alkyls such as, but not limited to, cyclopropylmethyl.

"Substituted alkyl" as used herein refers to an alkyl in which one or more hydrogen atoms are each independently replaced with a substituent. Typical substituents include, but are not limited to, F, Cl, Br, I, CN, $CF_3$, OR, R, =O, =S, =NR, =$N^+$(O)(R), =N(OR), =$N^+$(O)(OR), =N—NRR', —C(=O)R, —C(=O)OR, —C(=O)NRR', —NRR', —$N^+$RR'R", —N(R)C(=O)R', —N(R)C(=O)OR', —N(R)C(=O)NR'R", —SR, —OC(=O)R, —OC(=O)OR, —OC(=O)NRR', —OS(O)$_2$(OR), —OP(=O)(OR)$_2$, —OP(OR)$_2$, —P(=O)(OR)$_2$, —P(=O)(OR)NR'R", —S(O)R, —S(O)$_2$R, —S(O)$_2$NR, —S(O)(OR), —S(O)$_2$(OR), —SC(=O)R, —SC(=O)OR, =O and —SC(=O)NRR'; wherein each R, R' and R" is independently selected from H, alkyl, alkenyl, alkynyl, aryl and heterocyclyl. Alkenyl, alkynyl, alkyl, saturated or partially unsaturated cycloalkyl, heteroalkyl, heterocyclyl, arylalkyl, heteroarylalkyl, heterocyclylalkyl, cycloalkylalkyl, aryl and heteroaryl groups as described above may also be similarly substituted.

The term "halogen" as used herein includes fluorine (F), bromine (Br), chlorine (Cl), and iodine (I).

The term "a" as used herein means one or more.

In the compounds of the present invention, where a term such as $(CR^{13}R^{14})_q$ is used, $R^{13}$ and $R^{14}$ may vary with each iteration of q above 1. For instance, where q is 2, the term $(CR^{13}R^{14})_q$ may equal —$CH_2CH_2$— or —$CH(CH_3)C(CH_2CH_3)(CH_2CH_2CH_3)$— or any number of similar moieties falling within the scope of the definitions of $R^{13}$ and $R^{14}$.

ErbB Inhibitors

This invention relates to compounds that are useful for inhibiting type I receptor tyrosine kinases, such as EGFR (HER1), ErbB2 (HER2), ErbB3 (HER3), ErbB4 (HER4), VEGFR2, Flt3 and FGFR. The compounds of this invention may also be useful as inhibitors of serine, threonine, and dual specificity kinases such as Raf, MEK, and p38. Such compounds have utility as therapeutic agents for diseases that can be treated by the inhibition of the type I receptor tyrosine kinases signaling pathway and serine, threonine, and dual specificity kinase pathways.

In certain embodiments, this invention relates to compounds that are useful for inhibiting type I receptor tyrosine kinases such as EGFR (HER1), ErbB2 (HER2), ErbB3 (HER3), and ErbB4 (HER4).

In one embodiment, this invention includes compounds of Formula I

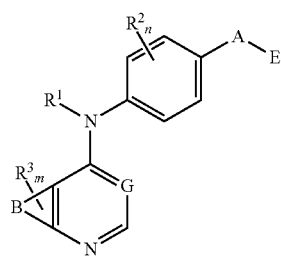

I and solvates, metabolites, and pharmaceutically acceptable salts thereof, wherein:

A is O, C(=O), S, SO or $SO_2$;

G is N or C—CN;

B represents a fused 6-membered aryl ring or a fused 5-6 membered heteroaryl ring;

E is

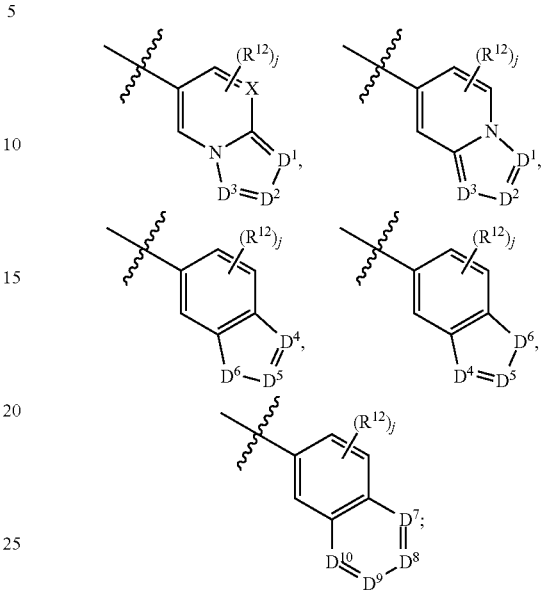

X is N or CH;

$D^1$, $D^2$ and $D^3$ are independently N or $CR^{19}$;

$D^4$ and $D^5$ are independently N or $CR^{19}$ and $D^6$ is O, S, or $NR^{20}$, wherein at least one of $D^4$ and $D^5$ is not $CR^{19}$;

$D^7$, $D^8$, $D^9$ and $D^{10}$ are independently N or $CR^{19}$, wherein at least one of $D^7$, $D^8$, $D^9$ and $D^{10}$ is N;

$R^1$ is H or alkyl;

each $R^2$ is independently halogen, cyano, nitro, trifluoromethyl, difluoromethyl, fluoromethyl, fluoromethoxy, difluoromethoxy, trifluoromethoxy, azido, —$SR^{18}$, —$OR^{15}$, —$C(O)R^{15}$, —$C(O)OR^{15}$, —$NR^{14}C(O)OR^{18}$, —$OC(O)R^{15}$, —$NR^{14}SO_2R^{18}$, —$SO_2NR^{15}R^{14}$, —$NR^{14}C(O)R^{15}$, —$C(O)NR^{15}R^{14}$, —$NR^{15}C(O)NR^{15}R^{14}$, —$NR^{13}C(NCN)NR^{15}R^{14}$, —$NR^{15}R^{14}$, alkyl, alkenyl, alkynyl, saturated or partially unsaturated cycloalkyl, cycloalkylalkyl, —S(O)$_p$(alkyl), —S(O)$_p(CR^{13}R^{14})_q$-aryl, aryl, arylalkyl, heteroaryl, heteroarylalkyl, saturated or partially unsaturated heterocyclyl, heterocyclylalkyl, —$O(CR^{13}R^{14})_q$-aryl, —$NR^{15}(CR^{13}R^{14})_q$-aryl, —$O(CR^{13}R^{14})_q$-heteroaryl, —$NR^{13}(CR^{13}R^{14})_q$-heteroaryl, —$O(CR^{13}R^{14})_q$-heterocyclyl or —$NR^{15}(CR^{13}R^{14})_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^{13}SO_2R^{18}$, —$SO_2NR^{15}R^{13}$, —$C(O)R^{15}$, —$C(O)OR^{15}$, —$OC(O)R^{15}$, —$NR^{13}C(O)OR^{18}$, —$NR^{13}C(O)R^{15}$, —$C(O)NR^{15}R^{13}$, —$NR^{15}R^{13}$, —$NR^{14}C(O)NR^{15}R^{13}$, —$NR^{14}C(NCN)NR^{15}R^{13}$, —$OR^{15}$, aryl, heteroaryl, arylalkyl, heteroarylalkyl, saturated and partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, $NR^{15}R^{13}$ and $OR^{15}$;

each $R^3$ is independently Q, Z, halogen, cyano, nitro, alkyl, alkenyl, alkynyl, heteroalkyl, heteroalkenyl, heteroalkynyl, saturated or partially unsaturated cycloalkyl, saturated or partially unsaturated heterocyclyl, aryl, arylalkyl, heteroaryl, heteroarylalkyl, trifluoromethoxy, difluoromethoxy, fluoromethoxy, trifluoromethyl, difluoromethyl, fluoromethyl, $OR^{15}$, $NR^{15}R^{16}$, $NR^{15}OR^{16}$, $NR^{15}C(=O)OR^{18}$, $NR^{15}C(=O)R^{16}$, $SO_2NR^{15}R^{16}$, $SR^{15}$, $SOR^{15}$, $SO_2R^{15}$, $C(=O)R^{15}$, $C(=O)OR^{15}$, $OC(=O)R^{15}$, $C(=O)NR^{15}R^{16}$, $NR^{15}C(=O)NR^{16}R^{17}$, $NR^{15}C(=NCN)NR^{16}R^{17}$, or $NR^{15}C(=NCN)R^{16}$, wherein said alkyl, alkenyl, alkynyl, heteroalkyl, heteroalkenyl, heteroalkynyl, cycloalkyl, heterocyclyl, aryl, arylalkyl, heteroaryl and heteroarylalkyl are optionally substituted with one or more groups independently selected from halogen, oxo, cyano, nitro, alkyl, alkenyl, alkynyl, heteroalkyl, heteroalkenyl, heteroalkynyl, saturated or partially unsaturated cycloalkyl, saturated and partially unsaturated heterocyclyl, aryl, arylalkyl, heteroaryl, heteroarylalkyl, trifluoromethoxy, difluoromethoxy, fluoromethoxy, trifluoromethyl, difluoromethyl, fluoromethyl, $OR^{15}$, $NR^{15}R^{16}$, $NR^{15}OR^{16}$, $NR^{15}C(O)R^{18}$, $NR^{15}C)=O)R^{16}$, $SO_2NR^{15}R^{16}$, $SR^{15}$, $SOR^{15}$, $SO_2R^{15}$, $C(=O)R^{15}$, $C(=O)OR^{15}$, $OC(=O)R^{15}$, $C(=O)NR^{15}R^{16}$, $NR^{15}C(=O)NR^{16}R^{17}$, $NR^{15}C(=NCN)NR^{16}R^{17}$, $NR^{15}C(=NCN)R^{16}$, ($C_1$-$C_4$ alkyl)$NR^aR^b$ and $NR^{15}C(O)CH_2OR^a$, or $R^3$ is a 5-6 membered heterocyclic ring containing from 1 to 4 heteroatoms selected from N, O, S, SO and $SO_2$ and substituted with -$M^1$-$M^2$-$M^3$-$M^4$ or -$M^1$-$M^5$, wherein $M^1$ is $C_1$-$C_4$ alkyl, wherein optionally a $CH_2$ is replaced by a $C(=O)$ group; $M^2$ is $NR^e$ or $CR^eR^f$; $M^3$ is $C_1$-$C_4$ alkyl; $M^4$ is CN, $NR^eS(O)_{0-2}R^f$, $S(O)_{0-2}NR^gR^h$, $COR^gR^h$, $S(O)_{0-2}R^f$, or $CO_2R^f$, and $M^5$ is $NR^gR^h$, wherein $R^e$, $R^f$, $R^g$ and $R^h$ are independently H or $C_1$-$C_4$ alkyl, or $R^g$ and $R^h$ together with the nitrogen atom to which they are attached form a 5- or 6-membered ring optionally containing 1 or 2 additional heteroatoms selected from N, O, S, SO and $SO_2$ in which any ring nitrogen atom present is optionally substituted with a $C_1$-$C_4$ alkyl group and which ring may optionally have one or two oxo or thiooxo substituents;

Q is

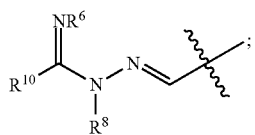

Z is selected from

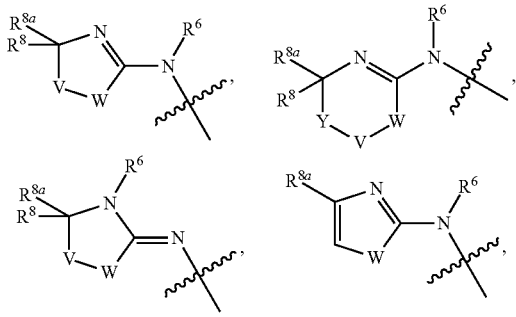

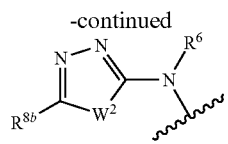

and tautomers thereof;

W and V are independently O, $NR^6$, S, SO, $SO_2$, $CR^7R^8$, $CR^8R^9$ or C=O;

$W^2$ is O or S;

Y is S, SO, $SO_2$, $CR^7CR^8$, or $CR^8R^9$, provided that when W is O, $NR^6$, S, SO, or $SO_2$, then V is $CR^8R^9$, and when V is O, $NR^6$, S, SO, or $SO_2$, then W and Y are each $CR^8R^9$;

$R^{8b}$ is H or $C_1$-$C_6$ alkyl;

each $R^6$, $R^8$, $R^{8a}$ and $R^9$ are independently hydrogen, trifluoromethyl, alkyl, saturated or partially unsaturated cycloalkyl, saturated or partially unsaturated heterocyclyl, aryl, arylalkyl, heteroaryl, heteroarylalkyl, or heterocyclylalkyl, wherein said alkyl, cycloalkyl, heterocyclyl, aryl, arylalkyl, heteroaryl, heteroarylalkyl, and heterocyclylalkyl are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, $OR^{15}$, $NR^{15}R^{16}$, $SR^{15}$, $S(=O)R^{15}$, $SO_2R^{15}$, trifluoromethyl, difluoromethyl, fluoromethyl, fluoromethoxy, difluoromethoxy, trifluoromethoxy, azido, aryl, heteroaryl, arylalkyl, heteroarylalkyl, and heterocyclylalkyl, or $R^8$ and $R^{8a}$ together with the atom to which they are attached form a 3 to 6 membered carbocyclic ring;

$R^7$ is hydrogen, halogen, cyano, nitro, alkyl, alkenyl, alkynyl, saturated or partially unsaturated cycloalkyl, saturated or partially unsaturated heterocyclyl, cycloalkylalkyl, aryl, arylalkyl, heteroaryl, heteroarylalkyl, heterocyclylalkyl, —$NR^{15}SO_2R^{16}$—$SO_2NR^{15}R^{16}$, —$C(O)R^{15}$, —$C(O)OR^{15}$, —$OC(O)R^{15}$, —$NR^{15}C(O)OR^{18}$, —$NR^{15}C(O)R^{16}$, —$C(O)NR^{15}R^{16}$, $NR^{15}R^{16}$, —$NR^{15}C(O)NR^{16}R^{17}$, —$OR^{15}$, —$S(O)R^{15}$, —$SO_2R^{15}$, or $SR^{15}$, wherein said alkyl, alkenyl, alkynyl, cycloalkyl, heterocyclyl, cycloalkylalkyl, aryl, arylalkyl, heteroaryl, heteroarylalkyl, and heterocyclylalkyl, are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, —$NR^{15}SO_2R^{16}$—$SO_2NR^{15}R^{16}$, —$C(O)R^{15}$, —$C(O)OR^{15}$, —$OC(O)R^{15}$, —$NR^{15}C(O)OR^{18}$, —$NR^{15}C(O)R^{16}$, —$C(O)NR^{15}R^{16}$, —$NR^{15}R^{16}$, —$NR^{15}C(O)NR^{16}R^{17}$, —$OR^{15}$, —$S(O)R^{15}$, —$SO_2R^{15}$, $SR^{15}$, aryl, arylalkyl, heteroaryl, heteroarylalkyl, and heterocyclylalkyl;

$R^{10}$ is hydrogen, alkyl, alkenyl, alkynyl, saturated or partially unsaturated cycloalkyl, saturated or partially unsaturated heterocyclyl, cycloalkylalkyl, aryl, arylalkyl, heteroaryl, heteroarylalkyl, heterocyclylalkyl, —$NR^{15}C(O)OR^{18}$, —$NR^{15}C(O)R^{16}$, —$NR^{15}R^{16}$, or —$OR^{15}$, wherein said alkyl, alkenyl, alkynyl, cycloalkyl, heterocyclyl, cycloalkylalkyl, aryl, arylalkyl, heteroaryl, heteroarylalkyl, heterocyclylalkyl, are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, —NR$^{15}$SO$_2$R$^{16}$—SO$_2$NR$^{15}$R$^{16}$, —C(O)R$^{15}$, —C(O)OR$^{15}$, —OC(O)R$^{15}$, —NR$^{15}$C(O)OR$^{18}$, —NR$^{15}$C(O)R$^{16}$, —C(O)NR$^{15}$R$^{16}$, —NR$^{15}$R$^{16}$, —N$^{15}$C(O)R$^{16}$R$^{17}$, —OR$^{15}$, —S(O)R$^{15}$, —SO$_2$R$^{15}$, SR$^{15}$, aryl, arylalkyl, heteroaryl, heteroarylalkyl, and heterocyclylalkyl;

or R$^6$ and R$^8$ together with the atoms to which they are attached form a 3 to 10 membered saturated or partially unsaturated heterocyclyl ring optionally containing one or more additional heteroatoms selected from N, O, S, SO, SO$_2$ and NR$^6$, wherein said carbocyclic and heterocyclic rings are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, OR$^{15}$, NR$^{15}$R$^{16}$, SR$^{15}$, heteroaryl, arylalkyl, heteroarylalkyl, and heterocyclylalkyl;

or R$^7$ and R$^8$ together with the atoms to which they are attached form a 3 to 10 membered saturated or partially unsaturated cycloalkyl or heterocyclyl ring optionally containing one or more additional heteroatoms selected from N, O, S, SO, SO$_2$ and NR$^6$, wherein said carbocyclic and heterocyclic rings are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, OR$^{15}$, NR$^{15}$R$^{16}$, SR$^{15}$, heteroaryl, arylalkyl, heteroarylalkyl, and heterocyclylalkyl;

or R$^8$ and R$^9$ together with the atoms to which they are attached form a 3 to 10 membered saturated or partially unsaturated cycloalkyl or heterocyclyl ring optionally containing one or more additional heteroatoms selected from N, O, S, SO, SO$_2$ and NR$^6$, wherein said carbocyclic and heterocyclic rings are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, OR$^{15}$, NR$^{15}$R$^{16}$, SR$^{15}$, heteroaryl, arylalkyl, heteroarylalkyl, and heterocyclylalkyl;

or R$^6$ and R$^{10}$ together with the atoms to which they are attached form a 3 to 10 membered saturated or partially unsaturated heterocyclyl ring optionally containing one or more additional heteroatoms selected from N, O, S, SO, SO$_2$ and NR$^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, OR$^{15}$, NR$^{15}$R$^{16}$, SR$^{15}$, heteroaryl, arylalkyl, heteroarylalkyl, and heterocyclylalkyl;

or R$^8$ and R$^{10}$ together with the atoms to which they are attached form a 3 to 10 membered saturated or partially unsaturated heterocyclyl ring optionally containing one or more additional heteroatoms selected from N, O, S, SO, SO$_2$ and NR$^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, OR$^{15}$, NR$^{15}$R$^{16}$, SR$^{15}$, heteroaryl, arylalkyl, heteroarylalkyl, and heterocyclylalkyl;

each R$^{12}$ is independently halogen, cyano, nitro, trifluoromethyl, difluoromethyl, fluoromethyl, fluoromethoxy, difluoromethoxy, trifluoromethoxy, azido, —SR$^{18}$, —OR$^{15}$, —C(O)R$^{15}$, —C(O)OR$^{15}$, —NR$^{14}$C(O)OR$^{18}$, —OC(O)R$^{15}$—NR$^{14}$SO$_2$R$^{18}$, —SO$_2$NR$^{15}$R$^{14}$, —NR$^{14}$C(O)R$^{15}$, —C(O)NR$^{15}$R$^{14}$, —NR$^{13}$C(O)NR$^{15}$R$^{14}$, —NR$^{13}$C(NCN)NR$^{15}$R$^{14}$, —NR$^{15}$R$^{14}$, alkyl, alkenyl, alkynyl, saturated or partially unsaturated cycloalkyl, cycloalkylalkyl, —S(O)$_p$(alkyl), —S(O)$_p$(CR$^{13}$R$^{14}$)$_q$-aryl, aryl, arylalkyl, heteroaryl, heteroarylalkyl, saturated or partially unsaturated heterocyclyl, heterocyclylalkyl, —O(CR$^{13}$R$^{14}$)$^q$-aryl, —NR$^{15}$(CR$^{13}$R$^{14}$)$_q$-aryl, —O(CR$^{13}$R$^{14}$)$_q$-heteroaryl, —NR$^{13}$(CR$^{13}$R$^{14}$)$_q$-heteroaryl, —O(CR$^{13}$R$^{14}$)$_q$-heterocyclyl or —NR$^{15}$(CR$^{13}$R$^{14}$)$_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —NR$^{13}$SO$_2$R$^{18}$, —SO$_2$NR$^{15}$R$^{13}$, —C(O)R$^{15}$, —C(O)OR$^{15}$, —OC(O)R$^{15}$, —NR$^{13}$C(O)OR$^{18}$, —NR$^{13}$C(O)R$^{15}$, —C(O)NR$^{15}$R$^{13}$, —NR$^{15}$R$^{13}$, —NR$^{14}$C(O)NR$^{15}$R$^{13}$, —NR$^{14}$C(NCN)NR$^{15}$R$^{13}$, OR$^{15}$, aryl, heteroaryl, arylalkyl, heteroarylalkyl, saturated and partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, NR$^{15}$R$^{13}$ and OR$^{15}$;

R$^{13}$ and R$^{14}$ are independently hydrogen or alkyl, or

R$^{13}$ and R$^{14}$ together with the atoms to which they are attached form a saturated or partially unsaturated cycloalkyl or a saturated or partially unsaturated heterocyclyl ring, wherein said alkyl, cycloalkyl and heterocyclyl portions are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, OR$^a$, NR$^a$R$^b$, NR$^a$OR$^b$, NR$^a$CO$_2$R$^b$, NR$^a$COR$^b$, SO$_2$NR$^a$R$^b$, SR$^a$, SOR$^a$, SO$_2$R$^a$, S—S—R$^a$, C(=O)R$^a$, C(=O)OR$^a$, OC(=O)R$^a$, C(=O)NR$^a$R$^b$, NR$^a$C(=O)R$^b$, and NR$^a$C(=O)NR$^b$R$^c$;

R$^{15}$, R$^{16}$ and R$^{17}$ are independently H, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, OR$^a$, NR$^a$R$^b$, NR$^a$OR$^b$, NR$^a$CO$_2$R$^b$, NR$^a$COR$^b$, SO$_2$NR$^a$R$^b$, SR$^a$, SOR$^a$, SO$_2$R$^a$, S—S—R$^a$, C(=O)R$^a$, C(=O)OR$^a$, OC(=O)R$^a$, C(=O)NR$^a$R$^b$, NR$^a$C(=O)R$^b$, NR$^a$C(=O)NR$^b$R$^c$, OC(=O)NR$^a$R$^b$, and C(=O)CH$_2$OR$^a$;

or any two of R$^{15}$, R$^{16}$ and R$^{17}$ together with the atom to which they are attached form a heterocyclic ring optionally containing one or more additional heteroatoms selected from N, O, S, SO, SO$_2$ and NR$^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^a$, $NR^aR^b$, $SR^a$, heteroaryl, arylalkyl, heteroarylalkyl, and heterocyclylalkyl, or $R^{13}$ and $R^{15}$ together with the atom to which they are attached form a saturated or partially unsaturated cycloalkyl or saturated or partially unsaturated heterocyclyl ring, wherein said alkyl, cycloalkyl and heterocyclyl are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, C(=O)$R^a$, C(=O)O$R^a$, OC(=O)$R^a$, C(=O)$NR^aR^b$, $NR^aC$(=O)$R^b$, and $NR^aC$(=O)$NR^bR^c$;

$R^{18}$ is $CF_3$, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, saturated or partially unsaturated heterocyclyl, cycloalkylalkyl, aryl, arylalkyl, heteroaryl, heteroarylalkyl and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, C(=O)$R^a$, C(=O)O$R^a$, OC(=O)$R^a$, C(=O)$NR^aR^b$, $NR^aC$(=O)$R^b$, $NR^aC$(=O)$NR^bR^c$, or $R^{15}$ and $R^{18}$ together with the atoms to which they are attached form a saturated or partially unsaturated cycloalkyl or saturated or partially unsaturated heterocyclyl ring, wherein said alkyl, cycloalkyl and heterocyclyl are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, C(=O)$R^a$, C(=O)O$R^a$, OC(=O)$R^a$, C(=O)$NR^aR^b$, $NR^aC$(=O)$R^b$, and $NR^aC$(=O)$NR^bR^c$;

each $R^{19}$ is independently H, halogen, cyano, nitro, trifluoromethyl, difluoromethyl, fluoromethyl, fluoromethoxy, difluoromethoxy, trifluoromethoxy, azido, —$SR^{18}$, —$OR^{15}$, —C(O)$R^{15}$, —C(O)O$R^{15}$, —$NR^{14}$C(O)O$R^{18}$, —OC(O)$R^{15}$—$NR^{14}SO_2R^{18}$, —$SO_2NR^{15}R^{14}$, —$NR^{14}$C(O)$R^{15}$, —C(O)$NR^{15}R^{14}$, —$NR^{13}$C(O)$NR^{15}R^{14}$, —$NR^{13}$C(NCN)$NR^{15}R^{14}$, —$NR^{15}R^{14}$, alkyl alkenyl, alkynyl, saturated or partially unsaturated cycloalkyl, cycloalkylalkyl, —S(O)$_p$(alkyl), —S(O)$_p(CR^{13}R^{14})_q$-aryl, aryl, arylalkyl, heteroaryl, heteroarylalkyl, saturated or partially unsaturated heterocyclyl, heterocyclylalkyl, —O(CR$^{13}R^{14})_q$-aryl, —$NR^{15}$(CR$^{13}R^{14})_q$-aryl, —O(CR$^{13}R^{14})_q$-heteroaryl, —$NR^{13}$(CR$^{13}R^{14})_q$-heteroaryl, —O(CR$^{13}R^{14})_q$-heterocyclyl or —$NR^{15}$(CR$^{13}R^{14})_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^{13}SO_2R^{18}$, —$SO_2NR^{15}R^{13}$, —C(O)$R^{15}$, —C(O)O$R^{15}$, —OC(O)$R^{15}$, —$NR^{13}$C(O)O$R^{18}$, —$NR^{13}$C(O)R, —C(O)$NR^{15}R^{13}$, —$NR^{15}R^{13}$ $NR^{14}$C(O)$NR^{15}R^{13}$, —$NR^{14}$C(NCN)$NR^{15}R^{13}$, —$OR^{15}$, aryl, heteroaryl, arylalkyl, heteroarylalkyl, saturated or partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, $NR^{15}R^{13}$ and $OR^{15}$;

each $R^{20}$ is independently $C_1$-$C_4$ alkyl, saturated or partially unsaturated cycloalkyl, trifluoromethyl, difluoromethyl, or fluoromethyl;

$R^a$, $R^b$ and $R^c$ are independently H, alkyl, alkenyl, alkynyl, saturated or partially unsaturated cycloalkyl, saturated or partially unsaturated heterocyclyl, aryl, or heteroaryl, or $NR^bR^c$ forms a 5-6 membered heterocyclic ring having 1-2 ring nitrogen atoms and optionally substituted with ($C_1$-$C_3$ alkyl), or $NR^bR^c$ forms a 5-6 membered heterocyclic ring having 1-2 ring nitrogen atoms;

j is 0, 1, 2 or 3;

m is 1, 2, 3, or 4;

n is 0, 1, 2, 3, or 4;

q is 0, 1, 2, 3, 4, or 5; and p is 0, 1 or 2;

wherein when said compound of Formula I is represented by the formula

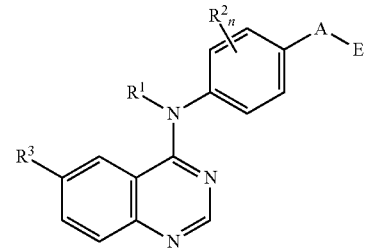

and $R^3$ is other than Q or Z, then E is not a benzofuranyl, indolyl, quinazolinyl, quinolinyl, or isoquinolinyl ring.

In certain embodiments, provided are compounds of Formula I

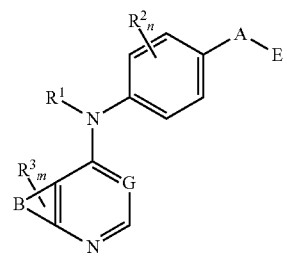

I and solvates, metabolites, and pharmaceutically acceptable salts thereof, wherein:

A is O, C(=O), S, SO or $SO_2$;

G is N or C—CN;

B represents a fused 6-membered aryl ring or a 5-6 membered heteroaryl ring;

E is

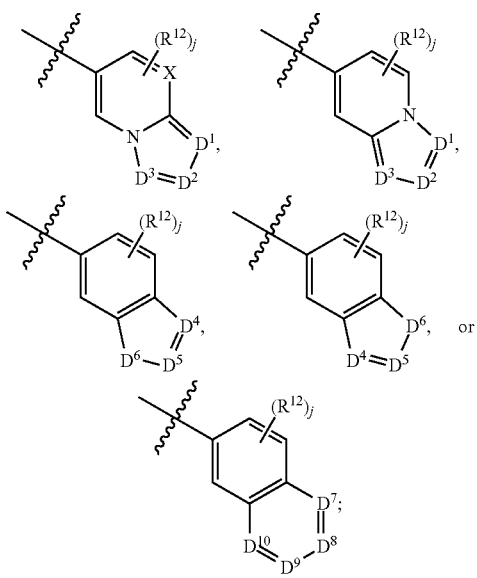

X is N or CH;
$D^1$, $D^2$ and $D^3$ are independently N or $CR^{19}$;
$D^4$ and $D^5$ are independently N or $CR^{19}$ and $D^6$ is O, S, or $NR^{20}$, wherein at least one of $D^4$ and $D^5$ is not $CR^{19}$;
$D^7$, $D^8$, $D^9$ and $D^{10}$ are independently N or $CR^{19}$, wherein at least one of $D^7$, $D^8$, $D^9$ and $D^{10}$ is N;
$R^1$ is H or alkyl;
each $R^2$ is independently halogen, cyano, nitro, trifluoromethyl, difluoromethyl, fluoromethyl, fluoromethoxy, difluoromethoxy, trifluoromethoxy, azido, —$SR^{18}$, —$OR^{15}$, —C(O)$R^{15}$, —C(O)O$R^{15}$, —$NR^{14}$C(O)O$R^{18}$, —OC(O)$R^{15}$, —$NR^{14}$SO$_2R^{18}$, —SO$_2$N$R^{15}R^{14}$, —$NR^{14}$C(O)$R^{15}$, —C(O)N$R^{15}R^{14}$, —$NR^{15}$C(O)N$R^{15}R^{14}$, —$NR^{13}$C(NCN)N$R^{15}R^{14}$, —N$R^{15}R^{14}$, alkyl, alkenyl, alkynyl, saturated or partially unsaturated cycloalkyl, cycloalkylalkyl, —S(O)$_p$(alkyl), —S(O)$_p$(C$R^{13}R^{14}$)$_q$-aryl, aryl, arylalkyl, heteroaryl, heteroarylalkyl, saturated or partially unsaturated heterocyclyl, heterocyclylalkyl, —O(C$R^{13}R^{14}$)$_q$-aryl, —N$R^{15}$(C$R^{13}R^{14}$)$_q$-aryl, —O(C$R^{13}R^{14}$)$_q$-heteroaryl, —N$R^{13}$(C$R^{13}R^{14}$)$_q$-heteroaryl, —O(C$R^{13}R^{14}$)$_q$-heterocyclyl or —N$R^{15}$(C$R^{13}R^{14}$)$_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^{13}$SO$_2R^{18}$, —SO$_2$N$R^{15}R^{13}$, —C(O)$R^{15}$, —C(O)O$R^{15}$, —OC(O)$R^{15}$, —$NR^{13}$C(O)O$R^{18}$, —$NR^{13}$C(O)$R^{15}$, —C(O)N$R^{15}R^{13}$, —N$R^{15}R^{13}$, —$NR^{14}$C(O)N$R^{15}R^{13}$, —$NR^{14}$C(NCN)N$R^{15}R^{13}$, O$R^{15}$, aryl, heteroaryl, arylalkyl, heteroarylalkyl saturated and partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, N$R^{15}R^{13}$ and O$R^{15}$;
each $R^3$ is independently Q, Z, halogen, cyano, nitro, alkyl, alkenyl, alkynyl, heteroalkyl, heteroalkenyl, heteroalkynyl, saturated or partially unsaturated cycloalkyl, saturated or partially unsaturated heterocyclyl, aryl, arylalkyl, heteroaryl, heteroarylalkyl, trifluoromethoxy, difluoromethoxy, fluoromethoxy, trifluoromethyl, difluoromethyl, fluoromethyl, O$R^{15}$, N$R^{15}R^{16}$, N$R^{15}R^{16}$, N$R^{15}$C(=O)O$R^{18}$, N$R^{15}$C(=O)$R^{16}$, SO$_2$N$R^{15}R^{16}$, S$R^{15}$, SO$R^{15}$, SO$_2R^{15}$, C(=O)$R^{15}$, C(=O)O$R^{15}$, OC(=O)$R^{15}$, C(=O)N$R^{15}R^{16}$, N$R^{15}$C(=O)N$R^{16}R^{17}$, N$R^{15}$C(=NCN)N$R^{16}R^{17}$, or N$R^{15}$C(=NCN)$R^{16}$,
wherein said alkyl, alkenyl, alkynyl, heteroalkyl, heteroalkenyl, heteroalkynyl, cycloalkyl, heterocyclyl, aryl, arylalkyl, heteroaryl and heteroarylalkyl are optionally substituted with one or more groups independently selected from halogen, oxo, cyano, nitro, alkyl, alkenyl, alkynyl, heteroalkyl, heteroalkenyl, heteroalkynyl, saturated or partially unsaturated cycloalkyl, saturated and partially unsaturated heterocyclyl, aryl, arylalkyl, heteroaryl, heteroarylalkyl, trifluoromethoxy, difluoromethoxy, fluoromethoxy, trifluoromethyl, difluoromethyl, fluoromethyl, O$R^{15}$, N$R^{15}R^{16}$, N$R^{15}$O$R^{16}$, N$R^{15}$C(=O)O$R^{18}$, N$R^{15}$C(=O)$R^{16}$, SO$_2$N$R^{15}R^{16}$, S$R^{15}$, SO$R^{15}$, SO$_2R^{15}$, C(=O)$R^{15}$, C(=O)O$R^{15}$, OC(=O)$R^{15}$, C(=O)N$R^{15}R^{16}$, N$R^{15}$C(=O)N$R^{16}R^{17}$, N$R^{15}$C(=NCN)N$R^{16}R^{17}$, and N$R^{15}$C(=NCN)R$^{16}$;

Q is

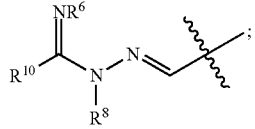

Z is selected from

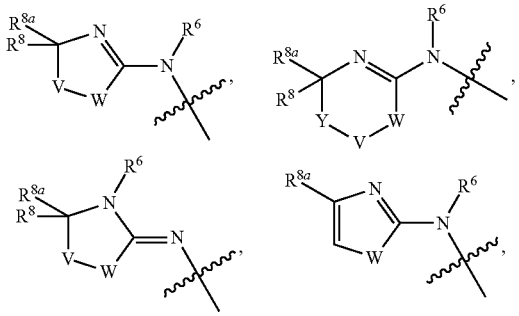

and tautomers thereof;
W and V are independently O, N$R^6$, S, SO, SO$_2$, C$R^7R^8$, C$R^8R^9$ or C=O;
Y is S, SO, SO$_2$, C$R^7$C$R^8$, or C$R^8R^9$,
provided that when W is O, N$R^6$, S, SO, or SO$_2$, then V is C$R^8R^9$, and
when V is O, N$R^6$, S, SO, or SO$_2$, then W and Y are each C$R^8R^9$;
each $R^6$, $R^8$, $R^{8a}$ and $R^9$ are independently hydrogen, trifluoromethyl, alkyl, saturated or partially unsaturated cycloalkyl, saturated or partially unsaturated heterocyclyl, aryl, arylalkyl, heteroaryl, heteroarylalkyl, or heterocyclylalkyl, wherein said alkyl, cycloalkyl, heterocyclyl, aryl, arylalkyl, heteroaryl, heteroarylalkyl, and heterocyclylalkyl are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, O$R^{15}$, N$R^{15}R^{16}$, S$R^{15}$, S(=O)$R^{15}$, SO$_2R^{15}$, trifluoromethyl, difluoromethyl, fluoromethyl, fluoromethoxy, difluoromethoxy, trifluoromethoxy, azido, aryl, heteroaryl, arylalkyl, heteroarylalkyl, and heterocyclylalkyl;

$R^7$ is hydrogen, halogen, cyano, nitro, alkyl, alkenyl, alkynyl, saturated or partially unsaturated cycloalkyl, saturated or partially unsaturated heterocyclyl, cycloalkylalkyl, aryl, arylalkyl, heteroaryl, heteroarylalkyl, heterocyclylalkyl, —$NR^{15}SO_2R^{16}$—$SO_2NR^{15}R^{16}$, —$C(O)R^{15}$, —$C(O)OR^{15}$, —$OC(O)R^{15}$, —$NR^{15}C(O)OR^{18}$, —$NR^{15}C(O)R^{16}$, —$C(O)NR^{15}R^{16}$, —$NR^{15}R^{16}$, —$NR^{15}C(O)NR^{16}R^{17}$, —$OR^{15}$, —$S(O)R^{15}$, —$SO_2R^{15}$, or $SR^{15}$, wherein said alkyl, alkenyl, alkynyl, cycloalkyl, heterocyclyl, cycloalkylalkyl, aryl, arylalkyl, heteroaryl, heteroarylalkyl, and heterocyclylalkyl, are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, —$NR^{15}SO_2R^{16}$— $SO_2NR^{15}R^{16}$, —$C(O)R^{15}$, —$C(O)OR^{15}$, —$OC(O)R^{15}$, —$NR^{15}C(O)OR^{18}$, —$NR^{15}C(O)R^{16}$, —$C(O)NR^{15}R^{16}$, —$NR^{15}R^{16}$, —$NR^{15}C(O)NR^{16}R^{17}$, —$OR^{15}$, —$S(O)R^{15}$, —$SO_2R^{15}$, $SR^{15}$, aryl, arylalkyl, heteroaryl, heteroarylalkyl, and heterocyclylalkyl;

$R^{10}$ is hydrogen, alkyl, alkenyl, alkynyl, saturated or partially unsaturated cycloalkyl, saturated or partially unsaturated heterocyclyl, cycloalkylalkyl, aryl, arylalkyl, heteroaryl, heteroarylalkyl, heterocyclylalkyl, —$NR^{15}C(O)OR^{18}$, —$NR^{15}C(O)R^{16}$, —$NR^{15}R^{16}$, or —$OR^{15}$, wherein said alkyl, alkenyl, alkynyl, cycloalkyl, heterocyclyl, cycloalkylalkyl, aryl, arylalkyl, heteroaryl, heteroarylalkyl, heterocyclylalkyl, are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, —$NR^{15}SO_2R^{16}$—$SO_2NR^{15}R^{16}$, —$C(O)R^{15}$, —$C(O)OR^{15}$, —$OC(O)R^{15}$, —$NR^{15}C(O)OR^{18}$, —$NR^{15}C(O)R^{16}$, $C(O)NR^{15}R^{16}$, —$N^{15}R^{16}$, —$NR^{15}C(O)NR^{16}R^{17}$, —$OR^{15}$, —$S(O)R^{15}$, —$SO_2R^{15}$, $SR^{15}$, aryl, arylalkyl, heteroaryl, heteroarylalkyl, and heterocyclylalkyl;

or $R^6$ and $R^8$ together with the atoms to which they are attached form a 3 to 10 membered saturated or partially unsaturated heterocyclyl ring optionally containing one or more additional heteroatoms selected from N, O, S, SO, $SO_2$ and $NR^6$, wherein said carbocyclic and heterocyclic rings are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^{15}$, $NR^{15}R^{16}$, $SR^{15}$, heteroaryl, arylalkyl, heteroarylalkyl, and heterocyclylalkyl;

or $R^7$ and $R^8$ together with the atoms to which they are attached form a 3 to 10 membered saturated or partially unsaturated cycloalkyl or heterocyclyl ring optionally containing one or more additional heteroatoms selected from N, O, S, SO, $SO_2$ and $NR^6$, wherein said carbocyclic and heterocyclic rings are optionally substituted with one or more groups independently selected from oxo, halogen, alkyl, alkenyl, alkynyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^{15}$, $NR^{15}R^{16}$, $SR^{15}$, heteroaryl, arylalkyl, heteroarylalkyl, and heterocyclylalkyl;

or $R^8$ and $R^9$ together with the atoms to which they are attached form a 3 to 10 membered saturated or partially unsaturated cycloalkyl or heterocyclyl ring optionally containing one or more additional heteroatoms selected from N, O, S, SO, $SO_2$ and $NR^6$, wherein said carbocyclic and heterocyclic rings are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^{15}$, $NR^{15}R^{16}$, $SR^{15}$, heteroaryl, arylalkyl, heteroarylalkyl, and heterocyclylalkyl;

or $R^6$ and $R^{10}$ together with the atoms to which they are attached form a 3 to 10 membered saturated or partially unsaturated heterocyclyl ring optionally containing one or more additional heteroatoms selected from N, O, S, SO, $SO_2$ and $NR^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^{15}$, $NR^{15}R^{16}$, $SR^{15}$, heteroaryl, arylalkyl, heteroarylalkyl, and heterocyclylalkyl;

or $R^8$ and $R^{10}$ together with the atoms to which they are attached form a 3 to 10 membered saturated or partially unsaturated heterocyclyl ring optionally containing one or more additional heteroatoms selected from N, O, S, SO, $SO_2$ and $NR^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^{15}$, $NR^{15}R^{16}$, $SR^{15}$, heteroaryl, arylalkyl, heteroarylalkyl, and heterocyclylalkyl;

each $R^{12}$ is independently halogen, cyano, nitro, trifluoromethyl, difluoromethyl, fluoromethyl, fluoromethoxy, difluoromethoxy, trifluoromethoxy, azido, —$SR^{18}$, —$OR^{15}$, —$C(O)R^{15}$, —$C(O)OR^{15}$, —$NR^{14}C(O)OR^{18}$, —$OC(O)R^{15}$—$NR^{14}SO_2R^{18}$, —$SO_2NR^{15}R^{14}$, $NR^{14}C(O)R^{15}$, —$C(O)NR^{15}R^{14}$, —$NR^{13}C(O)NR^{15}R^{14}$, —$NR^{13}C(NCN)NR^{15}R^{14}$, —$NR^{15}R^{14}$, alkyl, alkenyl, alkynyl, saturated or partially unsaturated cycloalkyl, cycloalkylalkyl, —$S(O)_p$(alkyl), —$S(O)_p(CR^{13}R^{14})_q$-aryl, aryl, arylalkyl, heteroaryl, heteroarylalkyl, saturated or partially unsaturated heterocyclyl, heterocyclylalkyl, —$O(CR^{13}R^{14})_q$-aryl, —$NR^{15}(CR^{13}R^{14})_q$-aryl, —$O(CR^{13}R^{14})_q$-heteroaryl, —$NR^{13}(CR^{13}R^{14})_q$-heteroaryl, —$O(CR^{13}R^{14})_q$-heterocyclyl or —$NR^{15}(CR^{13}R^{14})_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^{13}SO_2R^{18}$, —$SO_2NR^{15}R^{13}$, —$C(O)R^{15}$, —$C(O)OR^{15}$, —$OC(O)R^{15}$, —$NR^{13}C(O)OR^{18}$, —$NR^{13}C(O)R^{15}$, —$C(O)NR^{15}R^{13}$, —$NR^{15}R^{13}$, —$NR^{14}C(O)NR^{15}R^{13}$, —$NR^{14}C(NCN)NR^{15}R^{13}$, —$OR^{15}$, aryl, heteroaryl, arylalkyl, heteroarylalkyl, saturated and partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, $NR^{15}R^{13}$ and $OR^{15}$;

$R^{13}$ and $R^{14}$ are independently hydrogen or alkyl, or $R^{13}$ and $R^{14}$ together with the atoms to which they are attached form a saturated or partially unsaturated cycloalkyl, or saturated or partially unsaturated heterocyclyl ring, wherein said alkyl, cycloalkyl and heterocyclyl portions are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, C(=O)$R^a$, C(=O)O$R^a$, OC(=O)$R^a$, C(=O)N$R^aR^b$, $NR^aC$(=O)$R^b$, and $NR^aC$(=O)$NR^bR^c$;

$R^{15}$, $R^{16}$ and $R^{17}$ are independently H, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, $OR^a$, $NR^aR^b$, $N^aOR^b$, $NR^aCO_2R^b$, $NR^aCOR^b$, $SO_2NR^aR^b$, $SR^a$, $SOR^a$, $SO_2R^a$, S—S—$R^a$, C(=O)$R^a$, C(=O)O$R^a$, OC(=O)$R^a$, C(=O)N$R^aR^b$, $NR^aC$(=O)$R^b$, and $NR^aC$(=O)$NR^bR^c$, or any two of $R^{15}$, $R^{16}$ and $R^{17}$ together with the atom to which they are attached form a heterocyclic ring optionally containing one or more additional heteroatoms selected from N, O, S, SO, $SO_2$ and $NR^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^a$, $NR^aR^b$, $SR^a$, heteroaryl, arylalkyl, heteroarylalkyl, and heterocyclylalkyl, or $R^{13}$ and $R^{15}$ together with the atom to which they are attached form a saturated or partially unsaturated cycloalkyl or saturated or partially unsaturated heterocyclyl ring, wherein said alkyl, cycloalkyl and heterocyclyl are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, C(=O)$R^a$, C(=O)O$R^a$, OC(=O)$R^a$, C(=O)N$R^aR^b$, $NR^aC$(=O)$R^b$, and $NR^aC$(=O)$NR^bR^c$;

$R^{18}$ is $CF_3$, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, saturated or partially unsaturated heterocyclyl, cycloalkylalkyl, aryl, arylalkyl, heteroaryl, heteroarylalkyl and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, C(=O)$R^a$, C(=O)O$R^a$, OC(=O)$R^a$, C(=O)N$R^aR^b$, $NR^aC$(=O)$R^b$, $NR^aC$(=O)$NR^bR^c$, or $R^{15}$ and $R^{18}$ together with the atoms to which they are attached form a saturated or partially unsaturated cycloalkyl or saturated or partially unsaturated heterocyclyl ring, wherein said alkyl, cycloalkyl and heterocyclyl are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, C(=O)$R^a$, C(=O)O$R^a$, OC(=O)$R^a$, C(=O)N$R^aR^b$, $NR^aC$(=O)$R^b$, and $NR^aC$(=O)$NR^bR^c$;

each $R^{19}$ is independently H, halogen, cyano, nitro, trifluoromethyl, difluoromethyl, fluoromethyl, fluoromethoxy, difluoromethoxy, trifluoromethoxy, azido, —$SR^{18}$, —$OR^{15}$, —C(O)$R^{15}$, —C(O)O$R^{15}$, —$NR^{14}$C(O)O$R^{18}$, —OC(O)$R^{15}$—$NR^{14}SO_2R^{18}$, —$SO_2NR^{15}R^{14}$, —$NR^{14}$C(O)$R^{15}$, —C(O)$NR^{15}R^{14}$, —$NR^{13}$C(O)$NR^{15}R^{14}$, —$NR^{13}$C(NCN)$NR^{15}R^{14}$, —$NR^{15}R^{14}$, alkyl, alkenyl, alkynyl, saturated or partially unsaturated cycloalkyl, cycloalkylalkyl, —S(O)$_p$(alkyl), —S(O)$_p$(C$R^{13}R^{14}$)$_q$-aryl, aryl, arylalkyl, heteroaryl, heteroarylalkyl, saturated or partially unsaturated heterocyclyl, heterocyclylalkyl, —O(C$R^{13}R^{14}$)$_q$-aryl, —$NR^{15}$(C$R^{13}R^{14}$)$_q$-aryl, —O(C$R^{13}R^{14}$)$_q$-heteroaryl, —$NR^{13}$(C$R^{13}R^{14}$)$_q$-heteroaryl, —O(C$R^{13}R^{14}$)$_q$-heterocyclyl or —$NR^{15}$(C$R^{13}R^{14}$)$_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^{13}SO_2R^{18}$, —$SO_2NR^{15}R^{13}$, —C(O)$R^{15}$, —C(O)O$R^{15}$, —OC(O)$R^{15}$, —$NR^{13}$C(O)O$R^{18}$, —$NR^{13}$C(O)$R^{15}$, —C(O)$NR^{15}R^{13}$, —$NR^{15}R^{13}$, —$NR^{14}$C(O)$NR^{15}R^{13}$, —$NR^{14}$(NCN)$NR^{15}R^{13}$, —$OR^{15}$, aryl, heteroaryl, arylalkyl, heteroarylalkyl, saturated or partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, $NR^{15}R^{13}$ and $OR^{15}$;

each $R^{20}$ is independently $C_1$-$C_4$ alkyl, saturated or partially unsaturated cycloalkyl, trifluoromethyl, difluoromethyl, or fluoromethyl;

$R^a$, $R^b$ and $R^c$ are independently H, alkyl, alkenyl, alkynyl, saturated or partially unsaturated cycloalkyl, saturated or partially unsaturated heterocyclyl, aryl, or heteroaryl;

j is 0, 1, 2 or 3;

m is 1, 2, 3, or 4;

n is 0, 1, 2, 3, or 4;

q is 0, 1, 2, 3, 4, or 5; and p is 0, 1 or 2;

wherein when said compound of Formula I is represented by the formula

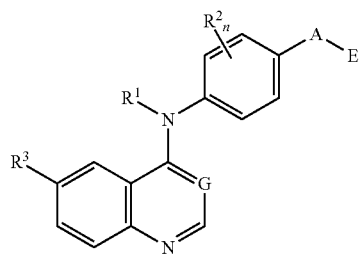

and $R^3$ is other than Q or Z, then E is not a benzofuranyl, indolyl, quinazolinyl, quinolinyl, or isoquinolinyl ring.

In certain embodiments of compounds of Formula I, G is N.

In certain embodiments of compounds of Formula I, $R^1$ is H.

In certain embodiments of compounds of Formula I, A is O.

In certain embodiments of compounds of Formula I, A is S.

In certain embodiments of compounds of Formula I, B is a fused 6 membered aryl ring.

In certain embodiments of compounds of Formula I, B is

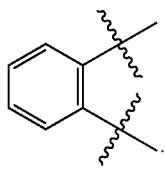 [SMILES: *c1ccccc1*]

In certain embodiments, Formula I has the structure:

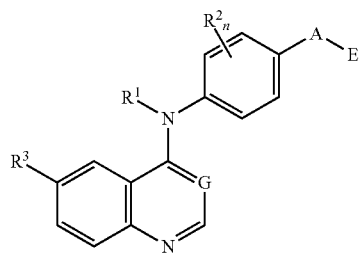

wherein $R^1$, $R^2$, $R^3$, G, A, E and n are as defined above.

In certain embodiments of compounds of Formula I, B is a fused 5-6 membered heteroaryl ring. In particular embodiments, B is a fused thieno ring.

In certain embodiment of compounds of Formula I, B is

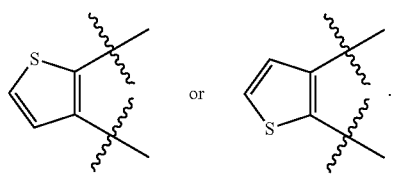 [SMILES: *c1ccsc1* ; *c1ccsc1*]

In certain embodiments, Formula I has the structure:

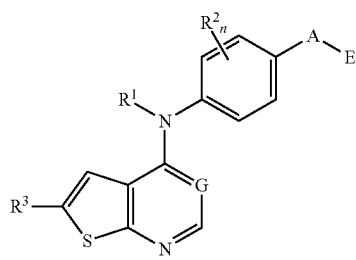

wherein $R^1$, $R^2$, $R^3$, G, A, E and n are as defined above.

In certain embodiments, Formula I has the structure:

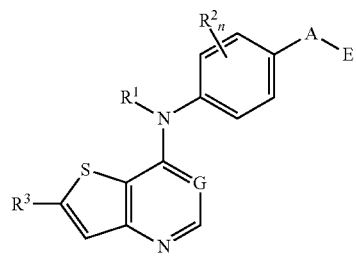

wherein $R^1$, $R^2$, $R^3$, G, A, E and n are as defined above.

In certain embodiments of compounds of Formula I, E is

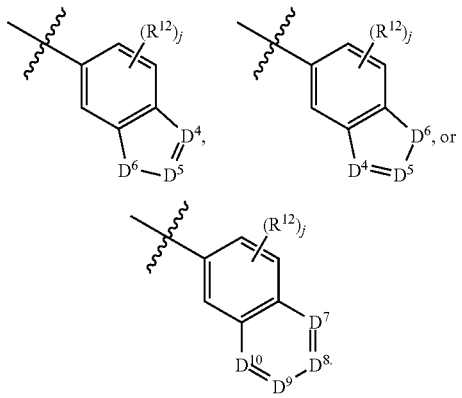

Exemplary embodiments of E include, but are not limited to, bicyclic heteroaryl rings selected from

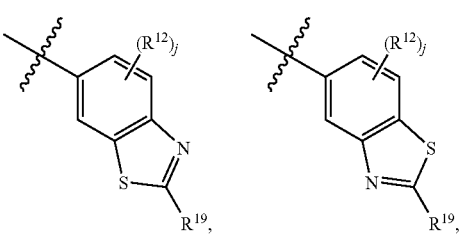

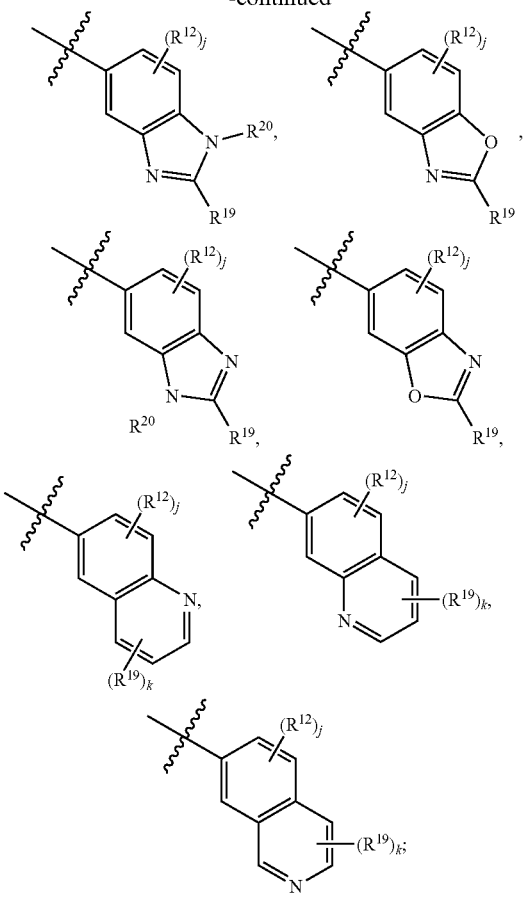

wherein k is 0, 1, 2, or 3. Examples of $R^{12}$ groups include, but are not limited to, amino, $C_1$-$C_4$ alkoxy, saturated or partially unsaturated cycloalkyl, CN, trifluoromethyl, difluoromethyl, and fluoromethyl. Example of $R^{19}$ groups include, but are not limited to, H, amino, $C_1$-$C_4$ alkoxy, saturated or partially unsaturated cycloalkyl, CN, trifluoromethyl, difluoromethyl, and fluoromethyl. Examples of $R^{20}$ include, but are not limited to, $C_1$-$C_4$ alkyl, saturated or partially unsaturated cycloalkyl, trifluoromethyl, difluoromethyl, and fluoromethyl.

In other embodiments, $R^{12}$ is halogen.
In other embodiments, $R^{20}$ is H.
In particular embodiments, $R^{12}$ is H.
In certain embodiments, $R^{19}$ is H or $C_1$-$C_6$ alkyl. In particular embodiments, $R^{19}$ is H or methyl.
In certain embodiments, $R^{20}$ is H or $C_1$-$C_6$ alkyl. In particular embodiments, $R^{20}$ is H, methyl or ethyl.
In particular embodiments, E is selected from the structures:

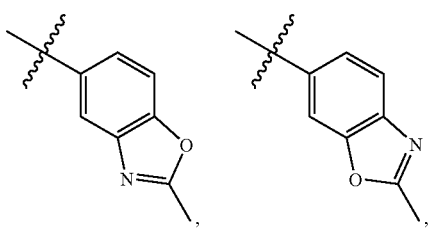

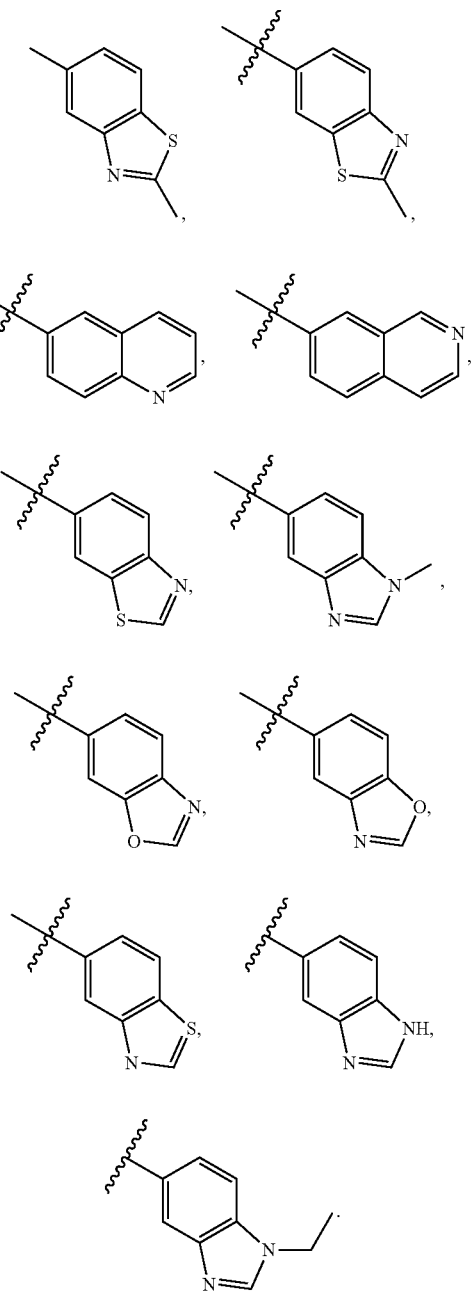

In certain embodiments of compounds of Formula I, E is

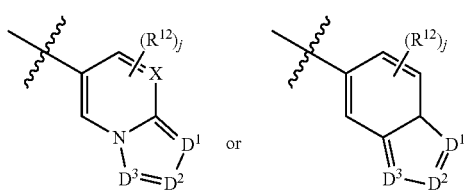

In one embodiment, at least one of $D^1$, $D^2$ and $D^3$ is N.

Exemplary embodiments of E further include heteroaryl rings selected from, but not limited to,

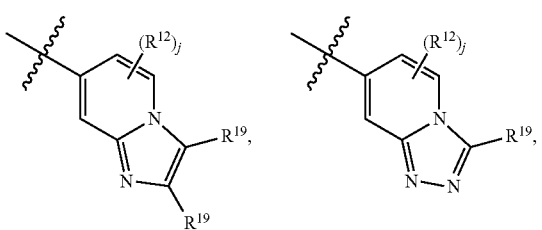

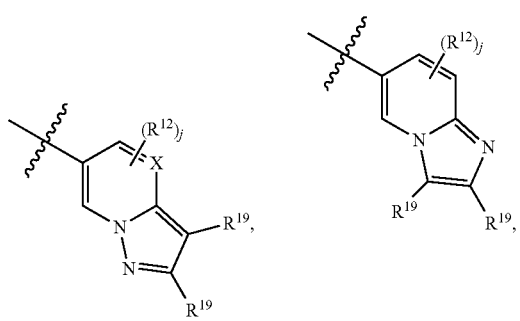

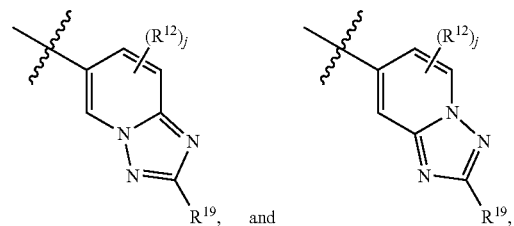

wherein each $R^{19}$ group is independent of the other. Examples of $R^{12}$ groups include, but are not limited to, amino, $C_1$-$C_4$ alkoxy, saturated or partially unsaturated cycloalkyl, CN, trifluoromethyl, difluoromethyl, and fluoromethyl. Example of $R^{19}$ groups include, but are not limited to, H, amino, $C_1$-$C_4$ alkoxy, saturated or partially unsaturated cycloalkyl, CN, trifluoromethyl, difluoromethyl, and fluoromethyl.

In certain embodiments, $R^{12}$ is halogen. In certain embodiments, j is 0 or 1. A particular example for $R^{12}$ is F.

In certain embodiments, $R^{19}$ is H, $C_1$-$C_6$ alkyl, or halogen. Particular examples for $R^{19}$ include H, methyl, Cl, and Br.

Particular examples of E include:

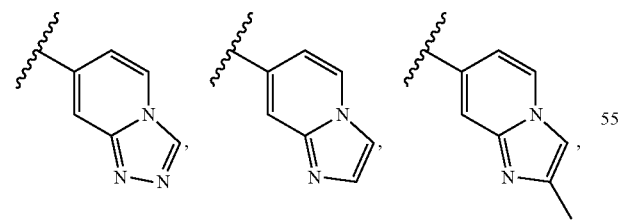

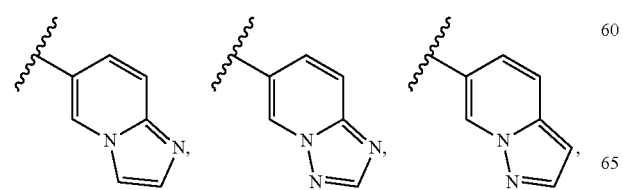

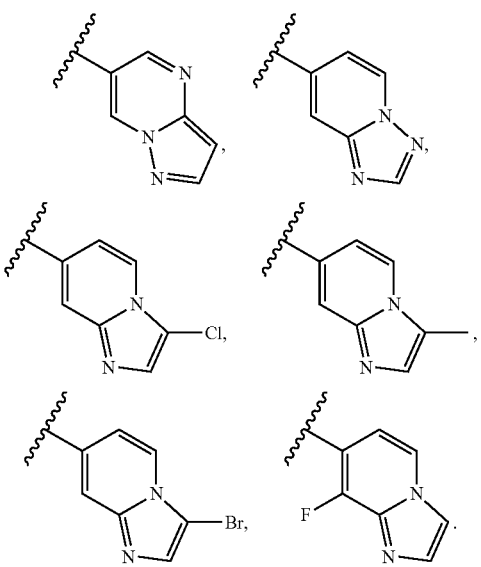

In one embodiment the compounds of Formula I are selected from compounds wherein E is selected from the groups E1, E2, E3, E4, E5, E6, E7 and E8:

E1

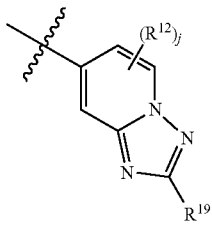

E2

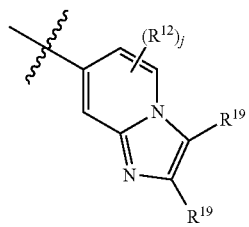

E3

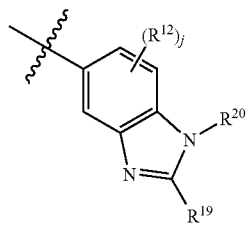

E4

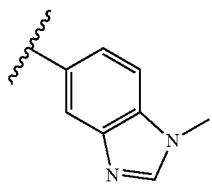

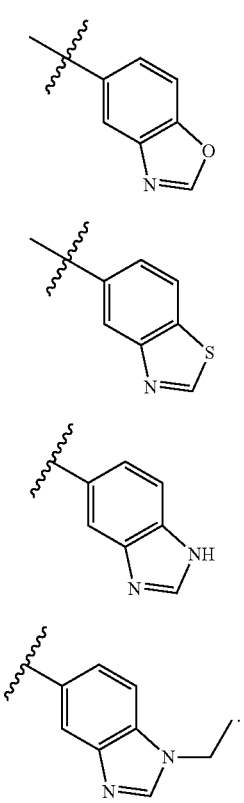

In certain embodiments, E is selected from the groups E1, E2 and E3, and j is 0 or 1. In certain embodiments of the groups E1, E2 and E3, $R^{12}$ is halogen. In certain embodiments of the groups E1, E2 and E3, $R^{19}$ is selected from H, halogen or $C_1$-$C_6$ alkyl. In certain embodiments of the groups E1, E2 and E3, $R^{20}$ is H. Particular examples of ErbB2 selective compounds include compounds of Formula I wherein E is selected from the groups

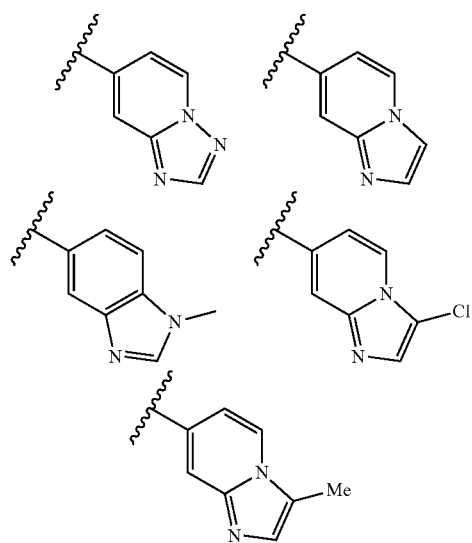

In another embodiment, provided are compounds of Formula I wherein E is selected from E1, E2 and E3, provided that $R^3$ of formual I is other than —$NR^{15}$C(=O)(CH=CH)$R^{16a}$ when $R^{16a}$ represents H, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, C(=O)$R^a$, C(=O)O$R^a$, OC(=O)$R^a$, C(=O)$NR^aR^b$, $NR^aC$(=O)$R^b$, $NR^aC$(=O)$NR^bR^c$, OC(=O)$NR^aR^b$, and C(=O)$CH_2OR^a$. Certain compounds belonging to this subgroup have been found to be highly potent inhibitors of ErbB2 and are highly selective for ErbB2 over EGFR. As used herein, the term "highly selective" refers to a compound wherein the $IC_{50}$ for EGFR is at least 20 fold higher than the $IC_{50}$ for ErbB2 as determined by the cellular ErbB2 and EGFR phosphorylation assays described in Examples B and C Particular compounds of this invention were found to have an $IC_{50}$ for EGFR that is at least 50 fold higher than the $IC_{50}$ for ErbB2. As a further example, particular compounds of this invention were found to have an $IC_{50}$ for EGFR that is at least 100 fold higher than the $IC_{50}$ for ErbB2.

Accordingly, this invention provides compounds of Formula I which are highly potent ErbB2 inhibitors and are highly selective for ErbB2 relative to EGFR. Such compounds would allow treatment of cancers which can be treated by inhibiting ErbB2, for example cancers which express or overexpress ErbB2, in a relatively selective manner, thereby minimizing potential side effects associated with the inhibition of other kinases such as EGFR.

However, compounds of Formula I where $R^3$ is —$NR^{15}$C(=O)(CH=CH)$R^{16a}$ and $R^{16a}$ represents H or a substituted or unsubstituted $C_2$-$C_6$ alkyl were found to be inhibitors of both ErbB2 and EGFR. In addition, such compounds are believed to bind irreversibly to ErbB2 and EGFR.

In certain embodiments of compounds of Formula I, m is 1.

In certain embodiments of compounds of Formula I, $R^3$ is $OR^{15}$. In certain embodiments, $R^{15}$ is alkyl, alkenyl or alkynyl, wherein said alkyl, alkenyl and alkynyl are optionally substituted with one or more groups independently selected from saturated and partially unsaturated cycloalkyl, heteroaryl, saturated and partially unsaturated heterocyclyl, $OR^a$, $SO_2R^a$, and $NR^aR^b$.

In certain embodiments of compounds of Formula I, $R^3$ is $OR^{15}$ and $R^{15}$ is (i) H;

(ii) $C_3$-$C_6$ cycloalkyl optionally substituted with $OR^a$;

(iii) cycloalkylalkyl;

(iv) $C_1$-$C_6$ alkyl optionally substituted with one or two groups independently selected from —$OR^a$, —OC(O)$R^a$, —$CO_2R^a$, —$SO_2R^a$, —$SR^a$, —C(O)$NR^aR^b$, —$NR^aR^b$, —$NR^aC$(O)$R^b$, —OC(O)$NR^aR^b$, and $NR^aC$(O)$NR^bR^c$;

(v) a 5-6 membered heterocyclic ring having a ring heteroatom selected from N and O and optionally substituted with —C(O)$R^a$, $C_1$-$C_6$ alkyl, —C(O)$NR^aR^b$, —$SO_2R^a$, or C(O)$CH_2OR^a$;

(vi) heterocyclylalkyl, wherein said heterocyclic portion is a 5-6 membered ring having 1 or 2 ring heteroatoms independently selected from N and O and is optionally substituted with $C_1$-$C_6$ alkyl, halogen, $OR^a$ or oxo;

(vii) a 5-6 membered heteroaryl ring having from 1 to three ring nitrogen atoms and optionally substituted with $C_1$-$C_6$ alkyl or halogen; or (viii) heteroarylalkyl, wherein said heteroaryl portion is a 5-6 membered ring having 1-2 ring nitrogen atoms and is optionally substituted with $C_1$-$C_6$ alkyl.

In certain embodiments, $R^3$ is OH.

Examples of $OR^{15}$ when $R^{15}$ represents a $C_3$-$C_6$ cycloalkyl group optionally substituted by $OR^a$ wherein $R^a$ represents H or $C_1$-$C_6$ alkyl include cyclohexanoxy and cyclopentanoxy groups optionally substituted with OH, for example, 2-hydroxycyclopentoxy.

Examples of $OR^{15}$ when $R^{15}$ represents a cycloalkylalkyl group include —O—($C_3$-$C_6$ cycloalkyl)$(CH_2)_p$— wherein p is 1, 2, or 3. A particular example is 1-cyclopropylmethoxy.

Examples of $OR^{15}$ when $R^{15}$ represents a $C_1$-$C_6$ alkyl group include $CH_3O$— and $CH_3CH_2O$—.

Examples of $OR^{15}$ when $R^{15}$ represents a $C_1$-$C_6$ alkyl group substituted with one or two $OR^a$ groups and $R^a$ represents H, $C_1$-$C_6$ alkyl or benzyl include $CH_3O(CH_2)_2O$—, $CH_3CH_2O(CH_2)_2O$—, $HO(CH_2)_2O$—, $HOCH_2CH(OH)CH_2O$—, $CH_3CH(OH)CH_2O$—, $HOC(CH_3)_2CH_2O$—, $(PhCH_2O)CH_2CH_2O$—, and $(PhCH_2)OCH_2CH(OH)CH_2O$—.

Examples of $OR^{15}$ when $R^{15}$ represents a $C_1$-$C_6$ alkyl group substituted with —OC(O)$R^a$ include —O—$(CH_2)_p$OC(O)$R^a$ wherein p is 1-6 and $R^a$ is H or $C_1$-$C_6$ alkyl. A particular example is —O—$(CH_2)_2$OC(O)$CH_3$.

Examples of $OR^{15}$ when $R^{15}$ represents a $C_1$-$C_6$ alkyl group substituted with —$CO_2R^a$ include —O—$(CH_2)_p$$CO_2R^a$ wherein p is 1-6 and $R^a$ is H or $C_1$-$C_6$ alkyl. A particular example is —O—$(CH_2)CO_2CH_3$.

Examples of $OR^{15}$ when $R^{15}$ represents a $C_1$-$C_6$ alkyl group substituted with —$SO_2R^a$ include —O—$(CH_2)_p$$SO_2R^a$ wherein p is 1-6 and $R^a$ is $C_1$-$C_6$ alkyl. A particular example is —O$(CH_2)_3SO_2CH_3$.

Examples of $OR^{15}$ when $R^{15}$ represents a $C_1$-$C_6$ alkyl group substituted with —$SR^a$ include O—$(CH_2)_p$$SR^a$ wherein p is 1-6 and $R^a$ is $C_1$-$C_6$ alkyl. A particular example is —O$(CH_2)_3SCH_3$.

Examples of $OR^{15}$ when $R^{15}$ represents a $C_1$-$C_6$ alkyl group substituted with —C(O)$NR^aR^b$ include —O—$(CH_2)_p$C(O)$NR^aR^b$ wherein p is 1-6 and $R^a$ and $R^b$ are independently H or $C_1$-$C_6$ alkyl, or $NR^aR^b$ represents a 5-6 membered heterocycle having 1-2 ring nitrogen atoms and optionally substituted with $C_1$-$C_6$ alkyl. Particular examples of $OR^{15}$ include $(CH_3)_2NC(O)CH_2O$—, $CH_3NHC(O)CH_2O$—, $NH_2C(O)CH_2O$—, and

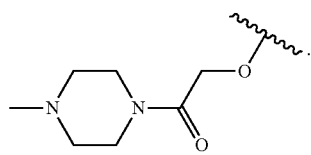 [SMILES: *OCC(=O)N1CCN(C)CC1]

Examples of $OR^{15}$ when $R^{15}$ represents a $C_1$-$C_6$ alkyl group substituted with —$NR^aC(O)R^b$ include —$O(CH_2)_p$N-$R^aC(O)R^b$ wherein p is 1-6 and $R^a$ and $R^b$ are independently H or $C_1$-$C_6$ alkyl. Particular examples of $OR^{15}$ include —$O(CH_2)_2NHC(O)CH_3$ and —$O(CH_2)_2NHC(O)CH_2CH_3$.

Examples of $OR^{15}$ when $R^{15}$ represents a $C_1$-$C_6$ alkyl group substituted with —$NR^aR^b$ include —$O$—$(CH_2)_p$N-$R^aR^b$ wherein p is 1-6 and $R^a$ and $R^b$ are independently H or $C_1$-$C_6$ alkyl (for example methyl or ethyl). Particular examples of $OR^{15}$ include —$O(CH_2)_3N(CH_3)_2$ and —$O(CH_2)_2N(CH_3)_2$.

Examples of $OR^{15}$ when $R^{15}$ represents a $C_1$-$C_6$ alkyl group substituted with —OC(O)$NR^aR^b$ include —O—$(CH_2)_p$—OC(O)$NR^aR^b$ wherein p is 1-6 and $R^a$ and $R^b$ are independently H or $C_1$-$C_6$ alkyl. A particular example is —$O(CH_2)_2OC(O)N(CH_3)_2$.

Examples of $OR^{15}$ when $R^{15}$ represents a $C_1$-$C_6$ alkyl group substituted with —$NR^aC(O)NR^bR^c$ include —O—$(CH_2)_p$—$NR^aC(O)NR^bR^c$ wherein p is 1-6, $R^a$ and $R^b$ are independently H or $C_1$-$C_6$ alkyl, and $R^c$ is H, $C_1$-$C_6$ alkyl or —O($C_1$-$C_6$ alkyl), or $NR^bR^c$ represents a 5-6 membered heterocycle having 1-2 ring nitrogen atoms (for example pyrrolidinyl). Particular examples of $OR^{15}$ include

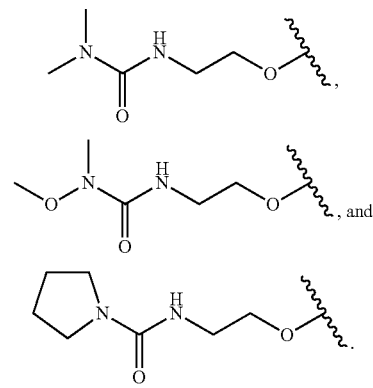

Examples of $OR^{15}$ when $R^{15}$ represents a 5-6 membered heterocyclic ring having a ring heteroatom selected from N and O and optionally substituted with —C(O)$R^a$, $C_1$-$C_6$ alkyl, oxo, —C(O)$NR^aR^b$, —$SO_2R^a$, or —C(O)$CH_2OR^a$ include pyrrolidinyl, piperidinyl, and tetrahydro-2H-pyranyl ring optionally substituted with —C(O)($C_1$-$C_6$ alkyl), oxo, $C_1$-$C_6$ alkyl, —C(O)N($C_1$-$C_6$ alkyl)$_2$, —$SO_2$($C_1$-$C_6$ alkyl), and —C(O)$CH_2O$($C_1$-$C_6$ alkyl). Particular examples include

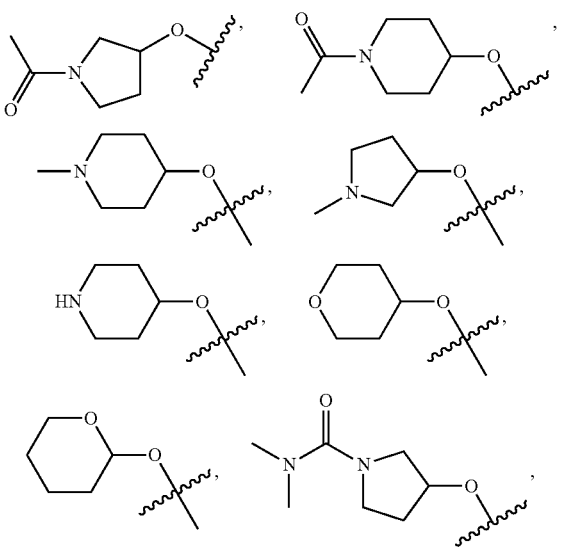

-continued

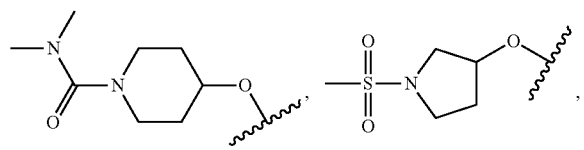

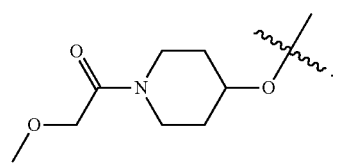

Examples of OR[15] when R[15] represents a heterocyclylalkyl group include O-Hetcyc)(CH$_2$)$_p$ wherein p is 1-6 and Hetcyc represents a 5-6 membered heterocyclic ring having 1-2 ring nitrogen atoms and optionally substituted with one or two groups selected from C$_1$-C$_6$ alkyl, halogen, OH, O—(C$_1$-C$_6$ alkyl) and oxo. Examples of the heterocyclic ring include pyrrolidinyl, piperidinyl, morpholinyl, tetrahydrofuranyl, pyrazinyl, and imidazolidinyl rings optionally substituted with one or two groups independently selected from methyl, F, OH and oxo. Particular examples of OR[15] include

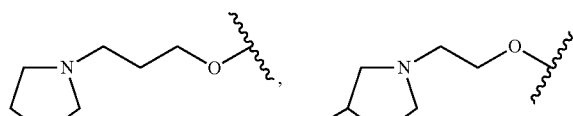

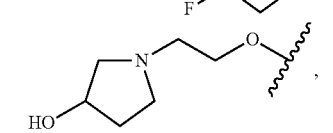

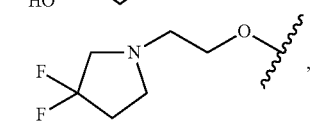

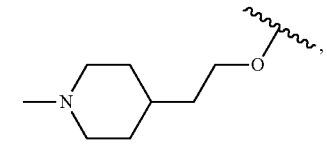

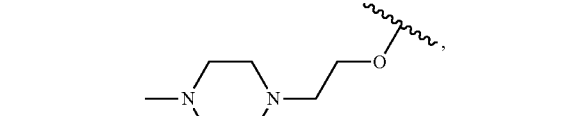

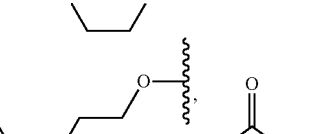

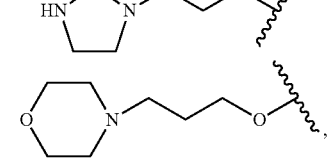

-continued

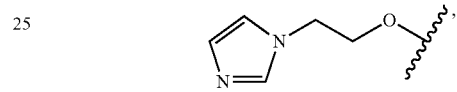

An example of OR[15] when R[15] represents a heteroaryl group includes groups wherein the heteroaryl is a pyridinyl group optionally substituted with C$_1$-C$_6$ alkyl or halogen. Particular examples include 2-methylpyridin-4-yloxy, 2-chloropyridin-4-yloxy, and 2-methylpyridin-4-yloxy.

An example of OR[15] when R[15] represents a heteroarylalkyl group includes —O—(CH$_2$)$_p$(heteroaryl) wherein p is 1-6 and the heteroaryl group is optionally substituted with C$_1$-C$_6$ alkyl. Examples of the heteroaryl group include 5-6 membered rings having 1 to 3 nitrogen atoms, for example imidazolyl and 1,2,4-triazolyl. Particular examples of OR[15] include

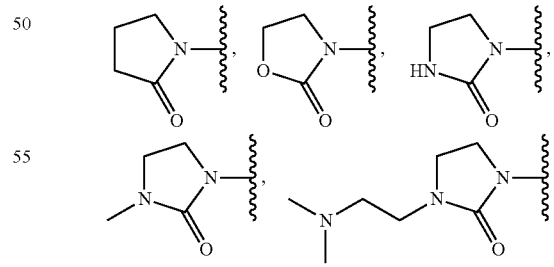

In certain embodiments, R$^3$ is a 5 membered heterocyclic ring bonded to the B ring through a nitrogen atom and optionally having a second ring heteroatom selected from N and O. In certain embodiments, the heterocyclic ring is substituted with one or two groups independently selected from C$_1$-C$_6$ alkyl, oxo and (CH$_2$)$_{1-2}$NR$^a$R$^b$, wherein R$^a$ and R$^b$ are independently H or C$_1$-C alkyl. Particular examples of OR[15] include In certain embodiments, R$^3$ is a 5-6 membered heteroaryl ring having 1-3 nitrogen atoms, wherein said heteroaryl is linked to the B ring by a ring nitrogen atom. An example includes 1H-pyrazolyl, for example 1H-pyrazol-1-yl.

In certain embodiment of compounds of Formula I, R$^3$ is Z. In certain embodiments, Z is selected from

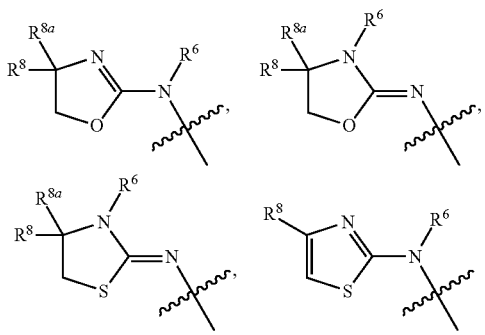

and tautomers thereof. Examples of tautomers of the above Z groups include those wherein $R^6$ is hydrogen, and can be represented by the following structures:

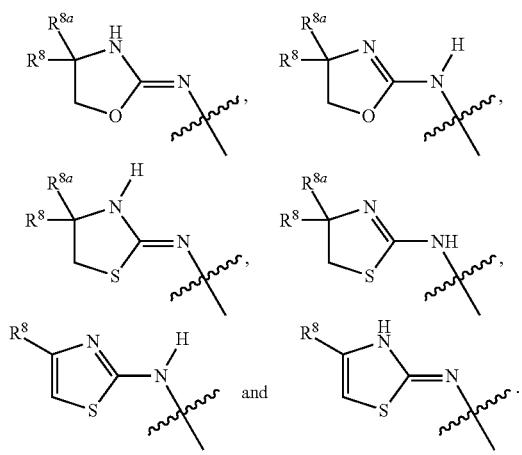

In certain embodiments, Z is selected from:

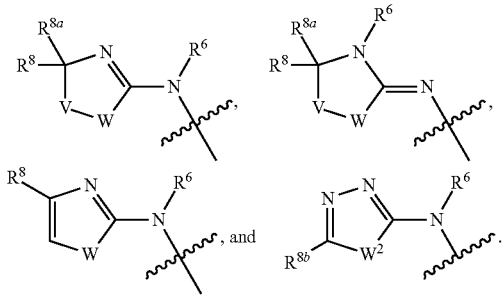

In certain embodiments, W is O or S.
In certain embodiments, $W^2$ is O or S.
In certain embodiments, V is $CR^8R^9$.
In certain embodiments, Z is selected from:

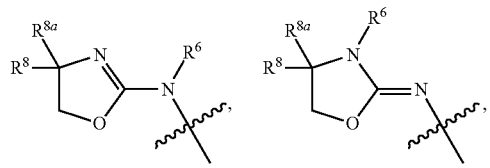

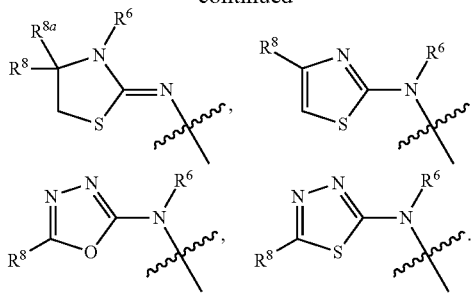

In certain embodiments, $R^6$ is H or $C_1$-$C_6$ alkyl.

In certain embodiments, $R^8$ and $R^{8a}$ are independently H or $C_1$-$C_6$ alkyl optionally substituted with $OR^a$ wherein $R^a$ is H or $C_1$-$C_6$ alkyl. In other embodiments, $R^8$ and $R^{8a}$ together with the atom to which they are attached form a $C_3$-$C_6$ cycloalkyl ring.

In certain embodiments, Z is selected from

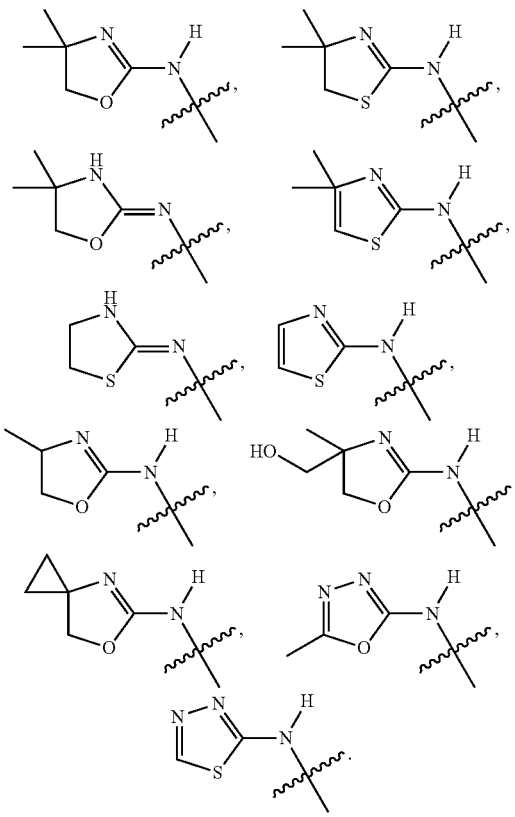

In certain embodiments, $R^3$ is $NR^{15}C(=O)R^{16}$. Examples of $R^{16}$ include, but are not limited to, alkyl, alkenyl or alkynyl, wherein said alkyl, alkenyl and alkynyl are optionally substituted with $NR^aR^b$.

In other embodiments, $R^3$ is —$NR^{15}C(=O)R^{16}$ wherein $R^{15}$ is H or methyl and $R^{16}$ represents $C_2$-$C_6$ alkenyl optionally substituted with $NR^aR^b$. Examples include —$NR^{15}C(=O)$—CH=$CH_2R^{16a}$ wherein $R^{16a}$ represents H or a substituted or unsubstituted $C_1$-$C_6$ alkyl. Particular examples of $R^3$ include —NHC(=O)—CH=$CH_2$ and —NHC(=O)—CH=$CHCH_2N(CH_3)_2$.

In other embodiments, $R^3$ is —$NR^{15}C(=O)R^{16}$ wherein $R^{15}$ is H or methyl and $R^{16}$ represents a 5-6 membered heterocyclic ring having one or two ring heteroatoms and optionally substituted with $C_1$-$C_6$ alkyl. Examples of heterocyclic rings include piperidinyl, tetrahydrofuranyl, and tetrahydropyranyl rings optionally substituted with $C_1$-$C_6$ alkyl. Particular examples of $R^3$ include

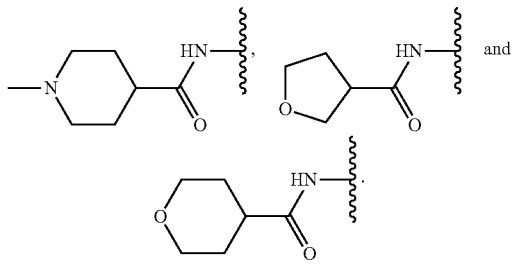

In other embodiments, $R^3$ is —$NR^{15}C(=O)^{16}$ wherein $R^{15}$ represents H or methyl and $R^{16}$ represents $C_1$-$C_6$ alkyl optionally substituted with one or more groups independently selected from $C_1$-$C_6$ alkyl and $OR^a$. In certain embodiments, $R^a$ is H or $C_1$-$C_6$ alkyl. Particular examples of $R^3$ include $CH_3C(O)NH—$, $(CH_3)_2C(O)NH—$, $CH_3CH_2C(O)N(CH_3)—$, $CH_3OCH_2C(O)NH—$, $CH_3OCH_2C(O)N(CH_3)—$, $CH_3CH(OCH_3)C(O)NH—$, $CH_3OCH_2CH_2C(O)NH—$, $CH_3OCH(CH_3)C(O)NH—$, and $CH_3OCH_2CH(CH_3)C(O)NH—$.

In certain embodiments, $R^3$ is —$C(=O)NR^{15}R^{16}$. In certain embodiments, $R^{15}$ and $R^{16}$ independently are H or $C_1$-$C_6$ alkyl. A particular example of $R^3$ is —$C(=O)N(CH_3)_2$. In other embodiments, $R^{15}$ and $R^{16}$ together with the atom to which they are attached form a 6 membered heterocyclic ring optionally having a second heteroatom selected from N and O and optionally substituted with $C_1$-$C_6$ alkyl. Examples of the heterocyclic ring include piperazinyl or morpholinyl optionally substituted with methyl. Particular embodiments of $R^3$ include —$C(=O)(4$-morpholinyl$)$ and —$C(=O)(1$-methylpiperazin-4-yl$)$.

In certain embodiments, $R^3$ is $SO_2R^{15}$. In certain embodiments, $R^{15}$ is $C_1$-$C_6$ alkyl or a phenyl group optionally substituted with $C_1$-$C_6$ alkyl. Particular examples of $R^3$ include 4-methylbenzenesulfonate or ethanesulfonate.

In certain embodiments, $R^3$ is $SOR^{15}$. In certain embodiments, $R^{15}$ is $C_1$-$C_6$ alkyl. A particular example of $R^3$ is ethysulfinyl.

In certain embodiments, $R^3$ is $SR^{15}$. In certain embodiments, $R^{15}$ is $C_1$-$C_6$ alkyl. A particular example of $R^3$ is EtS—.

In certain embodiments, $R^3$ is halogen. A particular example of $R^3$ is bromide.

In certain embodiments, $R^3$ is —$CO_2R^{15}$. In certain embodiments, $R^{15}$ is a 6 membered heterocyclic ring having one or two ring nitrogen atoms (for example piperidinyl or piperazinyl). In certain embodiments, the heterocyclic ring is substituted with $C_1$-$C_6$ alkyl (for example methyl). A particular example of $R^3$ is —$CO_2(1$-methylpiperazinyl$)$.

In certain embodiments, $R^3$ is a substituted or =substituted $C_1$-$C_6$ alkyl group. In certain embodiments, the alkyl group is substituted with $OR^{15}$, wherein $R^{15}$ is H or ($C_1$-$C_6$ alkyl), such as —($C_1$-$C_6$ alkyl$)$OH and —($C_1$-$C_6$ alkyl$)$O($C_1$-$C_6$ alkyl$)$. Particular examples of $R^3$ include —$(CH_2)_3OH$ and —$(CH_2)_3OCH_3$.

In certain embodiments, $R^3$ is a $C_3$-$C_6$ alkynyl group. In certain embodiments, the alkynyl group is substituted with $OR^{15}$. In certain embodiments, $R^{15}$ is H or ($C_1$-$C_6$ alkyl). Particular examples of $R^3$ include

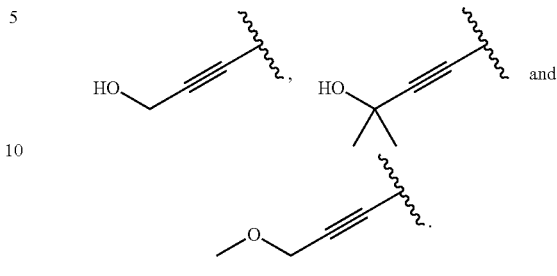

In certain embodiments, $R^3$ is a $C_3$-$C_6$ alkynyl group substituted with —$NR^{15}C(O)CH_2OR^a$. In certain embodiments, $R^{15}$ is H or $C_1$-$C_6$ alkyl. In certain embodiments, $R^a$ is H or $C_1$-$C_6$ alkyl. A particular example of $R^3$ is

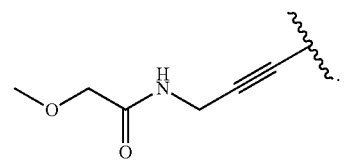 [SMILES: *C#CCNC(=O)COC]

In certain embodiments, $R^3$ is a $C_3$-$C_6$ alkynyl group substituted with a 6 membered heterocyclic ring having one or two ring heteroatoms independently selected from N, O, and $SO_2$. In certain embodiments, the heterocyclic ring has at least one ring nitrogen atom and is attached to the alkynyl group through the nitrogen atom. Particular examples of $R^3$ include

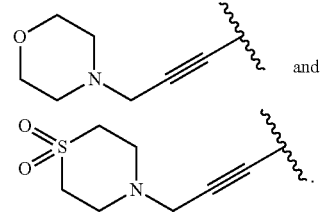

In certain embodiments, $R^3$ is a —$NR^{15}C(O)NR^{16}R^{17}$ group. In certain embodiments, $R^{15}$, $R^{16}$ and $R^{17}$ are independently H or $C_1$-$C_6$ alkyl. Particular examples of $R^3$ include

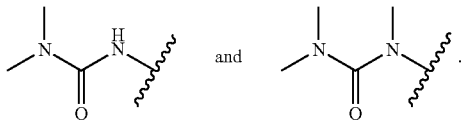

In certain embodiments, $R^3$ is a —$NR^{15}C(O)NR^{16}R^{17}$ group wherein $R^{15}$ is H or $C_1$-$C_6$ alkyl and $R^{16}$ and $R^{17}$ together with the nitrogen atom to which they are attached form a 5-6 membered heterocyclic ring optionally having a second heteroatom selected from N and O. Examples include pyrrolidinyl, morpholinyl and piperazinyl rings. In certain embodiments, the heterocyclic ring is substituted with $C_1$-$C_6$ alkyl. Particular examples of $R^3$ include

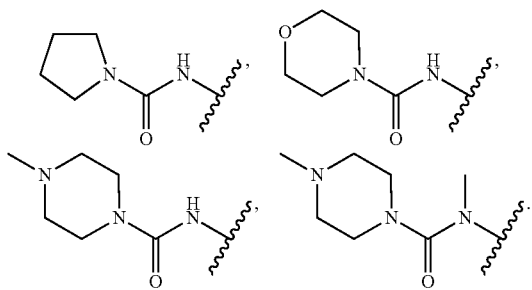

In certain embodiments, R³ is a heterocyclylalkyl group. Examples include $(CH_2)_p$-(hetCyc) wherein p is 1-6 and hetCyc is a 6 membered heterocyclic ring having a ring nitrogen atom and optionally having a second ring atom selected from N and $SO_2$. A particular example of R³ is

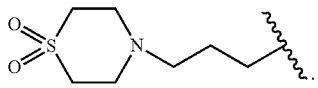

In certain embodiments, R³ is a 5-6 membered heterocyclic ring containing from 1 to 4 heteroatoms selected from N, O, S, SO and $SO_2$ and substituted with the group $M^1$-$M^2$-$M^3$-$M^4$, wherein $M^1$, $M^2$, $M^3$ and $M^4$ are as defined herein.

In certain embodiments, the 5-6 membered heterocyclic ring is furanyl, dihydrofuranyl, thienyl, imidazolyl, tetrazolyl, triazolyl, pyridinyl, pyrrolyl, pyrimidinyl, isoaxazoleyl or oxadiazolyl. In a particular embodiment, the heterocyclic ring is furanyl.

In certain embodiments, $M^1$ is $CH_2$, $CH_2CH_2$, C(O), or $CH_2C(O)$. In particular embodiments, $M^1$ is $CH_2$.

In certain embodiments, $M^2$ is NH or $N(C_1$-$C_6$ alkyl). In particular embodiments, $M^{12}$ is NH or NMe.

In certain embodiments, $M^3$ is methylene, ethylene or propylene.

In certain embodiments, $M^4$ is $SOR^f$, $SO_2R^f$, $NR^eSO_2R^f$, $SO_2NR^gR^h$, $CO_2R^f$, or $CONR^gR^h$, wherein $R^f$, $R^g$ and $R^h$ are independently H or $C_1$-$C_4$ alkyl.

Particular examples of R³ when it is represented by a 5-6 membered heterocyclic ring substituted with the group $M^1$-$M^2$-$M^3$-$M^4$ include:

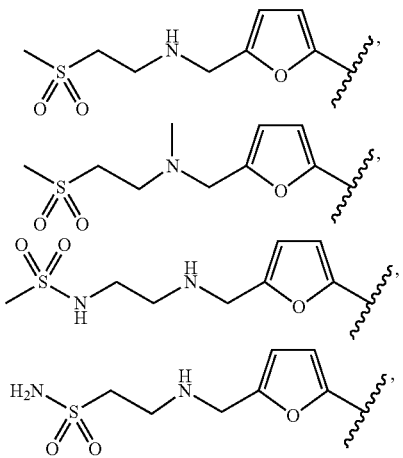

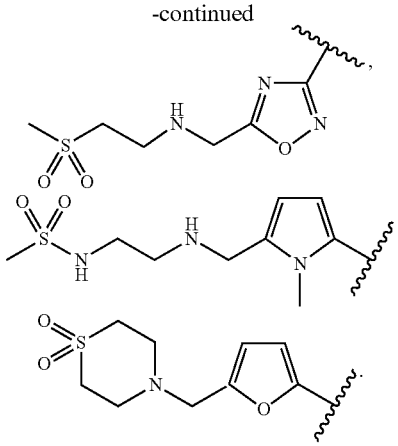

In a particular embodiment, R³ is

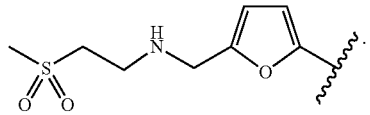 [SMILES: *c1ccc(CNCCS(C)(=O)=O)o1]

In certain embodiments, n is 1 and R² is halogen, CN, trifluoromethyl, difluoromethyl, fluoromethyl, $C_1$-$C_4$-alkyl, $C_1$-$C_4$-alkoxy, or cycloalkyl.

In certain embodiments, the phrase "R⁶ and R⁸ together with the atoms to which they are attached form a 3 to 10 membered saturated or partially unsaturated heterocyclic ring" refers to a ring formed from an R⁶ and R⁸ radical attached to different atoms on the same functional group, such as in a Q or Z group as defined above. The heterocyclic ring formed can be a fused ring or a spirocyclic ring.

In certain embodiments, the phrase "R⁷ and R⁸ together with the atoms to which they are attached form a 3 to 10 membered saturated or partially unsaturated cycloalkyl or heterocyclic ring" refers to a spirocyclic ring formed from an R⁷ and R⁸ radical attached to the same carbon atom, for example such as in a Z group as defined above wherein W is $CR^7R^8$. In other embodiments, the ring can be a fused ring formed by the R⁷ atom that is part of the $CR^7R^8$ group and an R⁸ atom attached to an adjacent carbon on the Z group.

In certain embodiments, the phrase "R⁸ and R⁹ together with the atoms to which they are attached form a 3 to 10 membered saturated or partially unsaturated cycloalkyl or heterocyclyl ring" refers to a spirocyclic ring formed from an R⁸ and R⁹ radical attached to the same carbon atom, for example such as in a Z group as defined above wherein V is $CR^8R^9$. In other embodiments, the ring can be a fused ring formed by the R⁹ atom of the $CR^8R^9$ group and an R⁸ atom attached to an adjacent carbon on the Z group.

In certain embodiments, the phrase "R⁶ and R¹⁰ together with the atoms to which they are attached form a 3 to 10 membered saturated or partially unsaturated heterocyclyl ring" refers to a ring formed by the NR⁶ and the R¹⁰ groups on the group Q as defined above.

In certain embodiments, the phrase "R⁸ and R¹⁰ together with the atoms to which they are attached form a 3 to 10 membered saturated or partially unsaturated heterocyclyl ring" refers to a ring formed by the N—R⁸ and the R¹⁰ atoms on the group Q as defined above.

In certain embodiments, the phrase "$R^{13}$ and $R^{14}$ together with the atoms to which they are attached form a saturated or partially unsaturated cycloalkyl or a saturated or partially unsaturated heterocyclyl ring" refers to a carbocyclic ring formed from an $R^{13}$ and $R^{14}$ radical attached to the same carbon atom, such as in a group having the formula —$S(O)_p$ $(CR^{13}R^{14})_q$—, —$O(CR^{13}R^{14})_q$-aryl, —$NR^{15}(CR^{13}R^{14})_q$-aryl, —$O(CR^{13}R^{14})_q$-heteroaryl, —$NR^{13}(CR^{13}R^{14})_q$-heteroaryl, —$O(CR^{13}R^{14})_q$-heterocyclyl or —$NR^{15}(CR^{13}R^{14})_q$-heterocyclyl, or to a heterocyclic ring formed through an $R^{13}$ and $R^{14}$ radical attached to different atoms within the same group, such as in a group having the formula —$NR^{14}C(O)NR^{15}R^{13}$, —$NR^{13}C(NCN)NR^{15}R^{14}$, —$NR^{13}(CR^{13}R^{14})_q$-heteroaryl or —$NR^{15}(CR^{13}R^{14})_q$-heterocyclyl.

In certain embodiments, the phrase "$R^{13}$ and $R^{15}$ together with the atom to which they are attached form a saturated or partially unsaturated cycloalkyl or saturated or partially unsaturated heterocyclyl ring" refers to a heterocyclic ring formed through an $R^{13}$ and $R^{15}$ radical attached to different atoms within the same group, such as in a group having the formula —$NR^{13}C(NCN)NR^{15}R^{14}$, —$NR^{15}(CR^{13}R^{14})_q$-aryl, or —$NR^{15}(CR^{13}R^{14})_q$-heterocyclyl.

In certain embodiments, the phrase "any two of $R^{15}$, $R^{16}$ and $R^{17}$ together with the atom to which they are attached form a heterocyclic ring" refers to a heterocyclic ring formed from an $R^{15}$ and $R^{16}$ radical attached to the same nitrogen atom, such as in a group having the formula $NR^{15}R^{16}$, $SO_2NR^{15}R^{16}$, $C(=O)NR^{15}R^{16}$, or an $R^{16}$ or $R^{17}$ radical attached to the same nitrogen atom, such as in a group having the formula $NR^{15}C(=O)NR^{16}R^{17}$. In other embodiments the phrase refers to a heterocyclic ring formed from an $R^{15}$ and $R^{16}$ radical attached to different atoms on the same group, such as in the group $NR^{15}OR^{16}$, $NR^{15}C(=O)R^{16}$, $NR^{15}C(=NCN)NR^{16}R^{17}$, or $NR^{15}C(=NCN)R^{16}$.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures, pure diastereomers and pure enantiomers of the compounds of this invention.

The term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerization. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

In addition to compounds of Formula I, the invention also includes solvates, pharmaceutically acceptable prodrugs, and pharmaceutically acceptable salts of such compounds.

The phrase "pharmaceutically acceptable" indicates that the substance or composition is compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

A "pharmaceutically acceptable prodrug" is a compound that may be converted under physiological conditions or by solvolysis to the specified compound or to a pharmaceutically acceptable salt of such compound. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine. Particular examples of prodrugs of this invention include compounds of Formula I covalently joined to a phosphate residue or a valine residue.

Additional types of prodrugs are also encompassed. For instance, a free carboxyl group of a compound of Formula I can be derivatized as an amide or alkyl ester. As another example, compounds of this invention comprising free hydroxy groups may be derivatized as prodrugs by converting the hydroxy group into groups such as, but not limited to, phosphate ester, hemisuccinate, dimethylaminoacetate, or phosphoryloxymethyloxycarbonyl groups, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including, but not limited to, ether, amine and carboxylic acid functionalities, or where the acyl group is an amino acid ester as described above, are also encompassed. Prodrugs of this type are described in *J. Med. Chem.,* 1996, 39, 10. More specific examples include replacement of the hydrogen atom of the alcohol group with a group such as ($C_1$-$C_6$)alkanoyloxymethyl, 1-(($C_1$-$C_6$)alkanoyloxy)ethyl, 1-methyl-1-($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, $—P(O)(O(C_1-C_6)$ alkyl)$_2$ or glycosyl (the radical resulting from the removal of a hydroxyl group of the hemiacetal form of a carbohydrate).

Free amines of compounds of Formula I can also be derivatized as amides, sulfonamides or phosphonamides. All of these prodrug moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, $—C(OH)C(O)OY$ wherein Y is H, $(C_1-C_6)$alkyl or benzyl, $—C(OY_0)Y_1$ wherein $Y_0$ is $(C_1-C_4)$ alkyl and $Y_1$ is $(C_1-C_6)$alkyl, carboxy $(C_1-C_6)$alkyl, amino$(C_1-C_4)$alkyl or mono-N- or di-N,N—$(C_1-C_6)$alkylaminoalkyl, $—C(Y_2)Y_3$ wherein $Y_2$ is H or methyl and $Y_3$ is mono-N- or di-N,N—$(C_1-C_6)$alkylamino, morpholino, piperidin-1-yl or pyrrolidin-1-yl.

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "*Design and Application of Prodrugs*," by H. Bundgaard p. 113-191 (1991); c) H. Bundgaard, *Advanced Drug Delivery Reviews*, 8:1-38 (1992); d) H. Bundgaard, et al., *Journal of Pharmaceutical Sciences*, 77:285 (1988); and e) N. Kakeya, et al., *Chem. Pharm. Bull.*, 32:692 (1984), each of which is specifically incorporated herein by reference.

A "pharmaceutically acceptable salt," unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases or acids to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, for example an inorganic acid such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

The compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified is contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^3H$ and $^{14}C$) are useful in compound and/or substrate tissue distribution assays. Tritiated (i.e., $^3H$) and carbon-14 (i.e., $^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Metabolites of Compounds of Formula I

Also falling within the scope of this invention are the in vivo metabolic products of compounds of Formula I described herein. A "metabolite" is a pharmacologically active product produced through metabolism in the body of a specified compound or salt thereof. Such products may result, for example, from the oxidation, reduction, hydrolysis, amidation, deamidation, esterification, deesterification, glucoronidation, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Synthesis of Compounds of Formula I

Compounds of Formula I may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, Schemes 1-7 show general method for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

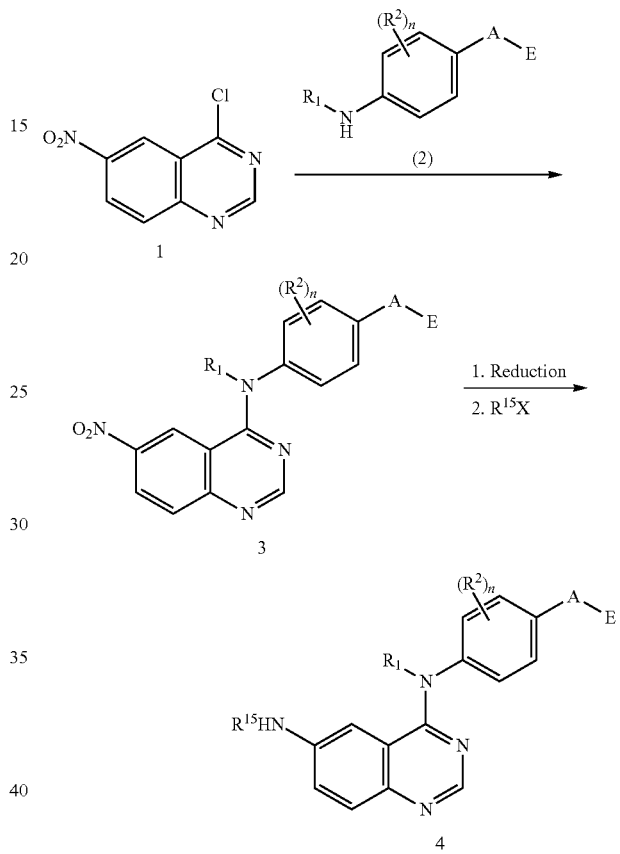

Scheme 1 illustrates synthesis of "N-linked" quinazoline compounds (4) of the present invention wherein A and E are as defined herein. According to Scheme 1, 4-anilino-6-nitroquinazoline (3) can be prepared by reacting an appropriate aniline (2) with a quinazoline (1) substituted in the 4 position with a suitable leaving group, for example a chloride, under standard coupling conditions. The coupling reaction can be performed in a variety of solvents, such as tBuOH, IPA or DCE and may require elevated temperatures and may require a mild base, such as EtN(iPr)$_2$. In one example, the reaction is achieved in a mixture of IPA and DCE heated to 80° C. Reduction of the nitro group of compound (3) can be accomplished by a variety of standard reduction protocols known in the art, such as Pd/C and H$_2$, Pd/C and hydrazine, Pt/C with NaOH and H$_2$, Zn/AcOH, Zn/NH$_4$Cl or Fe/HOAc. In one example, the reduction is accomplished with Pd/C and H$_2$. When R$^2$ is a halogen, the reduction can be accomplished Pt/C with NaOH and H$_2$ or Zn/NH$_4$Cl. The resulting aniline can be coupled with halides, or reacted with other suitable electrophiles such as aldehydes, acid chlorides, etc. to provide compound (4). These reactions may require a suitable base and/or elevated temperatures.

Scheme 2

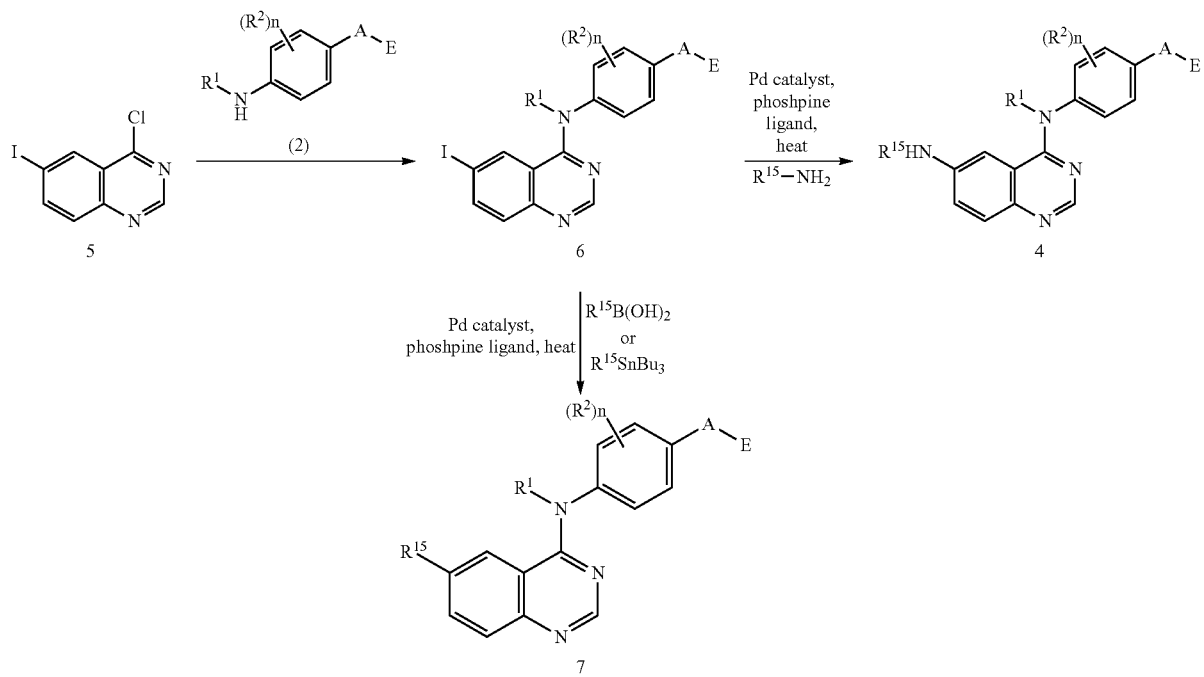

Scheme 2 illustrates an alternative route towards "N-linked" quinazoline compounds (4) wherein A and E are as defined herein. According to Scheme 2, 4-chloro-6-iodoquinazoline (5) can be used in place of 4-chloro-6-nitroquinazoline (1) in Scheme 1 to prepare 4-anilino-6-iodoquinazoline (6). The palladium mediated cross-coupling reaction of the resulting iodoquinazoline (6) with a suitable amine $R^{15}NH_2$ to give compound 4 can be accomplished by treatment with a palladium catalyst, for example $Pd(OAc)_2$, $Pd(PPh_3)_4$, $PdCl_2(dppf)_2$, $Pd_2(dba)_3$, a phosphine ligand and a base in a suitable organic solvent such as THF, DME or toluene. In one example, the coupling reaction is accomplished using $Pd_2(dba)_3$, X-PHOS and $Cs_2CO_3$ in THF and heating to 65° C. Scheme 2 also demonstrates the preparation of C-linked compounds (7). These analogs can be prepared from compound (6) by palladium mediated cross-coupling reactions with boronic acids or organo tin compounds using standard Suzuki or Stille reaction conditions well known in the art.

Scheme 3

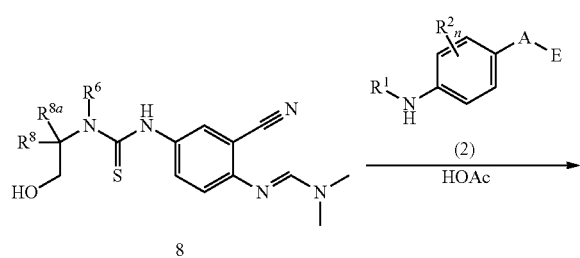

-continued

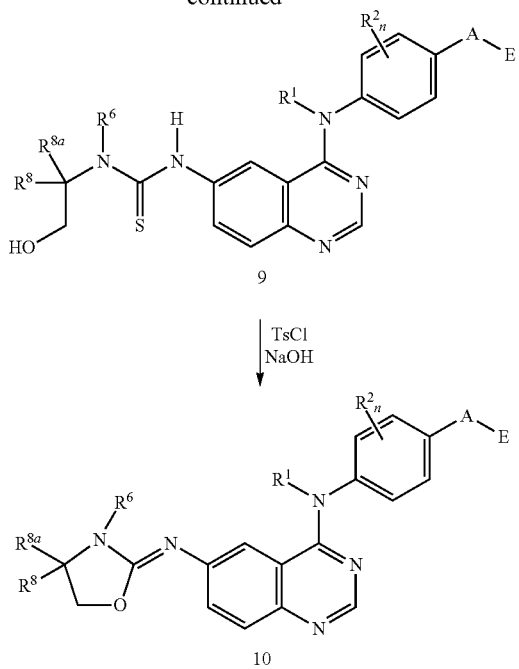

Scheme 3 illustrates a route towards "N-linked" oxazoline-quinazoline compounds wherein A and E are as defined herein. According to Scheme 3, amidine (8) can be condensed with suitable aniline (2) in the presence of an acid such as HOAc in a suitable organic solvent such as isopropyl acetate (IPAc) to provide the thiourea (9). The oxazoline (10) can be prepared by cyclizing the thiourea (9) under a variety of conditions, for example, by treating the thiourea (9) with TsCl and aqueous NaOH in THF.

Scheme 4

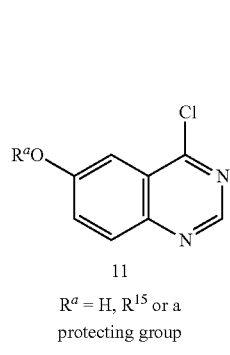

$R^a$ = H, $R^{15}$ or a protecting group

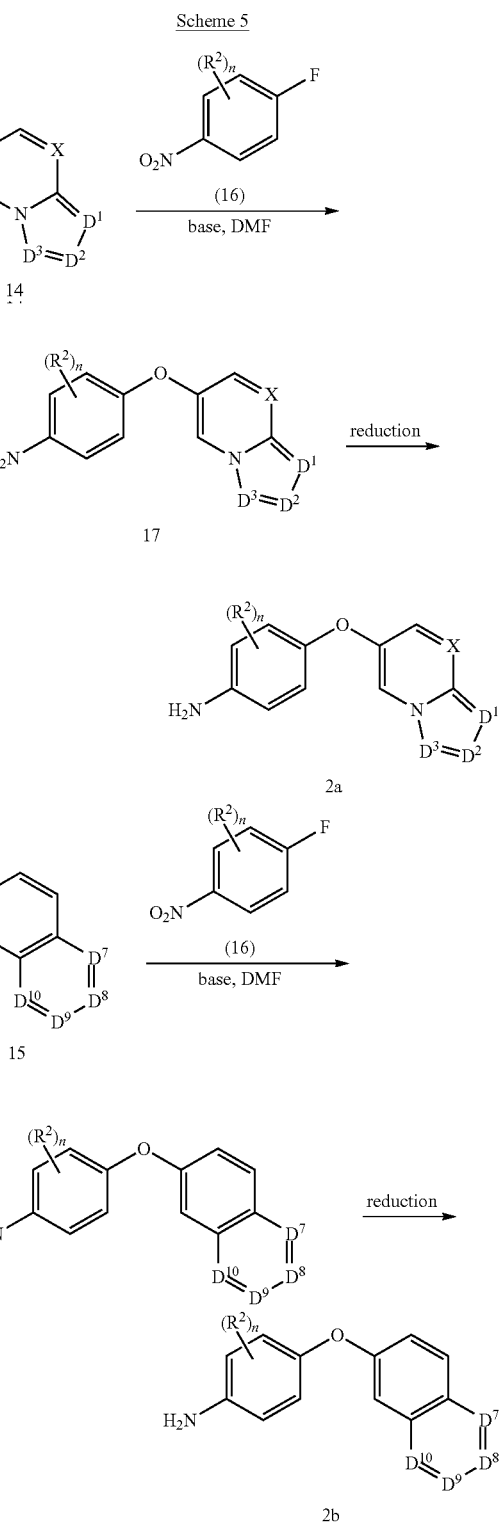

Scheme 4 illustrates the synthesis of an ether linked quinazoline (13) of the present invention wherein A and E are as defined herein. According to Scheme 4, 4-chloro-6-oxy-quinazoline (11) can be reacted with suitable aniline (2) under standard coupling conditions as described in Scheme 1 to provide compound (12). The oxygen moiety of compound (11) can be substituted with various $R^a$ groups, wherein $R^a$ is H, $R^{15}$ or a suitable alcohol protecting group, such as an acyl group. After reaction with the aniline, the optional protection group can be removed under suitable conditions, such as ammonia in MeOH in case of an acetate protecting group. The hydroxyl group of compound (12) can be coupled with a suitable alkyl halide $R^{15}$—X and an appropriate base, such as $K_2CO_3$, $Cs_2CO_3$ or $Cs(OH)_2$ in an organic solvent such as DMF or acetone to provide compound 13. In one example, the alkylation is achieved with $R^{15}$—Br using $Cs_2CO_3$ as a base in DMF. Alternatively, $R^{15}$—OH can be used in place of $R^{15}$—X if the alcohol has been converted to an activated leaving group, such as a tosylate. In yet another method, the hydroxyl group of 12 can be coupled with an alcohol $R^{15}$—OH under standard Mitsunobu conditions, such as DIAD/$PPh_3$ in THF, to provide compound 13.

Scheme 5 illustrates a method of preparing aniline intermediates (2a) and (2b) suitable for use in Schemes 1-4, from phenols (14) and (15), respectively. Phenols (14) and (15) are commercially available or known in the literature, or can be prepared by those skilled in the art by standard procedures. Phenol (14) can be reacted with an optionally substituted 4-fluoronitrobenzene (16) and a suitable base, for example $K_2CO_3$, NaH, or $Cs_2CO_3$ in a polar organic solvent such as DMF at elevated temperatures to provide the coupled product (17). In one example, phenol (14) is reacted with an optionally substituted 4-fluoronitrobenzene (16) in the presence of $Cs_2CO_3$ in DMF at 80° C. The nitro group of compound (17) can be reduced to the desired aniline compound (2a) using standard reduction methods such as Pd/C and $H_2$, Pd/C and hydrazine, Pt/C with NaOH and $H_2$, Zn/AcOH, $Zn/NH_4Cl$ or Fe/HOAc. In one example, the reduction is accomplished with Pd/C and $H_2$ (40 psi). When $R_2$ is a halogen, the reduction can be accomplished using Pt/C with NaOH and $H_2$ or $Zn/NH_4Cl$. In a similar manner, compound (2b) can be prepared from phenol (15).

80° C. The resulting compound can then be reacted with a carboxylic acid equivalent, such as triethyl orthoformate or trimethoxy methane and acid, such as HCl, HOAc or 4-methylbenzenesulfonic acid. In one example, the cyclization is achieved with trimethoxy methane and 4-methylbenzenesulfonic acid to furnish the triazole. The benzyl group can be removed under standard conditions, for example, Pd/C and $H_2$, to give (14a).

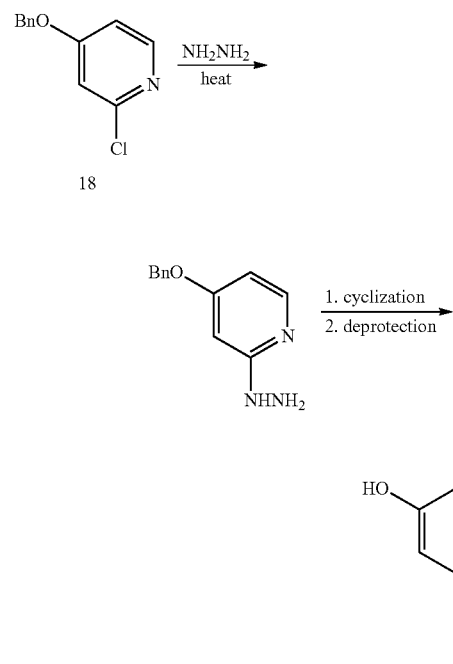

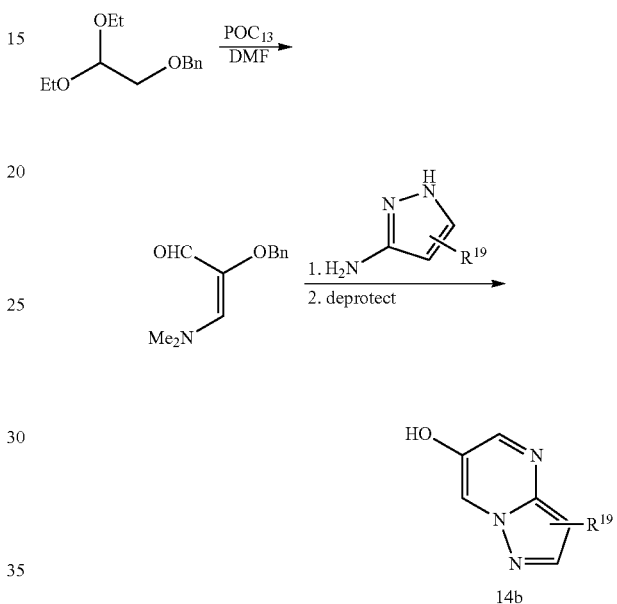

Scheme 6 illustrates a method of preparing phenol intermediate (14a) suitable for use in Scheme 5. Chloro-pyridine (18) can be reacted with hydrazine, for example in pyridine at Scheme 7 illustrates a method of preparing phenol intermediate (14b) suitable for use in Scheme 5. A suitably substituted acetal can reacted with DMF and $POCl_3$ to provide a dimethylamino-acrylaldehyde intermediate. Conversion of this intermediate to a pyrrazolo-pyrimidine can be accomplished by treatment with an optionally substituted 1H-pyrazol-3-amine in base at elevated temperatures, for example NaOMe in MeOH at 60° C. The benzyl group can be removed to give (14b) under standard conditions, such as Pd/C and $H_2$.

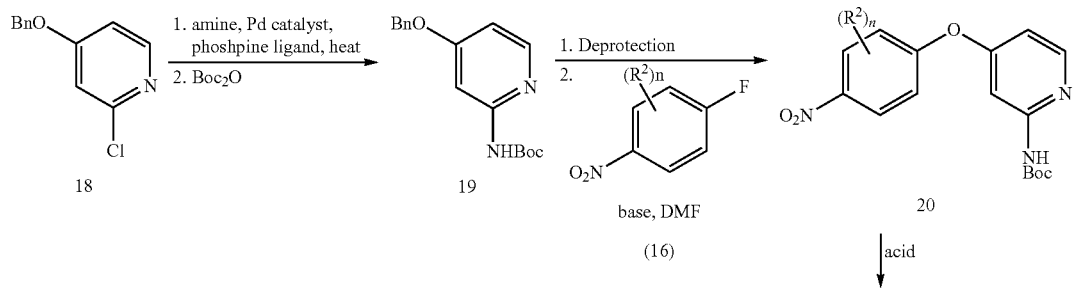

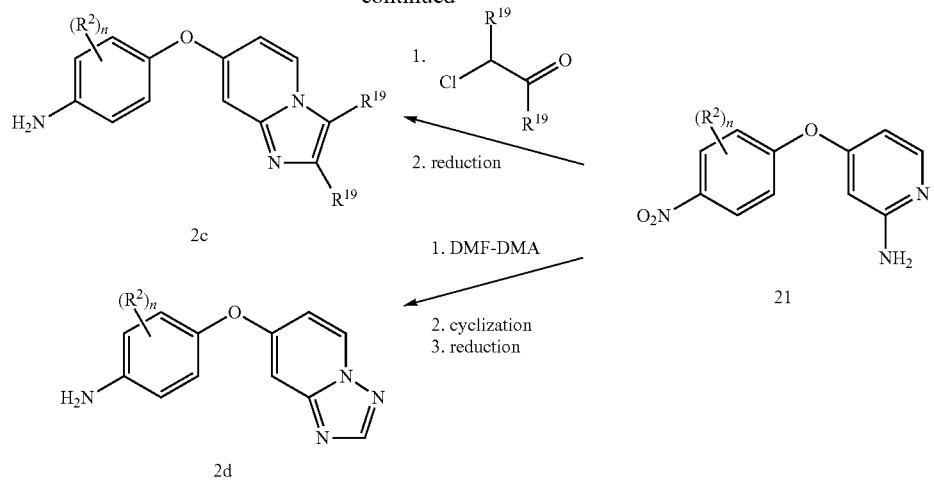

Scheme 8 illustrates the preparation of aniline intermediates (2c) and (2d) suitable for use in Schemes 1-4. According to Scheme 8, the palladium mediated cross-coupling reaction of 2-chloro-4-benzyloxy-pyridine (18) with a suitable amine to give compound (19) can be accomplished by treatment with a palladium catalyst, for example Pd(OAc)$_2$, Pd(PPh$_3$)$_4$, PdCl$_2$(dppf)$_2$, Pd$_2$(dba)$_3$, a phosphine ligand and a base in a suitable organic solvent such as THF, DME or toluene. In one example, the coupling is accomplished using LHMDS with Pd$_2$(dba)$_3$, X-PHOS and Cs$_2$CO$_3$ in THF and heating to 65° C. The resulting 2-aminopyridine can be optionally protected as the Boc-carbamate under standard conditions, for example Boc$_2$O in tBuOH. The benzyl group of compound (19) can be removed under standard conditions, such as Pd/C and H$_2$. The resulting phenol is then reacted with an optionally substituted 4-fluoro-nitrobenzene (16) as described in Scheme 5 to provide the coupled product (20). The Boc group of compound (20) can be removed with acid, for example TFA in DCM. The deprotected 2-aminopyridine (21) can be converted to an imidazopyridine derivative by reaction with a suitably substituted 2-halo-carbonyl compound. For example, compound (21) can be reacted with either chloroacetaldehyde, chloroacetone, or 2-chloropropanal in THF heated to reflux. Conversion of compound (21) into triazolopyridines can be achieved by two-step procedure that includes condensation of (21) with dimethylforamide dimethylacetal to provide a N,N-dimethyl-formimidamide derivative, which is then reacted with hydroxylamine sulfonic acid to provide the triazolopyridine. Reduction of the corresponding nitro group can be accomplished as described in Scheme 5 to provide compounds (2c) and (2d).

Scheme 9

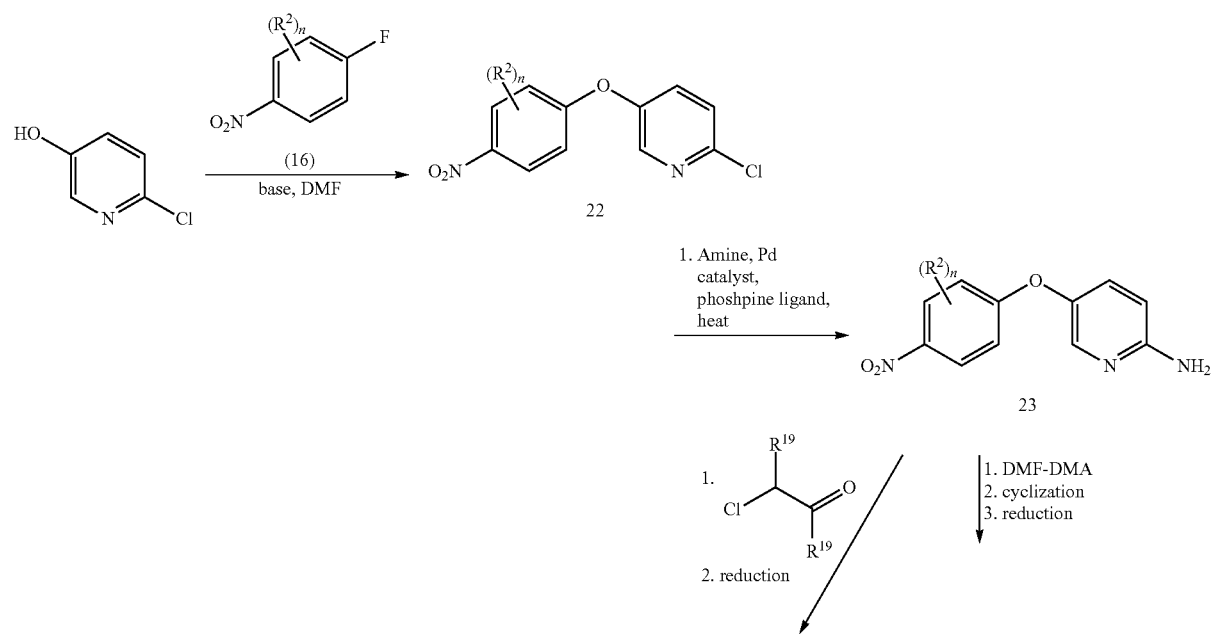

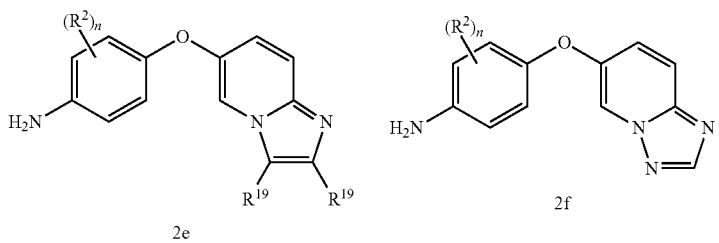

2e, 2f

Scheme 9 illustrates an alternative synthesis of intermediate aniline compound (2e) and (2f) suitable for use in Schemes 1-4. According to Scheme 9, 2-chloro-5-hydroxypyridine is reacted with an optionally substituted 4-fluoronitrobenzene (16) as described in Scheme 5. The chloro derivative (22) can be converted to the amino derivative (23) under palladium mediated cross coupling conditions as described in Scheme 8. Conversion of compound (23) to provide imidazopyridines or triazolopyridines can be accomplished under suitable conditions as described in Scheme 8. Reduction of the corresponding nitro groups can be accomplished as described in Scheme 5 to provide compounds (2e) and (2f).

carbonyl carbamate is accomplished by heating to elevated temperatures, for example 200° C., in diphenyl ether. The product is then hydrolyzed under basic conditions, such as KOH in MeOH heated to reflux. The thiol (24) can then be reacted with an optionally substituted 4-fluoronitrobenzene (16) as described in Scheme 5. Reduction of the nitro group can be accomplished as described in Scheme 5, for example with Fe/HOAc or Zn/NH$_4$Cl, to provide compound (2g). An alternative synthesis of aniline (2g) includes reacting a halo-substituted fused heterocyclic compound (25), where X=Br, with (iPr)$_3$SiSH and a palladium catalyst, for example Scheme 10

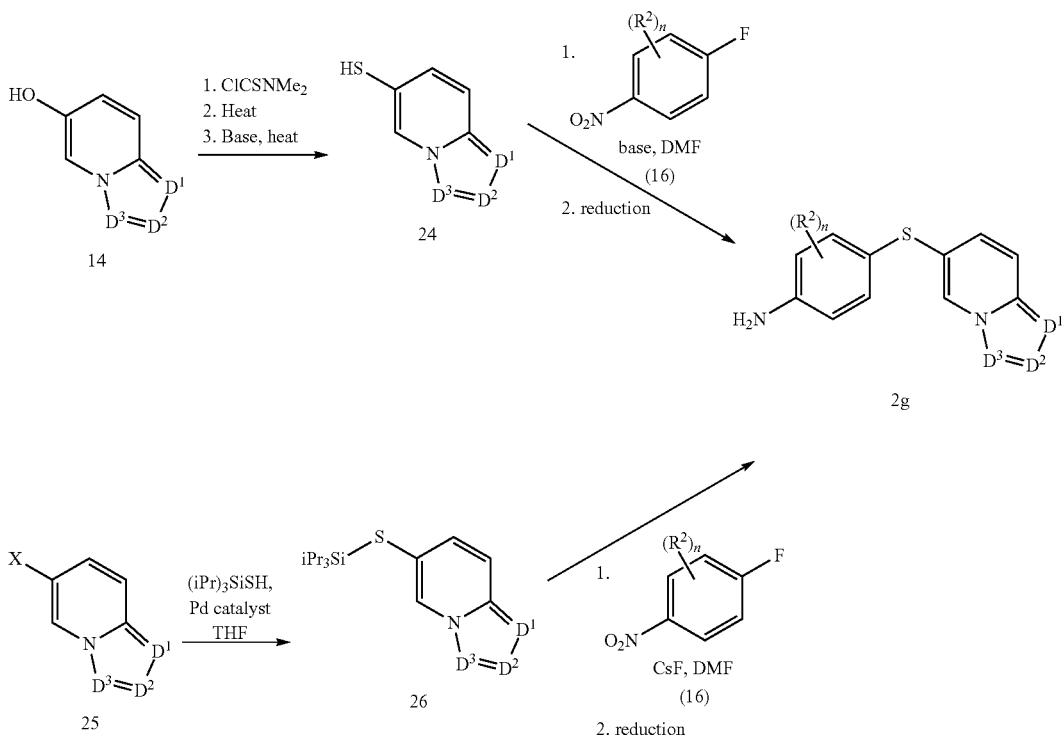

Scheme 10 illustrates an alternative synthesis of intermediate aniline compound (2g) suitable for use in Schemes 1-4. According to Scheme 10, phenol substituted benzofused-heterocycles (14) and (25) can be reacted with dimethyl thiocarbamoyl chloride and a base, for example, NaH in THF, with heating to reflux. Rearrangement of the resulting thio- Pd(PPh$_3$)$_4$ in THF, and heating to reflux. The resulting protected thiol (26) can be de-silated and reacted with an optionally substituted 4-fluoronitrobenzene (16) in situ with a fluoride source, such as CsF in DMF. Reduction of the nitro group to yield (2g) is accomplished under standard reaction conditions.

Scheme 11

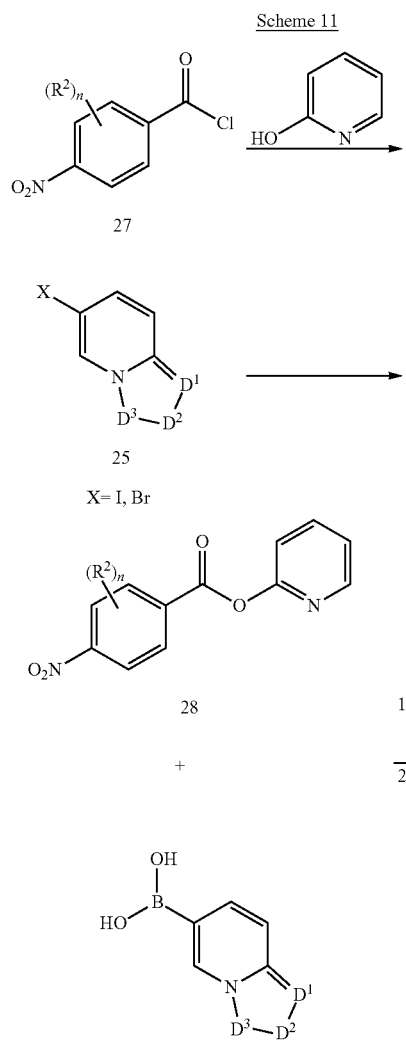

Scheme 12

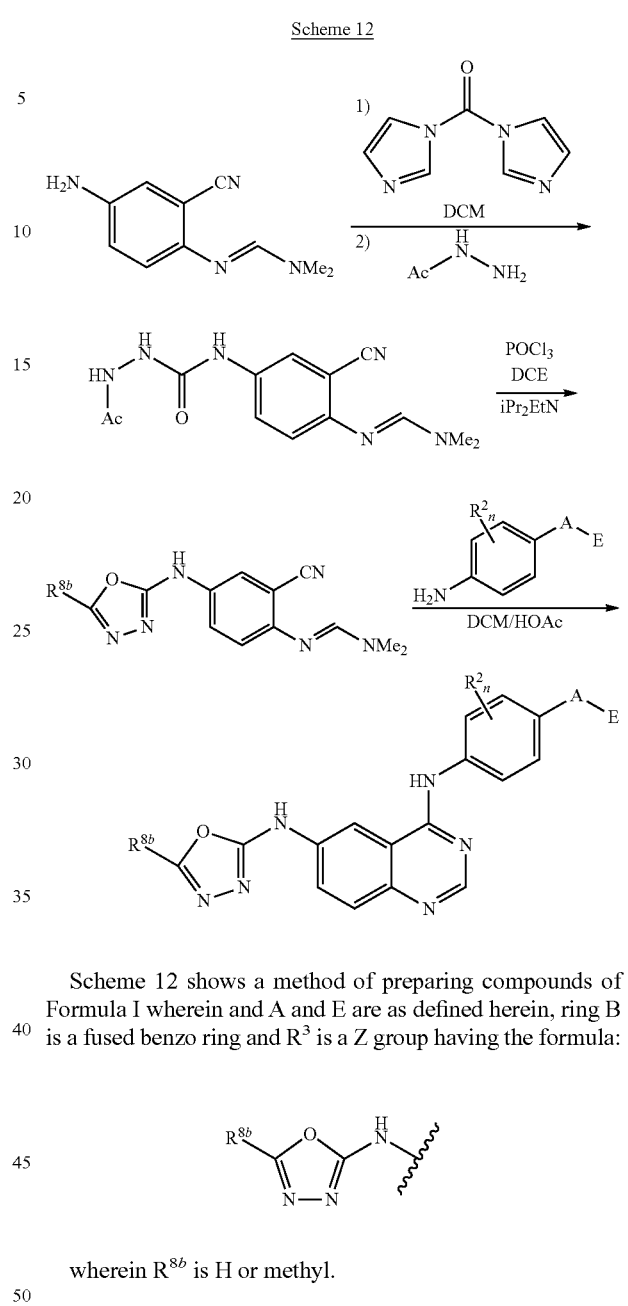

Scheme 12 shows a method of preparing compounds of Formula I wherein and A and E are as defined herein, ring B is a fused benzo ring and $R^3$ is a Z group having the formula:

wherein $R^{8b}$ is H or methyl.

Scheme 11 illustrates a method of preparing aniline (2h) suitable for use in Schemes 1-4. According to Scheme 11, acid chloride (27) is reacted with 2-pyridone and a base to yield ester (28), for example with $Et_3N$ in DCM. Boronic acid (29) is prepared from the halo substituted fused heterocycle (25) by standard conditions, for example by treatment with nBuLi at low temperatures followed by $B(OMe)_3$. Compound (28) is then coupled with boronic acid (29) under palladium mediated cross-coupling conditions, for example $Pd(OAc)_2$, $PPh_3$ and dioxane, and heating to 50° C. (Tatamidani, H.; Kakiuchi, F.; Chatani, N. *Org. Lett.* 2004, 6, 3597). The resulting nitro compound can be reduced under standard conditions as described in Scheme 5, such as Fe/HOAc or $Zn/NH_4Cl$, to provide compound (2h).

Scheme 13

-continued

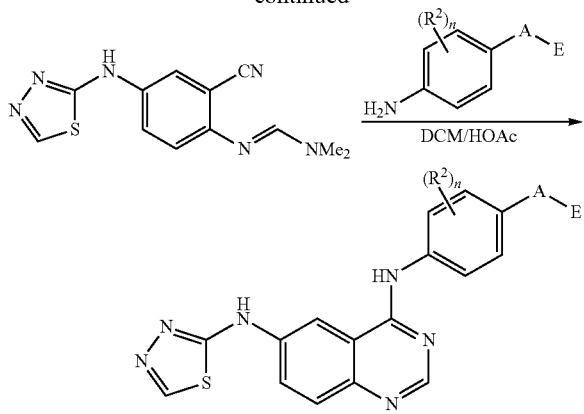

Scheme 13 shows a method of preparing compounds of Formula I wherein and A and E are as defined herein, ring B is a fused benzo ring and $R^3$ is a Z group having the formula:

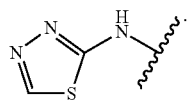

The compounds of Formula I may be prepared using reaction methods known in the art or by methods analogous to those known in the art. This invention also provides methods of preparing compounds of Formula I, comprising:

(a) reacting a compound of formula (F1)

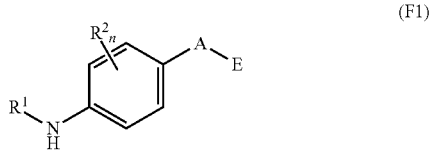

with a compound of formula (F2)

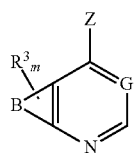

in which Z represents a leaving atom or group; or (b) for a compound of Formula I in which G is N, reacting a compound of formula (F3)

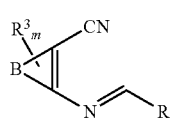

in which R represents a tertiary amino group, for example di(1-6C)alkylamino, such as dimethylamino, with a compound of formula (F1); followed if necessary, by converting the compound of Formula I into another compound of Formula I having a different $R^3$ group.

More particularly, this invention provides methods of preparing compounds of Formula I, comprising:

(c) for a compound of Formula I wherein $R^3$ is —$NHR^x$ and $R^x$ is $R^{15}$ or —$C(O)R^{15}$, and $R^{15}$ is as defined for Formula I, reacting a corresponding compound of Formula I wherein $R^3$ is —$NH_2$ with an alkylating agent or an acylating agent $R^{15}$—$X^1$ wherein $R^{15}$—$X^1$ is an acid or reactive derivative thereof (such as $R^{15}C(O)Cl$) or wherein $X^1$ is a leaving group such as halogen group, optionally in the presence of a base; or (d) for a compound of Formula I wherein $R^3$ is —$NHR^{15}$ and $R^{15}$ is as defined for Formula I, reacting a corresponding compound of Formula I wherein $R^3$ is an iodide group with a compound having the formula $R^{15}NH_2$ in the presence of a palladium catalyst and a phosphine ligand; or (e) for a compound of Formula I wherein $R^3$ is $R^{15}$ and $R^{15}$ is as defined for Formula I, reacting a corresponding compound of Formula I wherein $R^3$ is an iodide group with a compound having the formula $R^{15}B(OH)_2$ or $R^{15}SnBu_3$ in the presence of a palladium catalyst and a phosphine ligand; or (f) for a compound having the Formula I wherein $R^3$ is $OR^{15}$ and $R^{15}$ is alkyl, alkenyl, or alkynyl, reacting a corresponding compound of Formula I wherein $R^3$ is OH with $R^{15}$—$X^2$ wherein $R^{15}$ is alkyl, alkenyl or alkynyl and $X^2$ is a leaving group, in the presence of a base; or (g) for a compound having the Formula I wherein $R^3$ is $OR^{15}$ and $R^{15}$ is alkyl, alkenyl or alkynyl, reacting a corresponding compound of Formula I wherein $R^3$ is —$OR^{15a}$ and —$OR^{15a}$ is a sulfate group such as a tosylate group, with a compound having the formula $R^{15}OH$ in the presence of a base; or (h) for a compound having the Formula I wherein $R^3$ is a group of formula (F3)

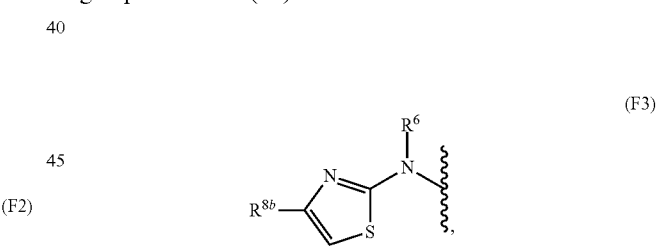

reacting a corresponding compound of Formula I wherein $R^3$ is an iodide group with a compound having the formula (F4)

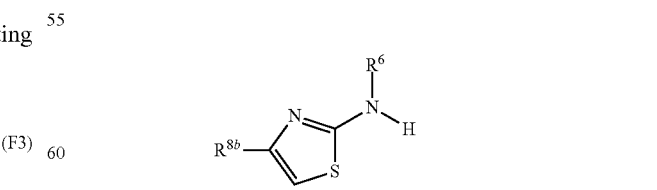

in the presence of a palladium catalyst, a phosphine ligand and a base; or (i) for a compound having the Formula I wherein $R^3$ is a group of Formula (F5)

(F5)

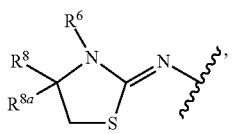

wherein R⁶ is methyl, cyclizing a corresponding compound of Formula I wherein R³ is a group of Formula (F6)

(F6)

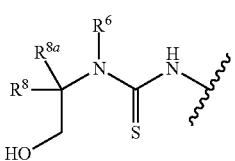

wherein R⁶ is methyl in the presence of a base and a sulfonyl chloride such as tosyl chloride; or (j) for a compound having the Formula I wherein R³ is a group of Formula (F5)

(F5)

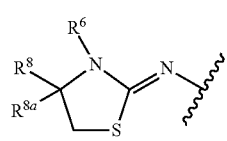

wherein R⁶ is H, cyclizing corresponding compound of Formula I wherein R³ is a group of the formula (F6) wherein R⁶ is H in the presence of diisopropyl azodicarboxylate and a phosphine ligand such as PPH₃; or (k) for a compound having the Formula I wherein R³ is a group of formula (F7)

(F7)

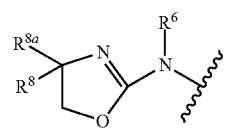

wherein R⁶ is H, reacting a corresponding compound having the Formula I wherein R³ is a group of formula (F6) and R⁶ is H in the presence of a base and a sulfonyl chloride.

Certain of the intermediates described in the above described Schemes and in the Examples are believed to be novel and are provided as further aspects of the invention. In particular, this invention further provides compound of formula (F1)

(F1)

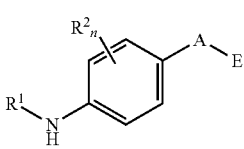

wherein R¹, R², A, E and n are as defined for Formula I. Compounds of Formula (F1) are useful for preparing pharmaceutical compounds such as the ErbB inhibitors of Formula I.

In preparing compounds of Formula I, protection of remote functionalities (e.g., primary or secondary amines, alcohols, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In any of the synthetic methods for preparing compounds of Formula I, it may be advantageous to separate reaction products from one another and/or from starting materials. The desired products of each step or series of steps is separated and/or purified to the desired degree of homogeneity by the techniques common in the art. Such separations involve, for example, multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a reaction mixture with a reagent selected to bind to or render otherwise separable a desired product, unreacted starting material, reaction by-product, or the like. Such reagents include adsorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate method(s) of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., *J. Chromatogr.*, (1975) 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−)menthyl chloroformate in the presence of base, or Mosher ester, α-methoxy-α-(trifluoromethyl)phenyl acetate (Jacob III. *J. Org. Chem.*, (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, *J. of Chromatogr.*, (1990) 513: 375-378). Enriched or purified enantiomers can be distinguished by methods used to distinguish other chiral molecules with asymmetric carbon atoms, such as optical rotation and circular dichroism.

Methods of Treatment with Compounds of Formula I

The compounds of the present invention can be used as prophylactics or therapeutic agents for treating diseases mediated by modulation or regulation of type I receptor tyrosine kinases and/or serine, threonine, and/or dual specificity kinases. An "effective amount" is intended to mean that amount of compound that, when administered to a mammal in need of such treatment, is sufficient to effect treatment for a disease mediated by the activity of one or more type I receptor tyrosine kinases and/or serine, threonine, and/or dual specificity kinases. Thus, for example, a therapeutically effective amount of a compound selected from Formula I or a solvate, metabolite, or pharmaceutically acceptable salt or prodrug thereof, is a quantity sufficient to modulate, regulate, or inhibit the activity of one or more type I receptor tyrosine kinases and/or serine, threonine, and/or dual specificity kinases such that a disease condition which is mediated by that activity is reduced or alleviated.

The terms "treat" or "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. The terms "treating," "treat," and "treatment" embrace both preventative, i.e., prophylactic, and palliative treatment.

The compounds of the present invention possess anti-cell-proliferation properties, which are believed to arise from their Class I receptor tyrosine kinase inhibitory activity. Accordingly the compounds of the present invention are expected to be useful in the treatment of diseases or medical conditions mediated alone or in part by Class I receptor tyrosine kinase enzymes, i.e. the compounds may be used to produce a Class I receptor tyrosine kinase inhibitory effect in a warm-blooded animal in need of such treatment. Thus the compounds of the present invention provide a method for treating the proliferation of malignant cells characterized by inhibition of Class I receptor tyrosine kinase enzymes, i.e., the compounds may be used to produce an anti-proliferative effect mediated alone or in part by the inhibition of Class I receptor tyrosine kinase. Accordingly, the compounds of the present invention are expected to be useful in the treatment of cancer by providing an anti-proliferative effect, particularly in the treatment of Class I receptor tyrosine kinase sensitive cancers such as cancers of the breast, lung, colon, rectum, stomach, prostate, bladder, pancreas and ovary. The compounds of the present invention are also expected to be useful in the treatment of other cell-proliferation diseases such as psoriasis.

Accordingly, one aspect of this invention relates to a pharmaceutical composition for the treatment of a hyperproliferative disorder or an abnormal cell growth in a mammal, which comprises a therapeutically effective amount of a compound of the present invention, or a solvate, metabolite, or pharmaceutically acceptable salt or prodrug thereof, and a pharmaceutically acceptable carrier.

The terms "abnormal cell growth" and "hyperproliferative disorder" are used interchangeably in this application.

"Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or over-expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/theroine kinase activation occurs.

In one embodiment, abnormal cell growth in cancer. According, this invention provides methods of treating cancer, comprising administering to a mammal in need thereof a therapeutic amount of a composition of this invention.

In certain embodiments, said cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancer.

The invention also relates to a pharmaceutical composition for the treatment of pancreatitis or kidney disease (including proliferative glomerulonephritis and diabetes-induced renal disease) or the treatment of pain in a mammal, which comprises a therapeutically effective amount of a compound of the present invention, or a solvate, metabolite, or pharmaceutically acceptable salt or prodrug thereof, and a pharmaceutically acceptable carrier.

The invention also relates to a method for the treatment of pancreatitis or kidney disease or the treatment of pain in a mammal as described above, which comprises administering to said mammal a therapeutically effective amount of a compound of the present invention, or a solvate, metabolite, or pharmaceutically acceptable salt or prodrug thereof in combination with a pharmaceutically acceptable carrier.

The invention also relates to a pharmaceutical composition for the prevention of blastocyte implantation in a mammal, which comprises a therapeutically effective amount of a compound of the present invention, or a solvate, metabolite, or pharmaceutically acceptable salt or prodrug thereof, and a pharmaceutically acceptable carrier.

The invention also relates to a method for the prevention of blastocyte implantation in a mammal, which comprises administering to said mammal a therapeutically effective amount of a compound of the present invention, or a solvate, metabolite, or pharmaceutically acceptable salt or prodrug thereof in combination with a pharmaceutically acceptable carrier.

The invention also relates to a pharmaceutical composition for treating a disease related to vasculogenesis or angiogenesis in a mammal, which comprises a therapeutically effective amount of a compound of the present invention, or a solvate, metabolite, or pharmaceutically acceptable salt or prodrug thereof, and a pharmaceutically acceptable carrier.

The invention also relates to a method for treating a disease related to vasculogenesis or angiogenesis in a mammal, which comprises administering to said mammal a therapeutically effective amount of a compound of the present invention, or a solvate, metabolite, or pharmaceutically acceptable salt or prodrug thereof in combination with a pharmaceutically acceptable carrier. Examples of such diseases include, but are not limited to, tumor angiogenesis, chronic inflammatory disease or other inflammatory condition such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a pharmaceutical composition for treating a disease or condition related to inflammatory disease, autoimmune disease, destructive bone disorders, proliferative disorders, infectious disease, viral disease, fibrotic disease or neurodegenerative disease in a mammal which comprises a therapeutically effective amount of a compound of the present invention, or a pharmaceutically acceptable salt, prodrug or hydrate thereof, and a pharmaceutically acceptable carrier. Examples of the above diseases and/or conditions include but is not limited to rheumatoid arthritis, atherosclerosis, inflammatory bowel disease, skin diseases such as psoriasis, eczema, and scleroderma, diabetes and diabetic complications, diabetic retinopathy, retinopathy of prematurity, age-related macular degeneration, hemangioma, chronic obstructive pulmonary disease, idiopathic pulmonary fibrosis, allergic responses including asthma allergic rhinitis and atopic dermatitis, renal disease and renal failure, polycystic kidney disease, acute coronary syndrome, congestive heart failure, osteoarthritis, neurofibromatosis, organ transplant rejection, cachexia and pain.

Patients that can be treated with compositions of the present invention include, for example, patients that have been diagnosed as having psoriasis, restenosis, atherosclerosis, BPH, lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

Further provided is a compound of Formula I for use as a medicament in the treatment of the diseases and conditions described above in a mammal, such as a human, suffering from such disorder. Also provided is the use of a compound of Formula I in the preparation of a medicament for the treatment of the diseases and conditions described above in a mammal, such as a human, suffering from such disorder.

Combination Therapy

The compounds of the present invention can be used in combination with one or more additional drugs such as described below. The dose of the second drug can be appropriately selected based on a clinically employed dose. The proportion of the compound of the present invention and the second drug can be appropriately determined according to the administration subject, the administration route, the target disease, the clinical condition, the combination, and other factors. In cases where the administration subject is a human, for instance, the second drug may be used in an amount of 0.01 to 100 parts by weight per part by weight of the compound of the present invention.

In certain embodiment of the invention, a method for the treatment of abnormal cell growth in a mammal comprises administering to a mammal an amount of a compound of Formula I that is effective in treating abnormal cell growth in combination with an anti-tumor agent selected from the following categories:

(i) antiproliferative/anti-neoplastic drugs and combinations thereof, as used in medical oncology, such as alkylating agents (for example, cis-platin, carboplatin, cyclophosphamide, nitrogen mustard, melphalan, chlorambucil, busulphan and nitrosoureas); anti-metabolites (for example, antifolates such as such as fluoropyrimidines like 5-fluorouracil and tegafur, raltitrexed, methotrexate, cytosine arabinside, hydroxyurea, or, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid); antitumor antibiotics (for example, anthracyclines like adriamycin, bleomycin, doxorubicin, daunomycin, epirubicin, idarubicin, mitomycin-C, dactinomycin and mithramycin); antimitotic agents (for example, vinca alkaloids like vincristine, vinblastine, vindesine and vinorelbine and taxoids like taxol and taxotere); topoisomerase inhibitors (for example epipodophyllotoxins like eptoposide and teniposide, amsacrine, topotecan and campothecin); and mitotic kinesin KSP inhibitors;

(ii) cytostatic agents such as antiestrogens (for example, tamoxifen, toremifene, raloxifene, droloxifene and iodoxyfene); estrogen receptor down regulators (for example, fulvestratrant); antiandrogens (for example, bicalutamide, flutamide, nilutamide, cyproxerone acetate and CASODEX™ (4'-cyano-3-(4-fluorophenylsulphonyl)-2-hydroxy-2-methyl-3'-(trifluoromethyl)propionanilide)); LHRH antagonists or LHRH agonists (for example, goserelin, leuporelin and buserelin); progestogens (for example, megestrol acetate); aromatase inhibitors (for example, asanastrozole, letrozole, vorazole and exemestane); inhibitors of 5α-reductase such as finasteride; and p38 inhibitors such as those disclosed in U.S. Publication Nos. 2004/0176325, 2004/0180896, and 2004/0192635;

(iii) agents which inhibit cancer cell invasion (for example, metalloproteinase inhibitors like marimastat and inhibitors of urokinase plasminogne activator receptor function);

(iv) inhibitors of growth factor function such as growth factor antibodies, growth factor receptor antibodies (for example, the anti-erbB2 antibody trastumuzab [HERCEPTIN™] and the anti-erbB1 antibody cetuximab [C225]), farnesyl transferase inhibitors, tyrosine kinase inhibitors and serine-threonine kinase inhibitors (for example, inhibitors of the epidermal growth factor family tyrosine kinases such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)); inhibitors of the platelet-derived growth factor family; inhibitors of the hepatocyte growth factor family; and MEK inhibitors such as PD325901 and compounds such as those disclosed in U.S. Patent Publication 2004/0116710;

(v) antiangiogenic agents such as those which inhibit the effects of vascular endothelial growth factor (for example, the anti-vascular endothelial cell growth factor antibody bevacizumab [AVASTIN™], compounds such as those disclosed in PCT Publication Nos. WO 97/22596, WO 97/30035, WO 97/32856, and WO 98/13354) and compounds that work by other mechanisms (for example, linomide, inhibitors of integrin αvβ3 function, MMP inhibitors, COX-2 inhibitors and angiostatin);

(vi) vascular damaging agents such as Combretastatin A4 and compounds disclosed in PCT Publication Nos. WO 99/02166, WO 0/40529, WO 00/41669, WO 01/92224, WO 02/04434, and WO 02/08213;

(vii) antisense therapies (for example, those which are directed to the targets listed above such as ISIS 2503, and anti-ras antisense);

(viii) gene therapy approaches, including for example GVAX™, approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) interferon; and (x) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches to using transfected immune cells such as cytokine-transfected dendritic cells, approaches using cytokine-transfected tumor cell lines and approaches using anti-idiotypic antibodies.

In one embodiment the second compound of the pharmaceutical combination formulation or dosing regimen has complementary activities to the compound of Formula I such that they do not adversely affect each other. Such drugs are suitably present in combination in amounts that are effective for the purpose intended. Accordingly, another aspect of the present invention provides a composition comprising a compound of Formula I, or a solvate, metabolite, or pharmaceutically acceptable salt or prodrug thereof, in combination with a second drug, such as described herein.

The compound(s) of Formula I and the additional pharmaceutically active agent(s) may be administered together in a unitary pharmaceutical composition or separately and, when administered separately this may occur simultaneously or sequentially in any order. Such sequential administration may be close in time or remote in time. The amounts of the compound(s) of Formula I and the second agent(s) and the relative timings of administration will be selected in order to achieve the desired combined therapeutic effect.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

The compounds of the present invention can be used, for example in combination with additional drug(s) such as a therapeutic agent for Administration of Compounds of Formula I The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Pharmaceutical Formulations

In order to use a compound of Formula I or a pharmaceutically acceptable salt, solvate, metabolite or prodrug thereof for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I, or a pharmaceutically acceptable salt, solvate, metabolite or prodrug thereof, in association with a pharmaceutically acceptable diluent or carrier.

The pharmaceutical compositions of the invention are formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the compound to be administered will be governed by such considerations, and is the minimum amount necessary to prevent, ameliorate, or treat the disorder. The compound of the present invention is typically formulated into pharmaceutical dosage forms to provide an easily controllable dosage of the drug and to enable patient compliance with the prescribed regimen.

The composition for use herein is preferably sterile. In particular, formulations to be used for in vivo administration must be sterile. Such sterilization is readily accomplished, for example, by filtration through sterile filtration membranes. The compound ordinarily can be stored as a solid composition, a lyophilized formulation or as an aqueous solution.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, a milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment. The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more excipients.

The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The formulations may also include one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug (such as the compounds disclosed herein and, optionally, a chemotherapeutic agent) to a mammal. The components of the liposome are commonly arranged in a bilayer formation, similar to the lipid arrangement of biological membranes.

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The compositions of the invention may also be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder)

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols. Formulations suitable for vaginal administration may be presented as pessaries, tampons, creams, gels, pastes, foams or spray formulations containing in addition to the active ingredient such carriers as are known in the art to be appropriate.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for transdermal administration may be in the form of those transdermal skin patches that are well known to those of ordinary skill in the art.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

The pharmaceutical composition (or formulation) for application may be packaged in a variety of ways depending upon the method used for administering the drug. For example, an article for distribution can include a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The formulations may also be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising a compound of Formula I together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. In one embodiment, a suitable amount of a compound of Formula I is administered to a mammal in need thereof. Administration in one embodiment occurs in an amount between about 0.001 mg/kg of body weight to about 60 mg/kg of body weight per day. In another embodiment, administration occurs in an amount between 0.5 mg/kg of body weight to about 40 mg/kg of body weight per day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. In one embodiment, a suitable amount of a compound of Formula I is administered to a mammal in need thereof. Administration in one embodiment occurs in an amount between about 0.001 mg/kg of body weight to about 60 mg/kg of body weight per day. In another embodiment, administration occurs in an amount between 0.5 mg/kg of body weight to about 40 mg/kg of body weight per day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

Articles of Manufacture

In another embodiment of the invention, an article of manufacture, or "kit", containing materials useful for the treatment of the disorders described above is provided. In one embodiment, the kit comprises a container comprising a compound of Formula I, or a solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. In one embodiment, the label or package inserts indicates that the composition comprising a compound of Formula I can be used to treat one or more of the diseases or disorders disclosed herein.

In one embodiment, the kit further comprises a container. Suitable containers include, for example, bottles, vials, syringes, blister pack, etc. The container may be formed from a variety of materials such as glass or plastic. The container may hold a compound of Formula I or a formulation thereof which is effective for treating one or more diseases or disorders disclosed herein and may have a sterile access port (for example, the container may be an intravenous solution bag or a vial having a stopper pierceable by a hypodermic injection needle).

The kit may further comprise directions for the administration of the compound of Formula I and, if present, the second pharmaceutical formulation. For example, when the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit can include a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, an article of manufacture may comprise (a) a first container with a compound of Formula I contained therein; and optionally (b) a second container with a second pharmaceutical formulation contained therein, wherein the second pharmaceutical formulation comprises a second compound having, for example, antihyperproliferative activity. Alternatively, or additionally, the article of manufacture may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

BIOLOGICAL EXAMPLES

Example A

EGFR/ErbB2 Enzymatic Assays

Thermo LabSystems Immulon 4HBX 96-well plates are coated by incubation overnight at room temperature with 100 µL per well of 0.25 mg/mL Poly (Glu, Tyr) 4:1 (PGT) (Sigma Chemical Co., St. Louis, Mo.) in PBS (phosphate buffered saline). Excess PGT is removed by aspiration, and the plate is washed three times with wash buffer (0.1% Tween 20 in PBS). The kinase reaction is performed in 100 µL of 50 mM HEPES (pH 7.3) containing 125 mM sodium chloride, 24 mM magnesium chloride, 0.1 mM sodium orthovanadate, 15 µM ATP (adenosine triphosphate) and 0.3 units/mL EGFR (epidermal growth factor receptor) (BIOMOL Research Laboratories, Inc., Plymouth Meeting, Pa.). The compound in DMSO (dimethylsulfoxide) is added to give a final DMSO concentration of about 1%. Phosporylation is initiated by the addition of ATP and incubated for 30 minutes at room temperature. The kinase reaction is terminated by aspiration of the reaction mixture and subsequent washing with wash buffer (see above). Phosphorylated PGT is detected by incubation with 100 µL per well HRP conjugated PY20 antiphosphotyrosine antibody (Zymed Laboratories, Inc., South San Francisco, Calif.) diluted to 0.2 µg/mL in 3% BSA and 0.05% Tween 20 in PBS. Antibody is removed by aspiration, and the plate is washed with wash buffer. The colorimetric signal is developed by the addition of 100 µL per well TMB Microwell Peroxidase Substrate (Kirkegaard and Perry, Gaithersburg, Md.), and stopped by the addition of 100 µL per well 1M phosphoric acid. Phosphotyrosine in measured by absorbance at 450 nm.

The ErbB2 kinase is as above using 250 ng/mL erbB2 intracellular domain in place of EGFR. The intracellular domain of the ErbB2 tyrosine kinase (amino acids 691-1255) is expressed as a his-tagged protein in Baculovirus and purified by nickel chelating, ion exchange and size exclusion chromatography.

Compounds of the present invention have $IC_{50}$'s from less than 1 nM to 50 mM.

Example B

Cellular ErbB2 Phosphorylation Assay

The cellular potency of compounds is measured by the inhibition of phosphorylated erbB2 (p-erbB2) in the BT474 cell line which overexpresses erbB2 and consequently, has high basal levels of p-erbB2. BT474 cells are plated in 96 well plates and incubated overnight at 37° C./5% $CO_2$. The next day, the medium is replaced with serum-free medium, followed by the addition of compounds for 2 hours. Cells are lysed by the addition of lysis buffer and freezing at −80° C. Thawed and clarified lysates are then added to 96-well plates that are coated with an anti-erbB2 antibody. Phosphorylated erbB2 is detected with a phospho-tyrosine antibody using an ELISA format. Compounds of the present invention have $IC_{50}$'s of less than 1 µM in this assay.

Example C

Cellular EGFR Phosphorylation Assay

This assay measures the inhibition of EGF-induced phosphorylated EGFR (pEGFR) in the A431 cell line which overexpresses EGFR. Cells are plated in 96 well plates and incubated for 6-8 hrs at 37° C./5% $CO_2$ before being serum-starved overnight. The next day, compounds are added for 1 hour before a 10 minute induction with EGF. Cells are lysed by the addition of lysis buffer and freezing at −80° C. Thawed and clarified lysates are then added to 96-well plates that are coated with an anti-EGFR antibody; p-EGFR is then detected by a phospho-tyrosine antibody using an ELISA format.

PREPARATIVE EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius.

Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane (DCM), dichloroethane (DCE), toluene, dioxane and 1,2-difluoroethane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters). $^1$H NMR spectra were recorded on a Varian instrument operating at 400 MHz. $^1$H-NMR spectra were obtained as CDCl$_3$, CD$_3$OD or d$_6$-DMSO solutions (reported in ppm), using TMS as the reference standard (0.0 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

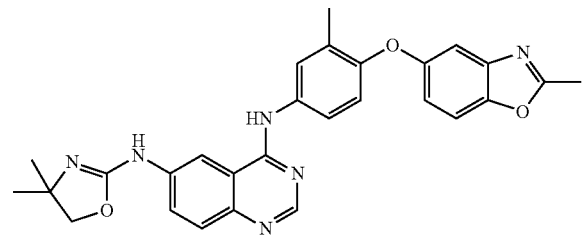

Synthesis of N6-(4,4-dimethyl-4,5-dihydrooxazol-2-yl)-N4-(3-methyl-4-(2-methylbenzo[d]oxazol-5-yloxy)phenyl)quinazoline-4,6-diamine Step A: Preparation of N'-(2-cyano-4-nitrophenyl)-N,N-dimethylformamidine: A mixture of 2-amino-5-nitrobenzonitrile (30.0 g, 184 mmol) and dimethoxy-N,N-dimethylmethanamine (29.6 mL, 223 mmol) was heated to 100° C. for 2 hours. The reaction mixture was concentrated under reduced pressure and dissolved in dichloromethane. The solution was run through a silica plug washing the plug with ethyl acetate. The filtrate was concentrated under reduced pressure, stirred with ether and filtered to provide the product (35.0 g, 87%) as yellow solid.

Step B: Preparation of N'-(4-amino-2-cyanophenyl)-N,N-dimethylformamidine: A solution of N'-(2-cyano-4-nitrophenyl)-N,N-dimethylformamidine (30.0 g, 137 mmol), cyclohexene (200 mL) and 10% Pd on carbon (3.0 g) in methanol (1 L) was refluxed for 10 hours under a hydrogen atmosphere. The hot solution was filtered through Celite and the filtrate was concentrated under reduced pressure. The residue was recrystallized from dichloromethane/carbon tetrachloride to provide the product (23.4 g, 90%) as pale gray crystals.

Step C: Preparation of 1-(3-cyano-4-((dimethylamino)methyleneamino)phenyl)-3-(1-hydroxy-2-methylpropan-2-yl)thiourea: To a cooled (−10° C.) solution of thiocarbonyldiimidazole (211 g, 1.178 mol) in THF (1.5 L) was added slowly via cannula a solution of N'-(4-amino-2-cyanophenyl)-N,N-dimethylformamidine (201.6 g, 1.071 mol) in THF (1.5 L). After stirring at −10° C. for 25 minutes, a solution of 2-amino-2-methylpropan-1-ol (120 g, 1.4 mol) in THF (500 mL) was slowly added to the mixture. After warming to room temperature and stirring for 16 hours, the mixture was washed with saturated sodium chloride (2×2 L). The combined aqueous layers were extracted with MTBE (2 L) and ethyl acetate (4×1 L). The combined organic layers were dried over MgSO$_4$ and concentrated under reduced pressure. The residue was crystallized with MTBE and ethyl acetate to provide the product (116.9 g, 34%) as yellow solid.

Step D: Preparation of 1-(2,5-dihydroxyphenyl)ethanone oxime: To a solution of 1-(2,5-dihydroxyphenyl)ethanone (10.0 g, 65.73 mmol) in ethanol (200 mL) was added hydroxylamine hydrochloride (13.7 g, 197.2 mmol). After heating to reflux for 16 hours, the solvent was reduced under reduced pressure. Ethyl acetate (200 mL) and water were added and the mixture was extracted with ethyl acetate (3×). The combined organic layers were dried and concentrated to provide the product (10 g, 91%) as yellow solid.

Step E: Preparation of 2-methylbenzo[d]oxazol-5-ol: To a cooled (0° C.) solution of 1-(2,5-dihydroxyphenyl)ethanone oxime (1.0 g, 5.98 mmol) in DMF (30 mL) was added dropwise POCl$_3$ (0.661 mL, 6.58 mmol). After stirring at 0° C. for 1 hour and then at room temperature for 2 hours, the mixture was washed with water. The aqueous layer was extracted with ethyl acetate and the combined organics were dried and concentrated under reduced pressure to provide the crude product that was used without further purification.

Step F: Preparation of 2-methyl-5-(2-methyl-4-nitrophenoxy)benzo[d]oxazole: 2-Methylbenzo[d]oxazol-5-ol (0.86 g, 5.77 mmol), 1-fluoro-2-methyl-4-nitrobenzene (0.98 g, 6.34 mmol) and K$_2$CO$_3$ (1.59 g, 11.53 mmol) were combined in DMF and heated to 50° C. for 16 hours. The reaction mixture was cooled to room temperature and poured into ice water. The mixture was extracted with ethyl acetate (3×). The combined organics were washed with brine, dried, and concentrated under reduced pressure. The residue was chromatographed (20% to 40% ethyl acetate in hexanes) to provide the product (0.671 g, 41%) as yellow solid.

Step G: Preparation of 3-methyl-4-(2-methylbenzo[d]oxazol-5-yloxy)benzenamine: To a solution of 2-methyl-5-(2-methyl-4-nitrophenoxy)benzo[d]oxazole (671 mg, 2.36 mmol) in ethanol (10 mL) was added 10% palladium on carbon (50 mg, 0.047 mmol). The reaction mixture was subjected to 40 psi of hydrogen for 2.5 hours. The mixture was filtered and the filtrate was concentrated under reduced pressure. The residue was chromatographed to provide the product (0.411 g, 69%) as yellow oil.

Step H: Preparation of 1-(1-hydroxy-2-methylpropan-2-yl)-3-(4-(3-methyl-4-(2-methylbenzo[d]oxazol-5-yloxy)phenylamino)quinazolin-6-yl)thiourea: To a solution of 1-(3-cyano-4-((dimethylamino)methyleneamino)phenyl)-3-(1-hydroxy-2-methylpropan-2-yl)thiourea (275 mg, 0.861 mmol) and 3-methyl-4-(2-methylbenzo[d]oxazol-5-yloxy)benzenamine (241 mg, 0.947 mmol) in isopropyl acetate (2 mL) was added acetic acid (0.2 mL, 3.44 mmol). After stirring at room temperature for 16 hours, hexanes was added and stirred with the mixture for 30 minutes. The mixture was filtered to provide the crude product (281 mg, 62%) as yellow solid.

Step I: Preparation of N6-(4,4-dimethyl-4,5-dihydrooxazol-2-yl)-N-4-(3-methyl-4-(2-methylbenzo[d]oxazol-5-yloxy)phenyl)quinazoline-4,6-diamine: To a solution of 1-(1-hydroxy-2-methylpropan-2-yl)-3-(4-(3-methyl-4-(2-methylbenzo[d]oxazol-5-yloxy)phenylamino)quinazolin-6- yl)thiourea (156 mg, 0.295 mmol) and NaOH (71 mg, 1.77 mmol) in THF (5 mL) was added tosylchloride (113 mg, 0.590 mmol). After stirring at room temperature for 3 hours, water was added and the mixture was extracted with ethyl acetate (2×). The combined organics were washed with 1M NaOH and then brine. The solution was dried and concentrated under reduced pressure. The yellow residue was chromatographed to isolate a white solid. The solid was triturated with ether and chromatographed again to provide the pure product (92 mg, 63%) as white solid. MS APCI (+) m/z 495 (M+1) detected; $^1$H NMR (400 MHz, DMSO-d6) δ 9.49 (br. s, 1H), 8.45 (s, 1H), 7.95 (br. s, 1H), 7.81 (br. s, 1H), 7.73 (br. m, 2H), 7.65 (s, 1H), 7.62 (s, 1H), 7.46 (br. s, 1H), 7.12 (d, 1H), 6.97 (dd, 1H), 6.93 (d, 1H), 4.08 (m, 2H), 2.60 (s, 3H), 2.21 (s, 3H), 1.28 (s, 6H).

Example 2

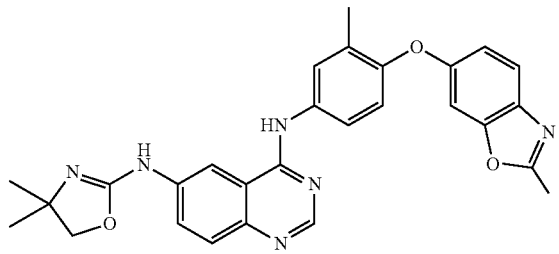

N6-(4,4-dimethyl-4,5-dihydrooxazol-2-yl)-N4-(3-methyl-4-(2-methylbenzo[d]oxazol-6-yloxy)phenyl)quinazoline-4,6-diamine Prepared according to the procedure for Example 1 using 1-(2,4-dihydroxyphenyl)ethanone in place of 1-(2,5-dihydroxyphenyl)ethanone. MS APCI (+) m/z 495 (M+1) detected; $^1$H NMR (400 MHz, DMSO-d6) δ 9.49 (s, 1H), 8.45 (s, 1H), 7.95 (br. s, 1H), 7.83 (br. s, 1H), 7.76 (br. s, 1H), 7.65 (br. s, 1H), 7.61 (d, 1H, J=8 Hz), 7.20 (d, 1H, J=2 Hz), 6.96 (d, 1H, J=8 Hz), 6.93 (dd, 1H, J=8 Hz, 2 Hz), 4.09 (br. s, 2H), 2.58 (s, 3H), 2.21 (s, 3H), 1.28 (s, 6H).

Example 3

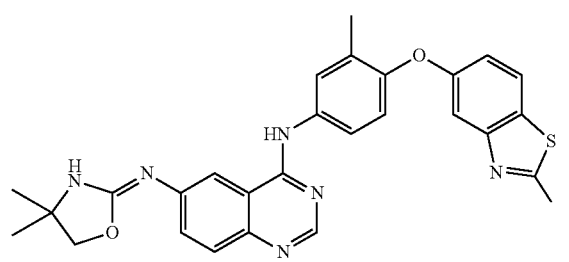

N6-(4,4-dimethyloxazolidin-2-ylidene)-N4-(3-methyl-4-(2-methylbenzo[d]thiazol-5-yloxy)phenyl)quinazoline-4,6-diamine Prepared according to the procedure for Example 1 using 2-methylbenzo[d]thiazol-5-ol in place of 2-methylbenzo[d]oxazol-5-ol. MS APCI (+) m/z 511 (M+1) detected; $^1$H NMR (400 MHz, DMSO-d6) δ 9.53 (s, 1H), 8.47 (s, 1H), 8.02 (s, 1H), 8.00 (d, 1H, J=8 Hz), 7.83 (s, 1H), 7.75 (d, 1H, J=7 Hz), 7.66 (d, 1H, J=8 Hz), 7.29 (d, 1H, J=2 Hz), 7.08 (dd, 1H, J=8 Hz, 2 Hz), 7.03 (d, 1H, J=8 Hz), 4.08 (s, 2H), 2.77 (s, 3H), 2.20 (s, 3H), 1.28 (s, 6-1).

Example 4

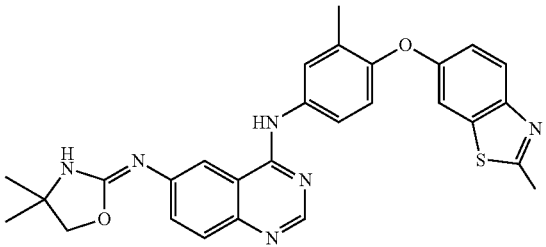

N6-(4,4-dimethyloxazolidin-2-ylidene)-N4-(3-methyl-4-(2-methylbenzo[d]thiazol-6-yloxy)phenyl)quinazoline-4,6-diamine Step A: Preparation of 2-methylbenzo[d]thiazol-6-ol: To a cooled (−78° C.) solution of 6-methoxy-2-methylbenzo[d]thiazole (0.861 g, 4.80 mmol) in dichloromethane (10 mL) was added BBr$_3$ (5 mL of 1.0 M solution in dichloromethane). After slowly warming to room temperature and stirring for 16 hours, the mixture was cooled to 0° C. and slowly quenched with methanol (20 mL). The reaction mixture was warmed to room temperature and concentrated under reduced pressure. The residue was partitioned between saturated NaHCO$_3$ and dichloromethane/isopropyl alcohol (85/15). The organic layer was dried over Na$_2$SO$_4$, filtered, and concentrated under reduced pressure to provide the crude product (0.351 g, 44%) that was used without further purification.

Step B: The title compound was prepared according to the procedure for Example 1 using 2-methylbenzo[d]thiazol-6-ol in place of 2-methylbenzo[d]oxazol-5-ol. MS APCI (+) m/z 511 (M+1) detected; $^1$H NMR (400 MHz, DMSO-d6) δ 9.51 (s, 1H), 8.46 (s, 1H), 8.03 (br. s, 1H), 7.87 (d, 1H, J=9 Hz), 7.83 (s, 1H), 7.75 (d, 1H, J=8 Hz), 7.65 (d, 1H, J=8 Hz), 7.50 (d, 1H, J=2 Hz), 7.10 (dd, 1H, J=8 Hz, 2 Hz), 7.00 (d, 1H, J=8 Hz), 4.07 (s, 2H), 2.76 (s, 3H), 2.20 (s, 3H), 1.28 (s, 6H).

Example 5

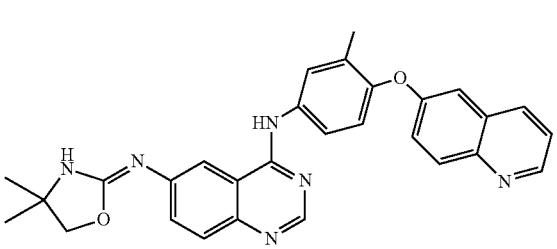 [SMILES: Cc1cc(Nc2ncnc3ccc(/N=C4/NC(C)(C)CO4)cc23)ccc1Oc1ccc2ncccc2c1]

N6-(4,4-dimethyloxazolidin-2-ylidene)-N4-(3-methyl-4-(quinolin-6-yloxy)phenyl)quinazoline-4,6-diamine Prepared according to the procedure for Example 1 using quinolin-6-ol in place of 2-methylbenzo[d]oxazol-5-ol. MS APCI (+) m/z 491 (M+1) detected; $^1$H NMR (400 MHz, DMSO-d6) δ 9.54 (s, 1H), 8.78 (dd, 1H, J=5 Hz, 2 Hz), 8.48 (s, 1H), 8.25 (d, 1H, J=9 Hz), 8.05 (d, 1H, J=9 Hz), 7.89 (s, 1H), 7.82 (d, 1H, J=8 Hz), 7.66 (d, 1H, J=9 Hz), 7.56 (dd, 2H, J=9 Hz, 3 Hz), 7.46 (dd, 2H, J=9 Hz, 5 Hz), 7.16 (d, 2H, J=2 Hz), 7.10 (d, 1H, J=9 Hz), 4.08 (s, 2H), 2.21 (s, 3H), 1.29 (s, 6H).

Example 6

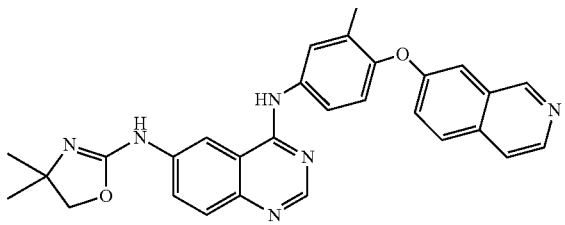 [SMILES: Cc1cc(Nc2ncnc3ccc(NC4=NC(C)(C)CO4)cc23)ccc1Oc1ccc2ccncc2c1]

N6-(4,4-dimethyl-4,5-dihydrooxazol-2-yl)-N4-(4-(isoquinolin-7-yloxy)-3-methylphenyl)quinazoline-4,6-diamine Prepared according to the procedure for Example 1 using isoquinolin-7-ol in place of 2-methylbenzo[d]oxazol-5-ol. MS APCI (+) m/z 491 (M+1) detected; $^1$H NMR (400 MHz, DMSO-d6) δ 9.58 (s, 1H), 9.18 (s, 1H), 8.49 (s, 1H), 8.41 (d, 1H), 8.04 (br. s, 1H), 8.03 (d, 1H), 7.90 (s, 1H), 7.85 (d, 1H), 7.81 (d, 2H), 7.67 (d, 1H), 7.60 (dd, 2H), 7.28 (d, 1H), 7.12 (d, 1H), 4.08 (s, 2H), 2.20 (s, 3H), 1.29 (s, 6H).

Example 7

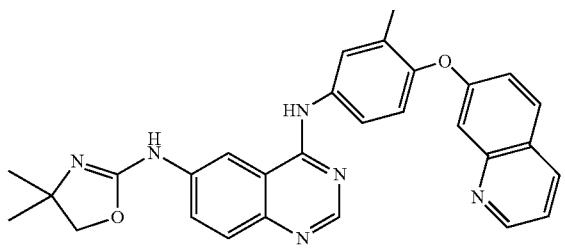 [SMILES: Cc1cc(Nc2ncnc3ccc(NC4=NC(C)(C)CO4)cc23)ccc1Oc1ccc2cccnc2c1]

N6-(4,4-dimethyl-4,5-dihydrooxazol-2-yl)-N4-(3-methyl-4-(quinolin-7-yloxy)phenyl)quinazoline-4,6-diamine Prepared according to the procedure for Example 1 using quinolin-7-ol in place of 2-methylbenzo[d]oxazol-5-ol. MS APCI (+) m/z 491 (M+1) detected; $^1$H NMR (400 MHz, DMSO-d6) δ 9.59 (s, 1H), 8.81 (dd, 1H, J=2 Hz, 5 Hz), 8.49 (s, 1H), 8.34 (d, 1H, J=8 Hz), 8.04 (br. s, 1H), 8.02 (d, 1H, J=9 Hz), 7.89 (br. s, 1H), 7.84 (d, 1H, J=9 Hz), 7.66 (d, 1H, J=9 Hz), 7.43 (m, 3H), 7.16 (d, 1H, J=9 Hz), 7.09 (d, 1H, J=2 Hz), 4.08 (s, 2H), 2.19 (s, 3H), 1.76 (s, 6H).

Example 8

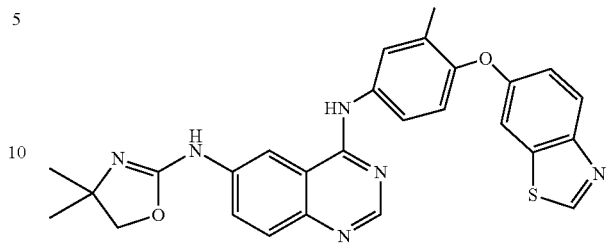

N4-(4-(benzo[d]thiazol-6-yloxy)-3-methylphenyl)-N-6-(4,4-dimethyl-4,5-dihydrooxazol-2-yl)quinazoline-4,6-diamine Step A: Preparation of benzo[d]thiazol-6-ol: 6-methoxybenzo[d]thiazole hydrobromide (1.00 g, 4.06 mmol) was dissolved in aqueous hydrobromide (10 mL of 48% solution). After heating to reflux for 10 hours, the mixture was cooled in an ice bath and diluted with water (50 mL). After adjusting the pH to 8 with the slow addition of solid NaHCO$_3$, the mixture was filtered, washing the solid with water and air-drying to provide the product (0.35 g, 57%) as white solid.

Step B: The title compound was prepared according to the procedure for Example 1 using benzo[d]thiazol-6-ol in place of 2-methylbenzo[d]oxazol-5-ol. MS APCI (+) m/z 497 (M+1) detected; $^1$H NMR (400 MHz, DMSO-d6) δ 9.55 (s, 1H), 9.26 (s, 1H), 8.47 (s, 1H), 8.06 (d, 1H, J=9 Hz), 8.01 (br. s, 1H), 7.85 (s, 1H), 7.77 (d, 1H, J=8 Hz), 7.66 (d, 1H, J=8 Hz), 7.61 (d, 1H, J=2 Hz), 7.20 (dd, 1H, J=9 Hz, 2 Hz), 7.03 (d, 1H, J=9 Hz), 4.07 (s, 2H), 2.21 (s, 3H), 1.28 (s, 6H).

Example 9

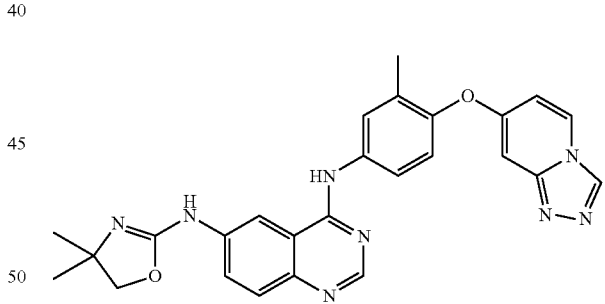

N4-(4-([1,2,4]triazolo[4,3-a]pyridin-7-yloxy)-3-methylphenyl)-N6-(4,4-dimethyl-4,5-dihydrooxazol-2-yl)quinazoline-4,6-diamine Step A: Preparation of 4-(benzyloxy)-2-chloropyridine: To a cooled (0° C.) slurry of washed (hexanes) sodium hydride (14.07 g, 352 mmol) in THF (650 mL) was added dropwise a solution of benzyl alcohol (35.2 mL, 337 mmol) in THF (200 mL). After stirring for 15 minutes, a solution of 2-chloro-4-nitropyridine (50 g, 306 mmol) in THF (200 mL) was added dropwise. After heating to reflux for 16 hours, the black slurry was diluted with water (200 mL) and concentrated to remove the THF. The resulting mixture was diluted with more water and filtered. The filtrate was extracted with ether and ethyl acetate. The combine organics were dried and concentrated. The residue was chromatographed (10% ethyl acetate in hexanes) to provide the product as orange solid.

Step B: Preparation of 1-(4-(benzyloxy)pyridin-2-yl)hydrazine: To a solution of 4-(benzyloxy)-2-chloropyridine (4.89 g, 22.30 mmol) in pyridine (120 mL) was added hydrazine (45 mL, 22.30 mmol). After heating to reflux for 18 hours, the mixture was concentrated to provide the crude product, which was used without further purification.

Step C: Preparation of 7-(benzyloxy)[1,2,4]triazolo[4,3-a]pyridine: To a solution of 1-(4-(benzyloxy)pyridin-2-yl)hydrazine (3.52 g, 16.35 mmol) in trimethoxymethane (20 mL, 16.35 mmol) was added 4-methylbenzenesulfonic acid (2.816 g, 16.35 mmol). After heating to 60° C. for 2 hours, the reaction mixture was concentrated under reduced pressure. The residue was chromatographed (ethyl acetate and 20:1 dichloromethane/methanol) to provide the product (2.33 g, 63%).

Step D: Preparation of [1,2,4]triazolo[4,3-a]pyridin-7-ol: To a solution of 7-(benzyloxy)-[1,2,4]triazolo[4,3-a]pyridine (0.512 g, 2.27 mmol) in ethanol (30 mL) was added Pd/C (0.5 g). After stirring under a hydrogen balloon for 3 hours, the mixture was filtered through celite and washed with ethanol (30 mL). The filtrate was concentrated under reduced pressure and chromatographed (20:1 dichloromethane/methanol) to provide the product.

Step E: The title compound was prepared according to the procedure for Example 1 using [1,2,4]triazolo[4,3-a]pyridin-7-ol in place of 2-methylbenzo[d]oxazol-5-ol. MS ESI (+) m/z 481 (M+1) detected; $^1$H NMR (400 MHz, CDCl$_3$) δ 8.79 (s, 1H), 8.58 (s, 1H), 8.19 (m 2H), 7.85 (s, 1H), 7.74 (m, 3H), 7.53 (d, 1H), 7.12 (d, 1H), 6.89 (dd, 1H), 6.79 (s, 1H), 4.14 (s, 2H), 2.26 (s, 3H), 1.46 (s, 6H).

Example 10

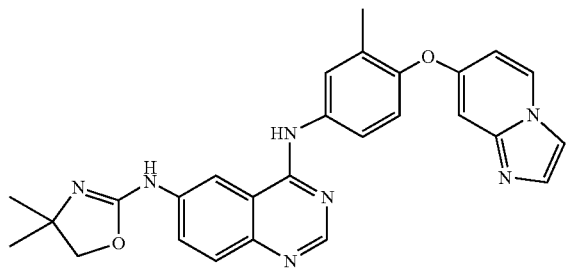 [SMILES: Cc1cc(Nc2ncnc3ccc(NC4=NC(C)(C)CO4)cc23)ccc1Oc1ccn2ccnc2c1]

Synthesis of N4-(4-(H-imidazo[1,2-a]pyridin-7-yloxy)-3-methylphenyl)-N6-(4,4-dimethyl-4,5-dihydrooxazol-2-yl)quinazoline-4,6-diamine Step A: Preparation of 4-(benzyloxy)pyridin-2-amine: To a mixture of 4-(benzyloxy)-2-chloropyridine (1.10 g, 5.01 mmol), Pd$_2$dba$_3$ (46 mg, 0.05 mmol) and 2-(dicyclohexylphosphino)-2',4',6'-tri-i-propyl-1,1'-biphenyl (57 mg, 0.120 mmol) in THF (10 mL) was added LHMDS (6 mL of 1.0 M solution). After heating to 65° C. for 30 minutes, the mixture was cooled to room temperature and concentrated onto silica gel. The product was eluted with 20:1 ethyl acetate/methanol to isolate a pale gold solid (0.97 g, 96%).

Step B: Preparation of tert-butyl 4-(benzyloxy)pyridin-2-ylcarbamate: To a solution of 4-(benzyloxy)pyridin-2-amine (4.6 g, 22.97 mmol) in tBuOH (50 mL) was added boc-anhydride (5.57 g, 25.5 mmol). After heating to 50° C. for 1 hour, ethanol (200 mL) was added to the reaction mixture. The room temperature mixture was filtered to provide the solid product (5.89 g, 85%).

Step C: Preparation of tert-butyl 4-hydroxypyridin-2-ylcarbamate: To a solution of tert-butyl 4-(benzyloxy)pyridin-2-ylcarbamate (5.89 g, 19.6 mmol) in methanol was added palladium on carbon (1.04 g, 0.981 mmol). After stirring under a hydrogen balloon at room temperature for 70 minutes, the solids were removed by filtration. The filtrate was concentrated under reduced pressure and solidified under high vacuum to provide the product (4.12 g, 99%) as white solid.

Step D: Preparation of tert-butyl 4-(2-methyl-4-nitrophenoxy)pyridin-2-ylcarbamate: To a solution of tert-butyl 4-hydroxypyridin-2-ylcarbamate (4.12 g, 19.6 mmol) and 1-fluoro-2-methyl-4-nitrobenzene (3.34 g, 21.6 mmol) in DMF (40 mL) was added K$_2$CO$_3$ (4.06 g, 29.04 mmol). After heating to 65° C. for 64 hours, the mixture was cooled to room temperature and poured into ice water (200 mL). The reaction mixture was extracted several times with ethyl acetate. The combined organics were concentrated under reduced pressure. The residue was chromatographed (20% ethyl acetate in hexanes) to provide the product (2.03 g, 30%).

Step E: Preparation of 4-(2-methyl-4-nitrophenoxy)pyridin-2-amine: To a solution of tert-butyl 4-(2-methyl-4-nitrophenoxy)pyridin-2-ylcarbamate (1.0 g, 2.90 mmol) in dichloromethane (28 mL) was added TFA (4 mL). After stirring at room temperature for 6 hours, the reaction mixture was concentrated under reduced pressure to provide the crude product that was used without further purification.

Step F: Preparation of 7-(2-methyl-4-nitrophenoxy)H-imidazol[1,2-a]pyridine: To a solution of 4-(2-methyl-4-nitrophenoxy)pyridin-2-amine (0.71 g, 2.90 mmol) in dichloromethane (25 mL) was added saturated NaHCO$_3$ (25 mL) followed by chloroacetaldehyde (1.14 g, 7.24 mmol). After stirring at room temperature for 16 hours, the mixture was diluted with water and dichloromethane. The aqueous layer was extracted with dichloromethane and the combined organics were dried and concentrated under reduced pressure. The residue was chromatographed to provide the product (0.61 g, 78%) as sticky yellow solid.

Step G: Preparation of 4H-imidazo[1,2-a]pyridin-7-yloxy)-3-methylbenzenamine: To a solution of 7-(2-methyl-4-nitrophenoxy)H-imidazo[1,2-a]pyridine (0.59 g, 2.19 mmol) in ethanol was added palladium on carbon (0.116 g, 0.11 mmol). After stirring at room temperature under a hydrogen balloon for 16 hours, the solids were removed by filtration. The filtrate was concentrated under reduced pressure and solidified under high vacuum to provide the product (0.51 g, 97%) as white foam.

Step H: Preparation of N4-(4-(H-imidazo[1,2-a]pyridin-7-yloxy)-3-methylphenyl)-N6-(4,4-dimethyl-4,5-dihydrooxazol-2-yl)quinazoline-4,6-diamine: To a mixture of 4-(H-imidazo[1,2-a]pyridin-7-yloxy)-3-methylbenzenamine (0.124 g, 0.518 mmol) and 1-(3-cyano-4-((dimethylamino)methyleneamino)phenyl)-3-(1-hydroxy-2-methylpropan-2-yl)thiourea (0.151 g, 0.471 mmol) in isopropyl acetate (2 mL) was added acetic acid (1 mL). After stirring at room temperature for 16 hours, hexanes were added to the mixture and the yellow solid was collected by filtration. To a solution of this product dissolved in THF (1 mL) was added tosyl chloride (0.180 g, 0.942 mmol) and NaOH (2.8 mL of 1 M solution). After stirring at room temperature for 30 minutes, water was added to the mixture and it was extracted with ethyl acetate twice. The combined organics were washed with NaOH (1 M) and brine. The solution was dried, filtered, and concentrated under reduced pressure. The yellow residue was triturated with ethyl acetate/MTBE to provide the product (0.10 g, 44%) as white solid. MS APCI (+) m/z 480 (M+1) detected; $^1$H NMR (400 MHz, DMSO-d6) δ 9.55 (s, 1H), 8.54 (d, 1H, J=7 Hz), 8.48 (s, 1H), 8.00 (br. s, 1H), 7.84 (m, 3H), 7.66 (d, 1H, J=8 Hz), 7.50 (br. s, 1H), 7.43 (s, 1H), 7.12 (d, 1H, J=8 Hz), 6.80 (dd, 1H, J=7 Hz, 2 Hz), 6.53 (d, 1H, J=2 Hz), 4.08 (br. s, 2H), 2.19 (s, 3H), 1.28 (s, 6H).

Example 11

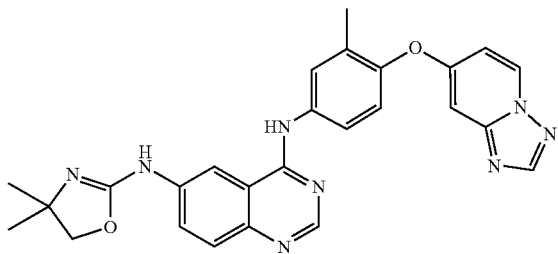 [SMILES: Cc1cc(Nc2ncnc3ccc(NC4=NC(C)(C)CO4)cc23)ccc1Oc1ccn2ncnc2c1]

N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Step A: Preparation of (Z)-N,N-dimethyl-N'-(4-(2-methyl-4-nitrophenoxy)pyridin-2-yl)formamidine: To a solution of 4-(2-methyl-4-nitrophenoxy)pyridin-2-amine (2.05 g, 8.34 mmol) in ethanol (9 mL) was added dimethoxy-N,N-dimethylmethanamine (1.18 mL, 8.34 mmol). After heating to 80° C. for 1 hour, the mixture was concentrated under reduced pressure to provide the crude product as dark oil.

Step B: Preparation of 7-(2-methyl-4-nitrophenoxy)-[1,2,4]triazolo[1,5-a]pyridine: To a cooled (0° C.) solution of (Z)-N,N-dimethyl-N'-(4-(2-methyl-4-nitrophenoxy)pyridin-2-yl)formamidine (1.00 g, 3.33 mmol) in methanol (5 mL) was added pyridine (0.54 mL, 6.66 mmol) and hydroxylamine sulfonic acid (0.427 g, 3.66 mmol). After stirring at room temperature for 2 hours, the precipitate was filtered to provide the product (0.442 g, 49%) as white solid.

Step C: The title compound was prepared according to the procedure for Example 1 using [7-(2-methyl-4-nitrophenoxy)-[1,2,4]triazolo[1,5-a]pyridine in place of 2-methyl-5-(2-methyl-4-nitrophenoxy)benzo[d]oxazole. MS APCI (+) m/z 481 (M+1) detected; $^1$H NMR (400 MHz, CDCl$_3$) δ 9.58 (s, 1H), 8.93 (d, 1H), 8.49 (s, 1H), 8.38 (s, 1H), 7.92 (br. m, 2H), 7.67 (br. s, 1H), 7.47 (br. s, 1H), 7.19 (d, 1H), 7.03 (dd, 1H), 6.79 (d, 1H), 4.08 (s, 2H), 2.19 (s, 3H), 1.28 (s, 6H).

Example 12

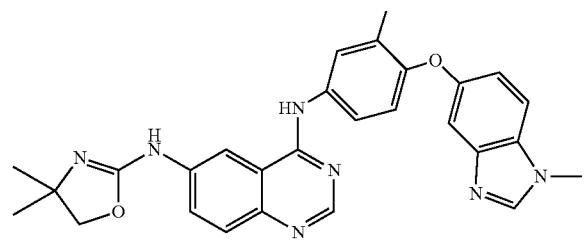

N6-(4,4-dimethyl-4,5-dihydrooxazol-2-yl)-N-4-(3-methyl-4-(1-methyl-1H-benzo[d]imidazol-5-yloxy)phenyl)quinazoline-4,6-diamine Step A: Preparation of 4-(2-methyl-4-nitrophenoxy)-2-nitrobenzenamine: To a solution of 1-fluoro-2-methyl-4-nitrobenzene (2.02 g, 13.0 mmol) and 4-amino-3-nitrophenol (2.22 g, 14.4 mmol) in DMF (20 mL) was added cesium carbonate (5.28 g, 16.2 mmol). After heating to 60° C. for 10 hours, the mixture was diluted with water (100 mL) and filtered. The precipitate was washed with water and air-dried to provide the product (3.28 g, 87%) as dark solid.

Step B: Preparation of N-methyl-4-(2-methyl-4-nitrophenoxy)-2-nitrobenzenamine: To a solution of sodium hydroxide (10.2 g in 10.5 mL water) was added toluene (15 mL), 4-(2-methyl-4-nitrophenoxy)-2-nitrobenzenamine (2.00 g, 6.92 mmol), dimethyl sulfate (750 µL, 7.88 mmol) and tetrabutylammonium sulfate (0.277 g, 0.816 mmol). After stirring at room temperature, the cooled (0° C.) reaction mixture was diluted with water (100 mL) and extracted with dichloromethane (100 mL). The organic layer was washed with water and brine, dried over Na$_2$SO$_4$, filtered, and concentrated under reduced pressure. The residue was chromatographed (dichloromethane) to provide the product (1.90 g, 91%).

Step C: Preparation of 4-(4-amino-2-methylphenoxy)-N1-methylbenzene-1,2-diamine: To a solution of N-methyl-4-(2-methyl-4-nitrophenoxy)-2-nitrobenzenamine (1.90 g, 6.27 mmol) in ethyl acetate (10 mL) and ethanol (20 mL) was added 10% Pd/C (0.342 g, 0.321 mmol). After shaking under 50 psi of hydrogen for 1 hour, the mixture was filtered and the filtrate was concentrated under reduced pressure to provide the product as clear oil.

Step D: Preparation of N-(3-methyl-4-(1-methyl-1H-benzo[d]imidazol-5-yloxy)phenyl)formamide: 4-(4-amino-2-methylphenoxy)-N1-methylbenzene-1,2-diamine (1.52 g, 6.25 mmol) was dissolved in formic acid (15 mL) and heated to reflux for 6 hours. After cooling to room temperature, the mixture was diluted water (100 mL) and neutralized with sodium bicarbonate. The mixture was partitioned between water and dichloromethane. The organic layer was washed with aqueous NaHCO$_3$, brine, dried over Na$_2$SO$_4$, filtered and concentrated under reduced pressure to provide the product (1.70 g, 97%).

Step E: Preparation of 3-methyl-4-(1-methyl-1H-benzo[d]imidazol-5-yloxy)benzenamine: To a solution of concentrated aqueous HCl (10 mL) in methanol (10 mL) was added N-(3-methyl-4-(1-methyl-1H-benzo[d]imidazol-5-yloxy)phenyl)formamide (1.70 g, 6.04 mmol). After heating to reflux for 2 hours, the reaction mixture was cooled to room temperature and diluted with water (100 mL). The mixture was neutralized with sodium bicarbonate and extracted with dichloromethane. The organic solution was dried over Na$_2$SO$_4$, filtered and concentrated under reduced pressure to provide the product.

Step F: The title compound was prepared according to the procedure for Example 1 using 3-methyl-4-(1-methyl-1H-benzo[d]imidazol-5-yloxy)benzenamine in place of 3-methyl-4-(2-methylbenzo[d]oxazol-5-yloxy)benzenamine. MS APCI (+) m/z 494 (M+1) detected; $^1$H NMR (400 MHz, DMSO-d6) δ 9.49 (s, 1H), 8.44 (s, 1H), 8.17 (s, 1H), 8.00 (br.

s, 1H), 7.78 (s, 1H), 7.66 (m, 2H), 7.56 (c, 1H), 7.08 (d, 1H), 6.98 (dd, 1H), 6.86 (d, 1H), 4.07 (s, 2H), 3.84 (s, 3H), 2.23 (s, 3H), 1.28 (s, 6H).

Example 13

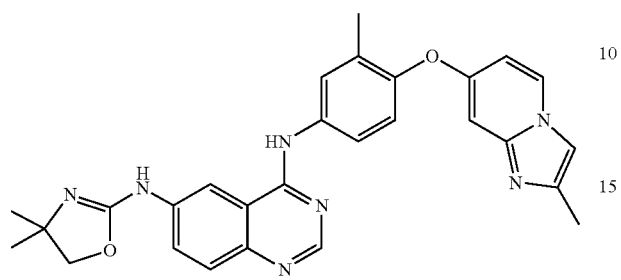

N6-(4,4-dimethyl-4,5-dihydrooxazol-2-yl)-N4-(3-methyl-4-(2-methylH-imidazo[1,2-a]pyridin-7-yloxy)phenyl)quinazoline-4,6-diamine Prepared according to the procedure for Example 10 using chloroacetone in place of chloroacetaldehyde. MS APCI (+) m/z 494 (M+1) detected; $^1$H NMR (400 MHz, DMSO-d6) δ 8.47 (s, 1H), 8.43 (d, 1H), 7.87 (m, 3H), 7.66 (br. s, 1H), 7.56 (s, 2H), 7.10 (d, 1H), 6.71 (dd, 1H), 6.45 (s, 1H), 4.09 (s, 2H), 2.25 (s, 3H), 2.18 (s, 3H), 1.11 (s, 6H).

Example 14

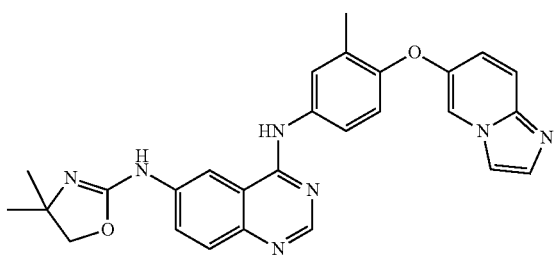 [SMILES: Cc1cc(Nc2ncnc3ccc(NC4=NC(C)(C)CO4)cc23)ccc1Oc1ccc2nccn2c1]

N4-(4-(H-imidazo[1,2-a]pyridin-6-yloxy)-3-methylphenyl)-N6-(4,4-dimethyl-4,5-dihydrooxazol-2-yl)quinazoline-4,6-diamine Step A: Preparation of 2-chloro-5-(2-methyl-4-nitrophenoxy)pyridine: To a suspension of 6-chloropyridin-3-ol (3.37 g, 26.0 mmol) and K$_2$CO$_3$ (7.19 g, 52.0 mmol) in DMF (200 mL) was added 1-fluoro-2-methyl-4-nitrobenzene (4.44 g, 28.6 mmol). After heating to 50° C. for 16 hours, the reaction mixture was cooled to room temperature and poured into water and extracted with ethyl acetate (2×). The organic layer was washed with brine, dried over Na$_2$SO$_4$, filtered, and concentrated under reduced pressure to provide the product as yellow oil.

Step B: Preparation of 5-(2-methyl-4-nitrophenoxy)pyridin-2-amine: To a solution of 2-chloro-5-(2-methyl-4-nitrophenoxy)pyridine (1.13 g, 4.27 mmol), XPHOS (0.097 g, 0.205 mmol) and Pd$_2$dba$_3$ (0.078 g, 0.0853 mmol) in THF (32 mL) was added LHMDS (8.53 mL, 8.53 mmol). After heating to 65° C. for 1 hour, the mixture was cooled to room temperature and stirred for 16 hours. The mixture was concentrated onto silica and chromatographed (10% methanol in ethyl acetate) to provide the product (0.336 g, 33%).

Step C: The title compound was prepared according to the procedure for Example 10 using 5-(2-methyl-4-nitrophenoxy)pyridin-2-amine in place of 4-(2-methyl-4-nitrophenoxy)pyridin-2-amine. MS APCI (+) m/z 480 (M+1) detected; $^1$H NMR (400 MHz, DMSO-d6) δ 9.51 (s, 1H), 8.45 (s, 1H), 8.21 (s, 1H), 7.91 (s, 1H), 7.83 (br. s, 1H), 7.73 (br. s, 1H), 7.66 (m, 2H), 7.60 (d, 1H), 7.55 (s, 1H), 7.15 (dd, 1H), 7.00 (d, 1H), 4.07 (s, 2H), 2.27 (s, 3H), 1.28 (s, 6H).

Example 15

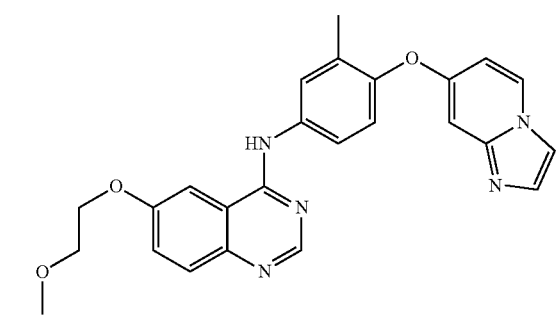 [SMILES: COCCOc1ccc2ncnc(Nc3ccc(Oc4ccn5ccnc5c4)c(C)c3)c2c1]

N-(4-(H-imidazo[1,2-a]pyridin-7-yloxy)-3-methylphenyl)-6-(2-methoxyethoxy)quinazolin-4-amine Step A: Preparation of quinazoline-4,6-diol: A mixture of 2-amino-5-hydroxybenzoic acid (19.64 g, 128 mmol), 1,3,5-triazine (15.6 g, 192 mmol), and piperidine (9 mL, 92.4 mmol) were heated to 60° C. in methanol (60 mL) for 2 hours. After cooling to 0° C., the mixture was filtered. The solid was washed with cold methanol and dried under high vacuum to provide the product (15 g, 72%) as white solid.

Step B: Preparation of 4-hydroxyquinazolin-6-yl acetate: A mixture of quinazoline-4,6-diol (20 g, 123 mmol) and acetic anhydride (186 mL, 1.97 mol) was heated to 100° C. in pyridine (30 mL) for 2 hours. After cooling to room temperature, ice (200 g) was slowly added to the reaction mixture. The precipitate was filtered, washed with cold water, and dried under high vacuum to provide the product (16.25 g, 65%) as pale yellow solid.

Step C: Preparation of 4-chloroquinazolin-6-yl acetate: To a solution of 4-hydroxyquinazolin-6-yl acetate (12.0 g, 58.8 mmol) in thionyl chloride (50 mL) was added DMF (0.5 mL). After heating to 90° C. for 3 hours, the reaction mixture was concentrated under reduced pressure and azeotroped with toluene to provide the product (11.8 g, 90%) as off-white solid.

Step D: Preparation of 4-(4-(H-imidazo[1,2-a]pyridin-7-yloxy)-3-methylphenylamino)quinazolin-6-yl acetate hydrochloride: A mixture of 4-chloroquinazolin-6-yl acetate (930 mg, 4.18 mmol) and 4-(H-imidazo[1,2-a]pyridin-7-yloxy)-3-methylbenzenamine (1.10 g, 4.60 mmol) dissolved in isopropanol (20 mL) was heated to reflux for 2 hours. After cooling to room temperature, the precipitate was collected via filtration and washed with isopropanol and ether. The precipitate was air-dried to provide the product (820 mg, 43%).

Step E: Preparation of 4-(4-(H-imidazo[1,2-a]pyridin-7-yloxy)-3-methylphenylamino)quinazolin-6-ol: To a solution of 4-(4-(H-imidazo[1,2-a]pyridin-7-yloxy)-3-methylphenylamino)quinazolin-6-yl acetate hydrochloride (820 mg, 1.78 mmol) in THF (30 mL) was added ammonium hydroxide (10 mL). After stirring at room temperature for several hours, the precipitate was collected via filtration and washed with THF. The precipitate was air-dried to provide the product (581 mg, 85%) as white solid.

Step F: Preparation of N-(4-(H-imidazo[1,2-a]pyridin-7-yloxy)-3-methylphenyl)-6-(2-methoxyethoxy)quinazolin-4-amine: A mixture of 4-(4-(H-imidazo[1,2-a]pyridin-7-yloxy)-3-methylphenylamino)quinazolin-6-ol (578 mg, 1.27 mmol), cesium carbonate (1.60 g, 4.91 mmol), sodium iodide (190 mg, 1.27 mmol) and 1-bromo-2-methoxyethane (150 µL, 1.58 mmol) in DMF (10 mL) was heated to 80° C. for 3 hours. After cooling to room temperature, the mixture was partitioned between dichloromethane and water. The organic layer was washed with water (4×) and brine, dried over $Na_2SO_4$, filtered and concentrated under reduced pressure. The residue was chromatographed (100:7:0.1 dichloromethane/methanol/triethylamine) to provide the product (365 mg, 65%) as foam. To 325 mg of this product dissolved in methanol (10 mL) was added tosylic acid monohydrate (280 mg). After stirring at room temperature for 45 minutes, the mixture was concentrated under reduced pressure. The residue was triturated with ether, filtered and air-dried to provide the product (576 mg) as the bis-tosylate salt. MS APCI (+) m/z 442 (M+1) detected; $^1$H NMR (400 MHz, $CD_3OD$) δ 7.46 (d, 1H, J=8 Hz), 7.43 (s, 1H), 6.79 (dd, 2H, J=11 Hz, 2 Hz), 6.54 (m, 2H), 6.52 (s, 1H), 6.49 (dd, 1H, J=9 Hz, 2 Hz), 6.45 (dd, 1H, J=9 Hz, 3 Hz), 6.38 (d, 4H, J=9 Hz), 6.02 (dd, 1H, J=7 Hz, 2 Hz), 5.99 (d, 1H, J=9 Hz), 5.89 (d, 4H, J=9 Hz), 5.71 (d, 1H, J=3 Hz), 3.07 (m, 2H), 2.51 (m, 2H), 2.15 (s, 3H), 1.04 (s, 6H), 0.95 (s, 3H).

Example 16

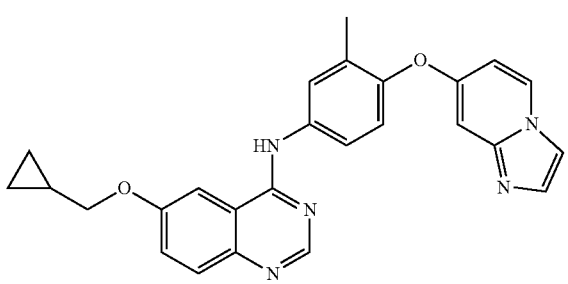 [SMILES: Cc1cc(Nc2ncnc3ccc(OCC4CC4)cc23)ccc1Oc1ccn2ccnc2c1]

N-(4-(H-imidazo[1,2-a]pyridin-7-yloxy)-3-methylphenyl)-6-(cyclopropylmethoxy)quinazolin-4-amine Prepared according to the procedure for Example 15 using (bromomethyl)cyclopropane in place of 1-bromo-2-methoxyethane. MS APCI (+) m/z 438 (M+1) detected; $^1$H NMR (400 MHz, $CDCl_3$) δ 8.97 (s, 1H), 8.67 (s, 1H), 8.07 (d, 1H, J=8 Hz), 7.82 (d, 1H, J=9 Hz), 7.65 (d, 1H, J=2 Hz), 7.50 (m, 3H), 7.44 (dd, 2H, J=9 Hz, 2 Hz), 6.93 (d, 1H, J=9 Hz), 6.74 (dd, 1H, J=7 Hz, 2 Hz), 6.54 (d, 1H, J=2 Hz), 3.72 (d, 2H, J=7 Hz), 2.11 (s, 3H), 1.24 (m, 1H), 0.59 (m, 2H), 0.21 (m, 2H).

Example 17

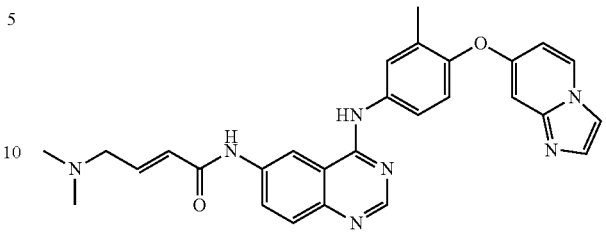

(E)-N-(4-(4-(H-imidazo[1,2-a]pyridin-7-yloxy)-3-methylphenylamino)quinazolin-6-yl)-4-(dimethylamino)but-2-enamide Step A: Preparation of 6-nitroquinazolin-4-ol: A mixture of 2-amino-5-nitrobenzoic acid (1000 g, 5 mol) and formamidine acetate (1000 g, 10 mol) were dissolved in methoxyethanol (4 L) and heated to 115° C. for 16 hours. After cooling the mixture to room temperature, ice water (5 L) was added and the mixture was stirred for 30 minutes before collecting the product (125 g, 14%) by filtration.

Step B: Preparation of 4-chloro-6-nitroquinazoline: To a solution of 6-nitroquinazolin-4-ol (4.40 g, 23.01 mmol) and N-ethyl-N-isopropylpropan-2-amine (11.89 g, 92.04 mmol) in dichloroethane (50 mL) was added phosphoryl trichloride (7.06 g, 46.02 mmol). After heating to 80° C. for 16 hours, the mixture was concentrated under reduced pressure. The residue was concentrated again with toluene (2×100 mL) to provide the product.

Step C: Preparation of N-(4-(H-imidazo[1,2-a]pyridin-7-yloxy)-3-methylphenyl)-6-nitroquinazolin-4-amine: To a solution of 4-chloro-6-nitroquinazoline (4.62 g, 22.02 mmol) in dichloroethane/t-butanol (20 mL, 1:1) was added 4-(H-imidazo[1,2-a]pyridin-7-yloxy)-3-methylbenzenamine (5.270 g, 22.02 mmol). After heating to 80° C. for 2 hours, the mixture was cooled to 0° C. and filtered. The solid was washed with cold dichloromethane (50 mL) to provide the product as the HCl salt. The solid was suspended in dichloromethane/isopropanol (50 mL/8 mL) and washed with saturated $NaHCO_3$ (50 mL). The aqueous layer was extracted with dichloromethane (2×50 mL). The combined organics were dried over $Na_2SO_4$ and concentrated to provide the product (7.05 g, 78%).

Step D: Preparation of N4-(4-(H-imidazo[1,2-a]pyridin-7-yloxy)-3-methylphenyl)quinazoline-4,6-diamine: To N-(4-(H-imidazo[1,2-a]pyridin-7-yloxy)-3-methylphenyl)-6-nitroquinazolin-4-amine (4.665 g, 11.31 mmol) in ethanol (100 mL) was added Pd/C (1 g). After stirring at room temperature under a hydrogen balloon for 4 hours, the mixture was filtered through celite and the solids were washed with ethanol (100 mL). The filtrate was concentrated under reduced pressure to provide the product (3.89 g, 90%).

Step E: Preparation of (E)-4-(dimethylamino)but-2-enoyl chloride hydrochloride: To (E)-4-(dimethylamino)but-2-enoic acid hydrochloride (110 mg, 0.664 mmol) in acetonitrile (1.5 mL) was added oxalyl dichloride (75.9 mg, 0.598 mmol) followed by one drop of DMF. After heating to 60° C. for 30 minutes, the mixture was cooled to room temperature and concentrated to 0.5 mL total volume. The resulting solution was used without further purification.

Step F: Preparation of (E)-N-(4-(4-(H-imidazo[1,2-a]pyridin-7-yloxy)-3-methylphenylamino)quinazolin-6-yl)-4-

(dimethylamino)but-2-enamide: To a cooled (0° C.) solution of (E)-4-(dimethylamino)but-2-enoyl chloride hydrochloride (0.122 g, 0.664 mmol) was added dropwise a solution of N4-(4-(H-imidazo[1,2-a]pyridin-7-yloxy)-3-methylphenyl)quinazoline-4,6-diamine (0.127 g, 0.332 mmol) in NMP (1.5 mL). After stirring at 0° C. for 2 hours, saturated NaHCO₃ (15 mL) was added to the mixture. The aqueous layer was extracted with ethyl acetate (2×10 mL). The combined organics were dried over Na₂SO₄ and concentrated under reduced pressure. The residue was chromatographed (dichloromethane/methanol/30% NH₄OH 20:1.5:0.01) to provide the product (16 mg, 10%). MS ESI (+) m/z 494 (M+1) detected; ¹H NMR (400 MHz, CDCl₃) δ 8.96 (s, 1H), 8.63 (s, 1H), 8.09 (d, 1H, J=7 Hz), 7.66 (d, 1H, J=9 Hz), 7.55 (d, 2H, J=14 Hz), 7.46 (d, 1H, J=9 Hz), 7.40 (s, 1H), 7.38 (d, 1H, J=9 Hz), 7.02 (m, 1H), 6.83 (d, 1H, J=9 Hz), 6.77 (dd, 1H, J=8 Hz, 2 Hz), 6.43 (s, 1H), 6.34 (d, 1H, J=14 Hz), 3.08 (d, 2H, J=5 Hz), 2.24 (s, 6H), 1.98 (s, 3H).

Example 18

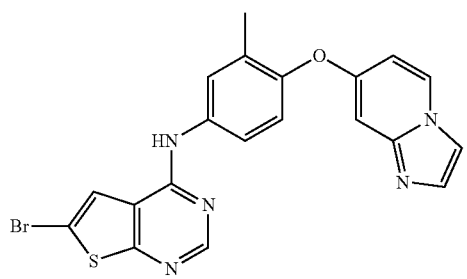 [SMILES: Cc1cc(Nc2ncnc3sc(Br)cc23)ccc1Oc1ccn2ccnc2c1]

N-(4-(H-imidazo[1,2-a]pyridin-7-yloxy)-3-methylphenyl)-6-bromothieno[2,3-d]pyrimidin-4-amine Step A: Preparation of 6-bromothieno[2,3-d]pyrimidin-4-ol: To a solution of thieno[2,3-d]pyrimidin-4-ol (3.0 g, 20 mmol) in glacial acetic acid (40 mL) was added bromine (6.3 g, 39 mmol). After heating to 80° C. for 1.5 hours, the reaction mixture was cooled to room temperature and poured into saturated NaHCO₃ and ice. The solid was filtered, washed with water and dried to provide the product.

Step B: Preparation of 6-bromo-4-chlorothieno[2,3-d]pyrimidine: To 6-bromothieno[2,3-d]pyrimidin-4-ol (3.0 g, 19.7 mmol) was added phosphorus oxychloride (5 mL). After heating to 80° C. for 1.5 hours, the reaction mixture was poured into saturated NaHCO₃ and ice. The solid was filtered, washed with water and dried to provide the product (4.06 g, 83%) as brown solid.

Step C: Preparation of N-(4-(H-imidazo[1,2-a]pyridin-7-yloxy)-3-methylphenyl)-6-bromothieno[2,3-d]pyrimidin-4-amine: To a solution of 6-bromo-4-chlorothieno[2,3-d]pyrimidine (0.569 g, 2.58 mmol) and 4-(H-imidazo[1,2-a]pyridin-7-yloxy)-3-methylbenzenamine (0.60 g, 2.51 mmol) in dichloroethane/isopropanol (11 mL) was added DIEA (0.44 mL, 2.51 mmol). After heating to 60° C. for 64 hours, the reaction mixture was worked up with isopropanol/dichloromethane. The organic solution was dried and concentrated under reduced pressure. The residue was chromatographed (gradient 0% to 8% methanol/7N NH₃/ethyl acetate). The crude product was purified further by reverse phase liquid chromatography. MS ESI (+) m/z 452, 454 (M+1, Br pattern) detected; ¹H NMR (400 MHz, DMSO-d6) δ 9.69 (s, 1H), 8.63 (d, 1H, J=7 Hz), 8.52 (s, 1H), 8.10 (s, 1H), 7.94 (s, 1H), 7.82 (d, 1H, J=3 Hz), 7.78 (dd, 1H, J=3 Hz, 9 Hz), 7.59 (s, 1H), 7.16 (d, 1H, J=9 Hz), 6.96 (dd, 1H, J=2 Hz, 7 Hz), 6.63 (s, 1H), 2.19 (s, 3H).

Example 19

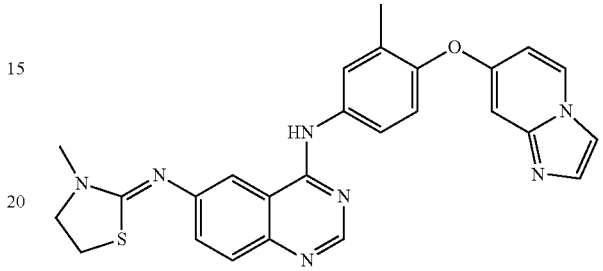

(Z)-N4-(4-(imidazo[1,2-a]pyridin-7-yloxy)-3-methylphenyl)-N6-(3-methylthiazolidin-2-ylidene)quinazoline-4,6-diamine Step A: Preparation of N-(4-(H-imidazo[1,2-a]pyridin-7-yloxy)-3-methylphenyl)-6-isothiocyanatoquinazolin-4-amine: To a solution of N4-(4-(H-imidazo[1,2-a]pyridin-7-yloxy)-3-methylphenyl)quinazoline-4,6-diamine (0.292 g, 0.764 mmol) in THF/dichloroethane (6 mL/3 mL) was added di(1H-imidazol-1-yl)methanethione (0.150 g, 0.840 mmol). After stirring at room temperature for 1 hour, 80% of the solvent was evaporated and DMF (4 mL) was added. The reaction solution was stirred for 1 hour more to provide the crude product.

Step B: Preparation of 3-(4-(4-(H-imidazo[1,2-a]pyridin-7-yloxy)-3-methylphenylamino)quinazolin-6-yl)-1-(2-hydroxyethyl)-1-methylthiourea: To N-(4-(H-imidazo[1,2-a]pyridin-7-yloxy)-3-methylphenyl)-6-isothiocyanatoquinazolin-4-amine (0.324 g, 0.763 mmol) was added 2-(methylamino)ethanol (0.115 g, 1.53 mmol). After stirring for 2 hours, the mixture was diluted with ethyl acetate (20 mL) and water (10 mL). The organic phase was dried over Na₂SO₄ and concentrated to provide the crude product.

Step C: Preparation of (Z)-N4-(4-(H-imidazo[1,2-a]pyridin-7-yloxy)-3-methylphenyl)-N6-(3-methylthiazolidin-2-ylidene)quinazoline-4,6-diamine: To a solution of 3-(4-(4-(imidazo[1,2-a]pyridin-7-yloxy)-3-methylphenylamino)quinazolin-6-yl)-1-(2-hydroxyethyl)-1-methylthiourea (0.38 g, 0.76 mmol) in THF (4 mL) was added NaOH (40%, 3.8 mmol) followed by 4-methylbenzene-1-sulfonyl chloride (0.29 g, 1.5 mmol). After stirring at room temperature for 2 hours, the reaction mixture was concentrated under reduced pressure. The residue was chromatographed (dichloromethane/methanol/30% NH₄OH 20:1:0.02) to provide the product. MS APCI (+) m/z 482 (M+1) detected; ¹H NMR (400 MHz, CDCl₃) δ 8.65 (m, 2H), 8.18 (m, 2H), 7.85 (d, 1H, J=7 Hz), 7.7 (s, 1H), 7.62 (m, 1H), 7.58 (s, 1H), 7.55 (s, 1H), 6.95 (m, 1H), 6.8 (m, 1H), 6.68 (m, 1H), 4.26 (m, 2H), 3.78 (m, 2H), 3.2 (s, 3H), 2.15 (s, 3H).

Example 20

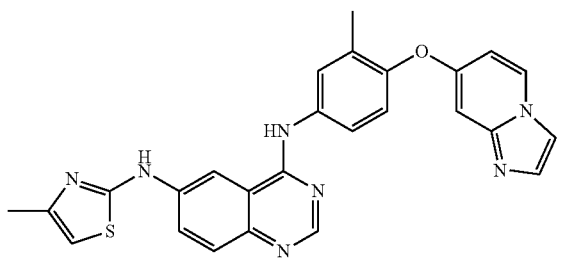 [SMILES: Cc1csc(Nc2ccc3ncnc(Nc4ccc(Oc5ccn6ccnc6c5)c(C)c4)c3c2)n1]

N4-(4-(imidazo[1,2-a]pyridin-7-yloxy)-3-methylphenyl)-N6-(4-methylthiazol-2-yl)quinazoline-4,6-diamine Step A: Preparation of 6-iodoquinazolin-4-ol: A mixture of 2-amino-5-iodobenzoic acid (125 g, 475 mmol) and formamide (200 mL) was heated to 190° C. for 2 hours. After cooling to room temperature, the reaction mixture was poured into water (500 mL) and stirred for 2 hours. The solids were filtered and dried under high vacuum to provide the product (108 g, 83%).

Step B: Preparation of 4-chloro-6-iodoquinazoline: To a cooled (0° C.) suspension of 6-iodoquinazolin-4-ol (107.6 g, 396 mmol) and DIEA (138 mL, 791 mmol) in dichloroethane (600 mL) was added POCl$_3$ (44.25 mL, 475 mmol). After heating to 90° C. for 16 hours, the reaction mixture was cooled to room temperature and the crystals (73.8 g) collected by filtration. The filtrate was concentrated under reduced pressure and azeotroped twice with toluene. The solids (8.3 g) were triturated with isopropanol (450 mL) and cooled in an ice bath before collecting by filtration and drying under high vacuum. The two solids were combined to provide the product (82.1 g, 71%) as white solid.

Step C: Preparation of N-(4-(H-imidazo[1,2-a]pyridin-7-yloxy)-3-methylphenyl)-6-iodoquinazolin-4-amine hydrochloride: To a solution of 4-chloro-6-iodoquinazoline (6.07 g, 20.9 mmol) in isopropanol (83 mL) was added 4-(H-imidazo[1,2-a]pyridin-7-yloxy)-3-methylbenzenamine (5.00 g, 20.9 mmol). After heating to 80° C. for 4 hours, the mixture was cooled to room temperature and filtered. The solid was washed with cold isopropanol and recrystallized from isopropanol to provide the product (2.66 g, 24%) as yellow solid.

Step D: Preparation of N4-(4-(imidazo[1,2-a]pyridin-7-yloxy)-3-methylphenyl)-N6-(4-methylthiazol-2-yl)quinazoline-4,6-diamine: A solution of N-(4-(imidazo[1,2-a]pyridin-7-yloxy)-3-methylphenyl)-6-iodoquinazolin-4-amine hydrochloride (0.20 g, 0.378 mmol) and 4-methylthiazol-2-amine (0.086 g, 0.755 mmol) and sodium 2-methylpropan-2-olate (0.145 g, 1.51 mmol), Xanthphos (0.016 g, 0.028 mmol), Pd$_2$ dba$_3$ (0.017 g, 0.018 mmol) in toluene (3.6 mL) was degassed and sealed. After heating to 100° C. for 16 hours, the mixture was diluted with water and ethyl acetate. The resulting solid was filtered to provide the product as brown solid. MS APCI (+) m/z 480 (M+1) detected; $^1$H NMR (400 MHz, DMSO-d6) δ 9.96 (s, 1H), 8.86 (s, 1H), 8.63 (s, 1H), 8.55 (d, 1H), 7.79 (m, 5H), 7.44 (s, 1H), 7.14 (d, 1H), 6.80 (dd, 1H), 6.55 (d, 1H), 2.50 (s, 3H), 2.21 (s, 3H).

Example 21

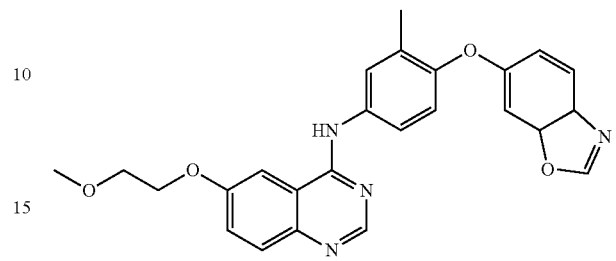

N-(4-(benzo[d]oxazol-6-yloxy)-3-methylphenyl)-6-(2-methoxyethoxy)quinazolin-4-amine Step A: Preparation of 2-aminobenzene-1,4-diol: To a solution of 2-nitrobenzene-1,4-diol (3.00 g, 19.34 mmol) in ethanol (100 mL) was added 10% palladium on carbon (0.600 g, 0.564 mmol). After shaking under 40 psi of hydrogen for 2 hours, the mixture was filtered and the filtrated was concentrated under reduced pressure to provide the product as solid.

Step B: Preparation of benzo[d]oxazol-5-ol: To a solution of 2-aminobenzene-1,4-diol (2.40 g, 19.2 mmol) in triethylorthoformate (10 mL) was added 3 drops of concentrated HCl. After heating to 65° C. for 30 minutes and stirring at room temperature for 16 hours, the mixture was poured into water and extracted with ethyl acetate (2×). The organic phase was washed with HCl (2N) and saturated NaHCO$_3$, dried, and concentrated under reduced pressure to provide the product (2.09 g, 81%) as red-black solid.

Step C: Preparation of 5-(2-methyl-4-nitrophenoxy)benzo[d]oxazole: To a solution of benzo[d]oxazol-5-ol (1.50 g, 11.10 mmol) and 1-fluoro-2-methyl-4-nitrobenzene (1.89 g, 12.21 mmol) in DMF was added cesium carbonate (1.81 g, 5.55 mmol) and potassium carbonate (2.30 g, 16.65 mmol). After heating to 50° C. for 16 hours, the mixture was poured into ice water and extracted with ethyl acetate (3×). The combined organics were washed with brine, dried, and concentrated under reduced pressure. The residue was chromatographed (30% ethyl acetate in hexanes) to provide the product (1.69 g, 56%) as white solid.

Step D: Preparation of 4-(benzo[d]oxazol-5-yloxy)-3-methylbenzenamine: To a solution of 5-(2-methyl-4-nitrophenoxy)benzo[d]oxazole (1.65 g, 6.12 mmol) in ethanol was added Pd/C (0.130 g, 0.122 mmol). After stirring under hydrogen atmosphere for 16 hours, the mixture was filtered and the filtrate was concentrated to provide the product (0.81 g, 55%) as yellow oil.

Step E: Preparation of 4-chloroquinazolin-6-ol: A mixture of 4-chloroquinazolin-6-yl acetate (10.0 g, 44.9 mmol) and ammonia (200 mL of 7N solution in methanol) were stirred together for 1 hour. The reaction mixture was concentrated to about 3 mL and triturated with diethyl ether to provide the product (6.50 g, 80%) as tan solid.

Step F: Preparation of 4-chloro-6-(2-methoxyethoxy)quinazoline: To a solution of 4-chloroquinazolin-6-ol (1.00 g, 5.54 mmol), triphenyl phosphine (1.45 g, 5.54 mmol) and 2-methoxyethanol (0.421 g, 5.54 mmol) in dichloromethane (83 mL) was added diisopropyl azodicarboxylate (1.18 g, 5.54 mmol). After stirring at room temperature for 16 hours, the mixture was concentrated under reduced pressure. The residue was chromatographed (30% ethyl acetate in hexanes) to provide the product (1.15 g, 87%) as white solid.

Step G: N-(4-(benzo[d]oxazol-5-yloxy)-3-methylphenyl)-6-(2-methoxyethoxy)quinazolin-4-amine: To a solution of 4-chloro-6-(2-methoxyethoxy)quinazoline (0.199 g, 0.83 mmol) and 4-(benzo[d]oxazol-5-yloxy)-3-methylbenzenamine (0.200 g, 0.83 mmol) in isopropanol (2 mL) and DCE (2 mL). After heating to 80° C. for 12 hours, the mixture was concentrated under reduced pressure. The residue was partitioned between saturated NaHCO$_3$ and EtOAc. The aqueous phase was extracted 2× with EtOAc, the combined organic phase was washed with brine, dried (Na$_2$SO$_4$), filtered and condensed. The residue was chromatographed to provide the product (0.100 g, 27%) as off-white solids. MS APCI (+) m/z 443 (M+1) detected; $^1$H NMR (400 MHz, DMSO-d6) δ 9.59 (s, 1H), 8.76 (s, 1H), 8.50 (s, 1H), 7.96 (s, 1H), 7.75 (m, 4H), 7.52 (dd, 1H), 7.26 (m, 1H), 7.10 (m, 1H), 6.97 (d, 1H), 4.30 (m, 2H), 3.76 (m, 2H), 3.36 (s, 3H), 2.24 (s, 3H).

Example 22

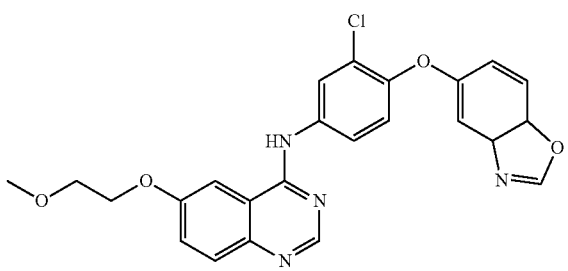 [SMILES: COCCOc1ccc2ncnc(Nc3ccc(OC4=CC5N=COC5C=C4)c(Cl)c3)c2c1]

N-(4-(benzo[d]oxazol-5-yloxy)-3-chlorophenyl)-6-(2-methoxyethoxy)quinazolin-4-amine Prepared according to the procedure for Example 21 using 1-fluoro-2-chloro-4-nitrobenzene in place of 1-fluoro-2-methyl-4-nitrobenzene, with the exception that the reduction of the nitro group was accomplished with Zn/NH$_4$Cl in MeOH/THF. MS APCI (+) m/z 463.3 (M+1) detected.

Example 23

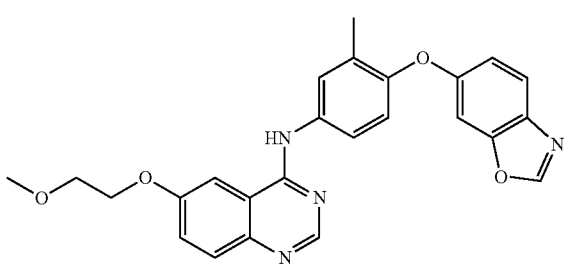 [SMILES: COCCOc1ccc2ncnc(Nc3ccc(Oc4ccc5ncoc5c4)c(C)c3)c2c1]

N-(4-(benzo[d]oxazol-6-yloxy)-3-methylphenyl)-6-(2-methoxyethoxy)quinazolin-4-amine Prepared according to the procedure for Example 21 using 2-aminobenzene-1,5-diol in place of 2-aminobenzene-1,4-diol. MS APCI (+) m/z 443 (M+1) detected; $^1$H NMR (400 MHz, DMSO-d6) δ 9.60 (s, 1H), 8.69 (s, 1H), 8.50 (s, 1H), 7.96 (s, 1H), 7.74 (m, 4H), 7.52 (dd, 1H), 7.29 (d, 1H), 7.05 (m, 2H), 4.30 (m, 2H), 3.77 (m, 2H), 3.36 (s, 3H), 2.23 (s, 31-1).

Example 24

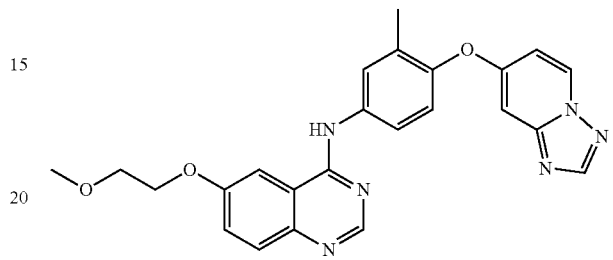

N-(4-([1,2,4]triazolo[1,5-a]pyridin-7-yloxy)-3-methylphenyl)-6-(2-methoxyethoxy)quinazolin-4-amine Prepared according to the procedure for Example 21 using 4-([1,2,4]triazolo[1,5-a]pyridin-7-yloxy)-3-methylbenzenamine in place of 4-(benzo[d]oxazol-5-yloxy)-3-methylbenzenamine. MS APCI (+) m/z 443.2.

Example 25

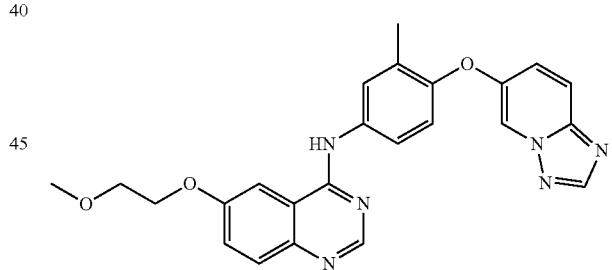

N-(4-([1,2,4]triazolo[1,5-a]pyridin-6-yloxy)-3-methylphenyl)-6-(2-methoxyethoxy)quinazolin-4-amine Step A. Preparation of 4-([1,2,4]triazolo[1,5-a]pyridin-6-yloxy)-3-methylbenzenamine: Prepared according to the procedure for Example 11 using 5-(2-methyl-4-nitrophenoxy)pyridin-2-amine in place of 4-(2-methyl-4-nitrophenoxy)pyridin-2-amine.

Step B. N-(4-([1,2,4]triazolo[1,5-a]pyridin-6-yloxy)-3-methylphenyl)-6-(2-methoxyethoxy)quinazolin-4-amine: Prepared according to the procedure for Example 21 using 4-([1,2,4]triazolo[1,5-a]pyridin-6-yloxy)-3-methylbenzenamine in place of 4-(benzo[d]oxazol-5-yloxy)-3-methylbenzenamine. MS APCI (+) m/z 443.3.

Example 26

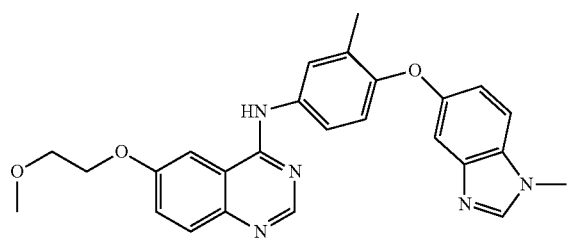 [SMILES: COCCOc1ccc2ncnc(Nc3ccc(Oc4ccc5c(c4)ncn5C)c(C)c3)c2c1]

6-(2-methoxyethoxy)-N-(3-methyl-4-(1-methyl-1H-benzo[d]imidazol-5-yloxy)phenyl)quinazolin-4-amine Prepared according to the procedure for Example 21 using 3-methyl-4-(1-methyl-1H-benzo[d]imidazol-5-yloxy)benzenamine in place of 4-(benzo[d]oxazol-5-yloxy)-3-methylbenzenamine. MS APCI (+) m/z 456 (M+1) detected; $^1$H NMR (400 MHz, CDCl$_3$) δ 8.68 (s, 1H), 7.85 (s, 1H), 7.83 (d, 1H, J=9 Hz), 7.56 (s, 1H), 7.53 (d, 1H, J=2 Hz), 7.49 (dd, 1H, J=9 Hz, 3 Hz), 7.38 (dd, 1H, J=9 Hz, 2 Hz), 7.34 (d, 1H, J=9 Hz), 7.30 (d, 1H, J=3 Hz), 7.08 (dd, 1H, J=9 Hz, 2 Hz), 6.87 (d, 1H, J=9 Hz), 4.23 (m, 2H), 3.85 (s, 3H), 3.80 (m, 2H), 3.47 (s, 3H), 2.30 (s, 3H).

Example 27

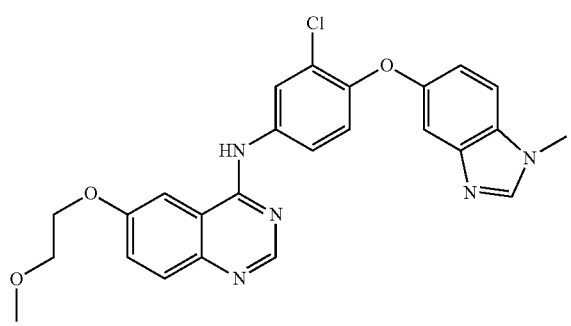 [SMILES: COCCOc1ccc2ncnc(Nc3ccc(Oc4ccc5c(c4)ncn5C)c(Cl)c3)c2c1]

N-(3-chloro-4-(1-methyl-1H-benzo[d]imidazol-5-yloxy)phenyl)-6-(2-methoxyethoxy)quinazolin-4-amine Prepared according to the procedure for Example 26 using 1-fluoro-2-chloro-4-nitrobenzene in place of 1-fluoro-2-methyl-4-nitrobenzene, with the exception that the reduction of the nitro group was accomplished with Zn/NH$_4$Cl in MeOH/THF. MS APCI (+) m/z 476.3 (M+1) detected.

Example 28

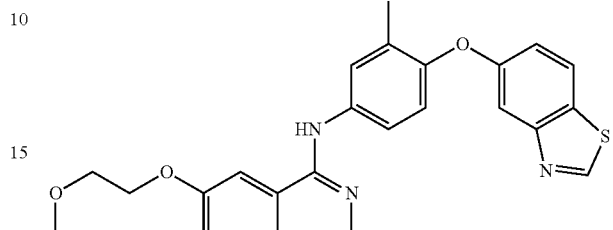

N-(4-(benzo[d]thiazol-5-yloxy)-3-methylphenyl)-6-(2-methoxyethoxy)quinazolin-4-amine hydrochloride Step A: Preparation of 4-(benzo[d]thiazol-5-yloxy)-3-methylbenzenamine: Prepared according to the procedure for Example 8 using 5-methoxybenzo[d]thiazole in place of 6-methoxybenzo[d]thiazole.

Step B: N-(4-(benzo[d]thiazol-5-yloxy)-3-methylphenyl)-6-(2-methoxyethoxy)quinazolin-4-amine: Prepared according to the procedure for Example 21 using 4-(benzo[d]thiazol-5-yloxy)-3-methylbenzenamine in place of 4-(benzo[d]oxazol-5-yloxy)-3-methylbenzenamine.

Example 29

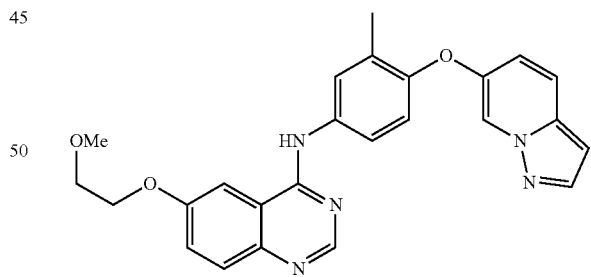

N-(4-(H-pyrazolo[1,5-a]pyridin-6-yloxy)-3-methylphenyl)-6-(2-methoxyethoxy)quinazolin-4-amine hydrochloride Prepared according to the procedure for Example 21 using pyrazolo[1,5-a]pyridin-6-ol (Miki, Y.; et al., *J. Heterocycles*, 1996, 43, 2249) in place of benzo[d]oxazol-5-ol. MS APCI (+) m/z 442.2 (M+1) detected.

Example 30

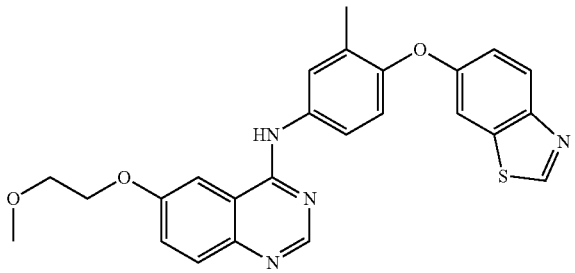 [SMILES: COCCOc1ccc2ncnc(Nc3ccc(Oc4ccc5ncsc5c4)c(C)c3)c2c1]

N-(4-(benzo[d]thiazol-6-yloxy)-3-methylphenyl)-6-(2-methoxyethoxy)quinazolin-4-amine Prepared according to the procedure for Example 21 using 4-(benzo[d]thiazol-6-yloxy)-3-methylbenzenamine in place of 4-(benzo[d]oxazol-5-yloxy)-3-methylbenzenamine.

Example 31

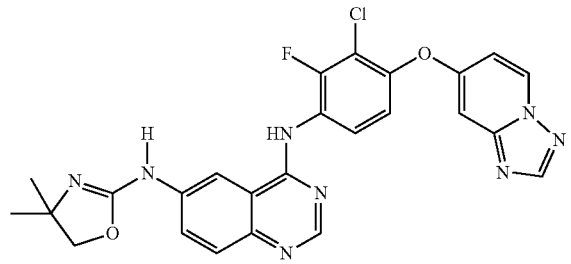 [SMILES: CC1(C)COC(Nc2ccc3ncnc(Nc4ccc(Oc5ccn6ncnc6c5)c(Cl)c4F)c3c2)=N1]

N4-(4-([1,2,4]triazolo[1,5-a]pyridin-7-yloxy)-3-chloro-2-fluorophenyl)-N6-(4,4-dimethyl-4,5-dihydrooxazol-2-yl)quinazoline-4,6-diamine Step A: Preparation of (Z)-N'-(4-(benzyloxy)pyridin-2-yl)-N,N-dimethylformamidine: A 250 mL, single-neck, round-bottomed flask was charged with 4-(benzyloxy)pyridin-2-amine (6.012 g, 30.02 mmol), dimethoxy-N,N-dimethylmethanamine (5.535 ml, 39.03 mmol) and ethanol (100.1 ml). A few drops of TFA were added and the reaction was heated to 50° C. for 4 hours. The reaction was cooled to ambient temperature and concentrated. The crude product was used in the next step without purification.

Step B: Preparation of (Z)-N'-(4-(benzyloxy)pyridin-2-yl)-N-hydroxyformamidine: A 100 mL, single-neck, round-bottomed flask was charged with (Z)-N'-(4-(benzyloxy)pyridin-2-yl)-N,N-dimethylformamidine (7.66 g, 30.0 mmol), hydroxyl amine hydrochloride (2.40 g, 34.5 mmol), propan-2-ol (33.3 ml), and THF (5 ml). The reaction was heated to 50° C. for 7 hours, then concentrated. The residue was titrated with EtOAc/THF and filtered. The filtrate was concentrated and triturated with dichloromethane to provide the product as a white solid.

Step C: Preparation of 7-(benzyloxy)-[1,2,4]triazolo[1,5-a]pyridine: Trifluoroacetic anhydride (2.62 mL, 18.9 mmol) was added dropwise to a solution of (Z)-N'-(4-(benzyloxy)pyridin-2-yl)-N-hydroxyformamidine (4.37 g, 17.9 mmol) in THF (180 mL), and the mixture was cooled to 0° C. The ice bath was then removed and the reaction was stirred for 12 hours. The reaction was concentrated to about 15-25 mL, then poured into 400 mL of iced 1 M NaOH. The mixture was stirred for 1 hour. The resulting white solids were collected by filtration, washed with hexanes, and dried under high vacuum for 1 hour to provide the desired product.

Step D: Preparation of [1,2,4]triazolo[1,5-a]pyridin-7-ol: A 250 mL, single-neck, round-bottomed flask was charged with 7-(benzyloxy)-[1,2,4]triazolo[1,5-a]pyridine (3.20 g, 14.2 mmol), Pd/C (0.756 g, 0.710 mmol), and THF (125 mL). The reaction was stirred under an atmosphere of hydrogen for 16 hours, then filtered (GF paper) and concentrated to a white solid. The solids were titrated with EtOAc and collected by filtration to provide the desired product.

Step E: Preparation of tert-butyl 3-chloro-2,4-difluorobenzoate: A 125 mL, single-neck, round-bottomed flask was charged with di-tert-butoxy-N,N-dimethylmethanamine (48.2 ml, 201 mmol), 3-chloro-2,4-difluorobenzoic acid (9.67 g, 50.2 mmol), and DMF (50 ml). The reaction was heated to 80° C. for 48 hours. After cooling to ambient temperature, the reaction was diluted with saturated NaHCO$_3$ and EtOAc. The aqueous phase was extracted with EtOAc, and the combined organic phases were washed with saturated NaHCO$_3$ and brine, dried, filtered and concentrated to provide the desired product as a gold oil.

Step F: Preparation of tert-butyl 4-([1,2,4]triazolo[1,5-a]pyridin-7-yloxy)-3-chloro-2-fluorobenzoate: A vial charged with tert-butyl 3-chloro-2,4-difluorobenzoate (0.210 g, 0.845 mmol), [1,2,4]triazolo[1,5-a]pyridin-7-ol (0.114 g, 0.845 mmol), cesium carbonate (0.413 g, 1.27 mmol), and DMF (1.7 ml). The reaction was heated to 80° C. for 12 hours, then poured into ice water. The resulting solids were collected by filtration and purified by flash chromatography, eluting with gradient of 10% EtOAc/Hexanes to 50% EtOAc/Hexanes to provide the desired product.

Step G: Preparation of 4-([1,2,4]triazolo[1,5-a]pyridin-7-yloxy)-3-chloro-2-fluorobenzoic acid: A 25 ml flask was charged with tert-butyl 4-([1,2,4]triazolo[1,5-a]pyridin-7-yloxy)-3-chloro-2-fluorobenzoate (0.060 g, 0.16 mmol) and dichloromethane (1.6 ml). The reaction was cooled to 0° C., and 2,2,2-trifluoroacetic acid (0.50 ml, 0.16 mmol) was added. The reaction was stirred for 20 minutes, then warmed to ambient temperature, stirred an additional 3 hours, and then concentrated to provide the desired product as a colorless oily residue.

Step H: Preparation of 4-([1,2,4]triazolo[1,5-a]pyridin-7-yloxy)-3-chloro-2-fluorobenzenamine: A vial was charged with 4-([1,2,4]triazolo[1,5-a]pyridin-7-yloxy)-3-chloro-2-fluorobenzoic acid (0.090 g, 0.2925 mmol), triethylamine (0.1223 ml, 0.8776 mmol) and DMF (1.5 ml). Diphenylphosphoryl azide (0.1630 ml, 0.7313 mmol) was added. The reaction was stirred at ambient temperature for 3 hours, then water (0.2199 ml, 0.2925 mmol) was added. The vial was sealed and heated to 100° C. for 1 hour, then cooled to ambient temperature and poured into 1 N NaOH/ice. The reaction was extracted with EtOAc, and the organic layer was dried, filtered and concentrated. The residue was purified by flash chromatography, eluting with a gradient from 100% EtOAc to 10% (with 6% NH$_4$OH) MeOH/EtOAc.

Step I: Preparation of N4-(4-([1,2,4]triazolo[1,5-a]pyridin-7-yloxy)-3-chloro-2-fluorophenyl)-N6-(4,4-dimethyl-4,5-dihydrooxazol-2-yl)quinazoline-4,6-diamine: Prepared according to the procedure for Example 1, using 4-([1,2,4]triazolo[1,5-a]pyridin-7-yloxy)-3-chloro-2-fluorobenzenamine in place of 3-methyl-4-(2-methylbenzo[d]oxazol-5-yloxy)benzenamine. MS APCI (+) m/z 519.3 (M+1, chlorine pattern) detected.

Example 32

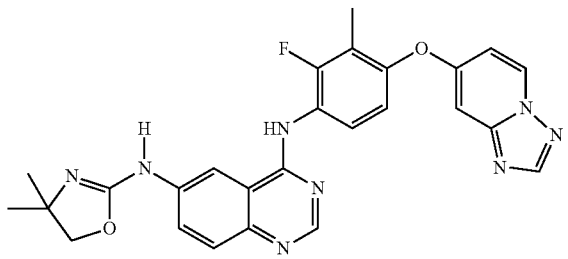 [SMILES: Cc1c(Oc2ccn3ncnc3c2)ccc(Nc2ncnc3ccc(NC4=NC(C)(C)CO4)cc23)c1F]

N4-(4-([1,2,4]triazolo[1,5-a]pyridin-7-yloxy)-2-fluoro-3-methylphenyl)-N6-(4,4-dimethyl-4,5-dihydrooxazol-2-yl)quinazoline-4,6-diamine Prepared according to the procedure of Example 31, using 2,4-difluoro-3-methylbenzoic in place of 3-chloro-2,4-difluorobenzoic acid. MS APCI (+) m/z 499.3 (M+1) detected.

Example 33

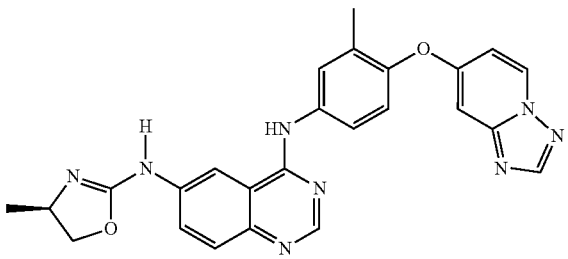 [SMILES: Cc1cc(Nc2ncnc3ccc(NC4=N[C@H](C)CO4)cc23)ccc1Oc1ccn2ncnc2c1]

(R)-N4-(4-([1,2,4]triazolo[1,5-a]pyridin-7-yloxy)-3-methylphenyl)-N6-(4-methyl-4,5-dihydrooxazol-2-yl)quinazoline-4,6-diamine Prepared according to the procedure for Example 1 using (R)-2-aminopropan-1-ol in place of 2-amino-2-methylpropan-1-ol and 4-([1,2,4]triazolo[1,5-a]pyridin-7-yloxy)-3-methylbenzenamine in place of 3-methyl-4-(2-methylbenzo[d]oxazol-5-yloxy)benzenamine. MS APCI (+) m/z 467.3 (M+1) detected.

Example 34

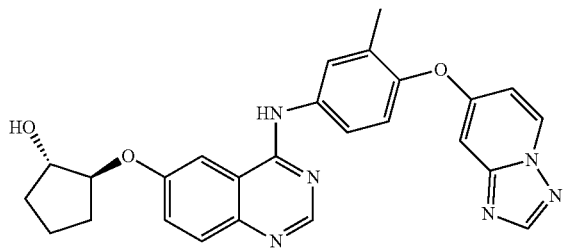 [SMILES: Cc1cc(Nc2ncnc3ccc(O[C@H]4CCC[C@@H]4O)cc23)ccc1Oc1ccn2ncnc2c1]

trans-2-(4-(4-([1,2,4]triazolo[1,5-a]pyridin-7-yloxy)-3-methylphenylamino)quinazolin-6-yloxy)cyclopentanol Step A: Preparation of 4-(4-([1,2,4]triazolo[1,5-a]pyridin-7-yloxy)-3-methylphenylamino)quinazolin-6-ol hydrochloride: Prepared according to Example 15 using 4-([1,2,4]triazolo[1,5-a]pyridin-7-yloxy)-3-methylbenzenamine in place of 4-(imidazo[1,2-a]pyridin-7-yloxy)-3-methylaniline.

Step B: Preparation of trans-2-(4-(4-([1,2,4]triazolo[1,5-a]pyridin-7-yloxy)-3-methylphenylamino)quinazolin-6-yloxy)cyclopentanol: A 50 mL flask was charged with 4-(4-([1,2,4]triazolo[1,5-a]pyridin-7-yloxy)-3-methylphenylamino)quinazolin-6-ol hydrochloride (3.117 g, 7.406 mmol), 6-oxa-bicyclo[3.1.0]hexane (0.6924 ml, 7.777 mmol), cesium hydroxide monohydrate (2.736 g, 16.29 mmol), DMF (20 mL). The reaction was heated to 92° C. for 12 hours, then cooled to room temperature and dilute with 200 mL of water. The mixture was stirred for 24 hours. The resulting precipitate was collected by filtration, washed with water and air dried to provide 2.80 g of the title compound as a racemic mixture. MS APCI (+) m/z 469.3 (M+1) detected.

Example 35

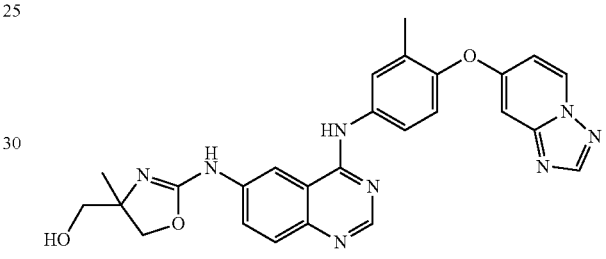

(2-(4-(4-([1,2,4]triazolo[1,5-a]pyridin-7-yloxy)-3-methylphenylamino)quinazolin-6-ylamino)-4-methyl-4,5-dihydrooxazol-4-yl)methanol Step A: Preparation of (E)-N'-(4-(3-(1-(tert-butyldiphenylsilyloxy)-3-hydroxy-2-methylpropan-2-yl)thioureido)-2-cyanophenyl)-N,N-dimethylformimidamide: Prepared according to the method of Example 1, using 2-amino-3-(tert-butyldiphenylsilyloxy)-2-methylpropan-1-ol in place of 2-amino-2-methylpropan-1-ol.

Step B: Preparation of N4-(4-([1,2,4]triazolo[1,5-a]pyridin-7-yloxy)-3-methylphenyl)-N6-(4-((tert-butyldiphenylsilyloxy)methyl)-4-methyl-4,5-dihydrooxazol-2-yl)quinazoline-4,6-diamine: Prepared according to the method of Example 1, using (E)-N'-(4-(3-(1-(tert-butyldiphenylsilyloxy)-3-hydroxy-2-methylpropan-2-yl)thioureido)-2-cyanophenyl)-N,N-dimethylformimidamide in place of 1-(3-cyano-4-((dimethylamino)methyleneamino)phenyl)-3-(1-hydroxy-2-methylpropan-2-yl)thiourea and 4-([1,2,4]triazolo[1,5-a]pyridin-7-yloxy)-3-methylbenzenamine in place of 4-(imidazo[1,2-a]pyridin-7-yloxy)-3-methylaniline.

Step C: Preparation of (2-(4-(4-([1,2,4]triazolo[1,5-a]pyridin-7-yloxy)-3-methylphenylamino)quinazolin-6-ylamino)-4-methyl-4,5-dihydrooxazol-4-yl)methanol: TBAF (7.799 mmol, 7.79 mL, 1M in THF) was added to a solution of N4-(4-([1,2,4]triazolo[1,5-a]pyridin-7-yloxy)-3-methylphenyl)-N6-(4-((tert-butyldiphenylsilyloxy)methyl)-4-methyl-4,5-dihydrooxazol-2-yl)quinazoline-4,6-diamine (2.866 g, 3.900 mmol) in THF (60 mL). The residue was stirred for 3 hours and then concentrated. The residue was purified by flash chromatography, eluting with EtOAc/Hex/

MeOH 9:1:1 with 0.1% H₂O to provide the title compound. MS APCI (+) m/z 497.4 (M+1) detected.

Example 36

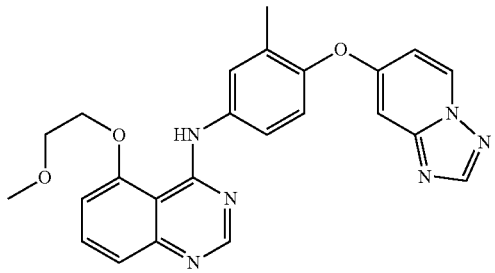 [SMILES: COCCOc1cccc2ncnc(Nc3ccc(Oc4ccn5ncnc5c4)c(C)c3)c12]

N-(4-([1,2,4]triazolo[1,5-a]pyridin-7-yloxy)-3-methylphenyl)-5-(2-methoxyethoxy)quinazolin-4-amine Step A: Preparation of 5-(2-methoxyethoxy)quinazolin-4-ol: To a solution of 2-methoxyethanol (0.528 ml, 6.70 mmol) in DMA (6 mL) was slowly added 514 mg of a 60% dispersion of NaH (0.308 g, 12.8 mmol), and the reaction mixture was stirred at room temperature for 30 minutes. 5-Fluoroquinazolin-4(3H)-one (1.0 g, 6.09 mmol) was added and the reaction mixture was heated at 80° C. for 2 hours. The reaction was concentrated and the residue was suspended in EtOH (75 mL) and then filtered through GF/F paper. The filtrate was concentrated to afford the desired product as a yellow solid.

Step B: Preparation of 4-chloro-5-(2-methoxyethoxy)quinazoline: Prepared according to the method of Example 15 using 5-(2-methoxyethoxy)quinazolin-4-ol in place of 4-hydroxyquinazolin-6-yl acetate.

Step C: Preparation of N-(4-([1,2,4]triazolo[1,5-a]pyridin-7-yloxy)-3-methylphenyl)-5-(2-methoxyethoxy)quinazolin-4-amine: Prepared according to the method of Example 24 using 4-chloro-5-(2-methoxyethoxy)quinazoline in place of 4-chloro-6-(2-methoxyethoxy)quinazoline. MS APCI (+) m/z 443.1 (M+1) detected.

The following compounds were also prepared according to the above-described methods.

| Ex. # | Structure | MS m/z |
|---|---|---|
| 37 | 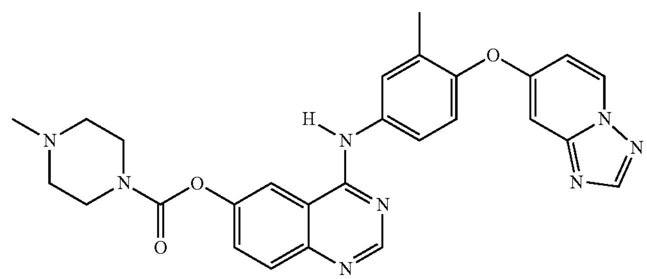 [SMILES: Cc1cc(Nc2ncnc3ccc(OC(=O)N4CCN(C)CC4)cc23)ccc1Oc1ccn2ncnc2c1] | 511.5 (M + 1) detected |
| 38 | 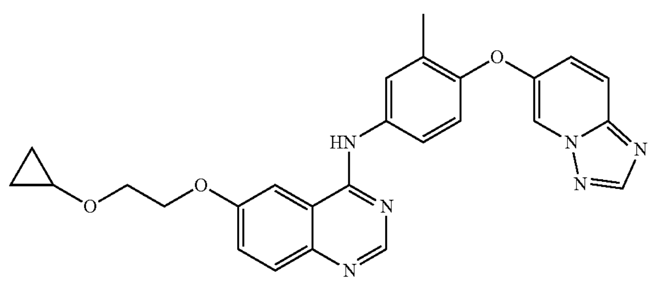 | 443.3 (M + 1) detected |
| 39 | 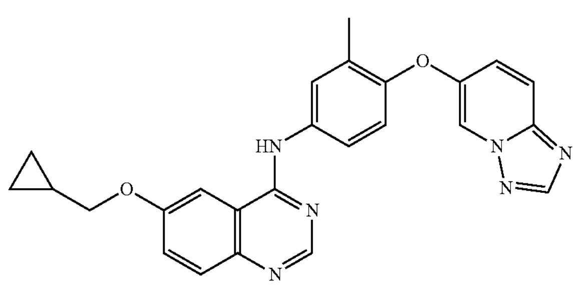 | 443.3 (M + 1) detected |

-continued

| Ex. # | Structure | MS m/z |
|---|---|---|
| 40 | 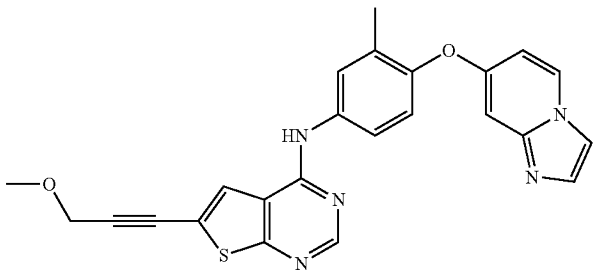 [SMILES: COCC#Cc1cc2c(Nc3ccc(Oc4ccn5ccnc5c4)c(C)c3)ncnc2s1] | 442.1 (M + 1) detected |
| 41 | 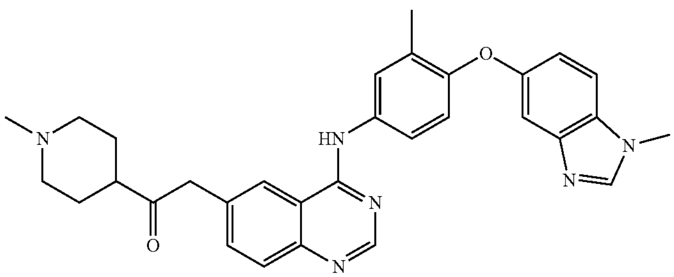 | 522.3 (M + 1) detected |
| 42 | 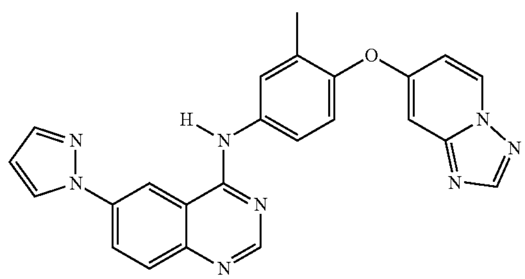 [SMILES: Cc1cc(Nc2ncnc3ccc(-n4cccn4)cc23)ccc1Oc1ccn2ncnc2c1] | 435.4 (M + 1) detected |
| 43 | 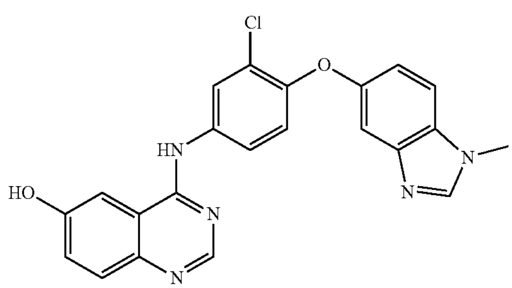 [SMILES: Cn1cnc2cc(Oc3ccc(Nc4ncnc5ccc(O)cc45)cc3Cl)ccc21] | 418.4 (M + 1) detected |
| 44 | 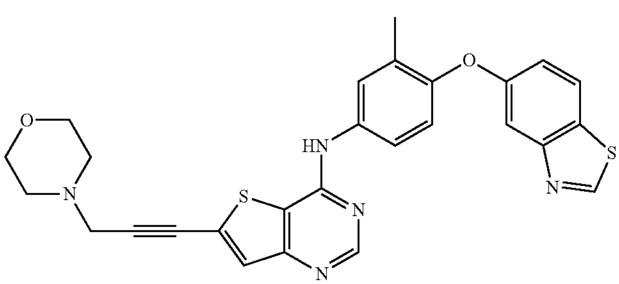 [SMILES: Cc1cc(Nc2ncnc3cc(C#CCN4CCOCC4)sc23)ccc1Oc1ccc2scnc2c1] | 514.1 (M + 1) detected |

-continued

| Ex. # | Structure | MS m/z |
|---|---|---|
| 45 | 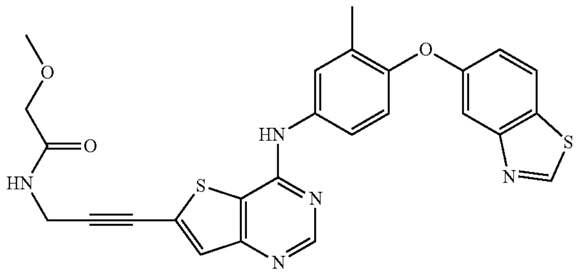 [SMILES: COCC(=O)NCC#Cc1cc2ncnc(Nc3ccc(Oc4ccc5scnc5c4)c(C)c3)c2s1] | 516.1 (M + 1) detected |
| 46 | 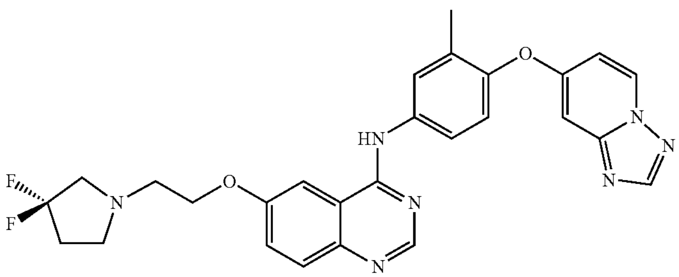 | 518.3 (M + 1) detected |
| 47 | 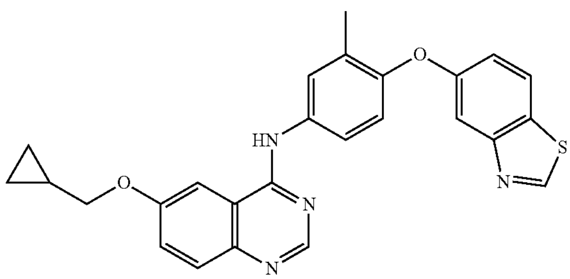 [SMILES: Cc1cc(Nc2ncnc3ccc(OCC4CC4)cc23)ccc1Oc1ccc2scnc2c1] | 455.2 (M + 1) detected |
| 48 | 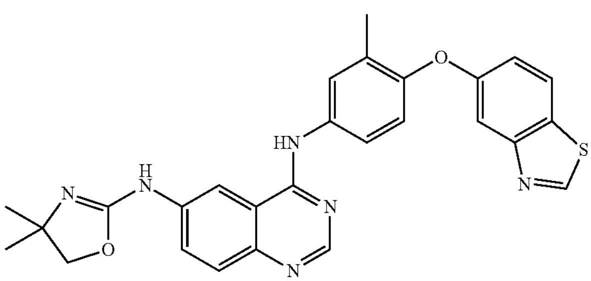 [SMILES: Cc1cc(Nc2ncnc3ccc(NC4=NC(C)(C)CO4)cc23)ccc1Oc1ccc2scnc2c1] | 498.0 (M + 1) detected |
| 49 | 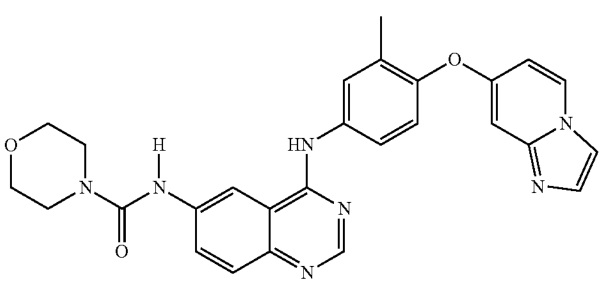 [SMILES: Cc1cc(Nc2ncnc3ccc(NC(=O)N4CCOCC4)cc23)ccc1Oc1ccn2ccnc2c1] | 496 (M + 1) detected |

-continued

| Ex. # | Structure | MS m/z |
|---|---|---|
| 50 | 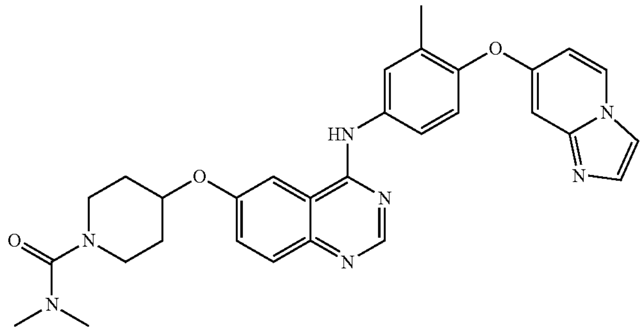 | 538.3 (M + 1) detected |
| 51 | 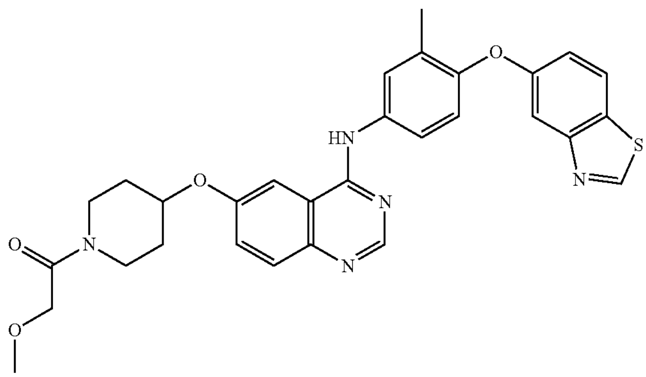 [SMILES: COCC(=O)N1CCC(Oc2ccc3ncnc(Nc4ccc(Oc5ccc6scnc6c5)c(C)c4)c3c2)CC1] | 556.2 (M + 1) detected |
| 52 | 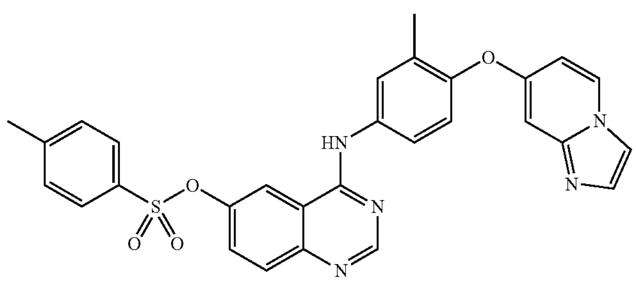 [SMILES: Cc1ccc(S(=O)(=O)Oc2ccc3ncnc(Nc4ccc(Oc5ccn6ccnc6c5)c(C)c4)c3c2)cc1] | 539.2 (M + 1) detected |
| 53 | 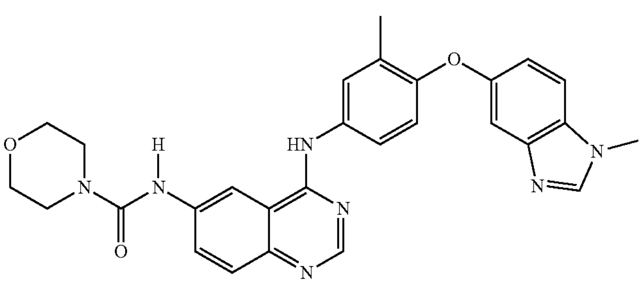 [SMILES: Cc1cc(Nc2ncnc3ccc(NC(=O)N4CCOCC4)cc23)ccc1Oc1ccc2c(c1)ncn2C] | 510.0 (M + 1) detected |
| 54 | 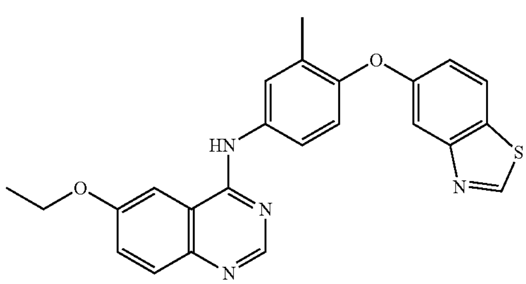 [SMILES: CCOc1ccc2ncnc(Nc3ccc(Oc4ccc5scnc5c4)c(C)c3)c2c1] | 429.3 (M + 1) detected |

| Ex. # | Structure | MS m/z |
|---|---|---|
| 55 | 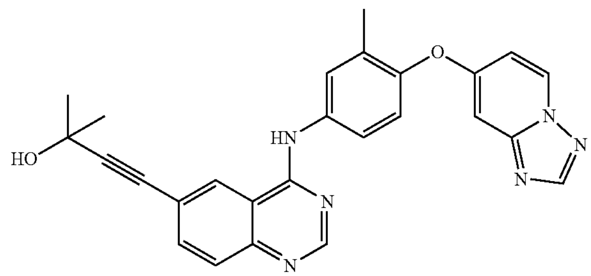 [SMILES: Cc1cc(Nc2ncnc3ccc(C#CC(C)(C)O)cc23)ccc1Oc1ccn2ncnc2c1] | 451.0 (M + 1) detected |
| 56 | 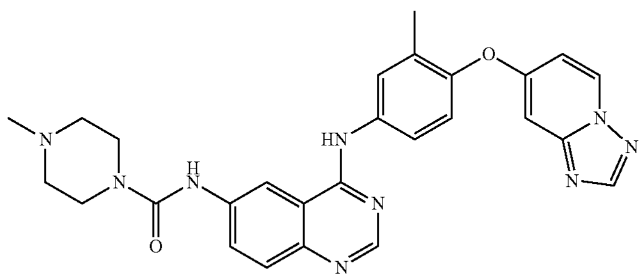 [SMILES: Cc1cc(Nc2ncnc3ccc(NC(=O)N4CCN(C)CC4)cc23)ccc1Oc1ccn2ncnc2c1] | 510.1 (M + 1) detected |
| 57 | 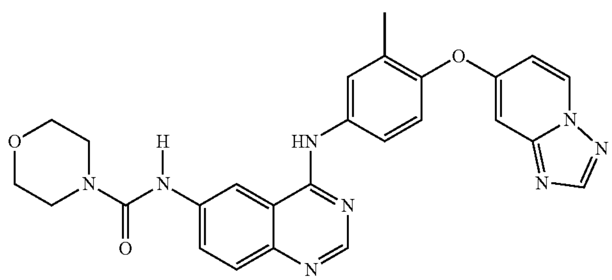 [SMILES: Cc1cc(Nc2ncnc3ccc(NC(=O)N4CCOCC4)cc23)ccc1Oc1ccn2ncnc2c1] | 497.0 (M + 1) detected |
| 58 | 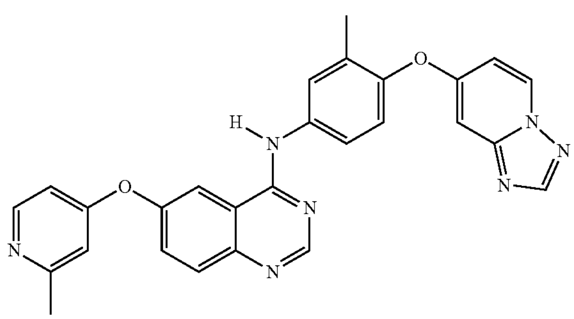 [SMILES: Cc1cc(Oc2ccc3ncnc(Nc4ccc(Oc5ccn6ncnc6c5)c(C)c4)c3c2)ccn1] | 476.1 (M + 1) detected |
| 59 | 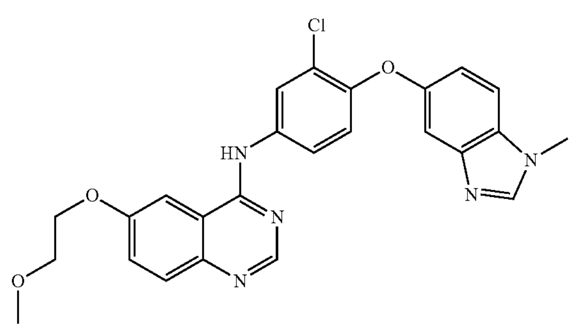 [SMILES: COCCOc1ccc2ncnc(Nc3ccc(Oc4ccc5c(c4)ncn5C)c(Cl)c3)c2c1] | 476.3 (M + 1) detected |

| Ex. # | Structure | MS m/z |
|---|---|---|
| 60 | 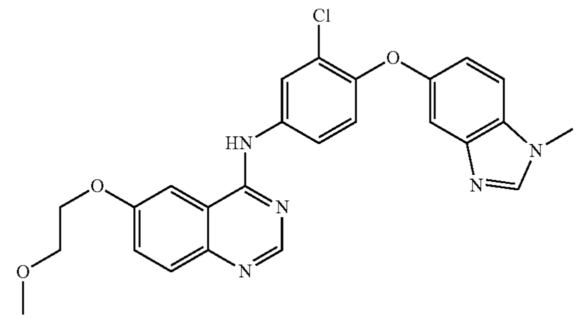 | 443.3 (M + 1) detected |
| 61 | 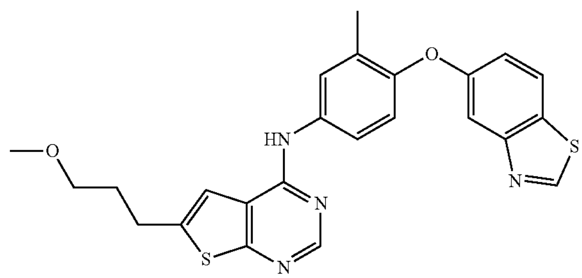 [SMILES: COCCCc1cc2c(Nc3ccc(Oc4ccc5scnc5c4)c(C)c3)ncnc2s1] | 463.3 (M + 1) detected |
| 62 | 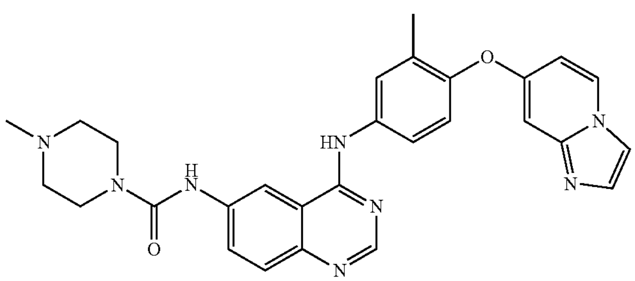 | 509.0 (M + 1) detected |
| 63 | 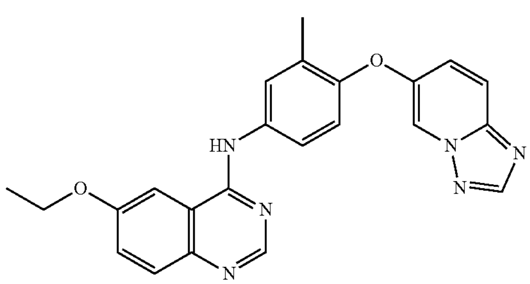 [SMILES: CCOc1ccc2ncnc(Nc3ccc(Oc4ccc5ncnn5c4)c(C)c3)c2c1] | 413.3 (M + 1) detected |
| 64 | 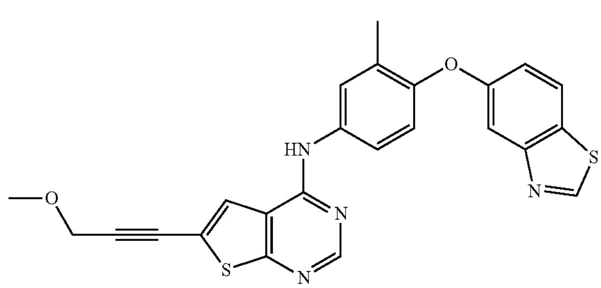 [SMILES: COCC#Cc1cc2c(Nc3ccc(Oc4ccc5scnc5c4)c(C)c3)ncnc2s1] | 459.1 (M + 1) detected |

-continued

| Ex. # | Structure | MS m/z |
|---|---|---|
| 65 | 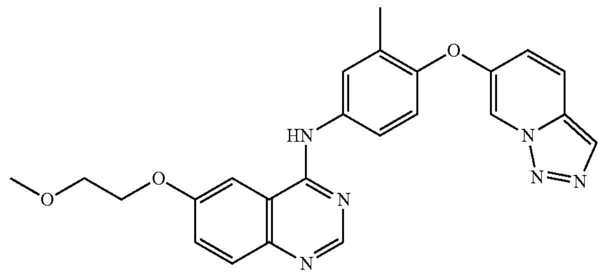 [SMILES: COCCOc1ccc2ncnc(Nc3ccc(Oc4ccc5cnnn5c4)c(C)c3)c2c1] | 443.0 (M + 1) detected |
| 66 | 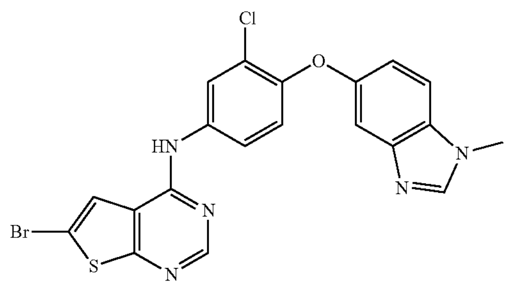 [SMILES: Cn1cnc2cc(Oc3ccc(Nc4ncnc5sc(Br)cc45)cc3Cl)ccc21] | 488.2 (M + 1) detected |
| 67 | 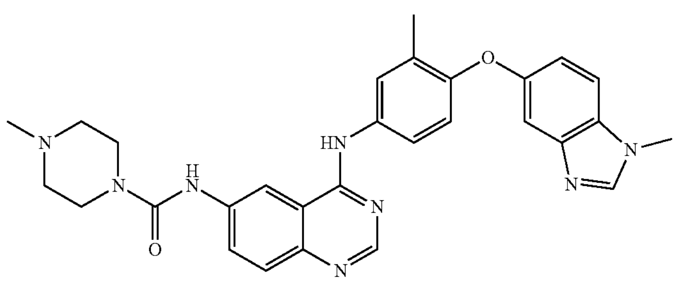 | 523.0 (M + 1) detected |
| 68 | 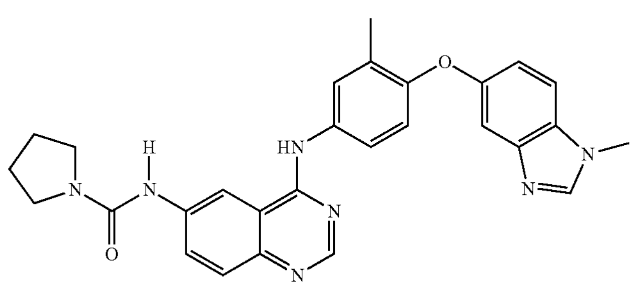 [SMILES: Cc1cc(Nc2ncnc3ccc(NC(=O)N4CCCC4)cc23)ccc1Oc1ccc2c(c1)ncn2C] | 494.1 (M + 1) detected |
| 69 | 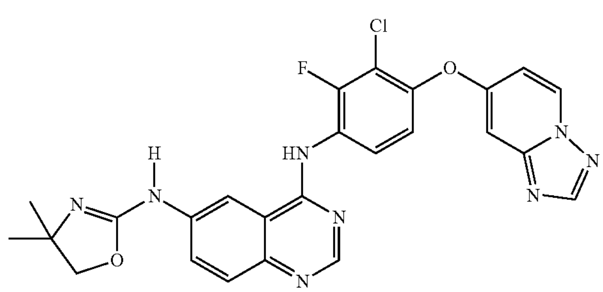 [SMILES: CC1(C)COC(Nc2ccc3ncnc(Nc4ccc(Oc5ccn6ncnc6c5)c(Cl)c4F)c3c2)=N1] | 519.3 (M + 1) detected |

-continued

| Ex. # | Structure | MS m/z |
|---|---|---|
| 70 | 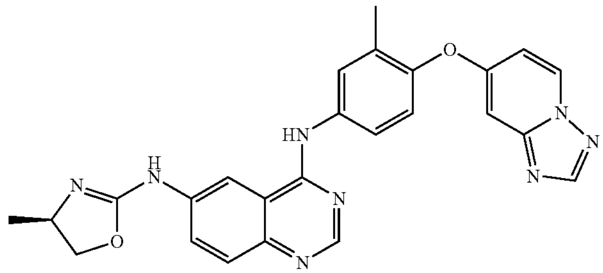 [SMILES: Cc1cc(Nc2ncnc3ccc(NC4=N[C@H](C)CO4)cc23)ccc1Oc1ccn2ncnc2c1] | 467.3 (M + 1) detected |
| 71 | 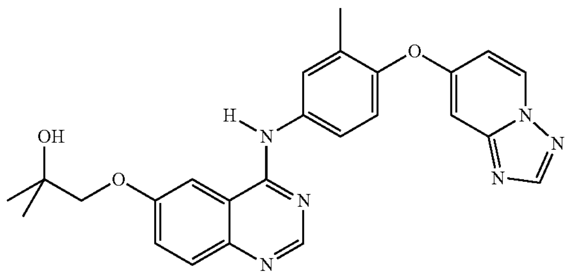 [SMILES: Cc1cc(Nc2ncnc3ccc(OCC(C)(C)O)cc23)ccc1Oc1ccn2ncnc2c1] | 457.3 (M + 1) detected |
| 72 | 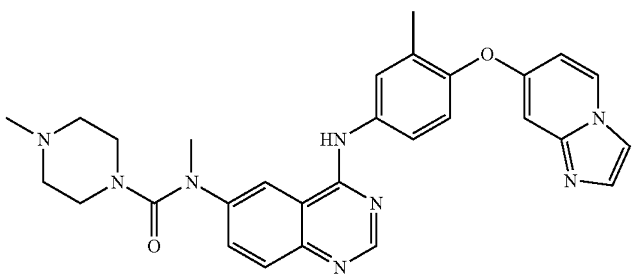 [SMILES: Cc1cc(Nc2ncnc3ccc(N(C)C(=O)N4CCN(C)CC4)cc23)ccc1Oc1ccn2ccnc2c1] | 523.3 (M + 1) detected |
| 73 | 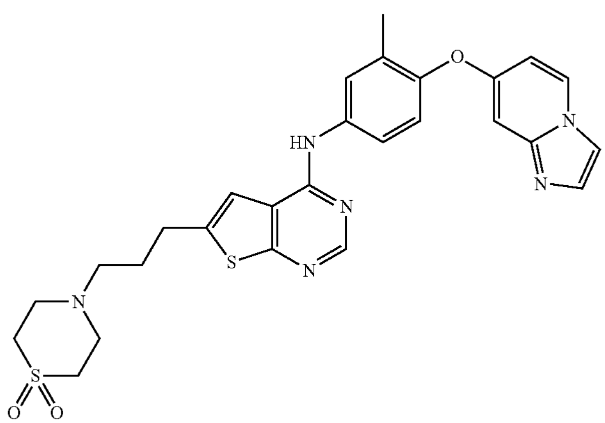 | 463.2 (M + 1) detected |
| 74 | 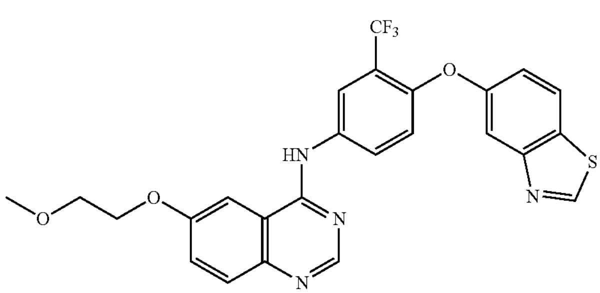 [SMILES: COCCOc1ccc2ncnc(Nc3ccc(Oc4ccc5scnc5c4)c(C(F)(F)F)c3)c2c1] | 513.2 (M + 1) detected |

-continued

| Ex. # | Structure | MS m/z |
| --- | --- | --- |
| 75 | 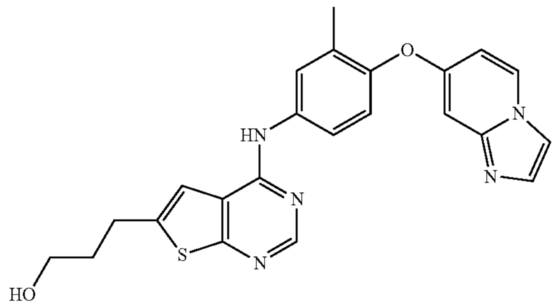 [SMILES: Cc1cc(Nc2ncnc3sc(CCCO)cc23)ccc1Oc1ccn2ccnc2c1] | 432.4 (M + 1) detected |
| 76 | 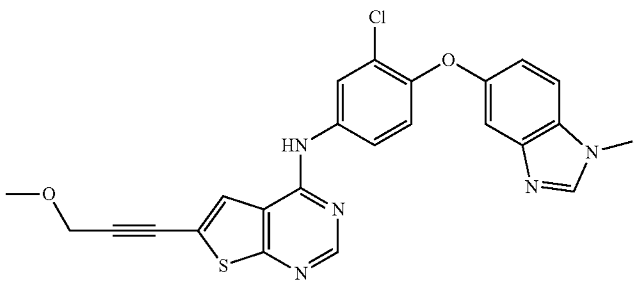 | 476.0 (M + 1) detected |
| 77 | 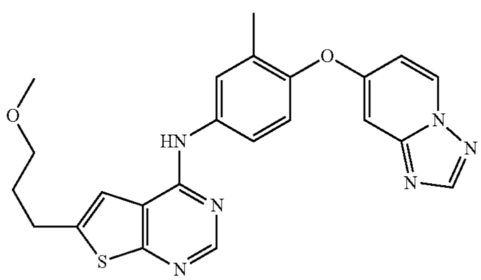 [SMILES: COCCCc1cc2c(Nc3ccc(Oc4ccn5ncnc5c4)c(C)c3)ncnc2s1] | 447.3 (M + 1) detected |
| 78 | 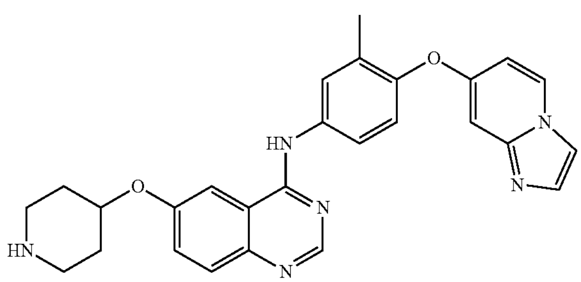 [SMILES: Cc1cc(Nc2ncnc3ccc(OC4CCNCC4)cc23)ccc1Oc1ccn2ccnc2c1] | 467.3 (M + 1) detected |
| 79 | 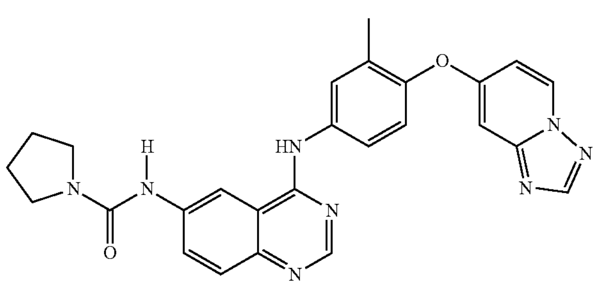 [SMILES: Cc1cc(Nc2ncnc3ccc(NC(=O)N4CCCC4)cc23)ccc1Oc1ccn2ncnc2c1] | 481.1 (M + 1) detected |

-continued

| Ex. # | Structure | MS m/z |
|---|---|---|
| 80 | 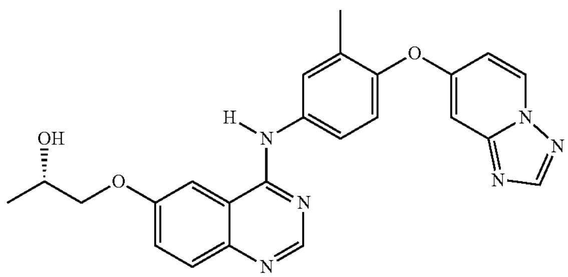 [SMILES: Cc1cc(Nc2ncnc3ccc(OC[C@H](C)O)cc23)ccc1Oc1ccn2ncnc2c1] | 443.3 (M + 1) detected |
| 81 | 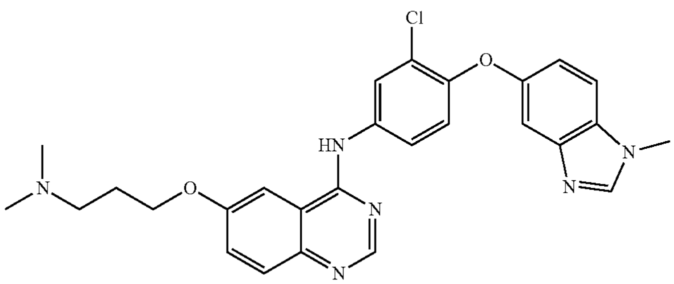 | 503.2 (M + 1) detected |
| 82 | 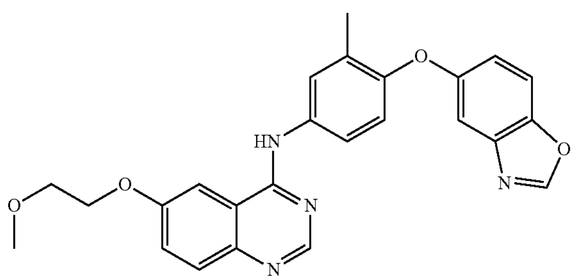 [SMILES: COCCOc1ccc2ncnc(Nc3ccc(Oc4ccc5ocnc5c4)c(C)c3)c2c1] | 443.3 (M + 1) detected |
| 83 | 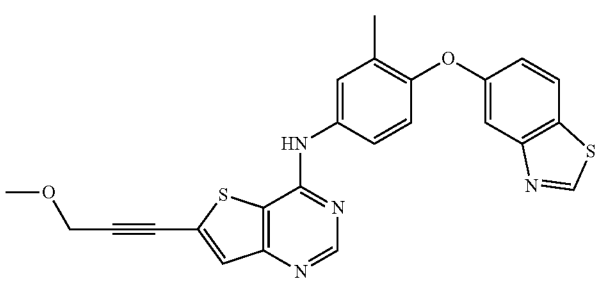 [SMILES: COCC#Cc1cc2ncnc(Nc3ccc(Oc4ccc5scnc5c4)c(C)c3)c2s1] | 459.2 (M + 1) detected |
| 84 | 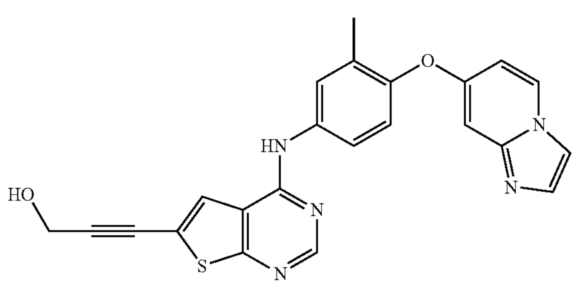 [SMILES: Cc1cc(Nc2ncnc3sc(C#CCO)cc23)ccc1Oc1ccn2ccnc2c1] | 428.1 (M + 1) detected |

-continued

| Ex. # | Structure | MS m/z |
|---|---|---|
| 85 | 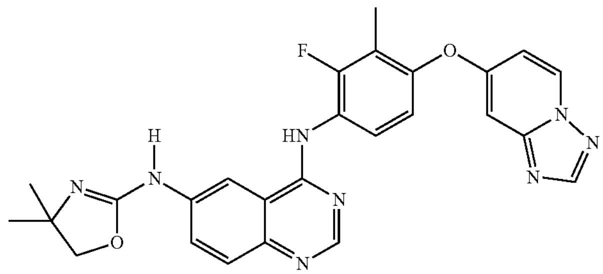 [SMILES: Cc1c(Oc2ccn3ncnc3c2)ccc(Nc2ncnc3ccc(NC4=NC(C)(C)CO4)cc23)c1F] | 499.3 (M + 1) detected |
| 86 | 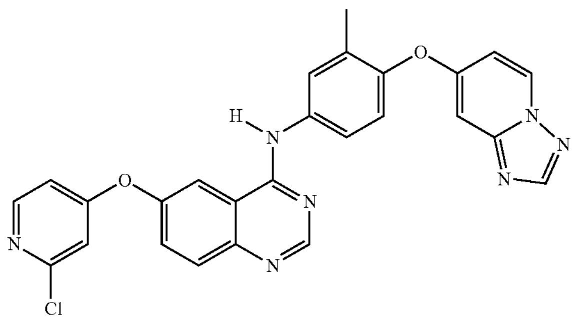 [SMILES: Cc1cc(Nc2ncnc3ccc(Oc4ccnc(Cl)c4)cc23)ccc1Oc1ccn2ncnc2c1] | 496.3 (M + 1) detected |
| 87 | 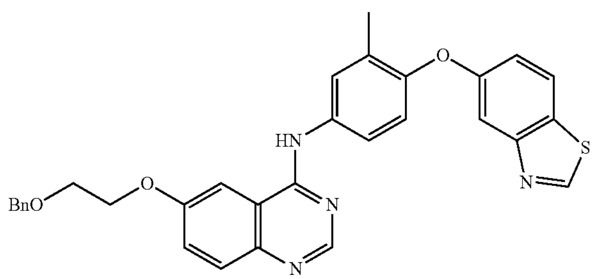 [SMILES: Cc1cc(Nc2ncnc3ccc(OCCOCc4ccccc4)cc23)ccc1Oc1ccc2scnc2c1] | 535.3 (M + 1) detected |
| 88 | 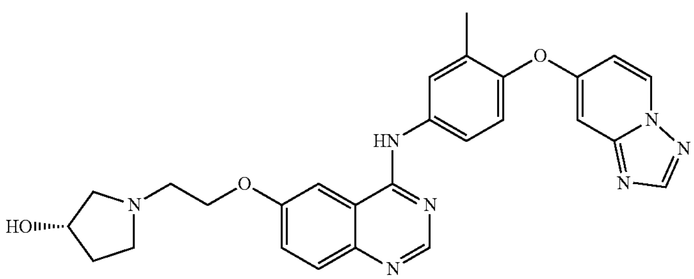 [SMILES: Cc1cc(Nc2ncnc3ccc(OCCN4CC[C@H](O)C4)cc23)ccc1Oc1ccn2ncnc2c1] | 498.3 (M + 1) detected |
| 89 | 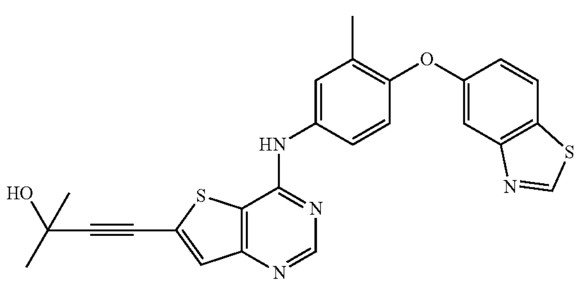 [SMILES: Cc1cc(Nc2ncnc3cc(C#CC(C)(C)O)sc23)ccc1Oc1ccc2scnc2c1] | 474.3 (M + 1) detected |

-continued

| Ex. # | Structure | MS m/z |
|---|---|---|
| 90 | 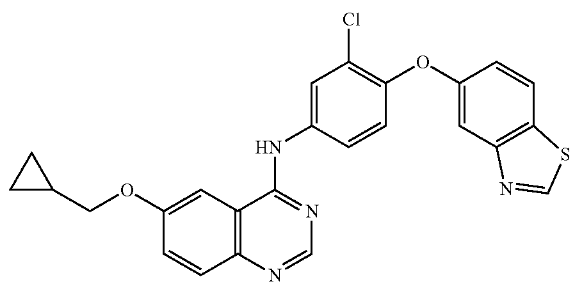 [SMILES: Clc1cc(Nc2ncnc3ccc(OCC4CC4)cc23)ccc1Oc1ccc2scnc2c1] | 475.2 (M + 1) detected |
| 91 | 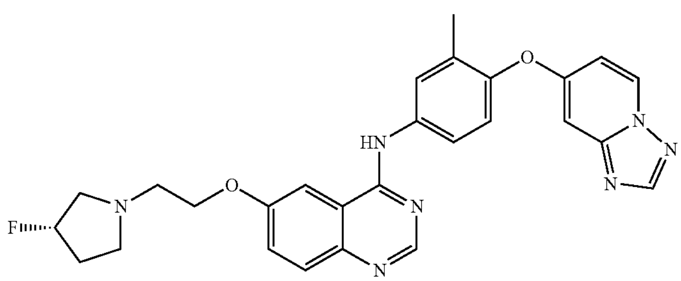 [SMILES: Cc1cc(Nc2ncnc3ccc(OCCN4CC[C@H](F)C4)cc23)ccc1Oc1ccn2ncnc2c1] | 500.2 (M + 1) detected |
| 92 | 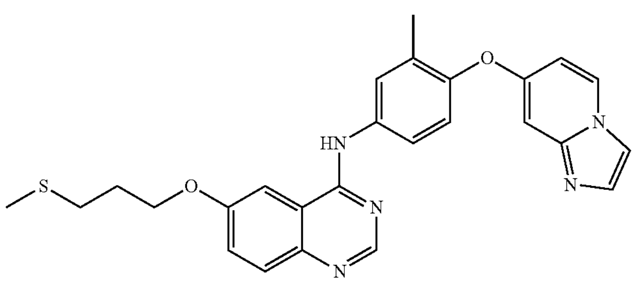 [SMILES: CSCCCOc1ccc2ncnc(Nc3ccc(Oc4ccn5ccnc5c4)c(C)c3)c2c1] | 472.4 (M + 1) detected |
| 93 | 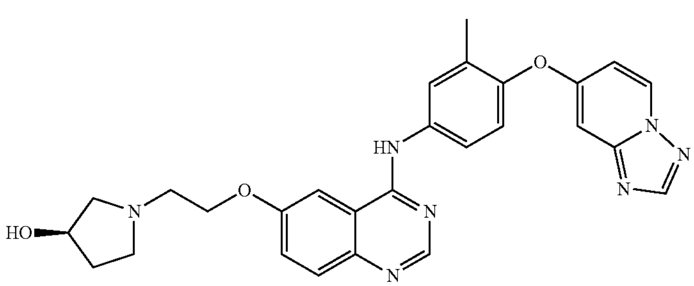 [SMILES: Cc1cc(Nc2ncnc3ccc(OCCN4CC[C@@H](O)C4)cc23)ccc1Oc1ccn2ncnc2c1] | 498.2 (M + 1) detected |
| 94 | 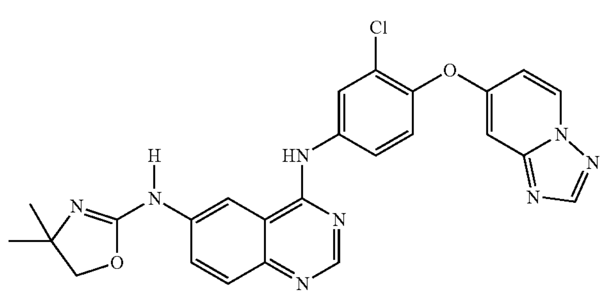 [SMILES: CC1(C)COC(Nc2ccc3ncnc(Nc4ccc(Oc5ccn6ncnc6c5)c(Cl)c4)c3c2)=N1] | 501.3 (M + 1) detected |

-continued
| Ex. # | Structure | MS m/z |
|---|---|---|
| 95 | 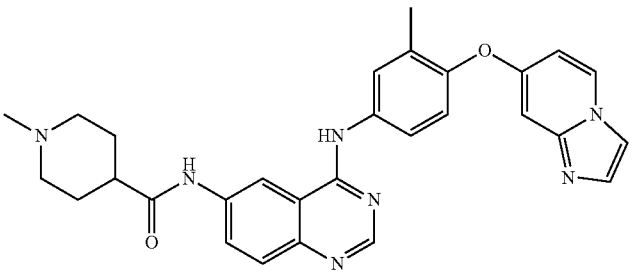 | 508.3 (M + 1) detected |
| 96 | 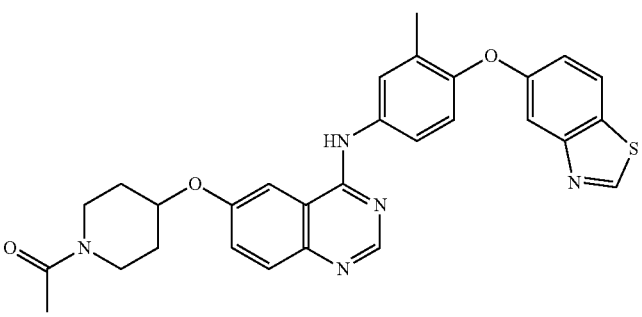 [SMILES: CC(=O)N1CCC(Oc2ccc3ncnc(Nc4ccc(Oc5ccc6scnc6c5)c(C)c4)c3c2)CC1] | 526.2 (M + 1) detected |
| 97 | 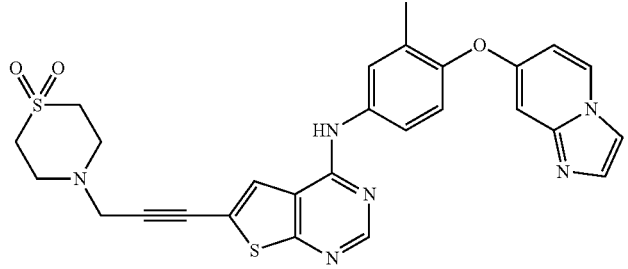 [SMILES: Cc1cc(Nc2ncnc3sc(C#CCN4CCS(=O)(=O)CC4)cc23)ccc1Oc1ccn2ccnc2c1] | 545.1 (M + 1) detected |
| 98 | 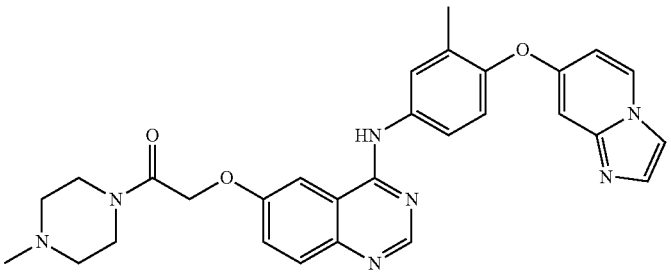 [SMILES: Cc1cc(Nc2ncnc3ccc(OCC(=O)N4CCN(C)CC4)cc23)ccc1Oc1ccn2ccnc2c1] | 524.4 (M + 1) detected |
| 99 | 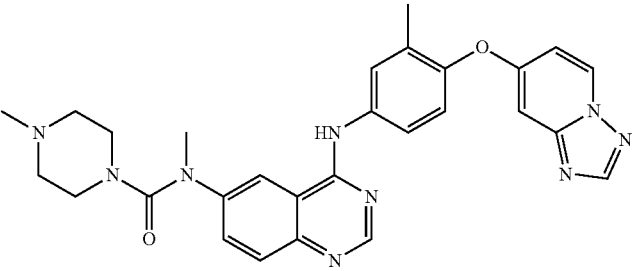 [SMILES: Cc1cc(Nc2ncnc3ccc(N(C)C(=O)N4CCN(C)CC4)cc23)ccc1Oc1ccn2ncnc2c1] | 524.2 (M + 1) detected |

-continued

| Ex. # | Structure | MS m/z |
|---|---|---|
| 100 | 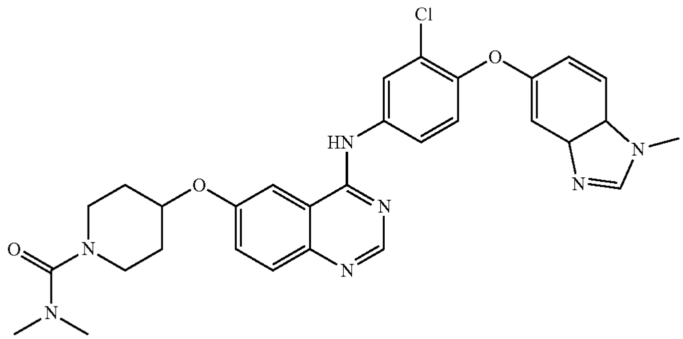 [SMILES: CN(C)C(=O)N1CCC(Oc2ccc3ncnc(Nc4ccc(OC5=CC6N=CN(C)C6C=C5)c(Cl)c4)c3c2)CC1] | 572.2 (M + 1) detected |
| 101 | 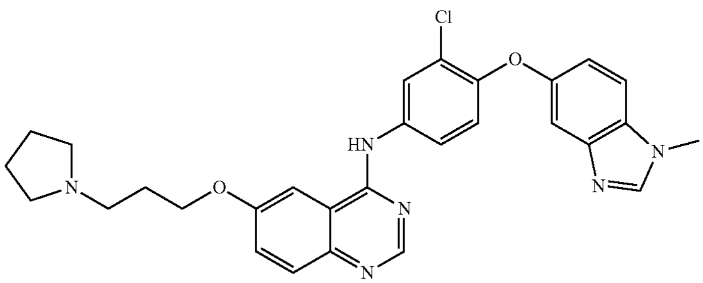 [SMILES: Cn1cnc2cc(Oc3ccc(Nc4ncnc5ccc(OCCCN6CCCC6)cc45)cc3Cl)ccc21] | 529.3 (M + 1) detected |
| 102 | 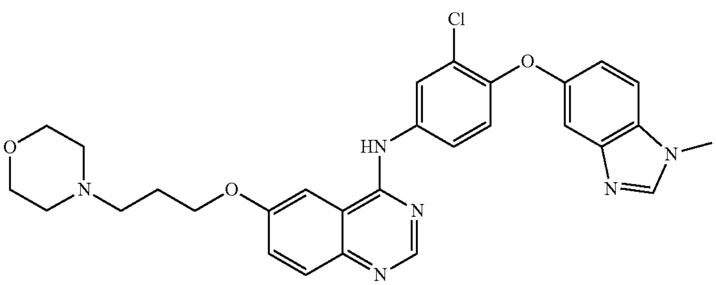 [SMILES: Cn1cnc2cc(Oc3ccc(Nc4ncnc5ccc(OCCCN6CCOCC6)cc45)cc3Cl)ccc21] | 545.3 (M + 1) detected |
| 103 | 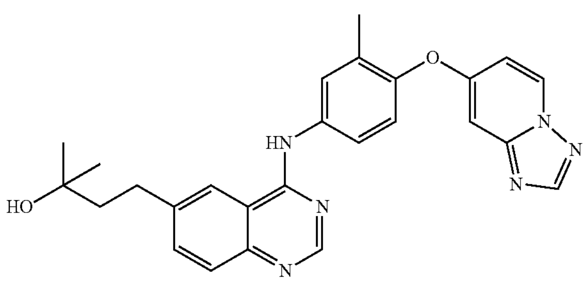 [SMILES: Cc1cc(Nc2ncnc3ccc(CCC(C)(C)O)cc23)ccc1Oc1ccn2ncnc2c1] | 455.2 (M + 1) detected |
| 104 | 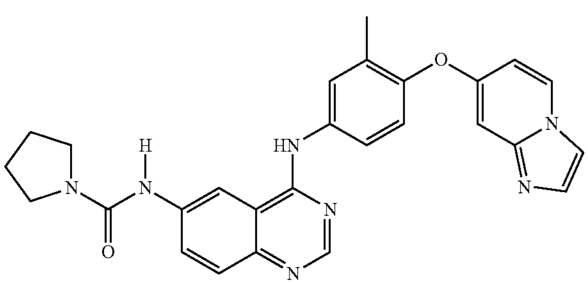 [SMILES: Cc1cc(Nc2ncnc3ccc(NC(=O)N4CCCC4)cc23)ccc1Oc1ccn2ccnc2c1] | 480.1 (M + 1) detected |

-continued

| Ex. # | Structure | MS m/z |
|---|---|---|
| 105 | 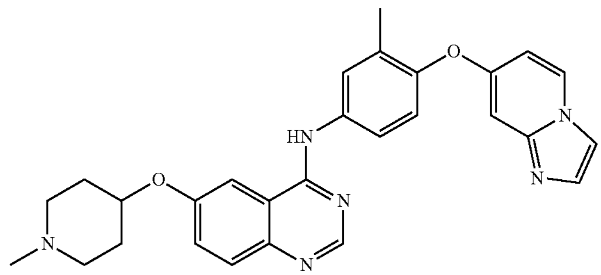 [SMILES: Cc1cc(Nc2ncnc3ccc(OC4CCN(C)CC4)cc23)ccc1Oc1ccn2ccnc2c1] | 481.3 (M + 1) detected |
| 106 | 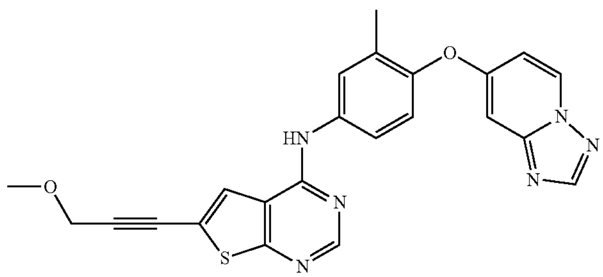 [SMILES: COCC#Cc1cc2c(Nc3ccc(Oc4ccn5ncnc5c4)c(C)c3)ncnc2s1] | 443.0 (M + 1) detected |
| 107 | 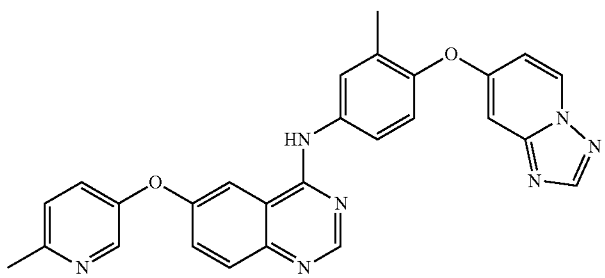 [SMILES: Cc1ccc(Oc2ccc3ncnc(Nc4ccc(Oc5ccn6ncnc6c5)c(C)c4)c3c2)cn1] | 476.4 (M + 1) detected |
| 108 | 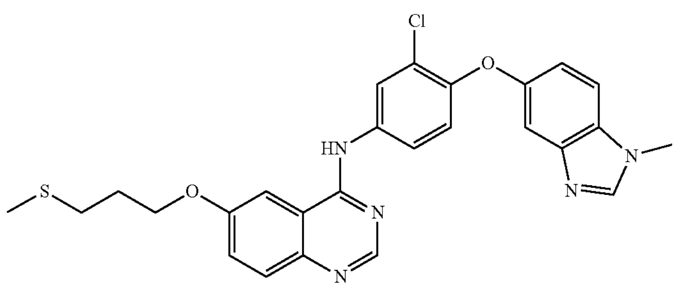 | 506.3 (M + 1) detected |
| 109 | 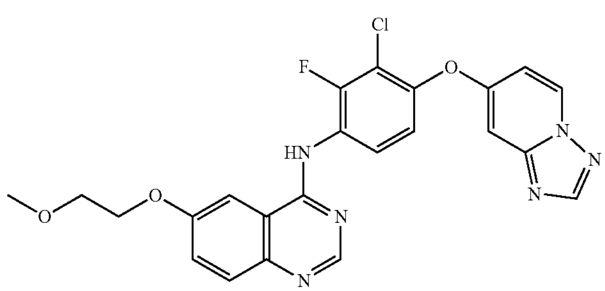 [SMILES: COCCOc1ccc2ncnc(Nc3ccc(Oc4ccn5ncnc5c4)c(Cl)c3F)c2c1] | 481.3 (M + 1) detected |

-continued

| Ex. # | Structure | MS m/z |
|---|---|---|
| 110 | 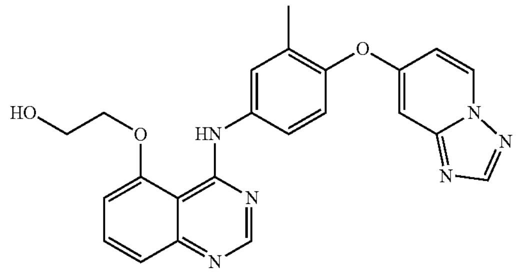 [SMILES: Cc1cc(Nc2ncnc3cccc(OCCO)c23)ccc1Oc1ccn2ncnc2c1] | 429.3 (M + 1) detected |
| 111 | 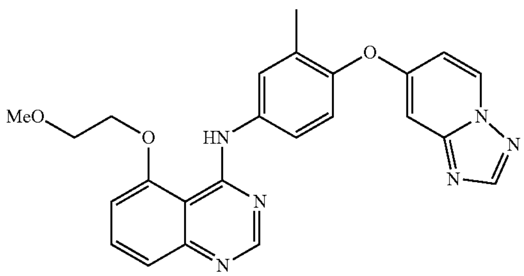 [SMILES: COCCOc1cccc2ncnc(Nc3ccc(Oc4ccn5ncnc5c4)c(C)c3)c12] | 443.1 (M + 1) detected |
| 112 | 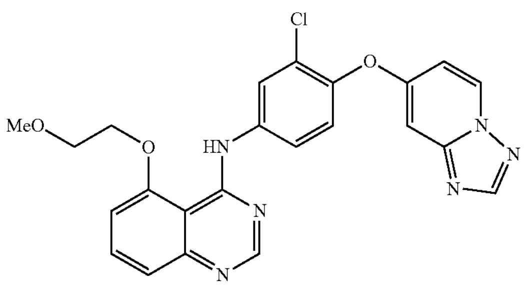 [SMILES: COCCOc1cccc2ncnc(Nc3ccc(Oc4ccn5ncnc5c4)c(Cl)c3)c12] | 463.1 (M + 1) detected |
| 113 | 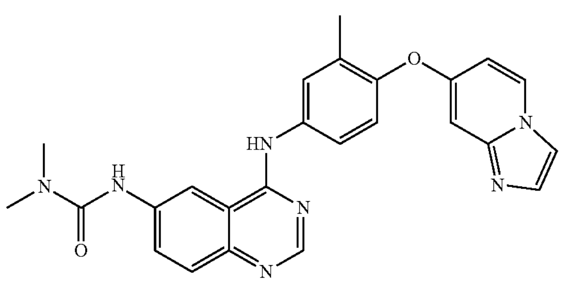 | 454.1 (M + 1) detected |
| 114 | 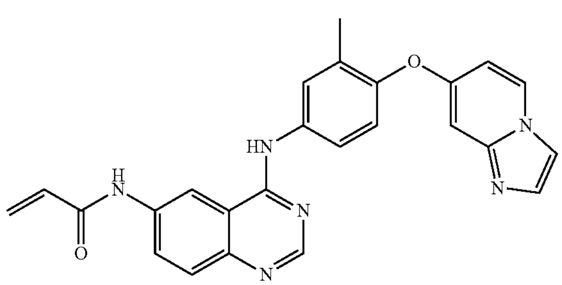 [SMILES: C=CC(=O)Nc1ccc2ncnc(Nc3ccc(Oc4ccn5ccnc5c4)c(C)c3)c2c1] | 437.4 (M + 1) detected |

-continued

| Ex. # | Structure | MS m/z |
|---|---|---|
| 115 | 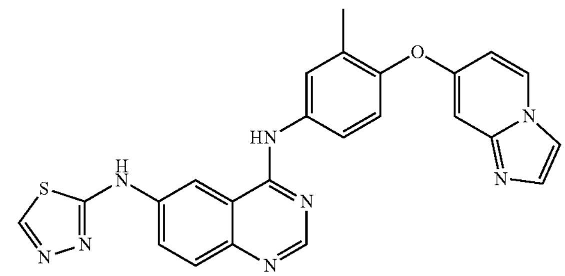 [SMILES: Cc1cc(Nc2ncnc3ccc(Nc4nncs4)cc23)ccc1Oc1ccn2ccnc2c1] | 467.2 (M + 1) detected |
| 116 | 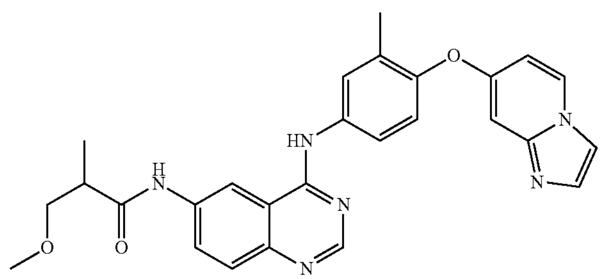 [SMILES: COCC(C)C(=O)Nc1ccc2ncnc(Nc3ccc(Oc4ccn5ccnc5c4)c(C)c3)c2c1] | 483.3 (M + 1) detected |
| 117 | 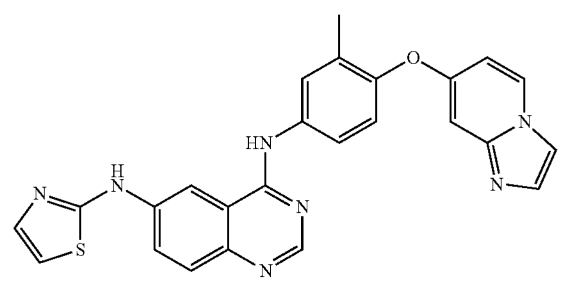 [SMILES: Cc1cc(Nc2ncnc3ccc(Nc4nccs4)cc23)ccc1Oc1ccn2ccnc2c1] | 466.4 (M + 1) detected |
| 118 | 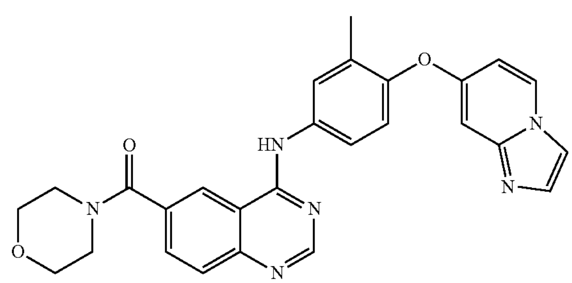 [SMILES: Cc1cc(Nc2ncnc3ccc(C(=O)N4CCOCC4)cc23)ccc1Oc1ccn2ccnc2c1] | 481.3 (M + 1) detected |
| 119 | 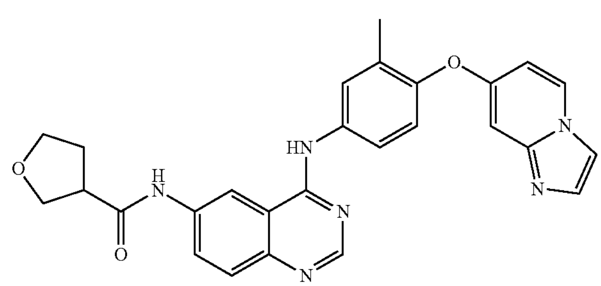 [SMILES: Cc1cc(Nc2ncnc3ccc(NC(=O)C4CCOC4)cc23)ccc1Oc1ccn2ccnc2c1] | 481.4 (M + 1) detected |

| Ex. # | Structure | MS m/z |
|---|---|---|
| 120 | 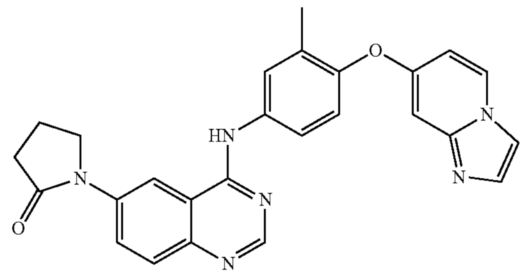 [SMILES: Cc1cc(Nc2ncnc3ccc(N4CCCC4=O)cc23)ccc1Oc1ccn2ccnc2c1] | 451.4 (M + 1) detected |
| 121 | 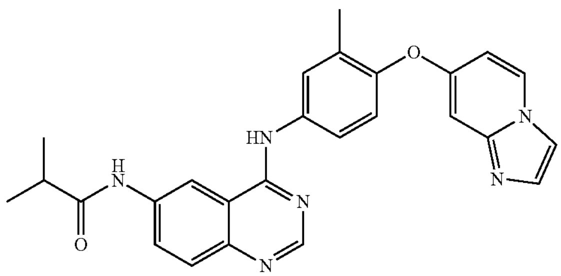 [SMILES: Cc1cc(Nc2ncnc3ccc(NC(=O)C(C)C)cc23)ccc1Oc1ccn2ccnc2c1] | 453.3 (M + 1) detected |
| 122 | 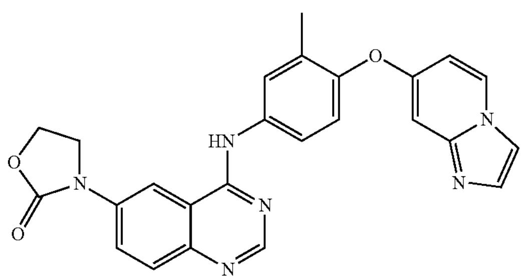 [SMILES: Cc1cc(Nc2ncnc3ccc(N4CCOC4=O)cc23)ccc1Oc1ccn2ccnc2c1] | 453.4 (M + 1) detected |
| 123 | 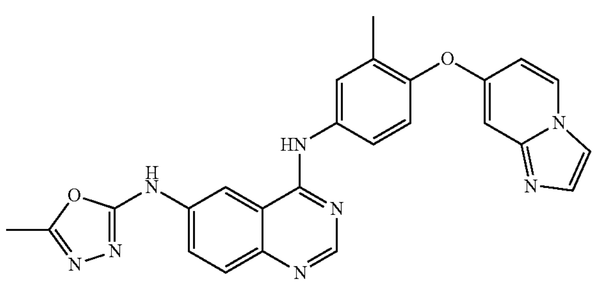 [SMILES: Cc1nnc(Nc2ccc3ncnc(Nc4ccc(Oc5ccn6ccnc6c5)c(C)c4)c3c2)o1] | 465.2 (M + 1) detected |
| 124 | 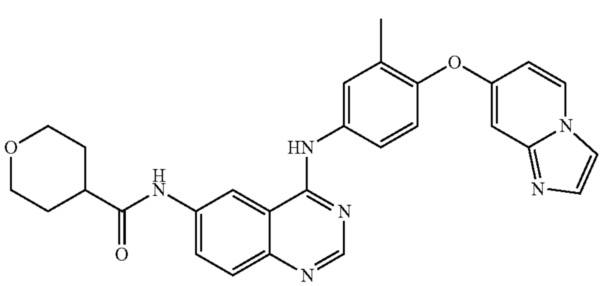 [SMILES: Cc1cc(Nc2ncnc3ccc(NC(=O)C4CCOCC4)cc23)ccc1Oc1ccn2ccnc2c1] | 495.3 (M + 1) detected |

-continued

| Ex. # | Structure | MS m/z |
|---|---|---|
| 125 | 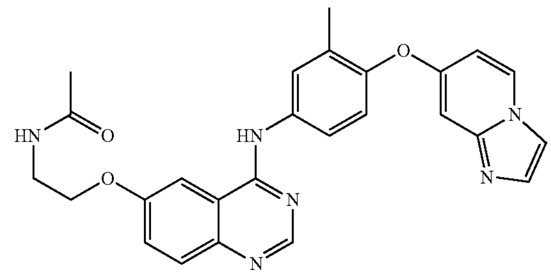 [SMILES: CC(=O)NCCOc1ccc2ncnc(Nc3ccc(Oc4ccn5ccnc5c4)c(C)c3)c2c1] | 469.2 (M + 1) detected |
| 126 | 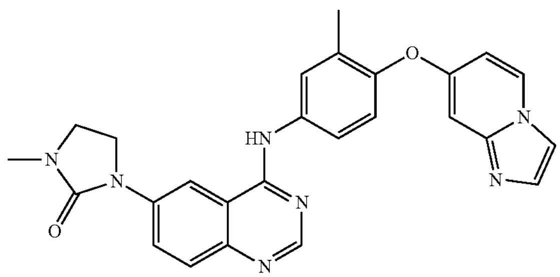 [SMILES: Cc1cc(Nc2ncnc3ccc(N4CCN(C)C4=O)cc23)ccc1Oc1ccn2ccnc2c1] | 466.3 (M + 1) detected |
| 127 | 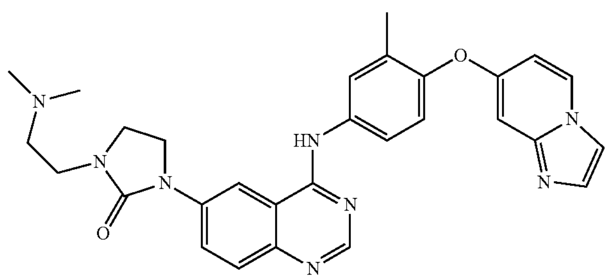 [SMILES: Cc1cc(Nc2ncnc3ccc(N4CCN(CCN(C)C)C4=O)cc23)ccc1Oc1ccn2ccnc2c1] | 523.3 (M + 1) detected |
| 128 | 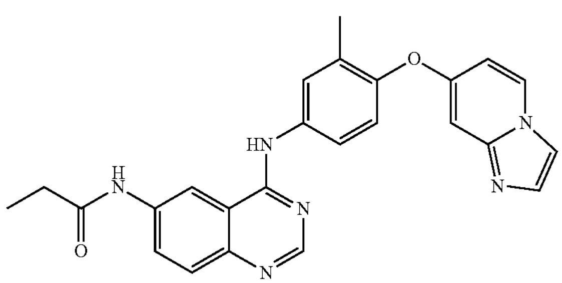 [SMILES: CCC(=O)Nc1ccc2ncnc(Nc3ccc(Oc4ccn5ccnc5c4)c(C)c3)c2c1] | 439.4 (M + 1) detected |
| 129 | 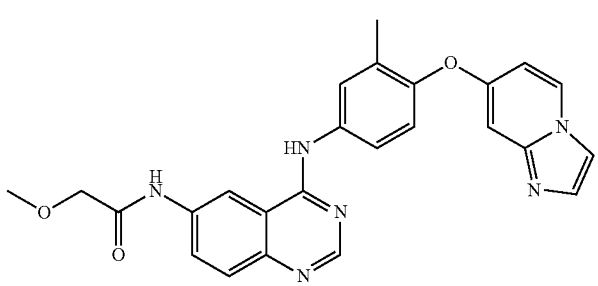 [SMILES: COCC(=O)Nc1ccc2ncnc(Nc3ccc(Oc4ccn5ccnc5c4)c(C)c3)c2c1] | 455.4 (M + 1) detected |

| Ex. # | Structure | MS m/z |
|---|---|---|
| 130 | 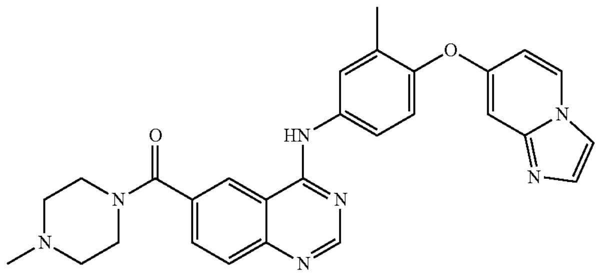 [SMILES: Cc1cc(Nc2ncnc3ccc(C(=O)N4CCN(C)CC4)cc23)ccc1Oc1ccn2ccnc2c1] | 494.3 (M + 1) detected |
| 131 | 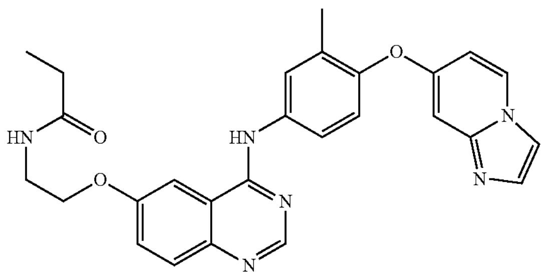 [SMILES: CCC(=O)NCCOc1ccc2ncnc(Nc3ccc(Oc4ccn5ccnc5c4)c(C)c3)c2c1] | 483.2 (M + 1) detected |
| 132 | 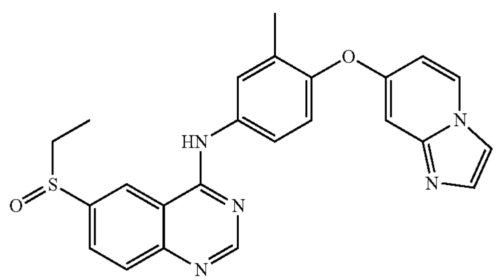 [SMILES: CCS(=O)c1ccc2ncnc(Nc3ccc(Oc4ccn5ccnc5c4)c(C)c3)c2c1] | 444.1 (M + 1) detected |
| 133 | 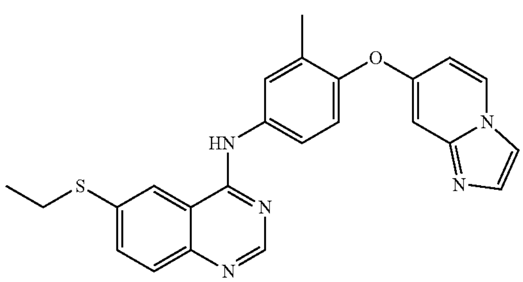 [SMILES: CCSc1ccc2ncnc(Nc3ccc(Oc4ccn5ccnc5c4)c(C)c3)c2c1] | 428.4 (M + 1) detected |
| 134 | 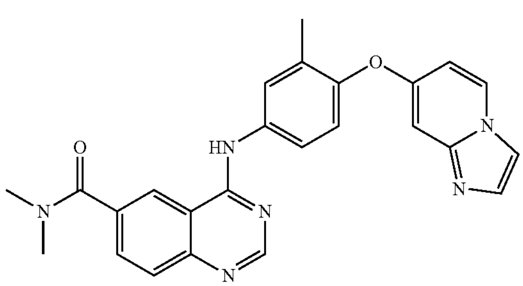 [SMILES: Cc1cc(Nc2ncnc3ccc(C(=O)N(C)C)cc23)ccc1Oc1ccn2ccnc2c1] | 439.3 (M + 1) detected |

| Ex. # | Structure | MS m/z |
|---|---|---|
| 135 | 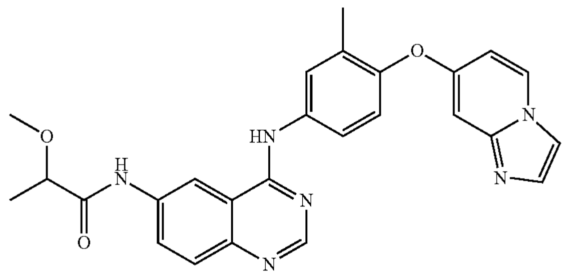 [SMILES: COC(C)C(=O)Nc1ccc2ncnc(Nc3ccc(Oc4ccn5ccnc5c4)c(C)c3)c2c1] | 469.2 (M + 1) detected |
| 136 | 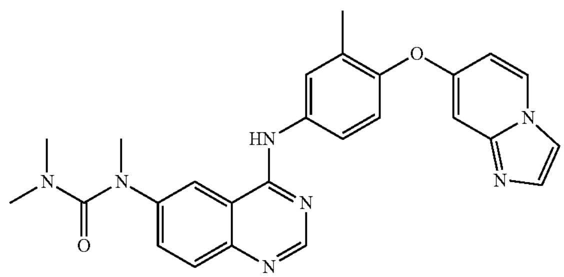 [SMILES: Cc1cc(Nc2ncnc3ccc(N(C)C(=O)N(C)C)cc23)ccc1Oc1ccn2ccnc2c1] | 468.3 (M + 1) detected |
| 137 | 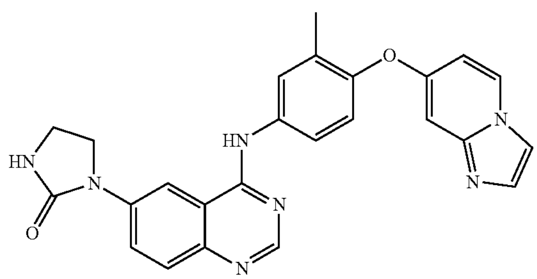 [SMILES: Cc1cc(Nc2ncnc3ccc(N4CCNC4=O)cc23)ccc1Oc1ccn2ccnc2c1] | 452.4 (M + 1) detected |
| 138 | 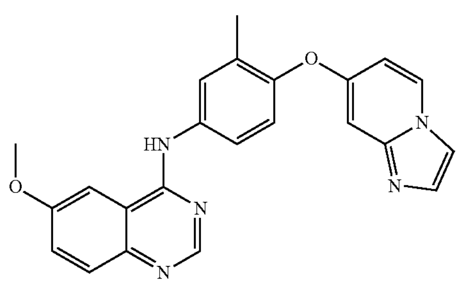 [SMILES: COc1ccc2ncnc(Nc3ccc(Oc4ccn5ccnc5c4)c(C)c3)c2c1] | 398.3 (M + 1) detected |
| 139 | 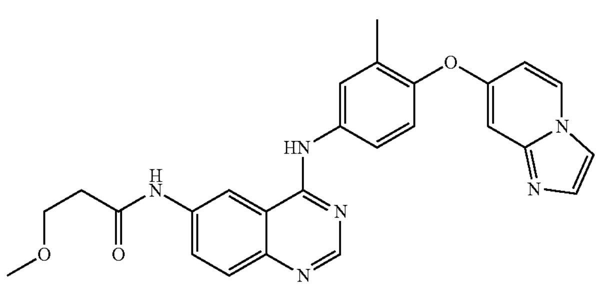 [SMILES: COCCC(=O)Nc1ccc2ncnc(Nc3ccc(Oc4ccn5ccnc5c4)c(C)c3)c2c1] | 469.3 (M + 1) detected |

| Ex. # | Structure | MS m/z |
|---|---|---|
| 140 | 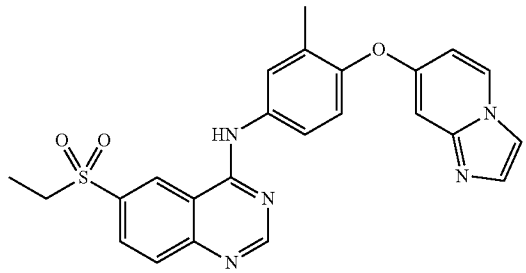 [SMILES: CCS(=O)(=O)c1ccc2ncnc(Nc3ccc(Oc4ccn5ccnc5c4)c(C)c3)c2c1] | 460.3 (M + 1) detected |
| 141 | 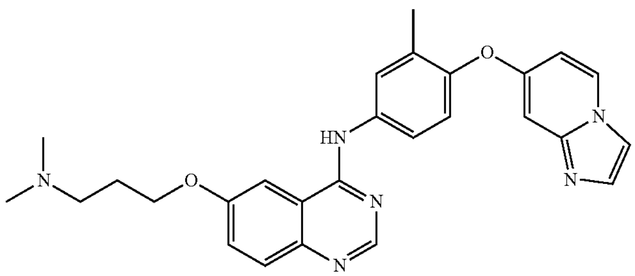 [SMILES: Cc1cc(Nc2ncnc3ccc(OCCCN(C)C)cc23)ccc1Oc1ccn2ccnc2c1] | 469.3 (M + 1) detected |
| 142 | 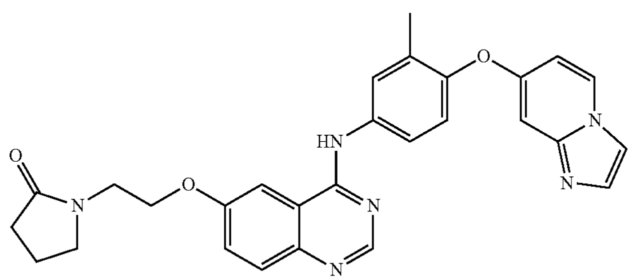 [SMILES: Cc1cc(Nc2ncnc3ccc(OCCN4CCCC4=O)cc23)ccc1Oc1ccn2ccnc2c1] | 495.2 (M + 1) detected |
| 143 | 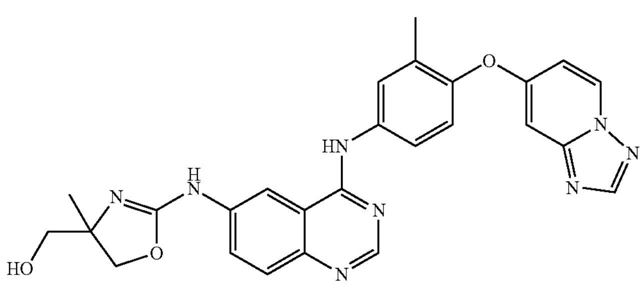 [SMILES: Cc1cc(Nc2ncnc3ccc(NC4=NC(C)(CO)CO4)cc23)ccc1Oc1ccn2ncnc2c1] | 497.3 (M + 1) detected |
| 144 | 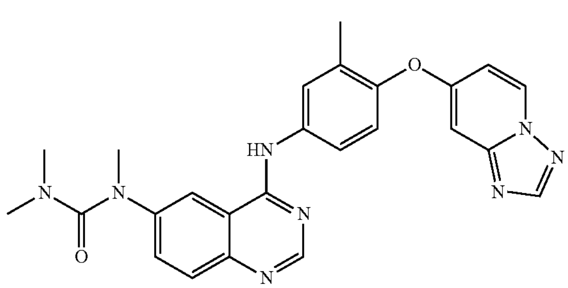 [SMILES: Cc1cc(Nc2ncnc3ccc(N(C)C(=O)N(C)C)cc23)ccc1Oc1ccn2ncnc2c1] | 469.2 (M + 1) detected |

| Ex. # | Structure | MS m/z |
|---|---|---|
| 145 | 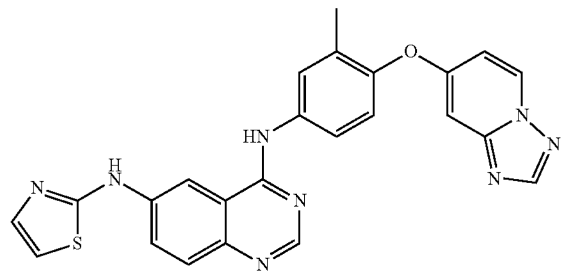 [SMILES: Cc1cc(Nc2ncnc3ccc(Nc4nccs4)cc23)ccc1Oc1ccn2ncnc2c1] | 467.4 (M + 1) detected |
| 146 | 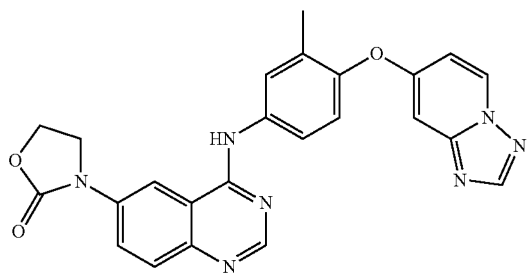 [SMILES: Cc1cc(Nc2ncnc3ccc(N4CCOC4=O)cc23)ccc1Oc1ccn2ncnc2c1] | 454.4 (M + 1) detected |
| 147 | 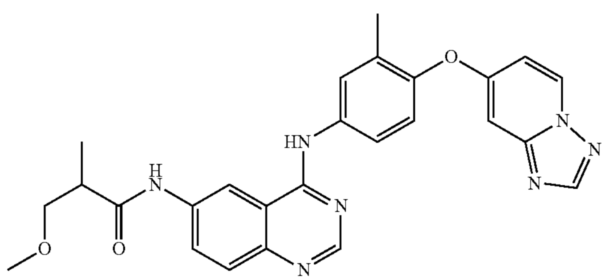 [SMILES: COCC(C)C(=O)Nc1ccc2ncnc(Nc3ccc(Oc4ccn5ncnc5c4)c(C)c3)c2c1] | 484.3 (M + 1) detected |
| 148 | 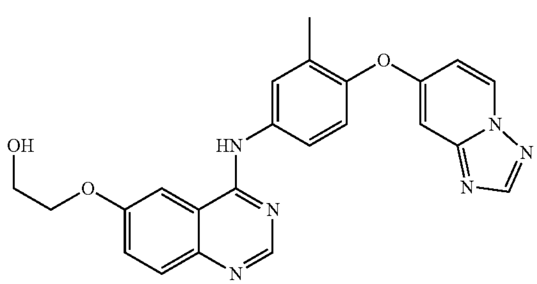 [SMILES: Cc1cc(Nc2ncnc3ccc(OCCO)cc23)ccc1Oc1ccn2ncnc2c1] | 429.3 (M + 1) detected |
| 149 | 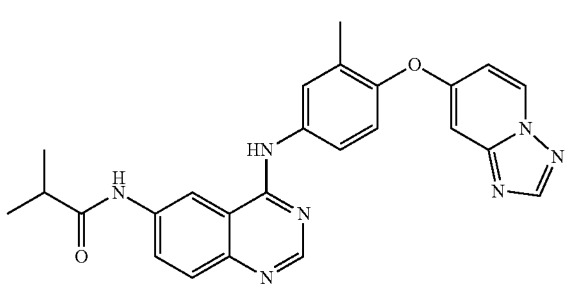 | 454.4 (M + 1) detected |

| Ex. # | Structure | MS m/z |
|---|---|---|
| 150 | 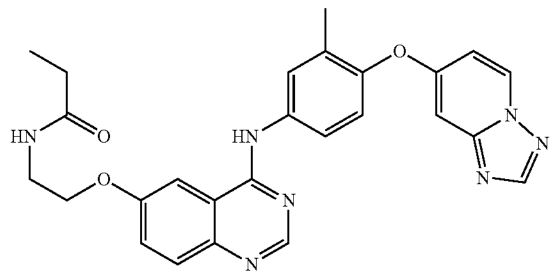 [SMILES: CCC(=O)NCCOc1ccc2ncnc(Nc3ccc(Oc4ccn5ncnc5c4)c(C)c3)c2c1] | 484.1 (M + 1) detected |
| 151 | 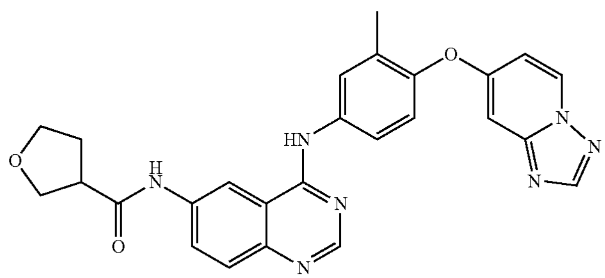 [SMILES: Cc1cc(Nc2ncnc3ccc(NC(=O)C4CCOC4)cc23)ccc1Oc1ccn2ncnc2c1] | 482.3 (M + 1) detected |
| 152 | 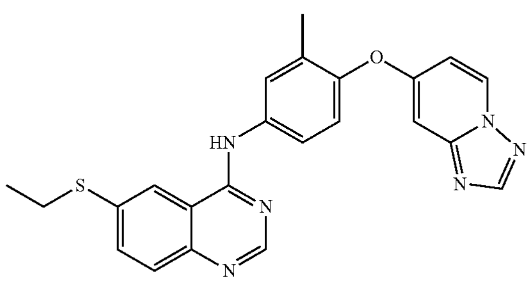 [SMILES: CCSc1ccc2ncnc(Nc3ccc(Oc4ccn5ncnc5c4)c(C)c3)c2c1] | 429.3 (M + 1) detected |
| 153 | 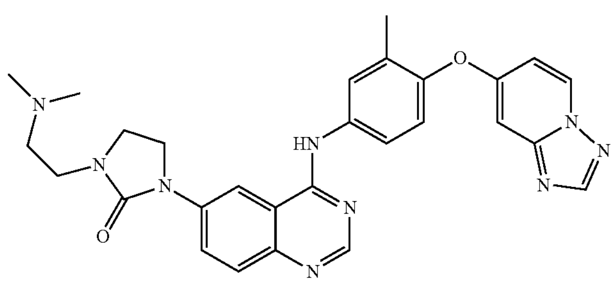 [SMILES: Cc1cc(Nc2ncnc3ccc(N4CCN(CCN(C)C)C4=O)cc23)ccc1Oc1ccn2ncnc2c1] | 524.2 (M + 1) detected |
| 154 | 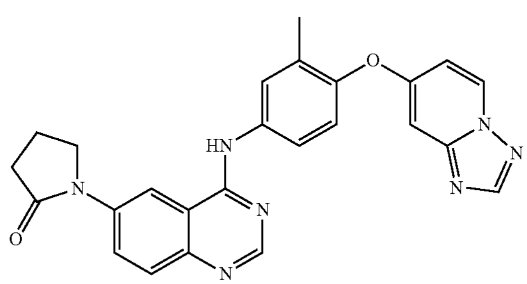 [SMILES: Cc1cc(Nc2ncnc3ccc(N4CCCC4=O)cc23)ccc1Oc1ccn2ncnc2c1] | 452.4 (M + 1) detected |

| Ex. # | Structure | MS m/z |
|---|---|---|
| 155 | 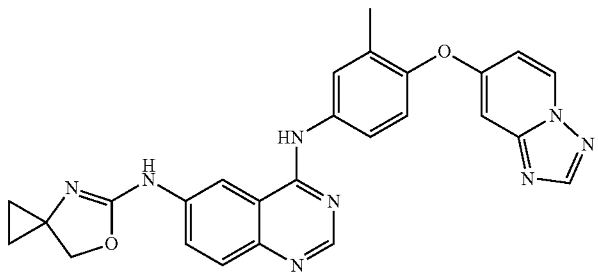 [SMILES: Cc1cc(Nc2ncnc3ccc(NC4=NC5(CC5)CO4)cc23)ccc1Oc1ccn2ncnc2c1] | 479.2 (M + 1) detected |
| 156 | 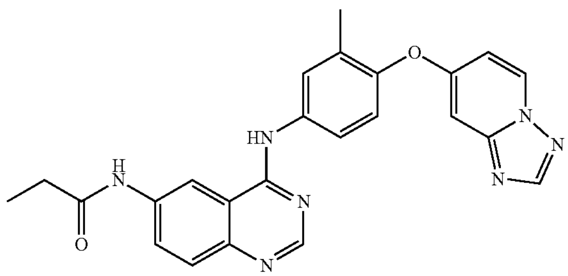 [SMILES: CCC(=O)Nc1ccc2ncnc(Nc3ccc(Oc4ccn5ncnc5c4)c(C)c3)c2c1] | 440.2 (M + 1) detected |
| 157 | 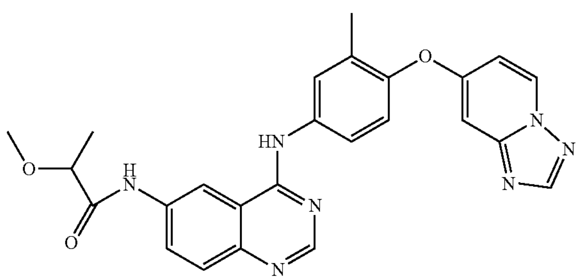 [SMILES: COC(C)C(=O)Nc1ccc2ncnc(Nc3ccc(Oc4ccn5ncnc5c4)c(C)c3)c2c1] | 470.3 (M + 1) detected |
| 158 | 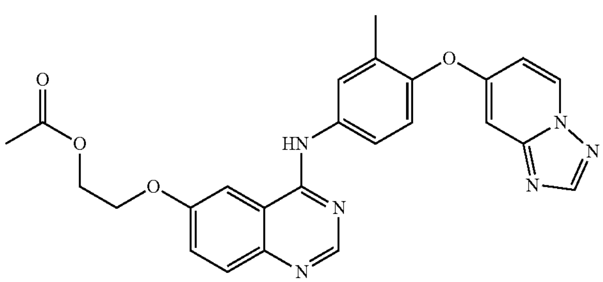 [SMILES: CC(=O)OCCOc1ccc2ncnc(Nc3ccc(Oc4ccn5ncnc5c4)c(C)c3)c2c1] | 471.2 (M + 1) detected |
| 159 | 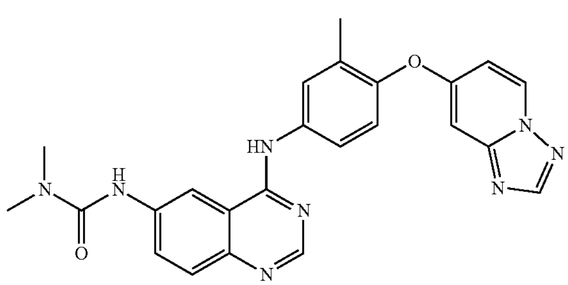 [SMILES: Cc1cc(Nc2ncnc3ccc(NC(=O)N(C)C)cc23)ccc1Oc1ccn2ncnc2c1] | 455.1 (M + 1) detected |

| Ex. # | Structure | MS m/z |
|---|---|---|
| 160 | 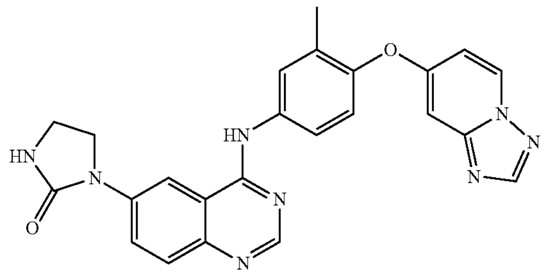 [SMILES: Cc1cc(Nc2ncnc3ccc(N4CCNC4=O)cc23)ccc1Oc1ccn2ncnc2c1] | 453.4 (M + 1) detected |
| 161 | 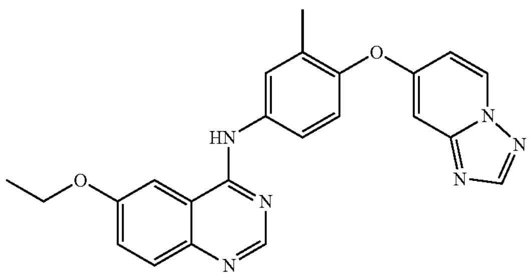 [SMILES: CCOc1ccc2ncnc(Nc3ccc(Oc4ccn5ncnc5c4)c(C)c3)c2c1] | 413.2 (M + 1) detected |
| 162 | 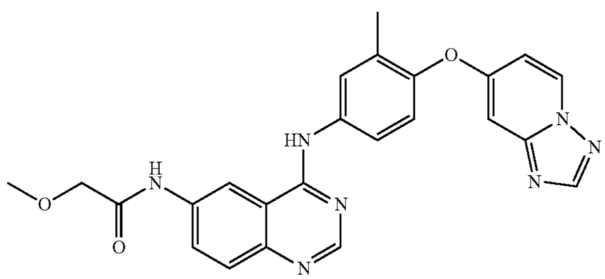 [SMILES: COCC(=O)Nc1ccc2ncnc(Nc3ccc(Oc4ccn5ncnc5c4)c(C)c3)c2c1] | 456.2 (M + 1) detected |
| 163 | 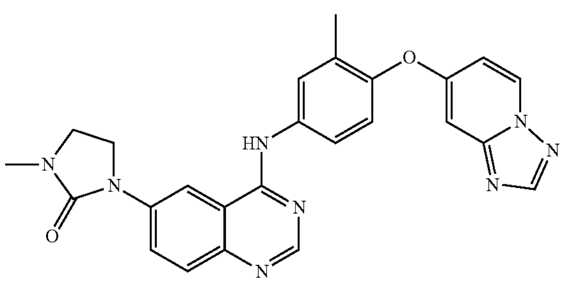 [SMILES: Cc1cc(Nc2ncnc3ccc(N4CCN(C)C4=O)cc23)ccc1Oc1ccn2ncnc2c1] | 467.3 (M + 1) detected |
| 164 | 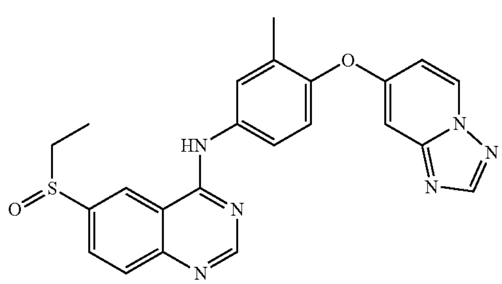 [SMILES: CCS(=O)c1ccc2ncnc(Nc3ccc(Oc4ccn5ncnc5c4)c(C)c3)c2c1] | 445.1 (M + 1) detected |

| Ex. # | Structure | MS m/z |
|---|---|---|
| 165 | 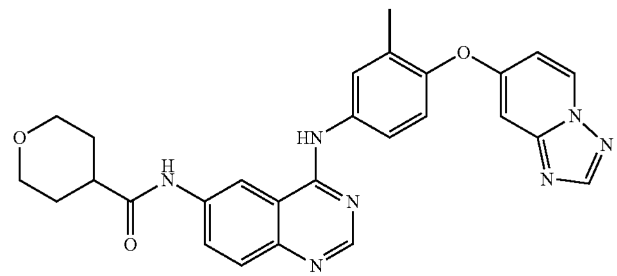 [SMILES: Cc1cc(Nc2ncnc3ccc(NC(=O)C4CCOCC4)cc23)ccc1Oc1ccn2ncnc2c1] | 496.4 (M + 1) detected |
| 166 | 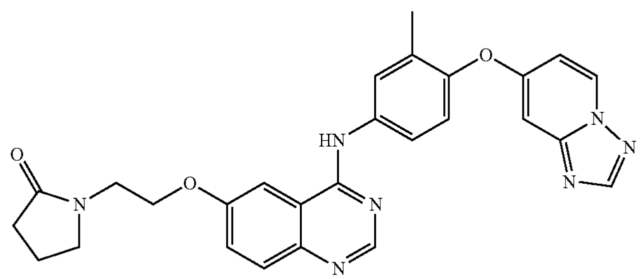 [SMILES: Cc1cc(Nc2ncnc3ccc(OCCN4CCCC4=O)cc23)ccc1Oc1ccn2ncnc2c1] | 496.2 (M + 1) detected |
| 167 | 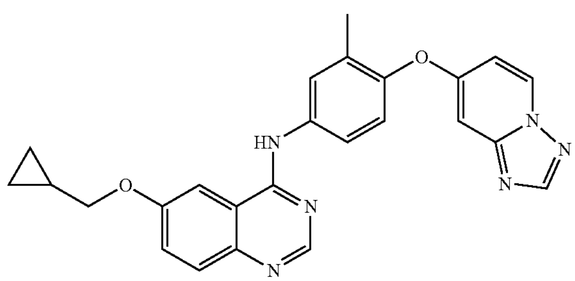 [SMILES: Cc1cc(Nc2ncnc3ccc(OCC4CC4)cc23)ccc1Oc1ccn2ncnc2c1] | 439.2 (M + 1) detected |
| 168 | 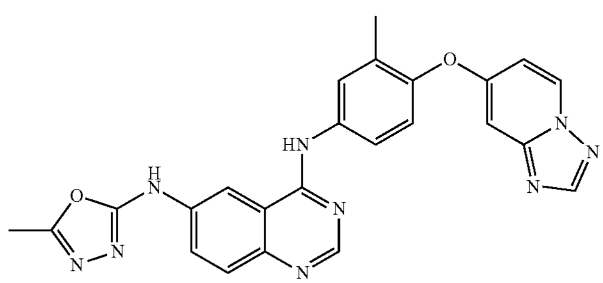 [SMILES: Cc1nnc(Nc2ccc3ncnc(Nc4ccc(Oc5ccn6ncnc6c5)c(C)c4)c3c2)o1] | 466.3 (M + 1) detected |
| 169 | 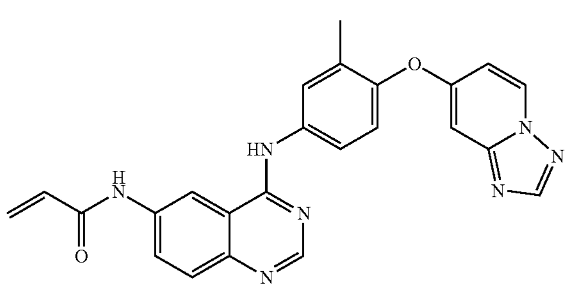 [SMILES: C=CC(=O)Nc1ccc2ncnc(Nc3ccc(Oc4ccn5ncnc5c4)c(C)c3)c2c1] | 438.4 (M + 1) detected |

| Ex. # | Structure | MS m/z |
|---|---|---|
| 170 | 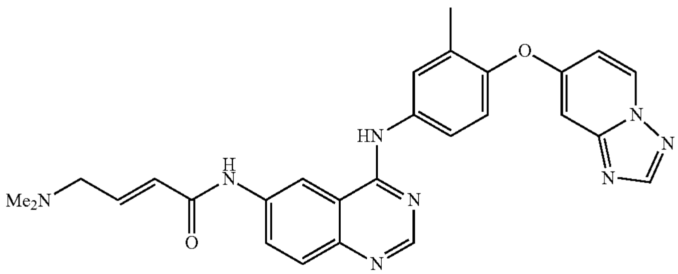 [SMILES: Cc1cc(Nc2ncnc3ccc(NC(=O)/C=C/CN(C)C)cc23)ccc1Oc1ccn2ncnc2c1] | 495.2 (M + 1) detected |
| 171 | 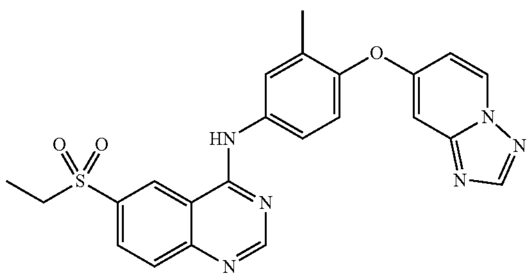 [SMILES: CCS(=O)(=O)c1ccc2ncnc(Nc3ccc(Oc4ccn5ncnc5c4)c(C)c3)c2c1] | 461.3 (M + 1) detected |
| 172 | 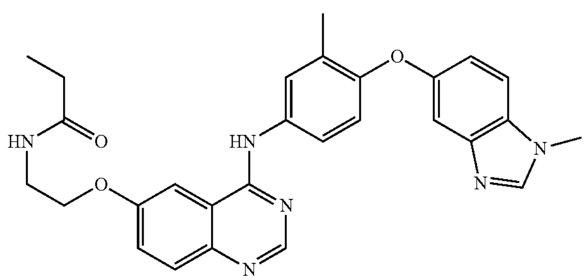 [SMILES: CCC(=O)NCCOc1ccc2ncnc(Nc3ccc(Oc4ccc5c(c4)ncn5C)c(C)c3)c2c1] | 497.1 (M + 1) detected |
| 173 | 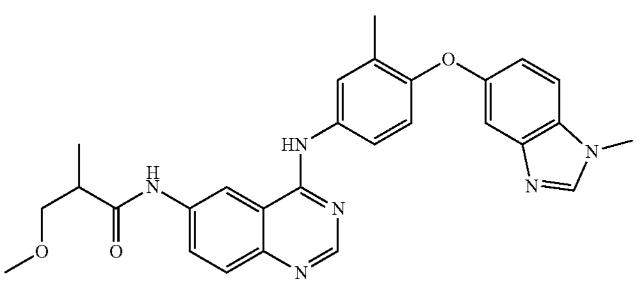 | 497.3 (M + 1) detected |
| 174 | 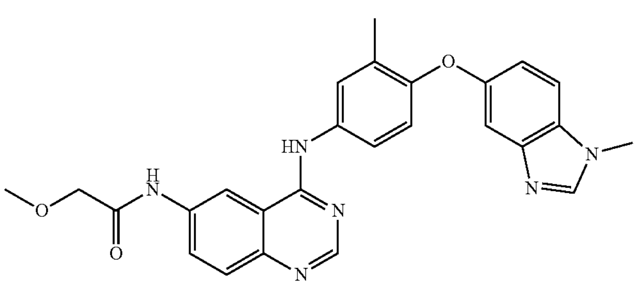 | 469.3 (M + 1) detected |

| Ex. # | Structure | MS m/z |
|---|---|---|
| 175 | 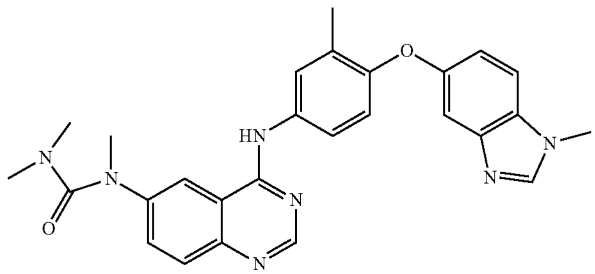 | 482.2 (M + 1) detected |
| 176 | 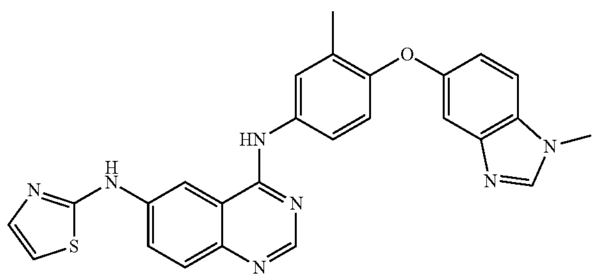 [SMILES: Cc1cc(Nc2ncnc3ccc(Nc4nccs4)cc23)ccc1Oc1ccc2c(c1)ncn2C] | 480.4 (M + 1) detected |
| 177 | 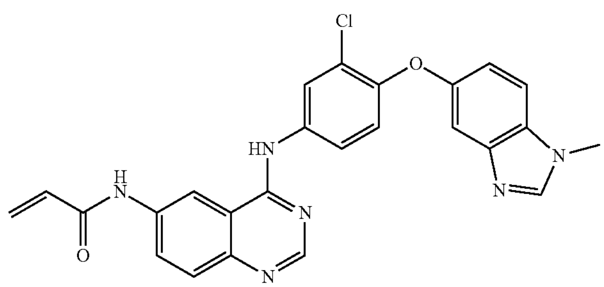 [SMILES: C=CC(=O)Nc1ccc2ncnc(Nc3ccc(Oc4ccc5c(c4)ncn5C)c(Cl)c3)c2c1] | 471.3 (M + 1) detected |
| 178 | 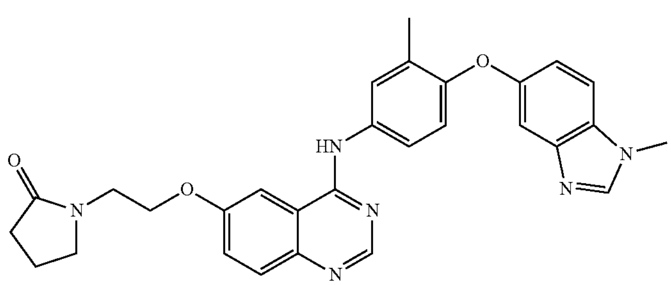 [SMILES: Cc1cc(Nc2ncnc3ccc(OCCN4CCCC4=O)cc23)ccc1Oc1ccc2c(c1)ncn2C] | 509.2 (M + 1) detected |
| 179 | 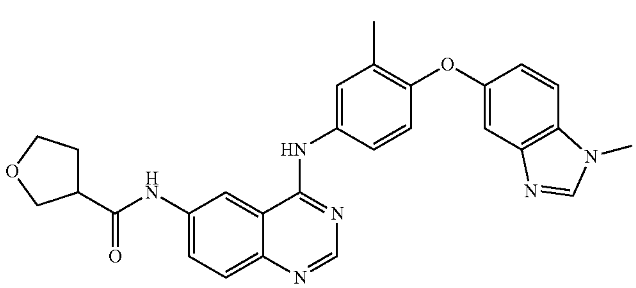 [SMILES: Cc1cc(Nc2ncnc3ccc(NC(=O)C4CCOC4)cc23)ccc1Oc1ccc2c(c1)ncn2C] | 495.3 (M + 1) detected |

-continued

| Ex. # | Structure | MS m/z |
|---|---|---|
| 180 | 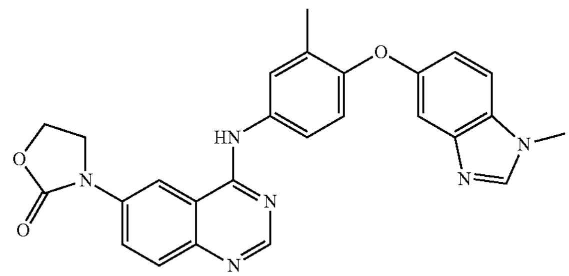 [SMILES: Cc1cc(Nc2ncnc3ccc(N4CCOC4=O)cc23)ccc1Oc1ccc2c(c1)ncn2C] | 467.3 (M + 1) detected |
| 181 | 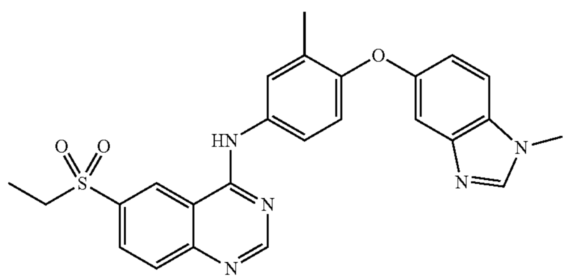 [SMILES: CCS(=O)(=O)c1ccc2ncnc(Nc3ccc(Oc4ccc5c(c4)ncn5C)c(C)c3)c2c1] | 474.3 (M + 1) detected |
| 182 | 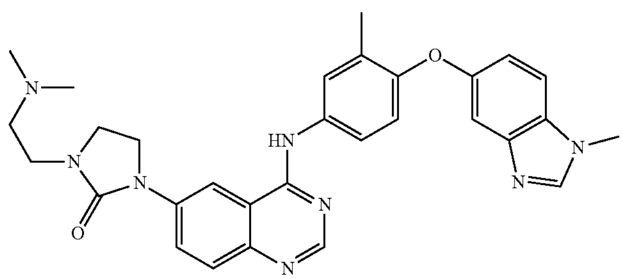 [SMILES: Cc1cc(Nc2ncnc3ccc(N4CCN(CCN(C)C)C4=O)cc23)ccc1Oc1ccc2c(c1)ncn2C] | 537.3 (M + 1) detected |
| 183 | 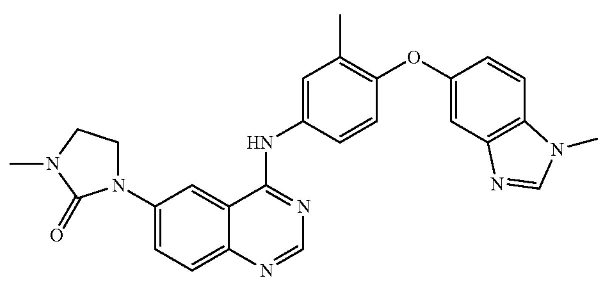 | 480.2 (M + 1) detected |
| 184 | 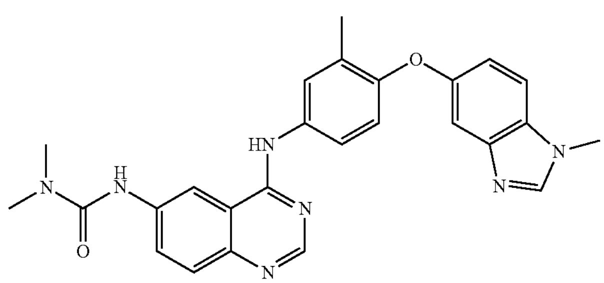 | 468.1 (M + 1) detected |

-continued

| Ex. # | Structure | MS m/z |
|---|---|---|
| 185 | 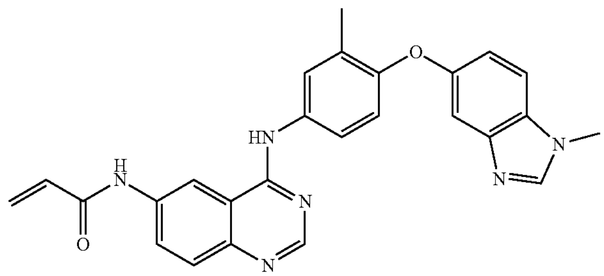 [SMILES: C=CC(=O)Nc1ccc2ncnc(Nc3ccc(Oc4ccc5c(c4)ncn5C)c(C)c3)c2c1] | 451.3 (M + 1) detected |
| 186 | 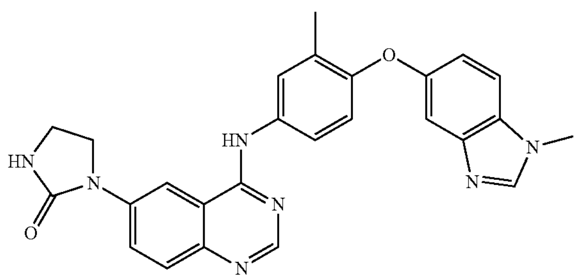 [SMILES: Cc1cc(Nc2ncnc3ccc(N4CCNC4=O)cc23)ccc1Oc1ccc2c(c1)ncn2C] | 466.3 (M + 1) detected |
| 187 | 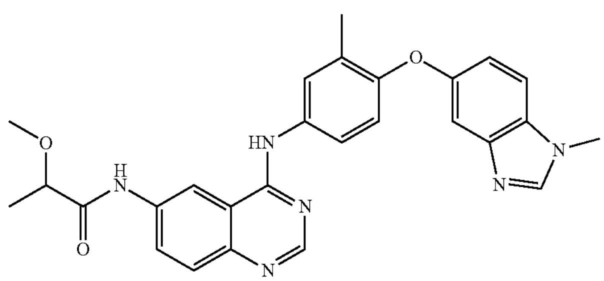 [SMILES: COC(C)C(=O)Nc1ccc2ncnc(Nc3ccc(Oc4ccc5c(c4)ncn5C)c(C)c3)c2c1] | 483.3 (M + 1) detected |
| 188 | 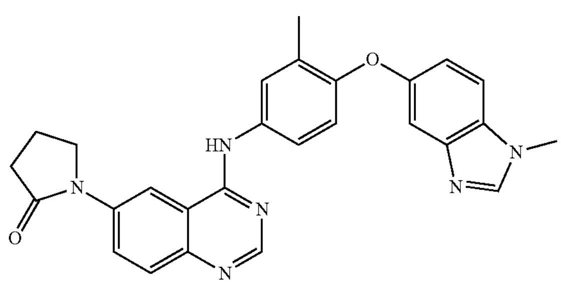 [SMILES: Cc1cc(Nc2ncnc3ccc(N4CCCC4=O)cc23)ccc1Oc1ccc2c(c1)ncn2C] | 465.4 (M + 1) detected |
| 189 | 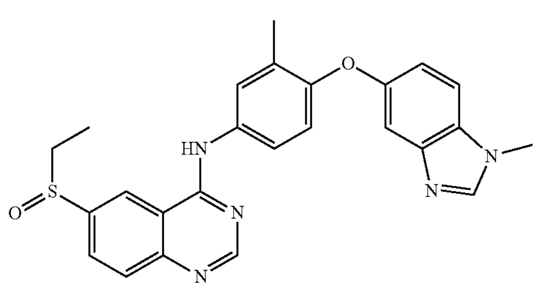 [SMILES: CCS(=O)c1ccc2ncnc(Nc3ccc(Oc4ccc5c(c4)ncn5C)c(C)c3)c2c1] | 458.1 (M + 1) detected |

-continued

| Ex. # | Structure | MS m/z |
|---|---|---|
| 190 | 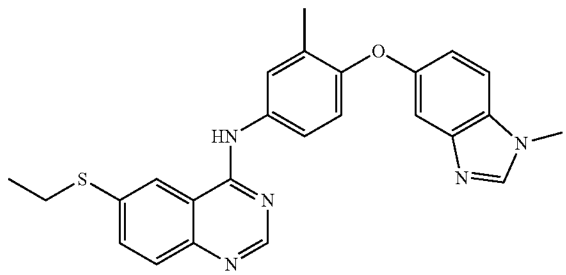 [SMILES: CCSc1ccc2ncnc(Nc3ccc(Oc4ccc5c(c4)ncn5C)c(C)c3)c2c1] | 442.3 (M + 1) detected |
| 191 | 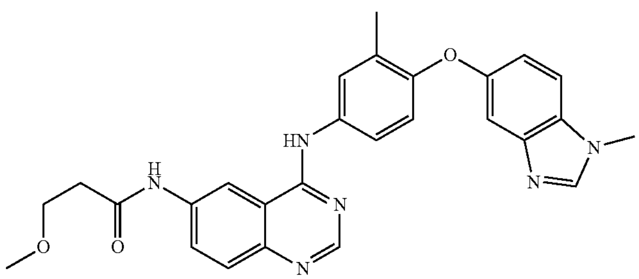 | 483.3 (M + 1) detected |
| 192 | 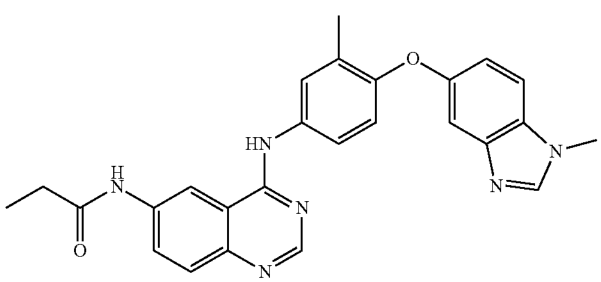 [SMILES: CCC(=O)Nc1ccc2ncnc(Nc3ccc(Oc4ccc5c(c4)ncn5C)c(C)c3)c2c1] | 453.3 (M + 1) detected |
| 193 | 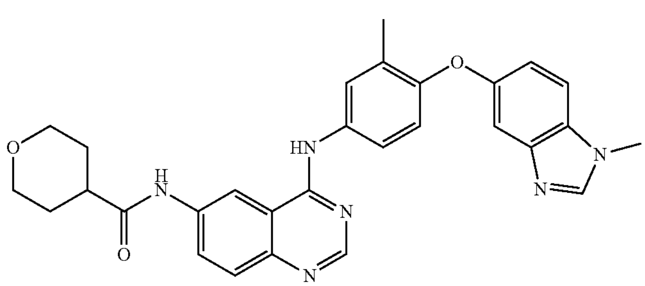 [SMILES: Cc1cc(Nc2ncnc3ccc(NC(=O)C4CCOCC4)cc23)ccc1Oc1ccc2c(c1)ncn2C] | 509.5 (M + 1) detected |
| 194 | 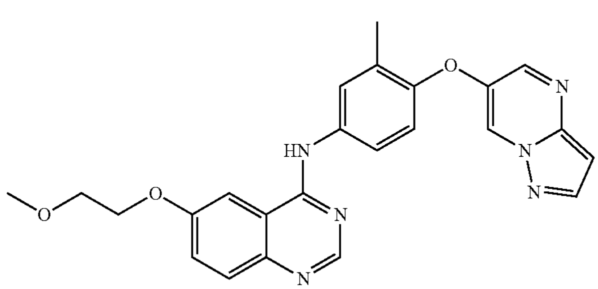 [SMILES: COCCOc1ccc2ncnc(Nc3ccc(Oc4cnc5ccnn5c4)c(C)c3)c2c1] | 443.3 (M + 1) detected |

| Ex. # | Structure | MS m/z |
|---|---|---|
| 195 | 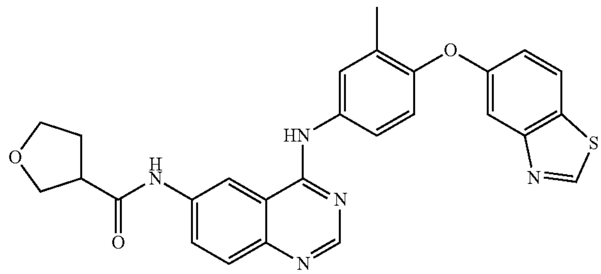 [SMILES: Cc1cc(Nc2ncnc3ccc(NC(=O)C4CCOC4)cc23)ccc1Oc1ccc2scnc2c1] | 498.3 (M + 1) detected |
| 196 | 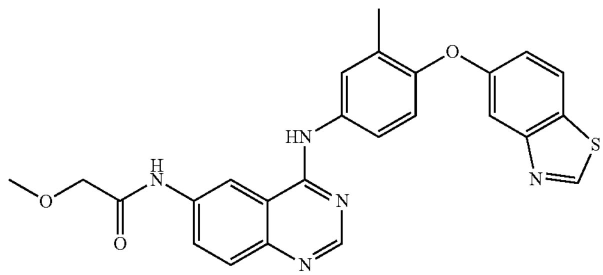 [SMILES: COCC(=O)Nc1ccc2ncnc(Nc3ccc(Oc4ccc5scnc5c4)c(C)c3)c2c1] | 472.2 (M + 1) detected |
| 197 | 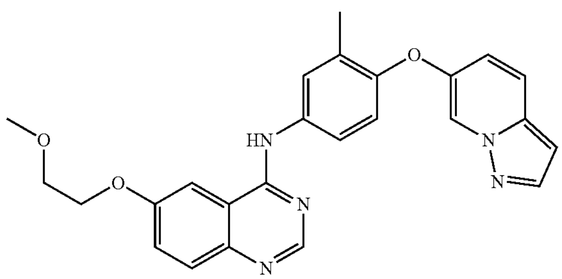 [SMILES: COCCOc1ccc2ncnc(Nc3ccc(Oc4ccc5ccnn5c4)c(C)c3)c2c1] | 442.2 (M + 1) detected |
| 198 | 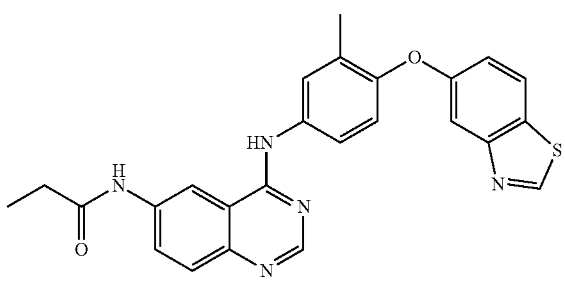 [SMILES: CCC(=O)Nc1ccc2ncnc(Nc3ccc(Oc4ccc5scnc5c4)c(C)c3)c2c1] | 456.2 (M + 1) detected |
| 199 | 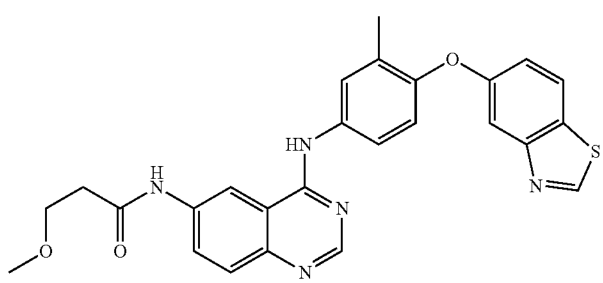 [SMILES: COCCC(=O)Nc1ccc2ncnc(Nc3ccc(Oc4ccc5scnc5c4)c(C)c3)c2c1] | 486.2 (M + 1) detected |

-continued

| Ex. # | Structure | MS m/z |
|---|---|---|
| 200 | 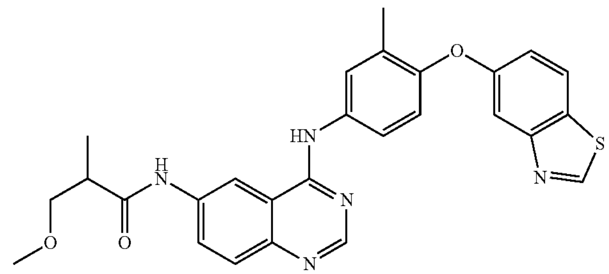 [SMILES: COCC(C)C(=O)Nc1ccc2ncnc(Nc3ccc(Oc4ccc5scnc5c4)c(C)c3)c2c1] | 500.2 (M + 1) detected |
| 201 | 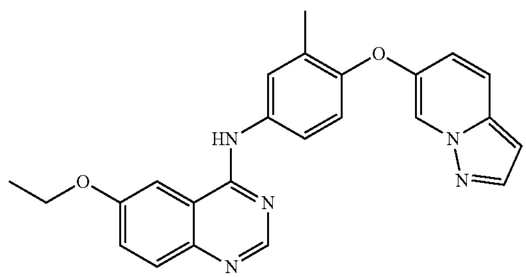 [SMILES: CCOc1ccc2ncnc(Nc3ccc(Oc4ccc5ccnn5c4)c(C)c3)c2c1] | 412.3 (M + 1) detected |
| 202 | racemic | 469.3 (M + 1) detected |
| 203 | racemic | 471.3 (M + 1) detected |
| 204 | 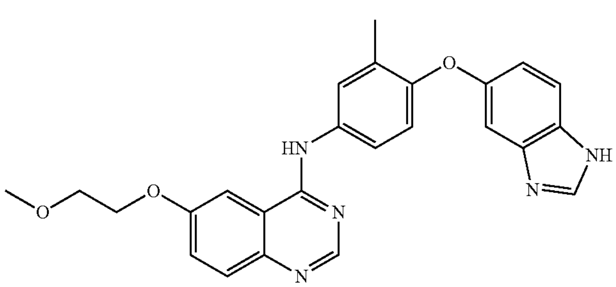 [SMILES: COCCOc1ccc2ncnc(Nc3ccc(Oc4ccc5[nH]cnc5c4)c(C)c3)c2c1] | 442.3 (M + 1) detected |

-continued
| Ex. # | Structure | MS m/z |
|---|---|---|
| 205 | 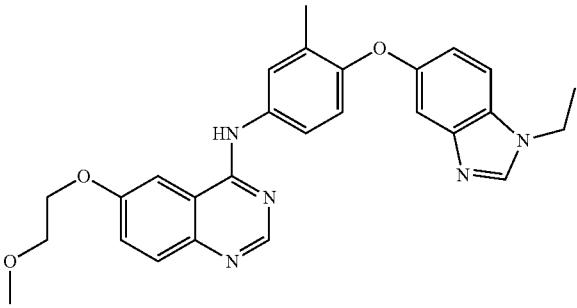 [SMILES: CCn1cnc2cc(Oc3ccc(Nc4ncnc5ccc(OCCOC)cc45)cc3C)ccc21] | 470.3 (M + 1) detected |
| 206 | 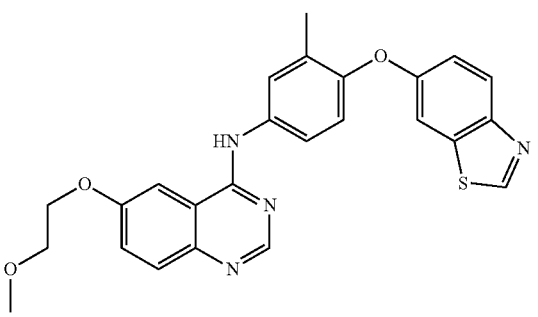 [SMILES: COCCOc1ccc2ncnc(Nc3ccc(Oc4ccc5ncsc5c4)c(C)c3)c2c1] | 459.3 (M + 1) detected |
| 207 | 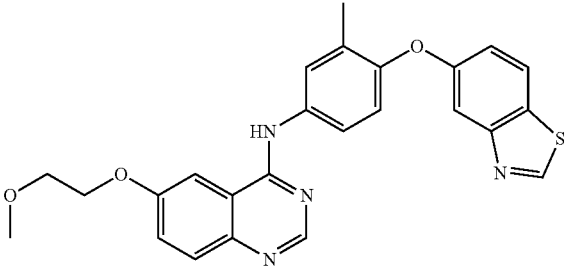 [SMILES: COCCOc1ccc2ncnc(Nc3ccc(Oc4ccc5scnc5c4)c(C)c3)c2c1] | 459.2 (M + 1) detected |
| 208 | 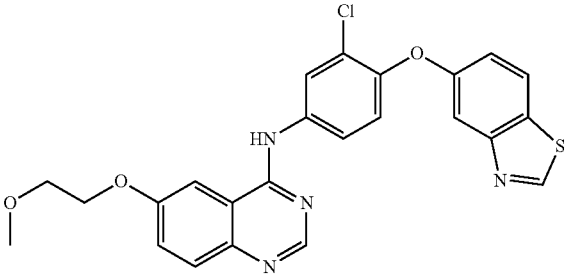 [SMILES: COCCOc1ccc2ncnc(Nc3ccc(Oc4ccc5scnc5c4)c(Cl)c3)c2c1] | 479.3 (M + 1) detected |
| 209 | 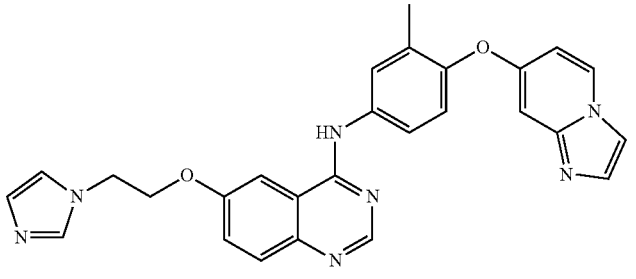 [SMILES: Cc1cc(Nc2ncnc3ccc(OCCn4ccnc4)cc23)ccc1Oc1ccn2ccnc2c1] | 478.2 (M + 1) detected |

-continued
| Ex. # | Structure | MS m/z |
|---|---|---|
| 210 | 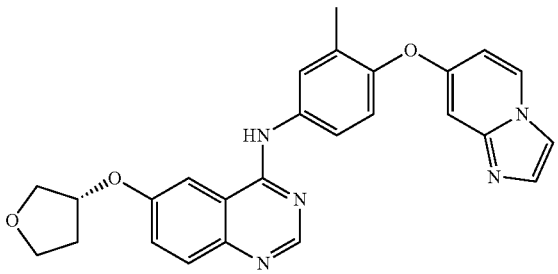 [SMILES: Cc1cc(Nc2ncnc3ccc(O[C@@H]4CCOC4)cc23)ccc1Oc1ccn2ccnc2c1] | 454.1 (M + 1) detected |
| 211 | 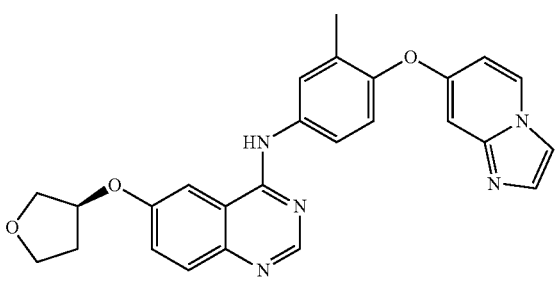 [SMILES: Cc1cc(Nc2ncnc3ccc(O[C@H]4CCOC4)cc23)ccc1Oc1ccn2ccnc2c1] | 454.2 (M + 1) detected |
| 212 | 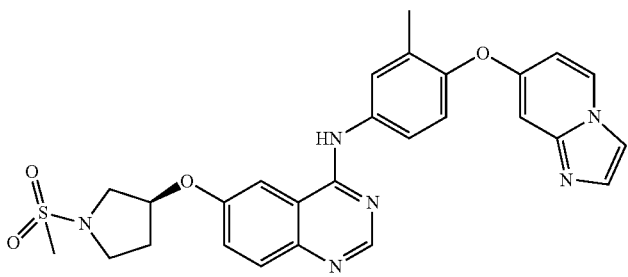 [SMILES: Cc1cc(Nc2ncnc3ccc(O[C@H]4CCN(S(C)(=O)=O)C4)cc23)ccc1Oc1ccn2ccnc2c1] | 531.2 (M + 1) detected |
| 213 | 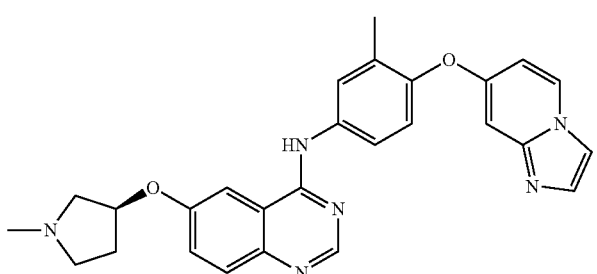 | 467.3 (M + 1) detected |
| 214 | 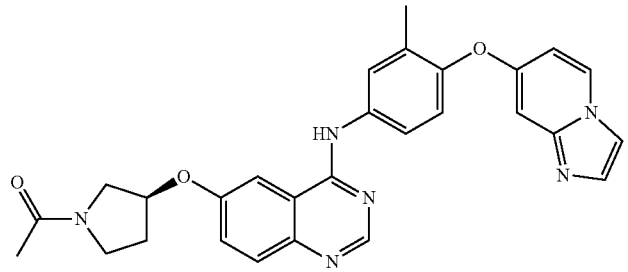 [SMILES: CC(=O)N1CC[C@H](Oc2ccc3ncnc(Nc4ccc(Oc5ccn6ccnc6c5)c(C)c4)c3c2)C1] | 495.2 (M + 1) detected |

-continued

| Ex. # | Structure | MS m/z |
|---|---|---|
| 215 | 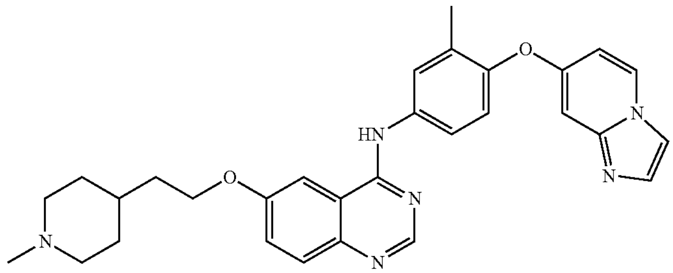 [SMILES: Cc1cc(Nc2ncnc3ccc(OCCC4CCN(C)CC4)cc23)ccc1Oc1ccn2ccnc2c1] | 509.3 (M + 1) detected |
| 216 | 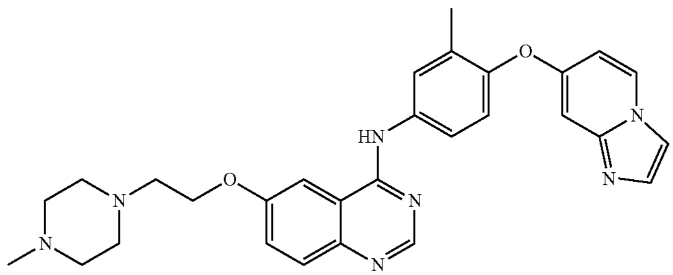 [SMILES: Cc1cc(Nc2ncnc3ccc(OCCN4CCN(C)CC4)cc23)ccc1Oc1ccn2ccnc2c1] | 510.1 (M + 1) detected |
| 217 | 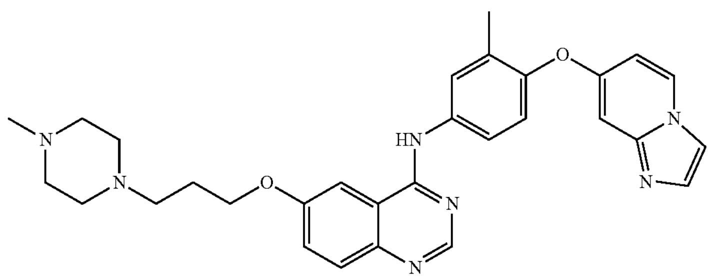 [SMILES: Cc1cc(Nc2ncnc3ccc(OCCCN4CCN(C)CC4)cc23)ccc1Oc1ccn2ccnc2c1] | 524.2 (M + 1) detected |
| 218 | 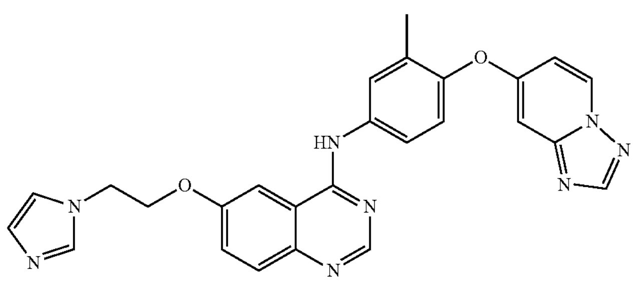 [SMILES: Cc1cc(Nc2ncnc3ccc(OCCn4ccnc4)cc23)ccc1Oc1ccn2ncnc2c1] | 479.2 (M + 1) detected |
| 219 | 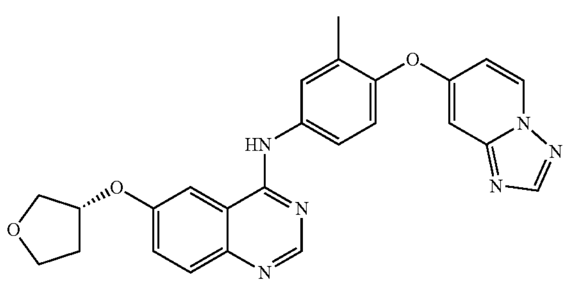 [SMILES: Cc1cc(Nc2ncnc3ccc(O[C@@H]4CCOC4)cc23)ccc1Oc1ccn2ncnc2c1] | 455.2 (M + 1) detected |

-continued
| Ex. # | Structure | MS m/z |
|---|---|---|
| 220 | 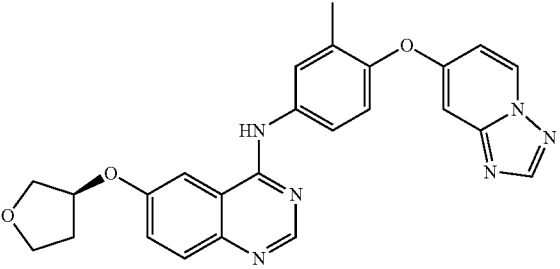 [SMILES: Cc1cc(Nc2ncnc3ccc(O[C@H]4CCOC4)cc23)ccc1Oc1ccn2ncnc2c1] | 455.2 (M + 1) detected |
| 221 | 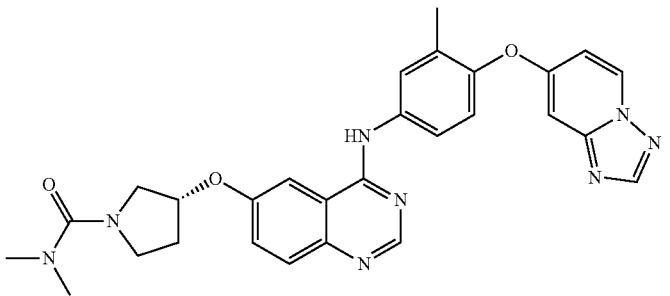 [SMILES: Cc1cc(Nc2ncnc3ccc(O[C@@H]4CCN(C(=O)N(C)C)C4)cc23)ccc1Oc1ccn2ncnc2c1] | 525.2 (M + 1) detected |
| 222 | 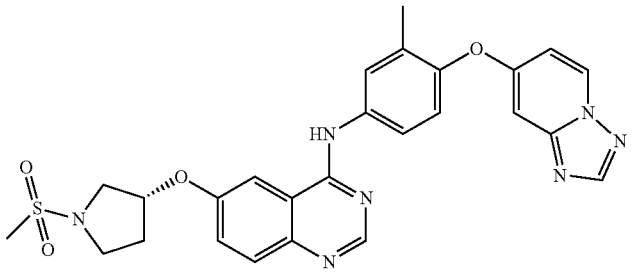 [SMILES: Cc1cc(Nc2ncnc3ccc(O[C@@H]4CCN(S(C)(=O)=O)C4)cc23)ccc1Oc1ccn2ncnc2c1] | 532.2 (M + 1) detected |
| 223 | 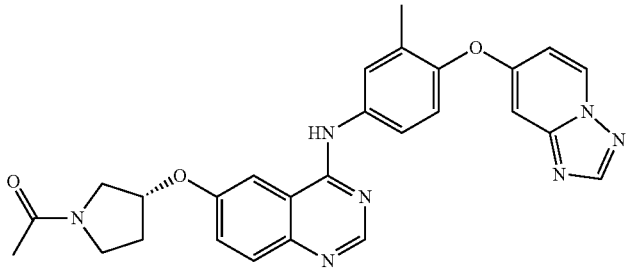 [SMILES: CC(=O)N1CC[C@@H](Oc2ccc3ncnc(Nc4ccc(Oc5ccn6ncnc6c5)c(C)c4)c3c2)C1] | 496.3 (M + 1) detected |
| 224 | 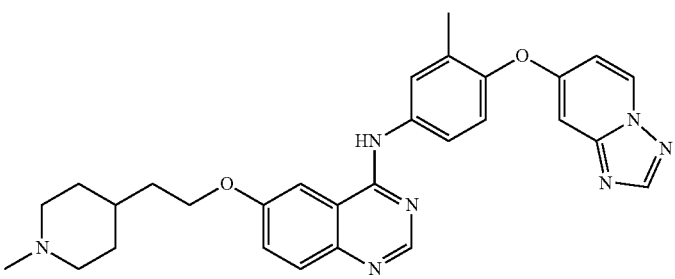 [SMILES: Cc1cc(Nc2ncnc3ccc(OCCC4CCN(C)CC4)cc23)ccc1Oc1ccn2ncnc2c1] | 510.1 (M + 1) detected |

-continued

| Ex. # | Structure | MS m/z |
|---|---|---|
| 225 | 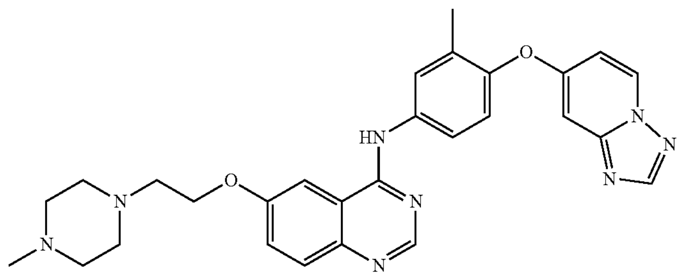 [SMILES: Cc1cc(Nc2ncnc3ccc(OCCN4CCN(C)CC4)cc23)ccc1Oc1ccn2ncnc2c1] | 511.2 (M + 1) detected |
| 226 | 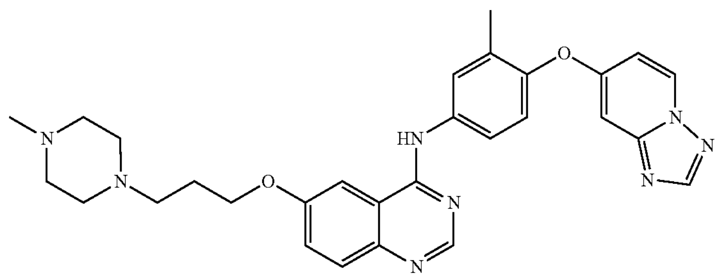 [SMILES: Cc1cc(Nc2ncnc3ccc(OCCCN4CCN(C)CC4)cc23)ccc1Oc1ccn2ncnc2c1] | 525.3 (M + 1) detected |
| 227 | 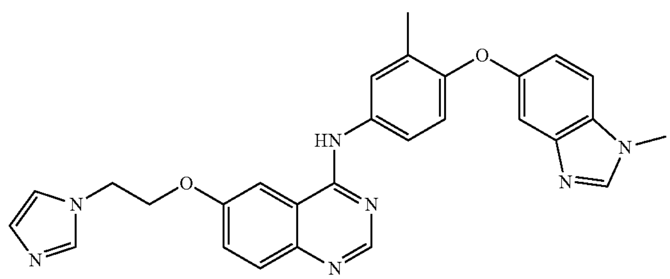 [SMILES: Cc1cc(Nc2ncnc3ccc(OCCn4ccnc4)cc23)ccc1Oc1ccc2c(c1)ncn2C] | 492.2 (M + 1) detected |
| 228 | 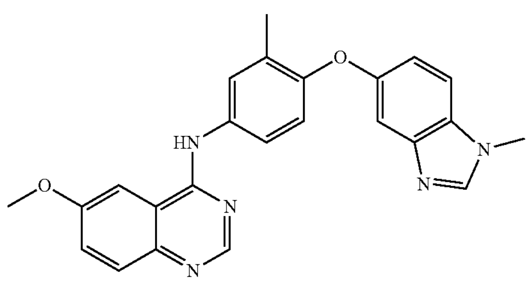 | 412.2 (M + 1) detected |
| 229 | 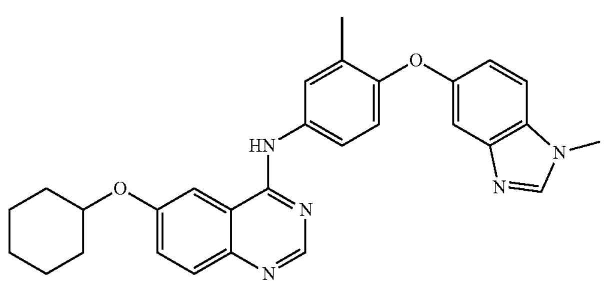 [SMILES: Cc1cc(Nc2ncnc3ccc(OC4CCCCC4)cc23)ccc1Oc1ccc2c(c1)ncn2C] | 480.2 (M + 1) detected |

| Ex. # | Structure | MS m/z |
|---|---|---|
| 230 | 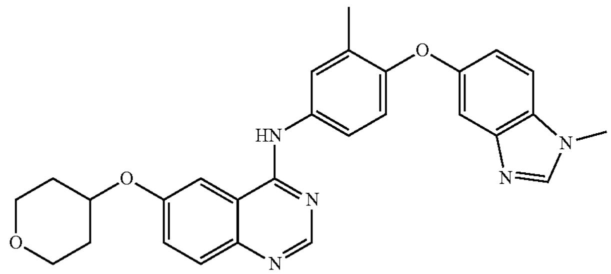 [SMILES: Cc1cc(Nc2ncnc3ccc(OC4CCOCC4)cc23)ccc1Oc1ccc2c(c1)ncn2C] | 482.2 (M + 1) detected |
| 231 | 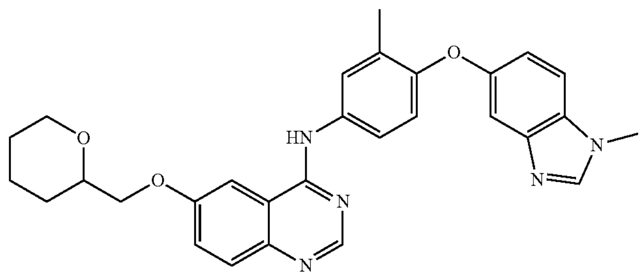 [SMILES: Cc1cc(Nc2ncnc3ccc(OCC4CCCCO4)cc23)ccc1Oc1ccc2c(c1)ncn2C] | 496.3 (M + 1) detected |
| 232 | 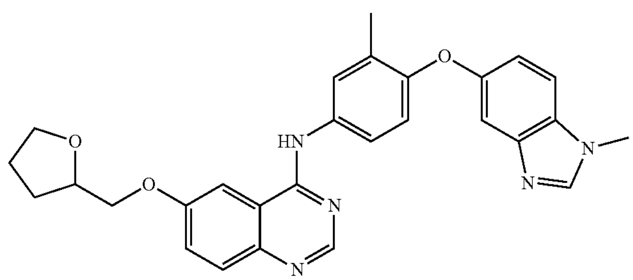 [SMILES: Cc1cc(Nc2ncnc3ccc(OCC4CCCO4)cc23)ccc1Oc1ccc2c(c1)ncn2C] | 482.3 (M + 1) detected |
| 233 | 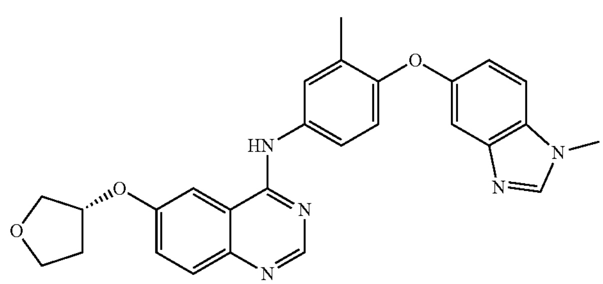 [SMILES: Cc1cc(Nc2ncnc3ccc(O[C@@H]4CCOC4)cc23)ccc1Oc1ccc2c(c1)ncn2C] | 468.2 (M + 1) detected |
| 234 | 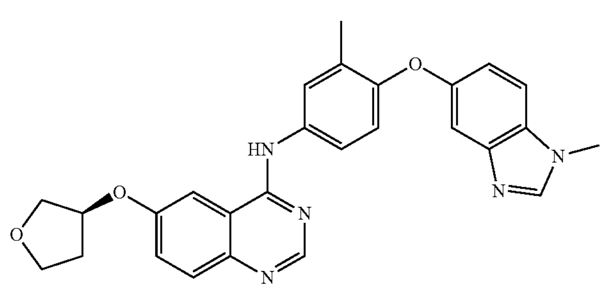 [SMILES: Cc1cc(Nc2ncnc3ccc(O[C@H]4CCOC4)cc23)ccc1Oc1ccc2c(c1)ncn2C] | 468.2 (M + 1) detected |

| Ex. # | Structure | MS m/z |
|---|---|---|
| 235 | 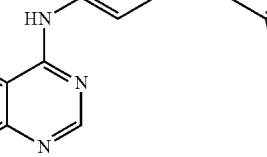 | 481.1 (M + 1) detected |
| 236 | 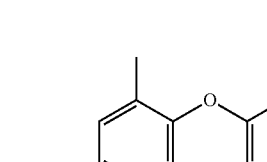 | 545.1 (M + 1) detected |
| 237 | 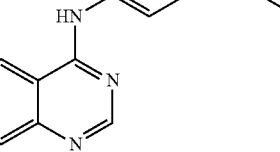 | 538.2 (M + 1) detected |
| 238 | 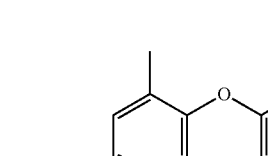 | 469.2 (M + 1) detected |
| 239 | 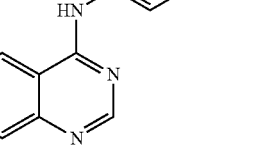 | 483.2 (M + 1) detected |

-continued

| Ex. # | Structure | MS m/z |
|---|---|---|
| 240 | 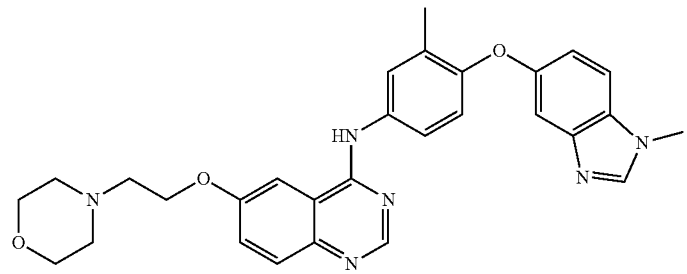 [SMILES: Cc1cc(Nc2ncnc3ccc(OCCN4CCOCC4)cc23)ccc1Oc1ccc2c(c1)ncn2C] | 511.1 (M + 1) detected |
| 241 | 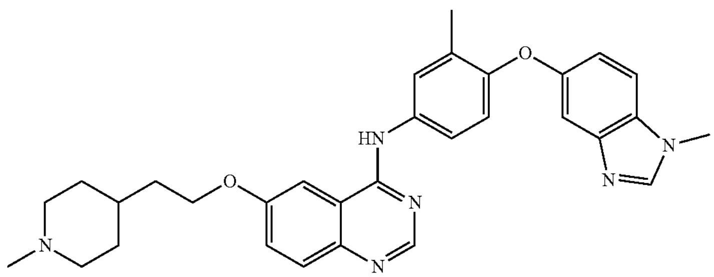 | 523.2 (M + 1) detected |
| 242 | 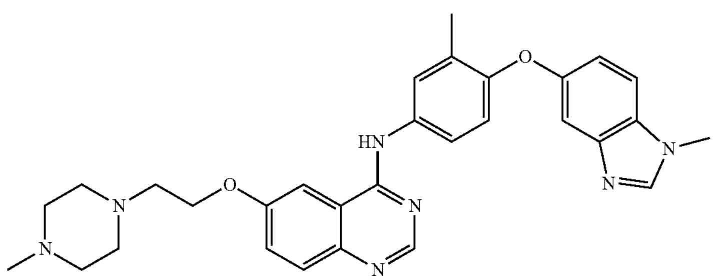 | 524.1 (M + 1) detected |
| 243 | 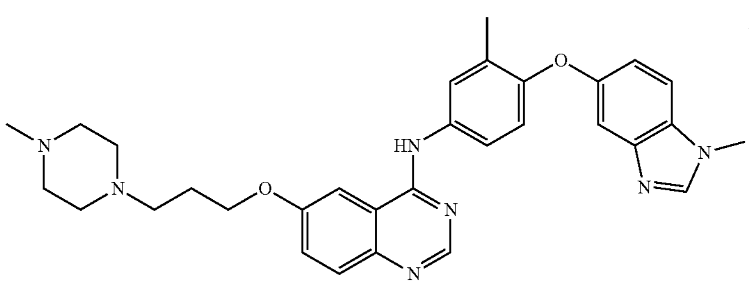 | 538.2 (M + 1) detected |
| 244 | 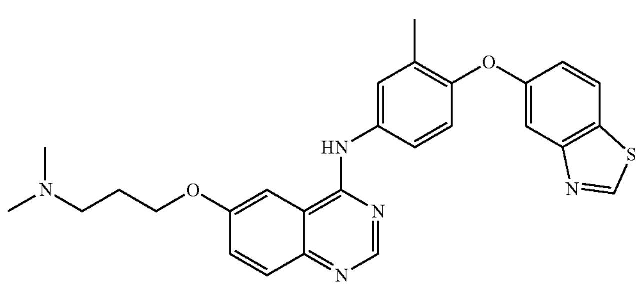 [SMILES: Cc1cc(Nc2ncnc3ccc(OCCCN(C)C)cc23)ccc1Oc1ccc2scnc2c1] | 486.1 (M + 1) detected |

| Ex. # | Structure | MS m/z |
|---|---|---|
| 245 | 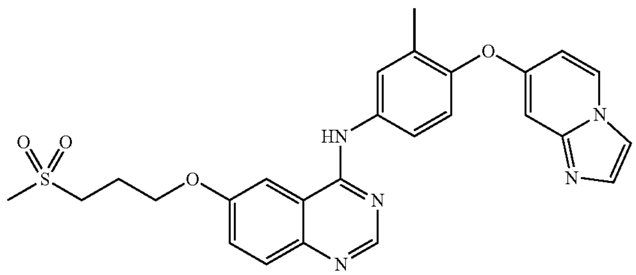 [SMILES: Cc1cc(Nc2ncnc3ccc(OCCCS(C)(=O)=O)cc23)ccc1Oc1ccn2ccnc2c1] | 504.3 (M + 1) detected |
| 246 | 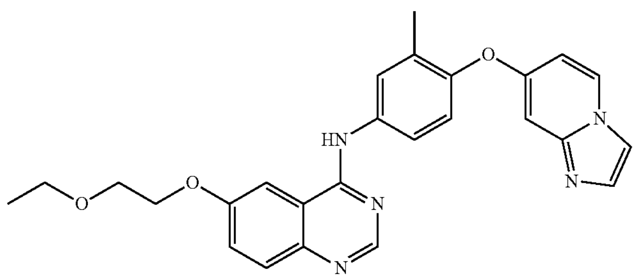 [SMILES: CCOCCOc1ccc2ncnc(Nc3ccc(Oc4ccn5ccnc5c4)c(C)c3)c2c1] | 456.4 (M + 1) detected |
| 247 | 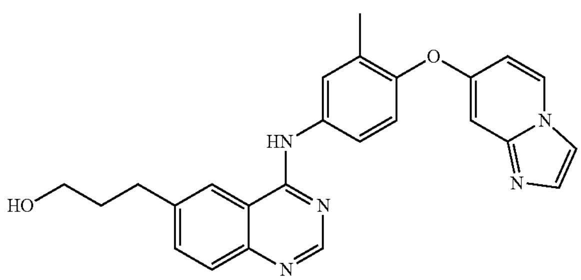 [SMILES: Cc1cc(Nc2ncnc3ccc(CCCO)cc23)ccc1Oc1ccn2ccnc2c1] | 426.4 (M + 1) detected |
| 248 | 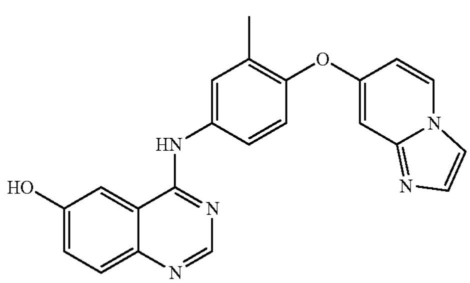 [SMILES: Cc1cc(Nc2ncnc3ccc(O)cc23)ccc1Oc1ccn2ccnc2c1] | 384.4 (M + 1) detected |
| 249 | 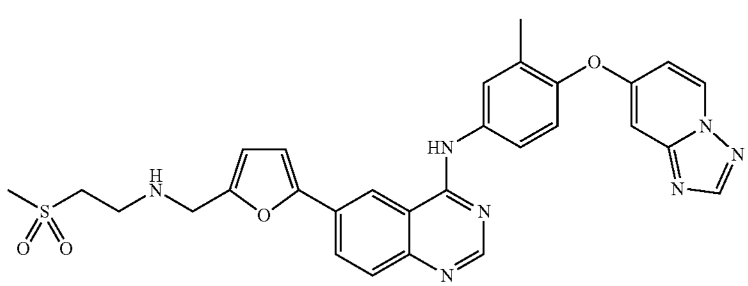 [SMILES: Cc1cc(Nc2ncnc3ccc(-c4ccc(CNCCS(C)(=O)=O)o4)cc23)ccc1Oc1ccn2ncnc2c1] | 570.0 (M + 1) detected |

-continued
| Ex. # | Structure | MS m/z |
|---|---|---|
| 250 | 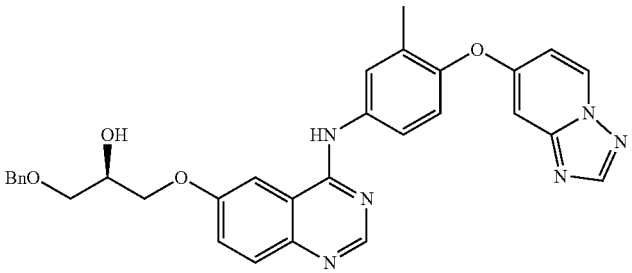 [SMILES: Cc1cc(Nc2ncnc3ccc(OC[C@H](O)COCc4ccccc4)cc23)ccc1Oc1ccn2ncnc2c1] | 549.2 (M + 1) detected |
| 251 | 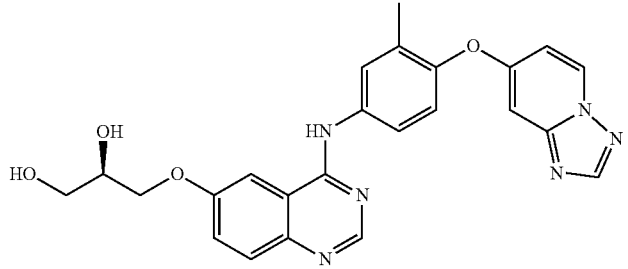 [SMILES: Cc1cc(Nc2ncnc3ccc(OC[C@H](O)CO)cc23)ccc1Oc1ccn2ncnc2c1] | 459.4 (M + 1) detected |
| 252 | 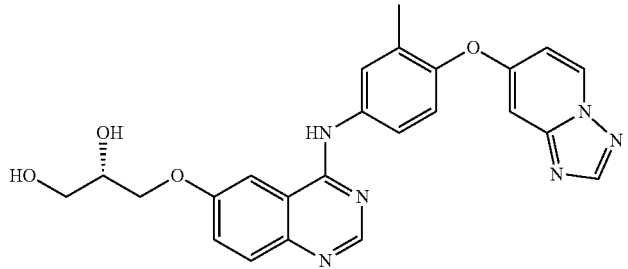 [SMILES: Cc1cc(Nc2ncnc3ccc(OC[C@@H](O)CO)cc23)ccc1Oc1ccn2ncnc2c1] | 459.4 (M + 1) detected |
| 253 | 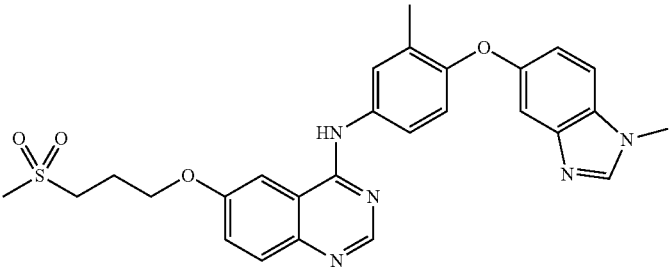 | 518.3 (M + 1) detected |
| 254 | 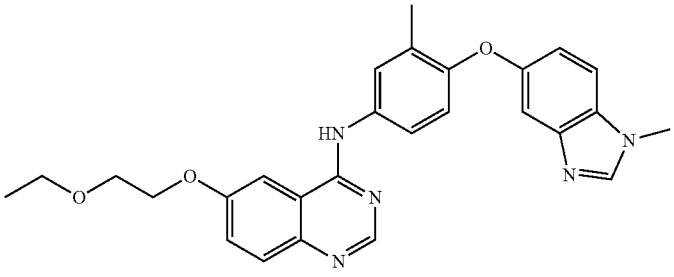 [SMILES: CCOCCOc1ccc2ncnc(Nc3ccc(Oc4ccc5c(c4)ncn5C)c(C)c3)c2c1] | 470.3 (M + 1) detected |

-continued

| Ex. # | Structure | MS m/z |
|---|---|---|
| 255 | 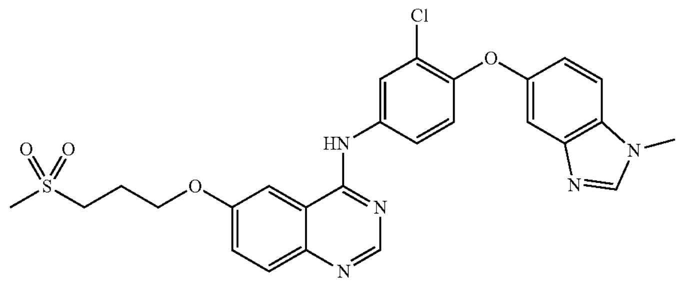 | 538.3, 540.2 (M+, Cl pattern) detected |
| 256 | 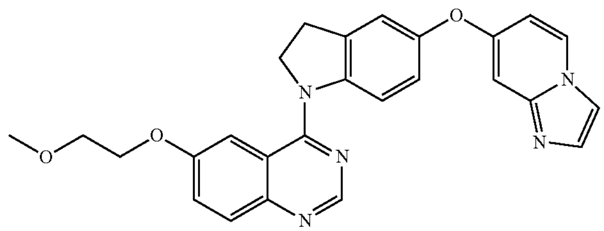 [SMILES: COCCOc1ccc2ncnc(N3CCc4cc(Oc5ccn6ccnc6c5)ccc43)c2c1] | 454.3 (M + 1) detected |
| 257 | 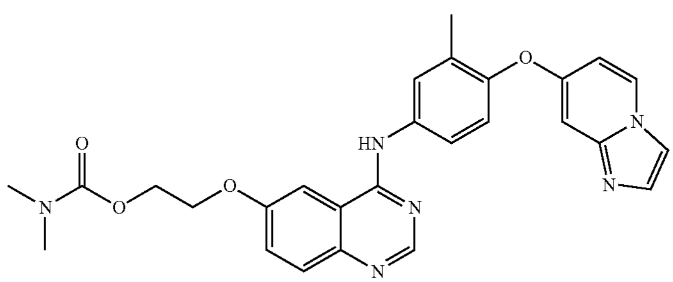 [SMILES: Cc1cc(Nc2ncnc3ccc(OCCOC(=O)N(C)C)cc23)ccc1Oc1ccn2ccnc2c1] | 499.2 (M + 1) detected |
| 258 | 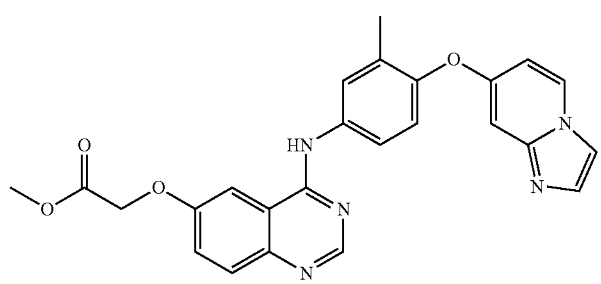 [SMILES: COC(=O)COc1ccc2ncnc(Nc3ccc(Oc4ccn5ccnc5c4)c(C)c3)c2c1] | 456.3 (M + 1) detected |
| 259 | 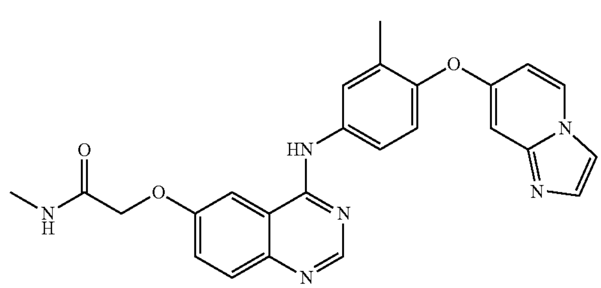 [SMILES: CNC(=O)COc1ccc2ncnc(Nc3ccc(Oc4ccn5ccnc5c4)c(C)c3)c2c1] | 455.2 (M + 1) detected |

-continued

| Ex. # | Structure | MS m/z |
|---|---|---|
| 260 | 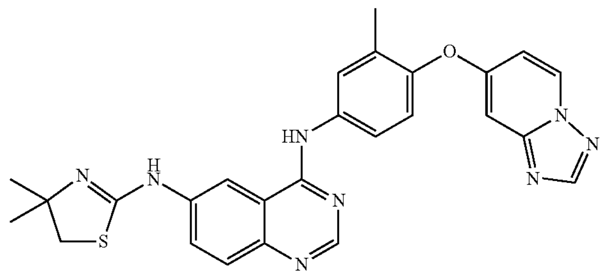 [SMILES: Cc1cc(Nc2ncnc3ccc(NC4=NC(C)(C)CS4)cc23)ccc1Oc1ccn2ncnc2c1] | 497.3 (M + 1) detected |
| 261 | 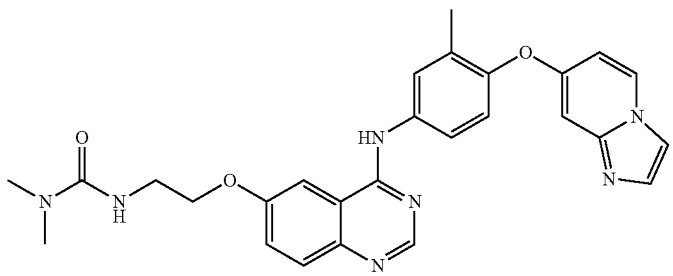 [SMILES: Cc1cc(Nc2ncnc3ccc(OCCNC(=O)N(C)C)cc23)ccc1Oc1ccn2ccnc2c1] | 498.1 (M + 1) detected |
| 262 | 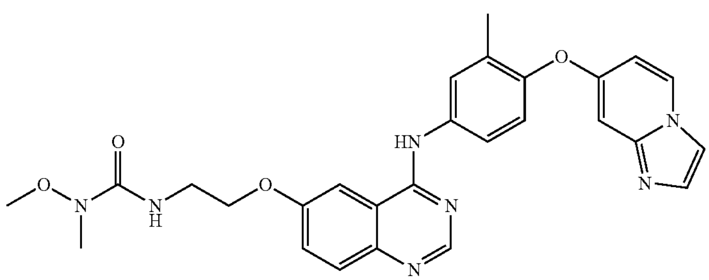 [SMILES: CON(C)C(=O)NCCOc1ccc2ncnc(Nc3ccc(Oc4ccn5ccnc5c4)c(C)c3)c2c1] | 514.1 (M + 1) detected |
| 263 | 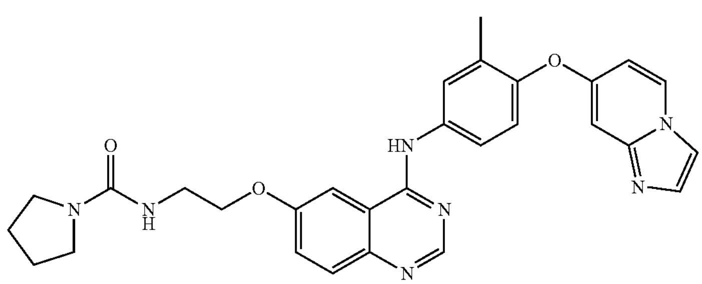 [SMILES: Cc1cc(Nc2ncnc3ccc(OCCNC(=O)N4CCCC4)cc23)ccc1Oc1ccn2ccnc2c1] | 524.0 (M + 1) detected |
| 264 | 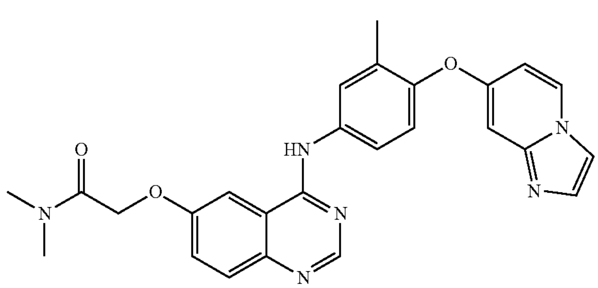 [SMILES: Cc1cc(Nc2ncnc3ccc(OCC(=O)N(C)C)cc23)ccc1Oc1ccn2ccnc2c1] | 469.2 (M + 1) detected |

-continued

| Ex. # | Structure | MS m/z |
|---|---|---|
| 265 | 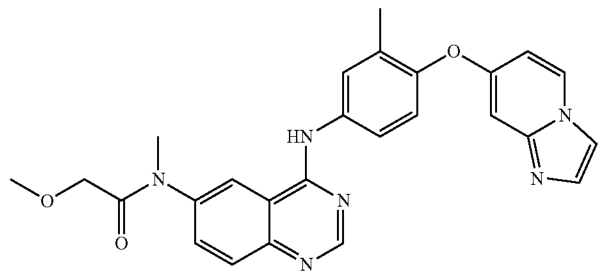 [SMILES: COCC(=O)N(C)c1ccc2ncnc(Nc3ccc(Oc4ccn5ccnc5c4)c(C)c3)c2c1] | 469.2 (M + 1) detected |
| 266 | 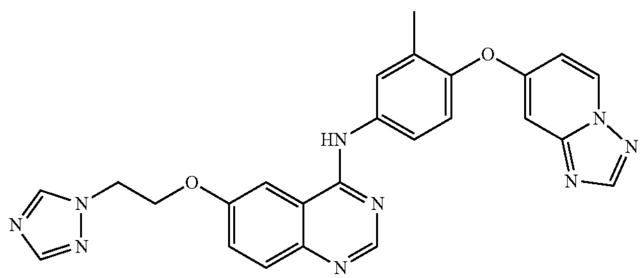 [SMILES: Cc1cc(Nc2ncnc3ccc(OCCn4cncn4)cc23)ccc1Oc1ccn2ncnc2c1] | 480.2 (M + 1) detected |
| 267 | 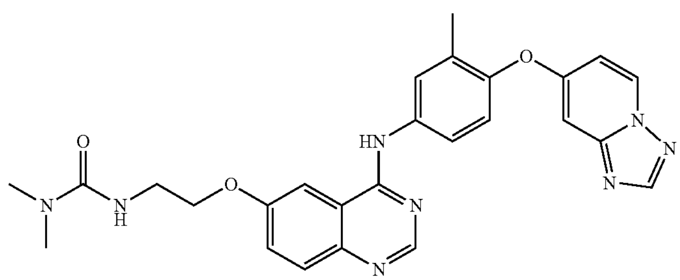 [SMILES: Cc1cc(Nc2ncnc3ccc(OCCNC(=O)N(C)C)cc23)ccc1Oc1ccn2ncnc2c1] | 499.1 (M + 1) detected |
| 268 | 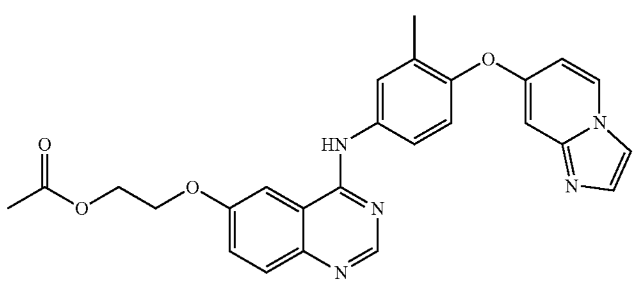 [SMILES: CC(=O)OCCOc1ccc2ncnc(Nc3ccc(Oc4ccn5ccnc5c4)c(C)c3)c2c1] | 470.2 (M + 1) detected |
| 269 | 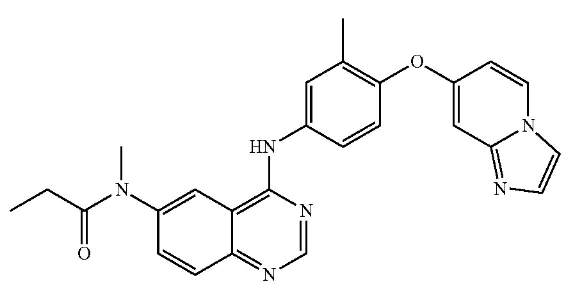 [SMILES: CCC(=O)N(C)c1ccc2ncnc(Nc3ccc(Oc4ccn5ccnc5c4)c(C)c3)c2c1] | 453.3 (M + 1) detected |

-continued
| Ex. # | Structure | MS m/z |
|---|---|---|
| 270 | 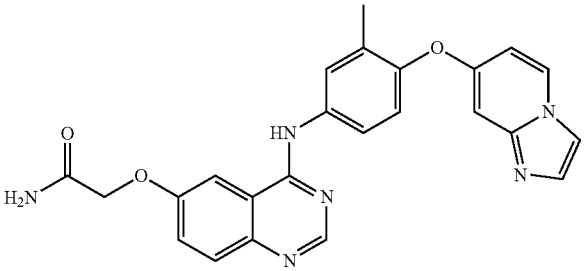 [SMILES: Cc1cc(Nc2ncnc3ccc(OCC(N)=O)cc23)ccc1Oc1ccn2ccnc2c1] | 441.2 (M + 1) detected |
| 271 | 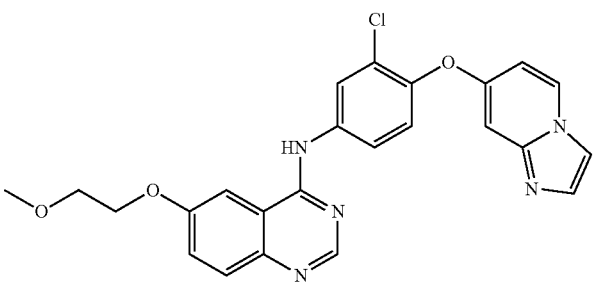 | 462.2, 464.2 (M+, Cl pattern) detected |
| 272 | 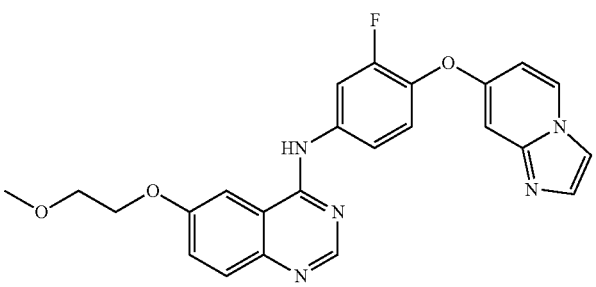 | 446.2 (M + 1) detected |
| 273 | 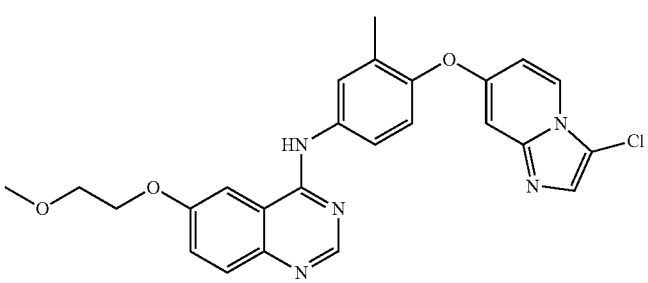 [SMILES: COCCOc1ccc2ncnc(Nc3ccc(Oc4ccn5c(Cl)cnc5c4)c(C)c3)c2c1] | 476.2, 478.1 (M+, Cl pattern) detected |
| 274 | 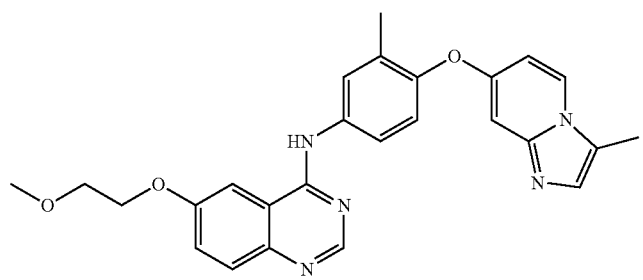 | 456.3 (M + 1) detected |

| Ex. # | Structure | MS m/z |
|---|---|---|
| 275 | 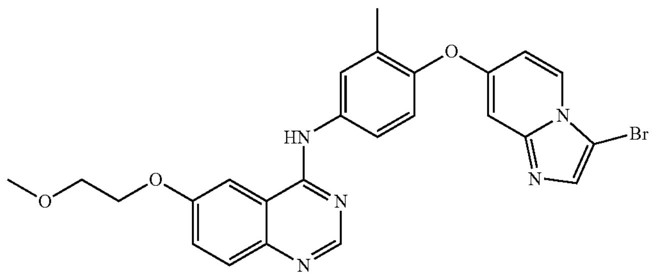 [SMILES: COCCOc1ccc2ncnc(Nc3ccc(Oc4ccn5c(Br)cnc5c4)c(C)c3)c2c1] | 522.1, 520.2 (M+, Br pattern) detected |
| 276 | 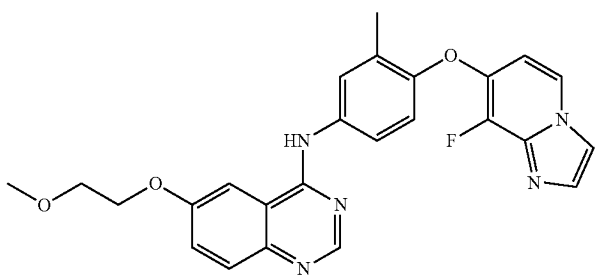 [SMILES: COCCOc1ccc2ncnc(Nc3ccc(Oc4ccn5ccnc5c4F)c(C)c3)c2c1] | 460.4 (M + 1) detected |
| 277 | 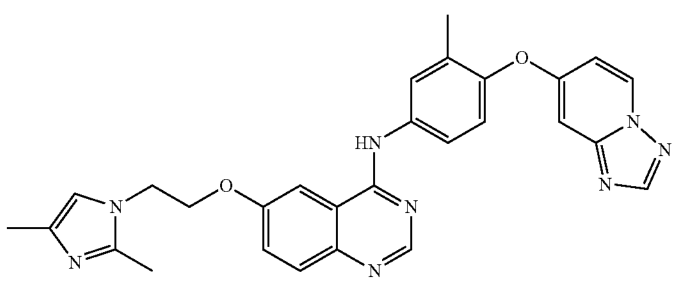 [SMILES: Cc1cn(CCOc2ccc3ncnc(Nc4ccc(Oc5ccn6ncnc6c5)c(C)c4)c3c2)c(C)n1] | 507.3 (M + 1) detected |
| 278 | 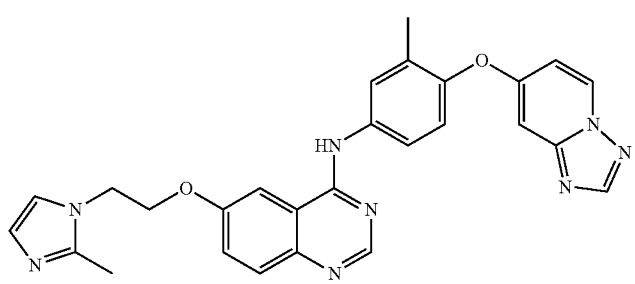 [SMILES: Cc1cc(Nc2ncnc3ccc(OCCn4ccnc4C)cc23)ccc1Oc1ccn2ncnc2c1] | 493.3 (M + 1) detected |
| 279 | 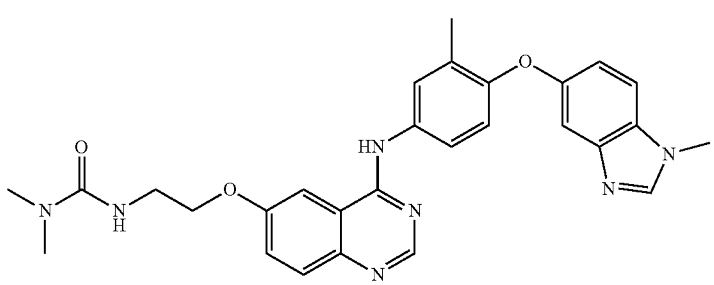 | 512.1 (M + 1) detected |

| Ex. # | Structure | MS m/z |
|---|---|---|
| 280 | 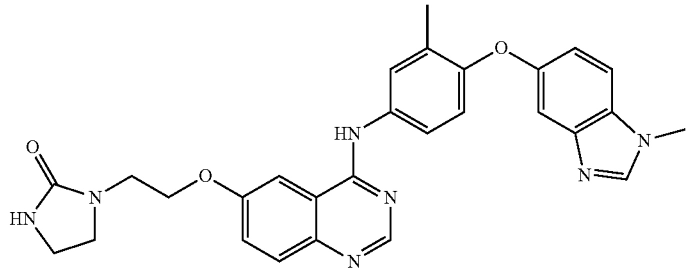 [SMILES: Cc1cc(Nc2ncnc3ccc(OCCN4CCNC4=O)cc23)ccc1Oc1ccc2c(c1)ncn2C] | 510.1 (M + 1) detected |
| 281 | 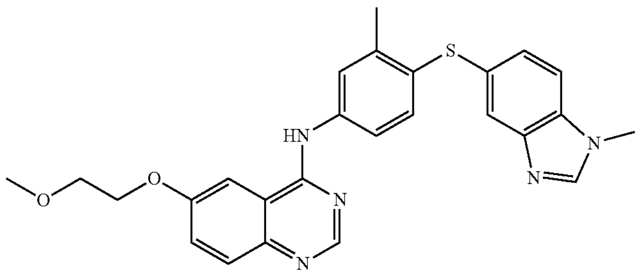 | 472.2 (M + 1) detected |

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound of Formula I

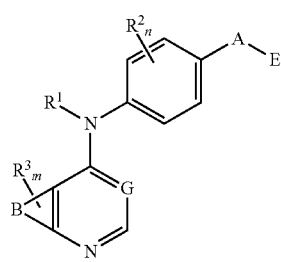

I or a pharmaceutically acceptable salt thereof, wherein:

A is O, C(=O), S, SO or $SO_2$;

G is N;

B represents a fused 6-membered aryl ring;

E is

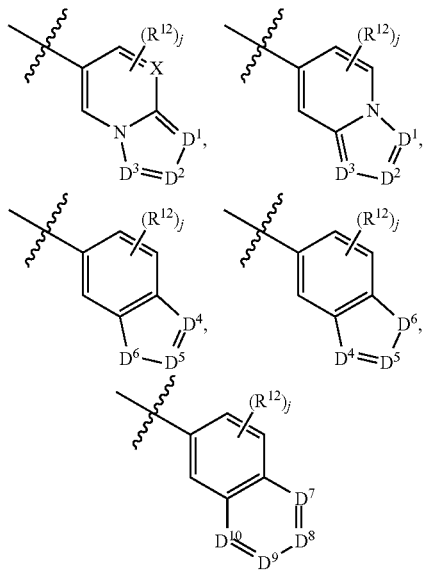

X is N or CH;

$D^1$, $D^2$ and $D^3$ are independently N or $CR^{19}$;

$D^4$ and $D^5$ are independently N or $CR^{19}$ and $D^6$ is O, S, or $NR^{20}$, wherein at least one of $D^4$ and $D^5$ is not $CR^{19}$;

$D^7$, $D^8$, $D^9$ and $D^{10}$ are independently N or $CR^{19}$, wherein at least one of $D^7$, $D^8$, $D^9$ and $D^{10}$ is N;

$R^1$ is H or alkyl;

each $R^2$ is independently halogen, cyano, nitro, trifluoromethyl, difluoromethyl, fluoromethyl, fluoromethoxy, difluoromethoxy, trifluoromethoxy, azido, —$SR^{18}$, —$OR^{15}$, —$C(O)R^{15}$, —$C(O)OR^{15}$, —$NR^{14}C(O)OR^{18}$, —$OC(O)R^{15}$, —$NR^{14}SO_2R^{18}$, —$SO_2NR^{15}R^{14}$, —NR$^{14}$C(O)R$^{15}$, —C(O)NR$^{15}$R$^{14}$, —NR$^{15}$C(O) NR$^{15}$R$^{14}$, —NR$^{13}$C(NCN)NR$^{15}$R$^{14}$, —NR$^{15}$R$^{14}$, alkyl, alkenyl, alkynyl, saturated or partially unsaturated cycloalkyl, cycloalkylalkyl, —S(O)$_p$(alkyl), —S(O)$_p$(CR$^{13}$R$^{14}$)$_q$-aryl, aryl, arylalkyl, heteroaryl, heteroarylalkyl, saturated or partially unsaturated heterocyclyl, heterocyclylalkyl, —O(CR$^{13}$R$^{14}$)$_q$-aryl, —NR$^{15}$(CR$^{13}$R$^{14}$)$_q$-aryl, —O(CR$^{13}$R$^{14}$)$_q$-heteroaryl, —NR$^{13}$(CR$^{13}$R$^{14}$)$_q$-heteroaryl, —O(CR$^{13}$R$^{14}$)$_q$heterocyclyl or —NR$^{15}$(CR$^{13}$R$^{14}$)$_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR$^{13}$SO$_2$R$^{18}$, —SO$_2$NR$^{15}$R$^{13}$, —C(O)R$^{15}$, —C(O)OR$^{15}$, —OC(O)R$^{15}$, —NR$^{13}$C(O)OR$^{18}$, —NR$^{13}$C(O)R$^{15}$, —C(O)NR$^{15}$R$^{13}$, —NR$^{15}$R$^{13}$, —NR$^{14}$C(O)NR$^{15}$R$^{13}$, —NR$^{14}$C(NCN)NR$^{15}$R$^{13}$, OR$^{15}$, aryl, heteroaryl, arylalkyl, heteroarylalkyl, saturated and partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, NR$^{15}$R$^{13}$ and OR$^{15}$;

each R$^3$ is independently Q, Z, halogen, cyano, nitro, alkyl, alkenyl, alkynyl, heteroalkyl, heteroalkenyl, heteroalkynyl, saturated or partially unsaturated cycloalkyl, saturated or partially unsaturated heterocyclyl, aryl, arylalkyl, heteroaryl, heteroarylalkyl, trifluoromethoxy, difluoromethoxy, fluoromethoxy, trifluoromethyl, difluoromethyl, fluoromethyl, OR$^{15}$, NR$^{15}$R$^{16}$, NR$^{15}$OR$^{16}$, NR$^{15}$C(═O)OR$^{18}$, NR$^{15}$C(═O)R$^{16}$, SO$_2$NR$^{15}$R$^{16}$, SR$^{15}$, SOR$^{15}$, SO$_2$R$^{15}$, C(═O)R$^{15}$, C(═O)OR$^{15}$, OC(═O)R$^{15}$, C(═O)NR$^{15}$R$^{16}$, NR$^{15}$C(O)NR$^{16}$R$^{17}$, NR$^{15}$C(═NCN)NR$^{16}$R$^{17}$, or NR$^{15}$C(═NCN)R$^{16}$, wherein said alkyl, alkenyl, alkynyl, heteroalkyl, heteroalkenyl, heteroalkynyl, cycloalkyl, heterocyclyl, aryl, arylalkyl, heteroaryl and heteroarylalkyl are optionally substituted with one or more groups independently selected from halogen, oxo, cyano, nitro, alkyl, alkenyl, alkynyl, heteroalkyl, heteroalkenyl, heteroalkynyl, saturated or partially unsaturated cycloalkyl, saturated and partially unsaturated heterocyclyl, aryl, arylalkyl, heteroaryl, heteroarylalkyl, trifluoromethoxy, difluoromethoxy, fluoromethoxy, trifluoromethyl, difluoromethyl, fluoromethyl, OR$^{15}$, NR$^{15}$R$^{16}$, NR$^{15}$OR$^{16}$, NR$^{15}$C(═O)OR$^{18}$, NR$^{15}$C(═O)R$^{16}$, SO$_2$NR$^{15}$R$^{16}$, SR$^{15}$, SOR$^{15}$, SO$_2$R$^{15}$, C(═O)R$^{15}$, C(═O)OR$^{15}$, OC(═O)R$^{15}$, C(═O)NR$^{15}$R$^{16}$, NR$^{15}$C(═O)NR$^{16}$R$^{17}$, NR$^{15}$C(═NCN)NR$^{16}$R$^{17}$, NR$^{15}$C(═NCN)R$^{16}$, (C$_1$-C$_4$ alkyl)NR$^a$R$^b$ and NR$^{15}$C(O)CH$_2$OR$^a$;

or R$^3$ is a 5-6 membered heterocyclic ring containing from 1 to 4 heteroatoms selected from N, O, S, SO and SO$_2$ and substituted with -M$^1$-M$^2$-M$^3$-M$^4$ or -M$^1$-M$^5$, wherein M$^1$ is C$_1$-C$_4$ alkyl, wherein optionally a CH$_2$ is replaced by a C(═O) group; M$^2$ is NR$^e$ or CR$^e$R$^f$; M$^3$ is C$_1$-C$_4$ alkyl; M$^4$ is CN, NR$^e$S(O)$_{0-2}$R$^f$, S(O)$_{0-2}$NR$^g$R$^h$, COR$^g$R$^h$, S(O)$_{0-2}$R$^f$, or CO$_2$R$^f$, and M$^5$ is NR$^g$R$^h$, wherein R$^e$, R$^f$, R$^g$ and R$^h$ are independently H or C$_1$-C$_4$ alkyl, or R$^g$ and R$^h$ together with the nitrogen atom to which they are attached form a 5- or 6-membered ring optionally containing 1 or 2 additional heteroatoms selected from N, O, S, SO and SO$_2$ in which any ring nitrogen atom present is optionally substituted with a C$_1$-C$_4$ alkyl group and which ring may optionally have one or two oxo or thiooxo substituents;

Q is

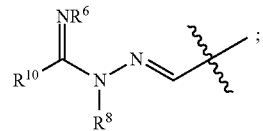

Z is selected from

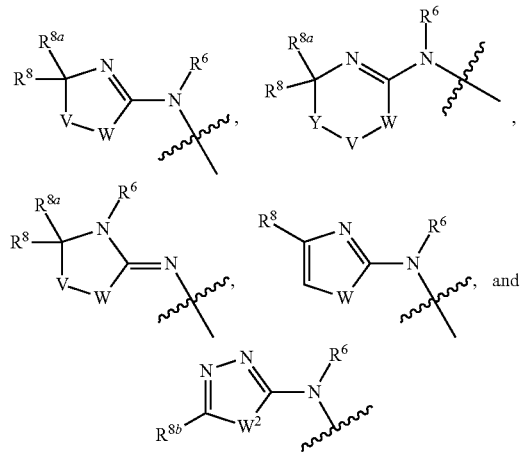

and tautomers thereof;

W and V are independently O, NR$^6$, S, SO, SO$_2$, CR$^7$R$^8$, CR$^8$R$^9$ or C═O;

W$^2$ is O or S;

Y is S, SO, SO$_2$, CR$^7$CR$^8$, or CR$^8$R$^9$, provided that when W is O, NR$^6$, S, SO, or SO$_2$, then V is CR$^8$R$^9$, and when V is O, NR$^6$, S, SO, or SO$_2$, then W and Y are each CR$^8$R$^9$;

R$^{8b}$ is H or C$_1$-C$_6$ alkyl;

each R$^6$, R$^8$, R$^{8a}$ and R$^9$ are independently hydrogen, trifluoromethyl, alkyl, saturated or partially unsaturated cycloalkyl, saturated or partially unsaturated heterocyclyl, aryl, arylalkyl, heteroaryl, heteroarylalkyl, or heterocyclylalkyl, wherein said alkyl, cycloalkyl, heterocyclyl, aryl, arylalkyl, heteroaryl, heteroarylalkyl, and heterocyclylalkyl are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, OR$^{15}$, NR$^{15}$R$^{16}$, SR$^{15}$, S(═O)R$^{15}$, SO$_2$R$^{15}$, trifluoromethyl, difluoromethyl, fluoromethyl, fluoromethoxy, difluoromethoxy, trifluoromethoxy, azido, aryl, heteroaryl, arylalkyl, heteroarylalkyl, and heterocyclylalkyl, or R$^8$ and R$^{8a}$ together with the atom to which they are attached form a 3 to 6 membered carbocyclic ring;

R$^7$ is hydrogen, halogen, cyano, nitro, alkyl, alkenyl, alkynyl, saturated or partially unsaturated cycloalkyl, saturated or partially unsaturated heterocyclyl, cycloalkylalkyl, aryl, arylalkyl, heteroaryl, heteroarylalkyl, heterocyclylalkyl, —$NR^{15}SO_2R^{16}$, —$SO_2NR^{15}R^{16}$, —$C(O)R^{15}$, —$C(O)OR^{15}$, —$OC(O)R^{15}$, —$NR^{15}C(O)OR^{18}$, —$NR^{15}C(O)R^{16}$, —$C(O)NR^{15}R^{16}$, —$NR^{15}R^{16}$, —$NR^{15}C(O)NR^{16}R^{17}$, —$OR^{15}$, —$S(O)R^{15}$, —$SO_2R^{15}$, or $SR^{15}$, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, —$NR^{15}SO_2R^{16}$, $SO_2NR^{15}R^{16}$, —$C(O)R^{15}$, —$C(O)OR^{15}$, —$OC(O)R^{15}$, —$NR^{15}C(O)OR^{18}$, —$NR^{15}C(O)R^{16}$, —$C(O)NR^{15}R^{16}$, —$NR^{15}R^{16}$, —$NR^{15}C(O)NR^{16}R^{17}$, —$OR^{15}$, —$S(O)R^{15}$, —$SO_2R^{15}$, $SR^{15}$, aryl, arylalkyl, heteroaryl, heteroarylalkyl, and heterocyclylalkyl;

$R^{10}$ is hydrogen, alkyl, alkenyl, alkynyl, saturated or partially unsaturated cycloalkyl, saturated or partially unsaturated heterocyclyl, cycloalkylalkyl, aryl, arylalkyl, heteroaryl, heteroarylalkyl, heterocyclylalkyl, —$NR^{15}C(O)OR^{18}$, —$NR^{15}C(O)R^{16}$, —$NR^{15}R^{16}$, or —$OR^{15}$, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, —$NR^{15}SO_2R^{16}$, —$SO_2NR^{15}R^{16}$, —$C(O)R^{15}$, —$C(O)OR^{15}$, —$OC(O)R^{15}$, —$NR^{15}C(O)OR^{18}$, —$NR^{15}C(O)R^{16}$, —$C(O)NR^{15}R^{16}$, —$NR^{15}R^{16}$, —$NR^{15}C(O)NR^{16}R^{17}$, —$OR^{15}$, —$S(O)R^{15}$, —$SO_2R^{15}$, $SR^{15}$, aryl, arylalkyl, heteroaryl, heteroarylalkyl, and heterocyclylalkyl;

or $R^6$ and $R^8$ together with the atoms to which they are attached form a 3 to 10 membered saturated or partially unsaturated heterocyclyl ring optionally containing one or more additional heteroatoms selected from N, O, S, SO, $SO_2$ and $NR^6$, wherein said carbocyclic and heterocyclic rings are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^{15}$, $NR^{15}R^{16}$, $SR^{15}$, heteroaryl, arylalkyl, heteroarylalkyl, and heterocyclylalkyl;

or $R^7$ and $R^8$ together with the atoms to which they are attached form a 3 to 10 membered saturated or partially unsaturated cycloalkyl or heterocyclyl ring optionally containing one or more additional heteroatoms selected from N, O, S, SO, $SO_2$ and $NR^6$, wherein said carbocyclic and heterocyclic rings are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^{15}$, $NR^{15}R^{16}$, $SR^{15}$, heteroaryl, arylalkyl, heteroarylalkyl, and heterocyclylalkyl;

or $R^8$ and $R^9$ together with the atoms to which they are attached form a 3 to 10 membered saturated or partially unsaturated cycloalkyl or heterocyclyl ring optionally containing one or more additional heteroatoms selected from N, O, S, SO, $SO_2$ and $NR^6$, wherein said carbocyclic and heterocyclic rings are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^{15}$, $NR^{15}R^{16}$, $SR^{15}$, heteroaryl, arylalkyl, heteroarylalkyl, and heterocyclylalkyl;

or $R^6$ and $R^{10}$ together with the atoms to which they are attached form a 3 to 10 membered saturated or partially unsaturated heterocyclyl ring optionally containing one or more additional heteroatoms selected from N, O, S, SO, $SO_2$ and $NR^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^{15}$, $NR^{15}R^{16}$, $SR^{15}$, heteroaryl, arylalkyl, heteroarylalkyl, and heterocyclylalkyl;

or $R^8$ and $R^{10}$ together with the atoms to which they are attached form a 3 to 10 membered saturated or partially unsaturated heterocyclyl ring optionally containing one or more additional heteroatoms selected from N, O, S, SO, $SO_2$ and $NR^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^{15}$, $NR^{15}R^{16}$, $SR^{15}$, heteroaryl, arylalkyl, heteroarylalkyl, and heterocyclylalkyl;

each $R^{12}$ is independently halogen, cyano, nitro, trifluoromethyl, difluoromethyl, fluoromethyl, fluoromethoxy, difluoromethoxy, trifluoromethoxy, azido, —$SR^{18}$, —$OR^{15}$, —$C(O)R^{15}$, —$C(O)OR^{15}$, —$NR^{14}C(O)OR^{18}$, —$OC(O)R^{15}$, —$NR^{14}SO_2R^{18}$, —$SO_2NR^{15}R^{14}$, —$NR^{14}C(O)R^{15}$, —$C(O)NR^{15}R^{14}$, —$NR^{13}C(O)NR^{15}R^{14}$, —$NR^{13}C(NCN)NR^{15}R^{14}$, —$NR^{15}R^{14}$, alkyl, alkenyl, alkynyl, saturated or partially unsaturated cycloalkyl, cycloalkylalkyl, —$S(O)_p$(alkyl), —$S(O)_p(CR^{13}R^{14})_q$-aryl, aryl, arylalkyl, heteroaryl, heteroarylalkyl, saturated or partially unsaturated heterocyclyl, heterocyclylalkyl, —$O(CR^{13}R^{14})_q$-aryl, —$NR^{15}(CR^{13}R^{14})_q$-aryl, —$O(CR^{13}R^{14})_q$-heteroaryl, —$NR^{13}(CR^{13}R^{14})_q$-heteroaryl, —$O(CR^{13}R^{14})_q$-heterocyclyl or —$NR^{15}(CR^{13}R^{14})_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^{13}SO_2R^{18}$, —$SO_2NR^{15}R^{13}$, —$C(O)R^{15}$, —$C(O)OR^{15}$, —$OC(O)R^{15}$, —$NR^{13}C(O)OR^{18}$, —$NR^{13}C(O)R^{15}$, —$C(O)NR^{15}R^{13}$, —$NR^{15}R^{13}$, —NR$^{14}$C(O)NR$^{15}$R$^{13}$, —NR$^{14}$C(NCN)NR$^{15}$R$^{13}$, —OR$^{15}$, aryl, heteroaryl, arylalkyl, heteroarylalkyl, saturated and partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, NR$^{15}$R$^{13}$ and OR$^{15}$;

R$^{13}$ and R$^{14}$ are independently hydrogen or alkyl, or

R$^{13}$ and R$^{14}$ together with the atoms to which they are attached form a saturated or partially unsaturated cycloalkyl, or saturated or partially unsaturated heterocyclyl ring, wherein said alkyl, cycloalkyl and heterocyclyl portions are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, OR$^a$, NR$^a$R$^b$, NR$^a$OR$^b$, NR$^a$CO$_2$R$^b$, NR$^a$COR$^b$, SO$_2$NR$^a$R$^b$, SR$^a$, SOR$^a$, SO$_2$R$^a$, S—S—R$^a$, C(=O)R$^a$, C(=O)OR$^a$, OC(=O)R$^a$, C(=O)NR$^a$R$^b$, NR$^a$C(=O)R$^b$, and NR$^a$C(=O)NR$^b$R$^c$;

R$^{15}$, R$^{16}$ and R$^{17}$ are independently H, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, OR$^a$, NR$^a$R$^b$, NR$^a$OR$^b$, NR$^a$CO$_2$R$^b$, NR$^a$COR$^b$, SO$_2$NR$^a$R$^b$, SR$^a$, SOR$^a$, SO$_2$R$^a$, S—S—R$^a$, C(=O)R$^a$, C(=O)OR$^a$, OC(=O)R$^a$, C(=O)NR$^a$R$^b$, NR$^a$C(=O)R$^b$, NR$^a$C(=O)NR$^b$R$^c$, OC(=O)NR$^a$R$^b$, and C(=O)CH$_2$OR$^a$;

or any two of R$^{15}$, R$^{16}$ and R$^{17}$ together with the atom to which they are attached form a heterocyclic ring optionally containing one or more additional heteroatoms selected from N, O, S, SO, SO$_2$ and NR$^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, OR$^a$, NR$^a$R$^b$, SR$^a$, heteroaryl, arylalkyl, heteroarylalkyl, and heterocyclylalkyl, or R$^{13}$ and R$^{15}$ together with the atom to which they are attached form a saturated or partially unsaturated cycloalkyl or saturated or partially unsaturated heterocyclyl ring, wherein said cycloalkyl and heterocyclyl are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, OR$^a$, NR$^a$R$^b$, NR$^a$OR$^b$, NR$^a$CO$_2$R$^b$, NR$^a$COR$^b$, SO$_2$NR$^a$R$^b$, SR$^a$, SOR$^a$, SO$_2$R$^a$, S—S—R$^a$, C(=O)R$^a$, C(=O)OR$^a$, OC(=O)R$^a$, C(=O)NR$^a$R$^b$, NR$^a$C(=O)R$^b$, and NR$^a$C(=O)NR$^b$R$^c$;

R$^{18}$ is CF$_3$, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, saturated or partially unsaturated heterocyclyl, cycloalkylalkyl, aryl, arylalkyl, heteroaryl, heteroarylalkyl and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, OR$^a$, NR$^a$R$^b$, NR$^a$OR$^b$, NR$^a$CO$_2$R$^b$, NR$^a$COR$^b$, SO$_2$NR$^a$R$^b$, SR$^a$, SOR$^a$, SO$_2$R$^a$, S—S—R$^a$, C(=O)R$^a$, C(=O)OR$^a$, OC(=O)R$^a$, C(=O)NR$^a$R$^b$, NR$^a$C(=O)R$^b$, and NR$^a$C(=O)NR$^b$R$^c$, or R$^{15}$ and R$^{18}$ together with the atoms to which they are attached form a saturated or partially unsaturated cycloalkyl or saturated or partially unsaturated heterocyclyl ring, wherein said cycloalkyl and heterocyclyl are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, OR$^a$, NR$^a$R$^b$, NR$^a$OR$^b$, NR$^a$CO$_2$R$^b$, NR$^a$COR$^b$, SO$_2$NR$^a$R$^b$, SR$^a$, SOR$^a$, SO$_2$R$^a$, S—S—R$^a$, C(=O)R$^a$, C(=O)OR$^a$, OC(=O)R$^a$, C(=O)NR$^a$R$^b$, NR$^a$C(=O)R$^b$, and NR$^a$C(=O)NR$^b$R$^c$;

each R$^{19}$ is independently H, halogen, cyano, nitro, trifluoromethyl, difluoromethyl, fluoromethyl, fluoromethoxy, difluoromethoxy, trifluoromethoxy, azido, —SR$^{18}$, —OR$^{15}$, —C(O)R$^{15}$, —C(O)OR$^{15}$, —NR$^{14}$C(O)OR$^{18}$, —OC(O)R$^{15}$, —NR$^{14}$SO$_2$R$^{18}$, —SO$_2$NR$^{15}$R$^{14}$, —NR$^{14}$C(O)R$^{15}$, —C(O)NR$^{15}$R$^{14}$, —NR$^{13}$C(O)NR$^{15}$R$^{14}$, —NR$^{13}$C(NCN)NR$^{15}$R$^{14}$, —NR$^{15}$R$^{14}$ alkyl, alkenyl, alkynyl, saturated or partially unsaturated cycloalkyl, cycloalkylalkyl, —S(O)$_p$(alkyl), —S(O)$_p$(CR$^{13}$R$^{14}$)$_q$-aryl, aryl, arylalkyl, heteroaryl, heteroarylalkyl, saturated or partially unsaturated heterocyclyl, heterocyclylalkyl, —O(CR$^{13}$R$^{14}$)$_q$-aryl, —NR$^{15}$(CR$^{13}$R$^{14}$)$_q$-aryl, —O(CR$^{13}$R$^{14}$)$_q$-heteroaryl, —NR$^{13}$(CR$^{13}$R$^{14}$)$_q$-heteroaryl, —O(CR$^{13}$R$^{14}$)$_q$-heterocyclyl or —NR$^{15}$(CR$^{13}$R$^{14}$)$_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR$^{13}$SO$_2$R$^{18}$, —SO$_2$NR$^{15}$R$^{13}$, —C(O)R$^{15}$, —C(O)OR$^{15}$, —OC(O)R$^{15}$, —NR$^{13}$C(O)OR$^{18}$, —NR$^{13}$C(O)R$^{15}$, —C(O)NR$^{15}$R$^{13}$, —NR$^{15}$R$^{13}$, —NR$^{14}$C(O)NR$^{15}$R$^{13}$, —NR$^{14}$C(NCN)NR$^{15}$R$^{13}$, —OR$^{15}$, aryl, heteroaryl, arylalkyl, heteroarylalkyl, saturated or partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, NR$^{15}$R$^{13}$ and OR$^{15}$;

each $R^{20}$ is independently $C_1$-$C_4$ alkyl, saturated or partially unsaturated cycloalkyl, trifluoromethyl, difluoromethyl, or fluoromethyl;

$R^a$, $R^b$ and $R^c$ are independently H, alkyl, alkenyl, alkynyl, saturated or partially unsaturated cycloalkyl, saturated or partially unsaturated heterocyclyl, aryl, or heteroaryl, or $NR^aR^b$ forms a 5-6 membered heterocyclic ring having 1-2 ring nitrogen atoms and optionally substituted with ($C_1$-$C_3$ alkyl), or $NR^bR^c$ forms a 5-6 membered heterocyclic ring having 1-2 ring nitrogen atoms;

j is 0, 1, 2 or 3;

m is 1, 2, 3, or 4;

n is 0, 1, 2, 3, or 4;

q is 0, 1, 2, 3, 4, or 5; and p is 0, 1 or 2;

wherein when said compound of Formula I is represented by the formula

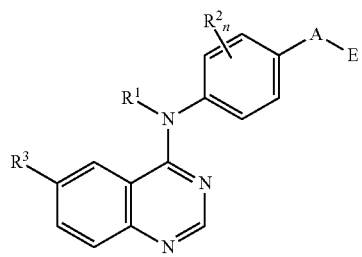

and $R^3$ is other than Q or Z, then E is not a benzofuranyl, indolyl, quinazolinyl, quinolinyl, or isoquinolinyl ring.

2. The compound of claim 1, wherein:

each $R^3$ is independently Q, Z, halogen, cyano, nitro, alkyl, alkenyl, alkynyl, heteroalkyl, heteroalkenyl, heteroalkynyl, saturated or partially unsaturated cycloalkyl, saturated or partially unsaturated heterocyclyl, aryl, arylalkyl, heteroaryl, heteroarylalkyl, trifluoromethoxy, difluoromethoxy, fluoromethoxy, trifluoromethyl, difluoromethyl, fluoromethyl, $OR^{15}$, $NR^{15}R^{16}$, $NR^{15}OR^{16}$, $NR^{15}C(=O)OR^{18}$, $NR^{15}C(=O)R^{16}$, $SO_2NR^{15}R^{16}$, $SR^{15}$, $SOR^{15}$, $SO_2R^{15}$, $C(=O)R^{15}$, $C(=O)OR^{15}$, $OC(=O)R^{15}$, $C(=O)NR^{15}R^{16}$, $NR^{15}C(=O)NR^{16}R^{17}$, $NR^{15}C(=NCN)NR^{16}R^{17}$, or $NR^{15}C(=NCN)R^{16}$, wherein said alkyl, alkenyl, alkynyl, heteroalkyl, heteroalkenyl, heteroalkynyl, cycloalkyl, heterocyclyl, aryl, arylalkyl, heteroaryl and heteroarylalkyl are optionally substituted with one or more groups independently selected from halogen, oxo, cyano, nitro, alkyl, alkenyl, alkynyl, heteroalkyl, heteroalkenyl, heteroalkynyl, saturated or partially unsaturated cycloalkyl, saturated and partially unsaturated heterocyclyl, aryl, arylalkyl, heteroaryl, heteroarylalkyl, trifluoromethoxy, difluoromethoxy, fluoromethoxy, trifluoromethyl, difluoromethyl, fluoromethyl, $OR^{15}$, $NR^{15}R^{16}$, $NR^{15}OR^{16}$, $NR^{15}C(=O)OR^{18}$, $NR^{15}C(=O)R^{16}$, $SO_2NR^{15}R^{16}$, $SR^{15}$, $SOR^{15}$, $SO_2R^{15}$, $C(=O)R^{15}$, $C(=O)OR^{15}$, $OC(=O)R^{15}$, $C(=O)NR^{15}R^{16}$, $NR^{15}C(=O)NR^{16}R^{17}$, $NR^{15}C(=NCN)NR^{16}R^{17}$, and $NR^{15}C(=NCN)R^{16}$;

Z is selected from

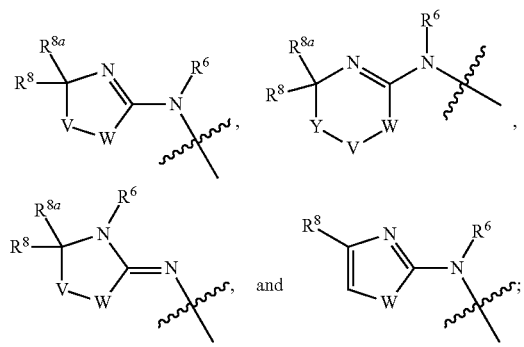

each $R^6$, $R^8$, $R^{8a}$ and $R^9$ are independently hydrogen, trifluoromethyl, alkyl, saturated or partially unsaturated cycloalkyl, saturated or partially unsaturated heterocyclyl, aryl, arylalkyl, heteroaryl, heteroarylalkyl, or heterocyclylalkyl, wherein said alkyl, cycloalkyl, heterocyclyl, aryl, arylalkyl, heteroaryl, heteroarylalkyl, and heterocyclylalkyl are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, $OR^{15}$, $NR^{15}R^{16}$, $SR^{15}S(=O)R^{15}$, $SO_2R^{15}$, trifluoromethyl, difluoromethyl, fluoromethyl, fluoromethoxy, difluoromethoxy, trifluoromethoxy, azido, aryl, heteroaryl, arylalkyl, heteroarylalkyl, and heterocyclylalkyl;

$R^{15}$, $R^{16}$ and $R^{17}$ are independently H, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, $C(=O)R^a$, $C(=O)OR^a$, $OC(=O)R^a$, $C(=O)NR^aR^b$, $NR^aC(=O)R^b$, and $NR^aC(=O)NR^bR^c$; and $R^a$, $R^b$ and $R^c$ are independently H, alkyl, alkenyl, alkynyl, saturated or partially unsaturated cycloalkyl, saturated or partially unsaturated heterocyclyl, aryl, or heteroaryl.

3. A compound of claim 1, wherein G is N and A is O or S.

4. A compound according to claim 1 having the formula

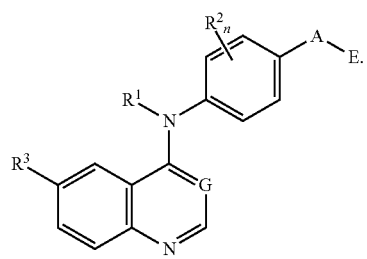

5. A compound according to claim 1, wherein E is selected from
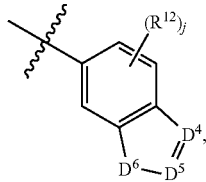 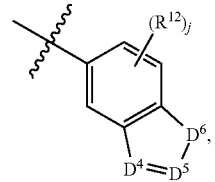 and
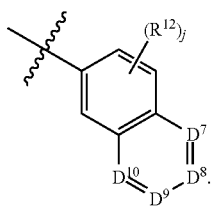
6. The compound of claim 5, wherein E is selected from structures:
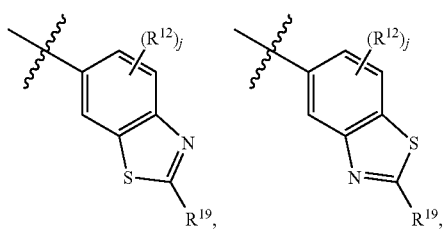
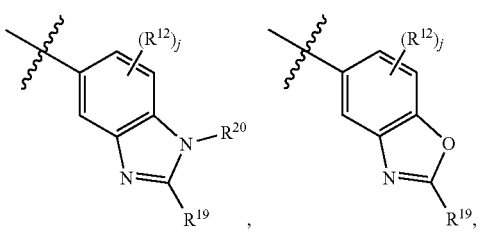
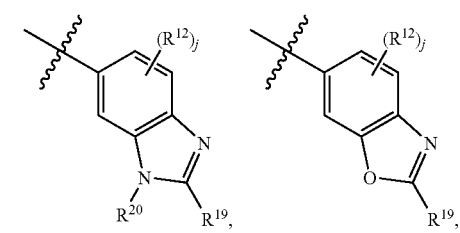
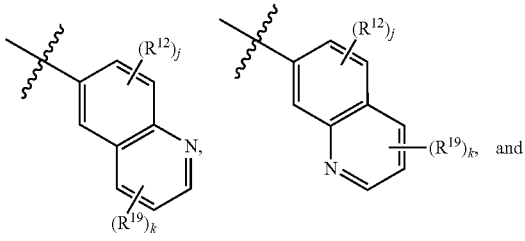
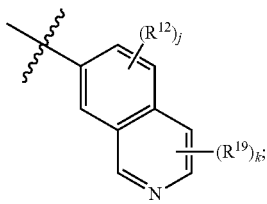
wherein k is 0, 1, 2, or 3.
7. The compound of claim 6, wherein E is selected from the structures:
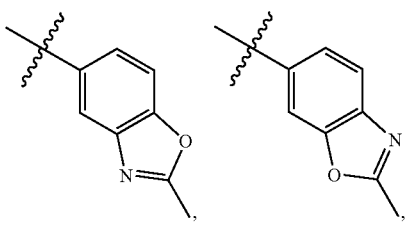
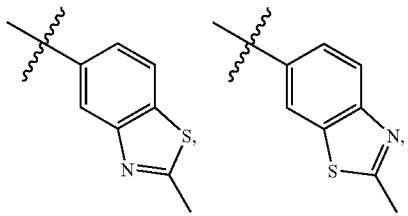
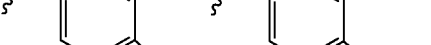
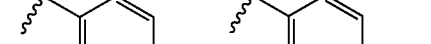
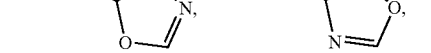

8. A compound according to claim 1, wherein E is selected from

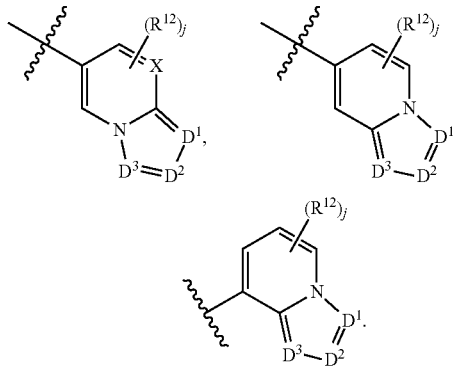

and

9. The compound of claim 8, wherein E is selected from the structures:

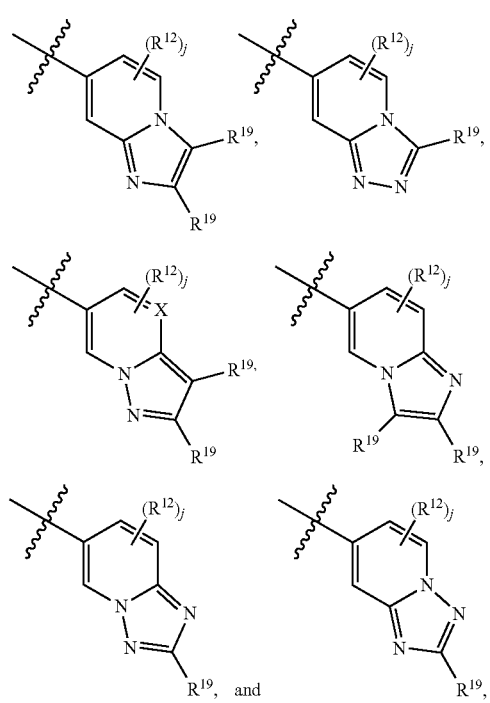

wherein each $R^{12}$ group and each $R^{19}$ group is independent of the other.

10. The compound of claim 9, wherein E is selected from:

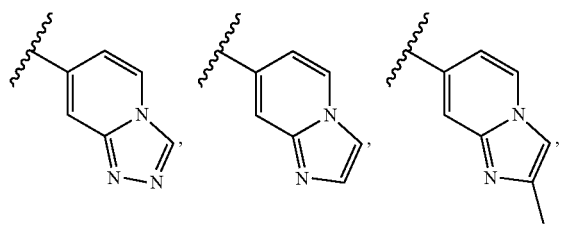

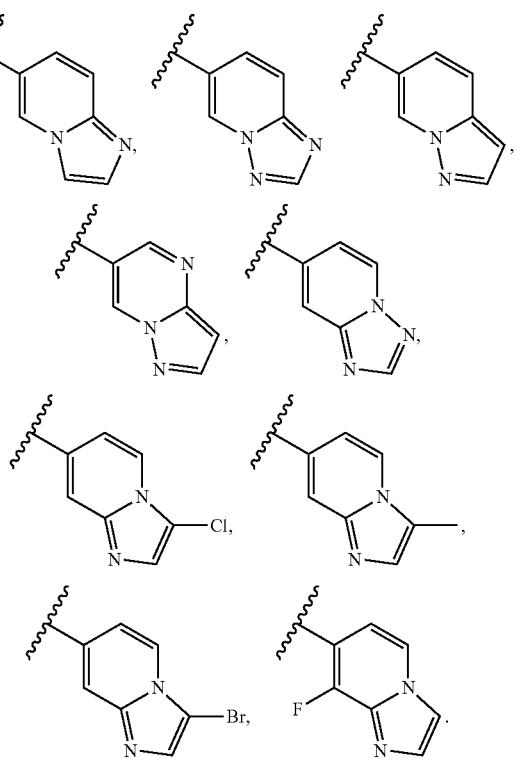

11. A compound according to claim 1, wherein m is 1 and $R^3$ is Z.

12. The compound of claim 11, wherein Z is selected from

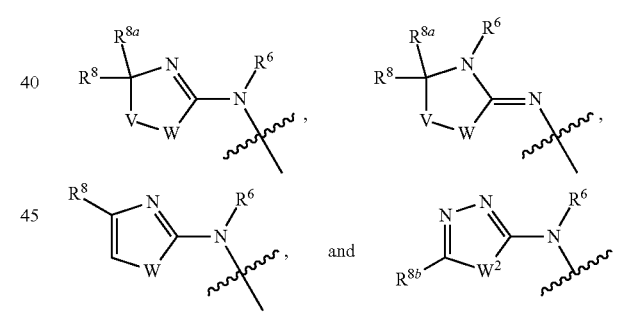

in which

W is O or S;
$W^2$ is O or S; and
V is $CR^8R^9$.

13. The compound of claim 12, wherein:

Z is selected from the structures:

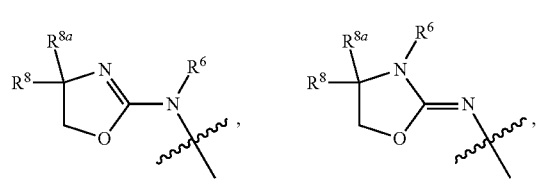

213

-continued

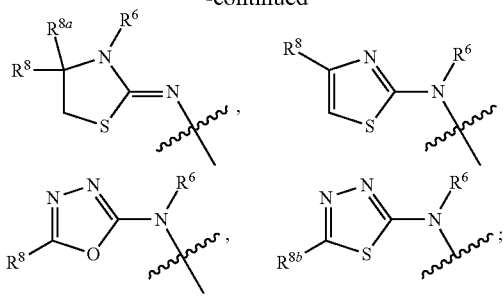

R⁶ is H or C₁-C₆ alkyl; and
R⁸ and R⁸ᵃ are independently H or C₁-C₆ alkyl optionally substituted with ORᵃ in which Rᵃ is H or C₁-C₆ alkyl, or R⁸ and R⁸ᵃ together with the atom to which they are attached form a C₃-C₆ cycloalkyl ring.

14. The compound of claim 13, wherein m is 1 and R³ is selected from the structures:

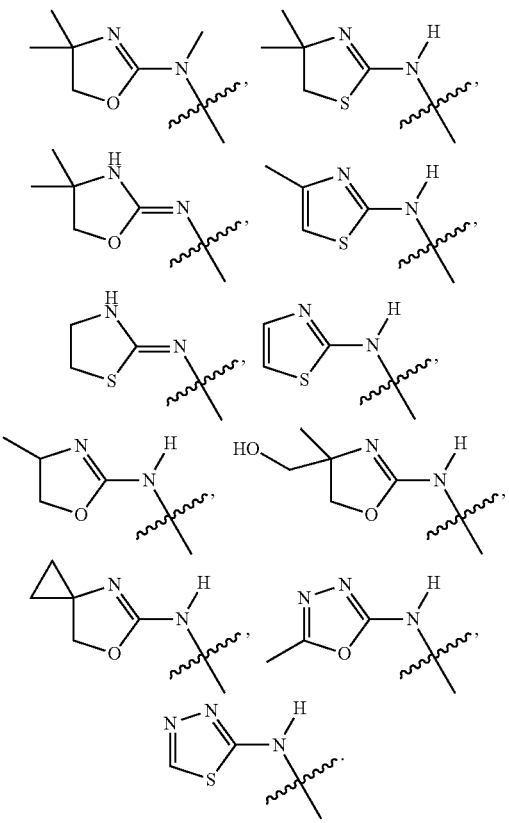

15. A compound according to claim 1, wherein m is 1 and R³ is OR¹⁵.

16. The compound of claim 15, wherein R¹⁵ is
(i) H;
(ii) C₃-C₆ cycloalkyl optionally substituted with ORᵃ;
(iii) cycloalkylalkyl;
(iv) C₁-C₆ alkyl optionally substituted with one or two groups independently selected from —ORᵃ, —OC(O)Rᵃ, —CO₂Rᵃ, —SO₂Rᵃ, —SRᵃ, —C(O)NRᵃRᵇ, —NRᵃRᵇ, —NRᵃC(O)Rᵇ, —OC(O)NRᵃRᵇ, and NRᵃC(O)NRᵇRᶜ;
(v) a 5-6 membered heterocyclic ring having a ring heteroatom selected from N and O and optionally substi-

214 tuted with —C(O)Rᵃ, C₁-C₆ alkyl, —C(O)NRᵃRᵇ, —SO₂Rᵃ, or C(O)CH₂ORᵃ;
(vi) heterocyclylalkyl, wherein said heterocyclic portion is a 5-6 membered ring having 1 or 2 ring heteroatoms independently selected from N and O and is optionally substituted with C₁-C₆ alkyl, halogen, ORᵃ or oxo;
(vii) a 5-6 membered heteroaryl ring having from 1 to three ring nitrogen atoms and optionally substituted with C₁-C₆ alkyl or halogen; or
(viii) heteroarylalkyl, wherein said heteroaryl portion is a 5-6 membered ring having 1-2 ring nitrogen atoms and is optionally substituted with C₁-C₆ alkyl.

17. The compound of claim 16, wherein R³ is:
(i) OH;
(ii) cyclopentanoxy, 2-hydroxycyclopentoxy, or cyclohexanoxy;
(iii) 1-cyclopropylmethoxy;
(iv) CH₃O—, CH₃CH₂O—, CH₃O(CH₂)₂O—, CH₃CH₂O(CH₂)₂O—, HO(CH₂)₂O—, HOCH₂CH(OH)CH₂O—, CH₃CH(OH)CH₂O—, HOC(CH₃)₂CH₂O—, (PhCH₂O)CH₂CH₂O—, (PhCH₂)OCH₂CH(OH)CH₂O—, —O—(CH₂)₂OC(O)CH₃, —O—(CH₂)CO₂CH₃, —O(CH₂)₃SO₂CH₃, —O(CH₂)₃SCH₃, —OCH₂C(O)N(CH₃)₂, —OCH₂C(O)NH(CH₃), —OCH₂C(O)NH₂,

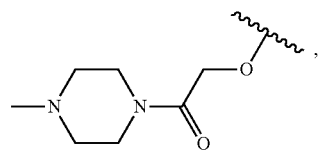 [SMILES: *OCC(=O)N1CCN(C)CC1]

—O(CH₂)₃N(CH₃)₂, —O(CH₂)₂N(CH₃)₂, —O(CH₂)₂NHC(O)CH₃, —O(CH₂)₂NHC(O)CH₂CH₃, —O(CH₂)₂OC(O)N(CH₃)₂,

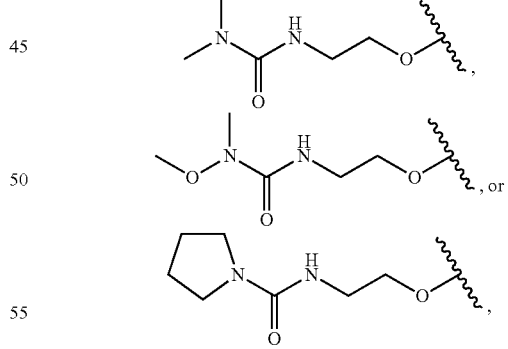

(v)

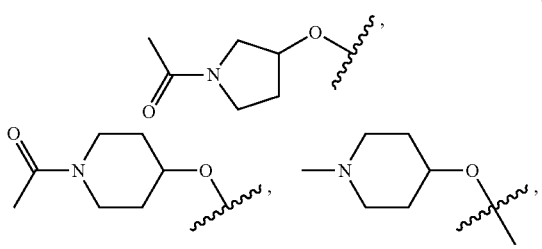

-continued

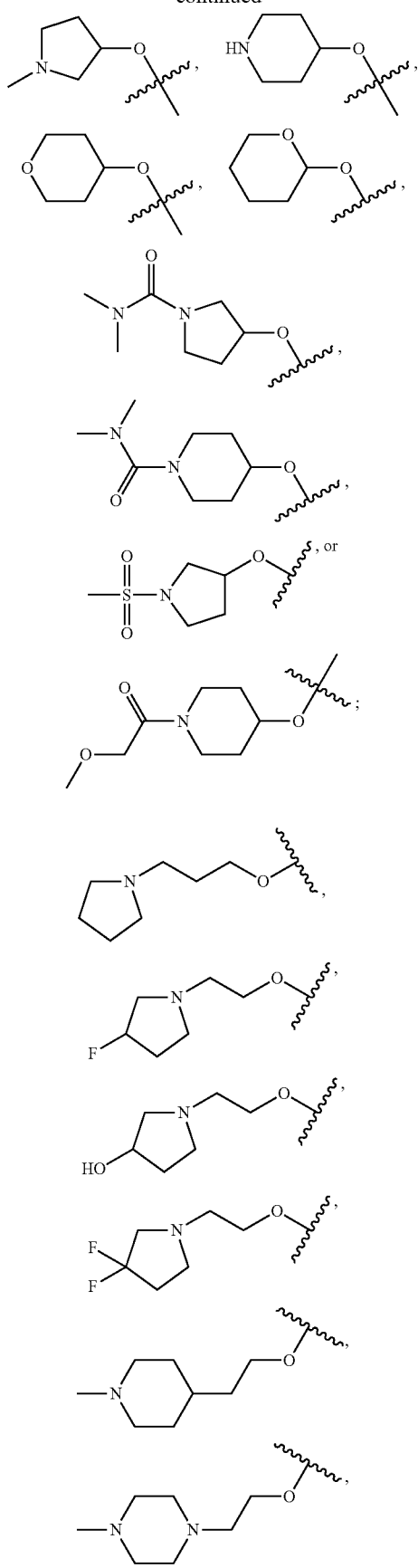

-continued

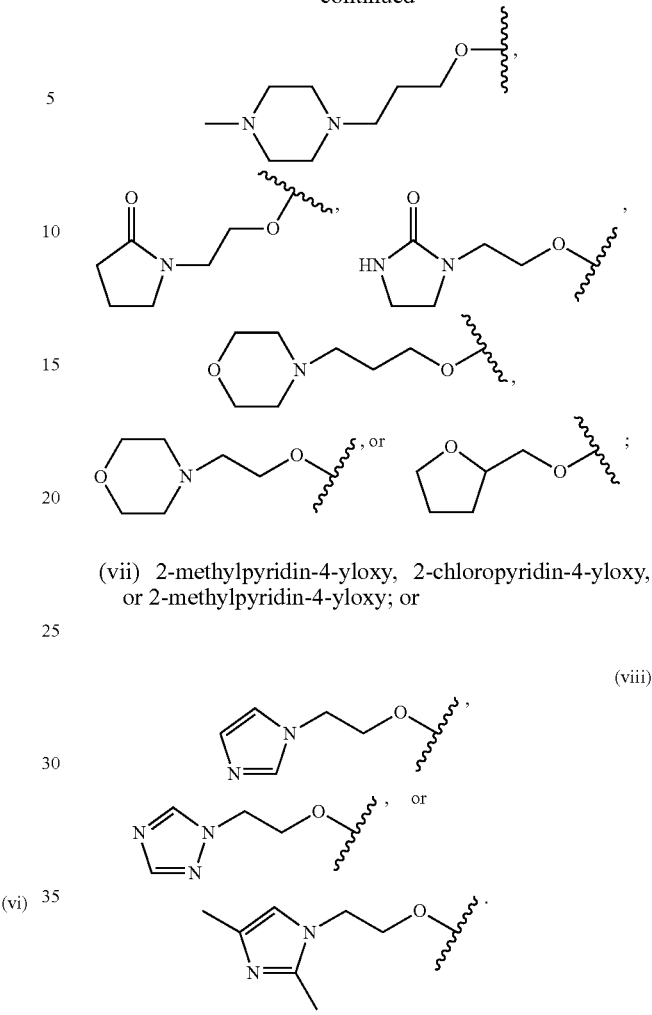

(vii) 2-methylpyridin-4-yloxy, 2-chloropyridin-4-yloxy, or 2-methylpyridin-4-yloxy; or (viii)

18. A compound according to claim 17, wherein m is 1 and $R^3$ is:
  (i) a 5 membered heterocyclic ring having a ring nitrogen atom and optionally having a second ring heteroatom selected from N and O, wherein said heterocyclic ring is optionally substituted with one or two groups independently selected from $C_1$-$C_6$ alkyl, oxo and $(CH_2)_{1-2}$ $NR^aR^b$;
  (ii) a 5-6 membered heteroaryl ring having 1-3 nitrogen atoms, wherein said heteroaryl is linked to the B ring by a ring nitrogen atom;
  (iii) —$NR^{15}C(O)R^{16}$ wherein $R^{15}$ is H or methyl and $R^{16}$ is selected from:
    (a) $C_2$-$C_6$ alkenyl optionally substituted with $NR^aR^b$;
    (b) a 5-6 membered heterocyclic ring optionally substituted with $C_1$-$C_6$ alkyl; and
    (c) $C_1$-$C_6$ alkyl optionally substituted with one or more groups independently selected from $C_1$-$C_6$ alkyl or $OR^a$;
  (iv) —$C(=O)NR^{15}R^{16}$ wherein $R^{15}$ and $R^{16}$ independently are H or $C_1$-$C_6$ alkyl, or $R^{15}$ and $R^{16}$ together with the atom to which they are attached form a 6 membered heterocyclic ring optionally having a second heteroatom selected from N and O and optionally substituted with $C_1$-$C_6$ alkyl;
  (v) $SO_2R^{15}$ wherein $R^{15}$ is $C_1$-$C_6$ alkyl or a phenyl group optionally substituted with $C_1$-$C_6$ alkyl;

(vi) SOR$^{15}$ wherein R$^{15}$ is C$_1$-C$_6$ alkyl;
(vii) SR$^{15}$ wherein R$^{15}$ is C$_1$-C$_6$ alkyl;
(viii) halogen;
(ix) R$^3$ is —CO$_2$R$^{15}$, wherein R$^{15}$ is a 6 membered heterocyclic ring having one or two ring nitrogen atoms and optionally substituted with C$_1$-C$_6$ alkyl;
(x) C$_1$-C$_6$ alkyl optionally substituted with OR$^{15}$ wherein R$^{15}$ is H or C$_1$-C$_6$ alkyl;
(xi) C$_3$-C$_6$ alkynyl optionally substituted with OR$^{15}$, NR$^{15}$C(O)CH$_2$OR$^a$ or a 6 membered heterocyclic ring having one or two ring heteroatoms independently selected from N, O, and SO$_2$, wherein R$^{15}$ and R$^{17}$ are independently H or C$_1$-C$_6$ alkyl, and R$^a$ is C$_1$-C$_6$ alkyl;
(xii) —NR$^{15}$C(O)NR$^{16}$R$^{17}$, wherein R$^{15}$, R$^{16}$ and R$^{17}$ are independently H or C$_1$-C$_6$ alkyl, or R$^{16}$ and R$^{17}$ together with the nitrogen atom to which they are attached form a 5-6 membered heterocyclic ring optionally having a second heteroatom selected from N and O and which is optionally substituted with C$_1$-C$_6$ alkyl; or
(xiii) heterocyclylalkyl wherein said heterocyclyl portion is a 6 membered ring having a ring nitrogen atom and optionally having a second ring heteroatom selected from N and SO$_2$.

19. The compound of claim 18, wherein R$^3$ is:

(i)

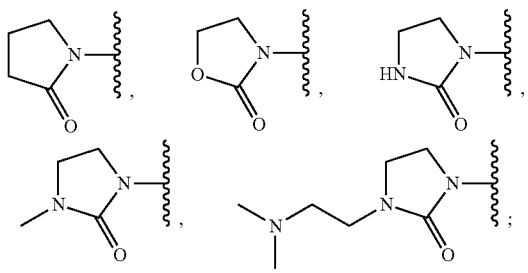

(ii) 1H-pyrazol-1-yl;
(iii) (CH$_2$=CH)—C(O)NH—, (CH$_3$)$_2$NCH$_2$(CH=CH)C(O)NH—,

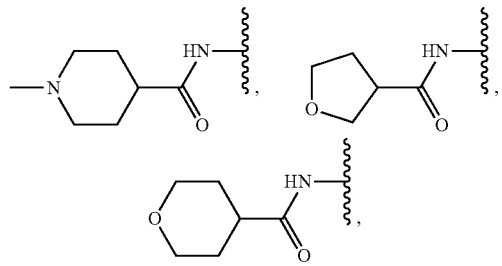

CH$_3$C(O)NH—, (CH$_3$)$_2$C(O)NH—, CH$_3$CH$_2$C(O)N(CH$_3$)—, CH$_3$OCH$_2$C(O)NH—, CH$_3$OCH$_2$C(O)N(CH$_3$)—, CH$_3$CH(OCH$_3$)C(O)NH—, CH$_3$OCH$_2$CH$_2$C(O)NH—, CH$_3$OCH(CH$_3$)C(O)NH—, CH$_3$OCH$_2$CH(CH$_3$)C(O)NH—;

(iv) (CH$_3$)$_2$NC(O)—, (4-morpholinyl)C(O)—, or (1-methylpiperazin-4-yl)C(O)—;
(v) 4-methylbenzenesulfonate, ethanesulfonate;
(vi) ethysulfinyl;
(vii) EtS—;
(viii) Br;

(ix) (1-methylpiperazin-4-yl)CO$_2$—;
(x) HO(CH$_2$)$_3$— or CH$_3$O(CH$_2$)$_3$—;

(xi)

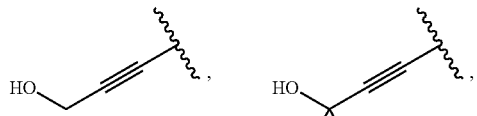

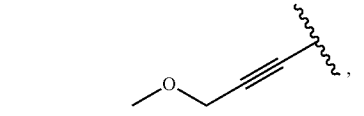

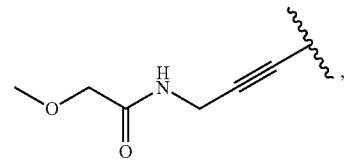

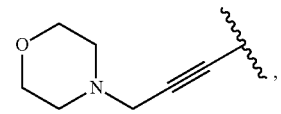

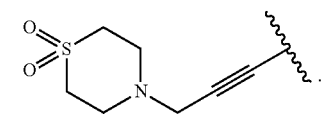

(xii)

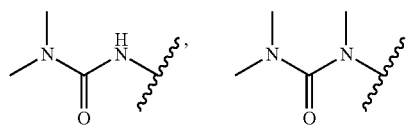

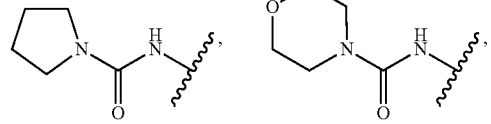

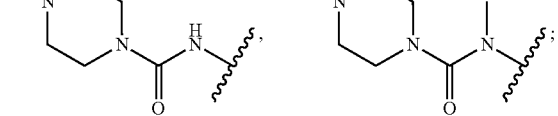

or (xiii)

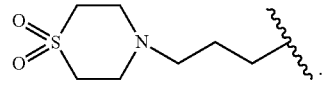

20. A compound according to claim 1 wherein:

E is selected from

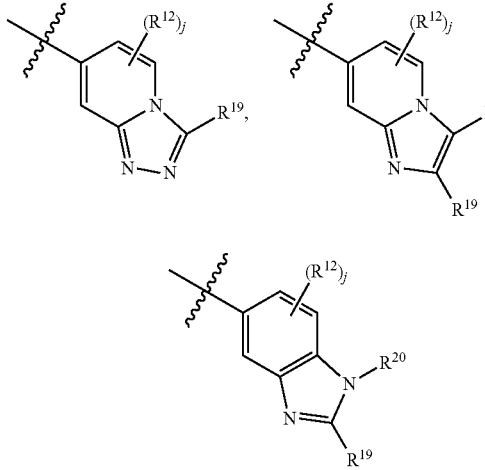

$R^{12}$ is halogen;

j is 0 or 1;

$R^{19}$ is H, $C_1$-$C_6$ alkyl, or halogen; and $R^{20}$ is H;

provided that $R^3$ of Formula I is not $NR^{15}C(=O)(CH=CH)R^{16a}$ wherein $R^{16a}$ is H, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, $C(=O)R^a$, $C(=O)OR^a$, $OC(=O)R^a$, $C(=O)NR^aR^b$, $NR^aC(=O)R^b$, $NR^aC(=O)NR^bR^c$, $OC(=O)NR^aR^b$, and $C(=O)CH_2OR^a$.

21. A composition comprising a compound according to claim 1 and a pharmaceutically acceptable carrier.

22. A composition comprising a compound according to claim 1 and a pharmaceutically acceptable diluent or carrier.

23. A method of preparing a compound of Formula I according to claim 1, comprising:

(a) reacting a compound of formula (F1)

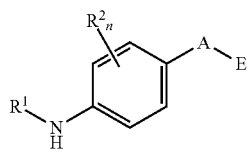

with a compound of formula (F2)

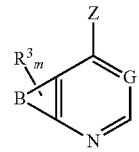

in which Z represents a leaving atom or group; or (b) for a compound of Formula I in which G is N, reacting a compound of formula (F3)

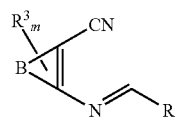

in which R represents a tertiary amino group, for example di(1-6C)alkylamino, such as dimethylamino, with a compound of formula (F1); followed if necessary, by converting the compound of Formula I into another compound of Formula I having a different $R^3$ group.

24. A compound of Formula I as defined in claim 1 and selected from the structures:

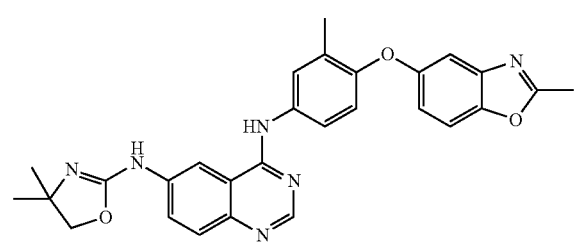

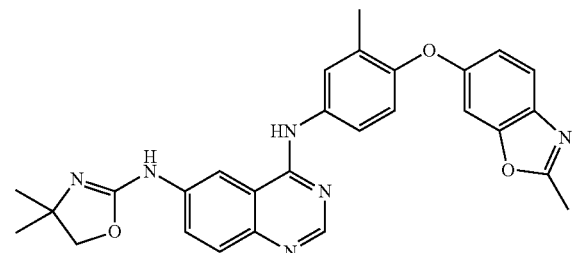

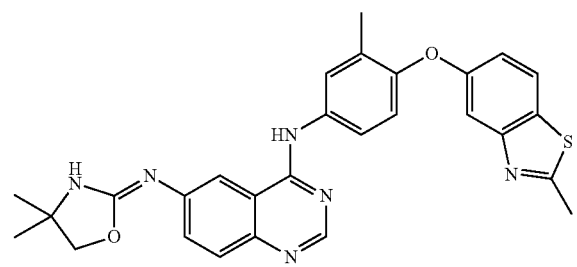

-continued
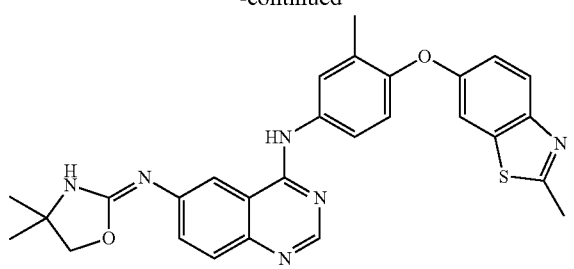
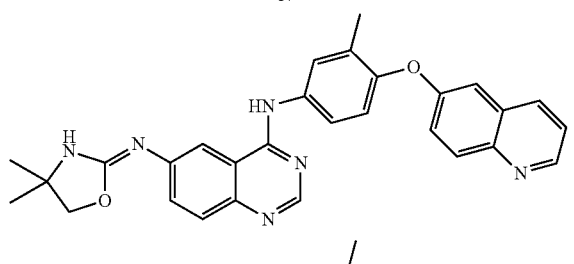
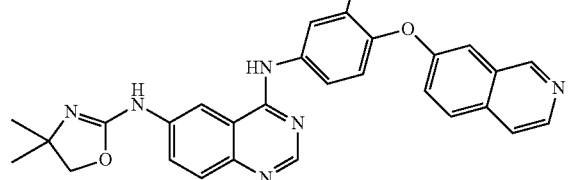
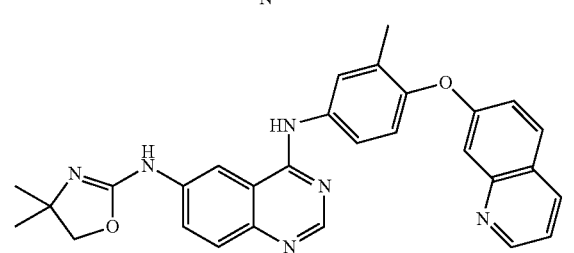
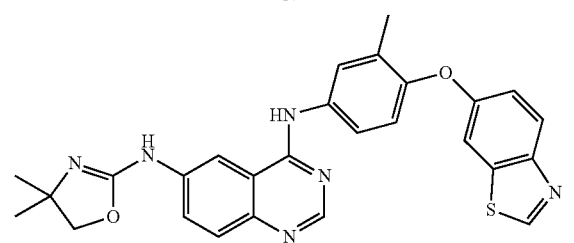
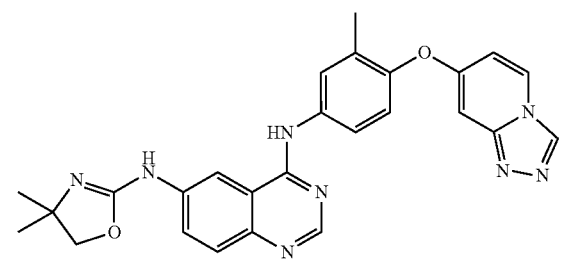
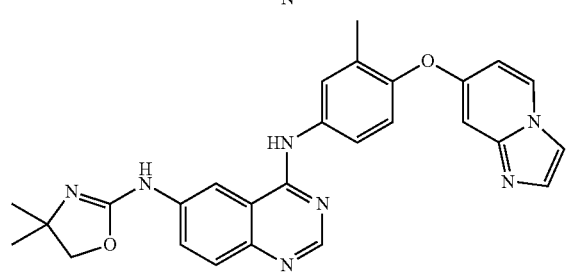
-continued
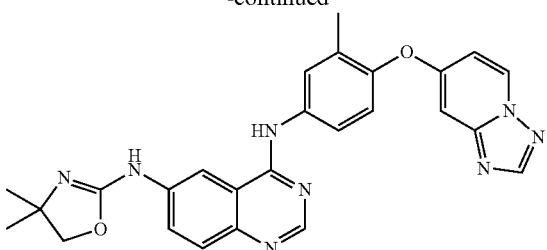
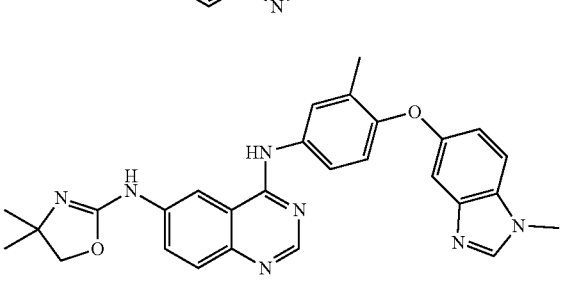
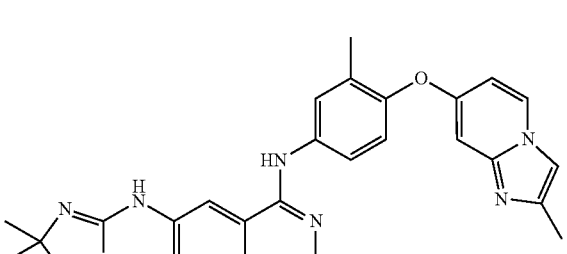
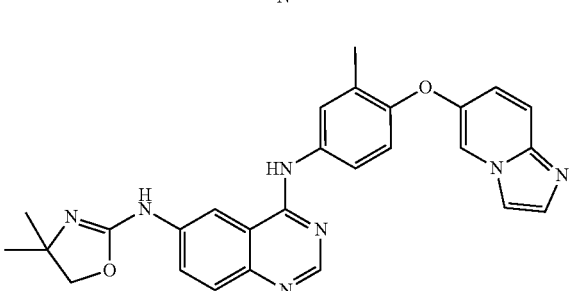
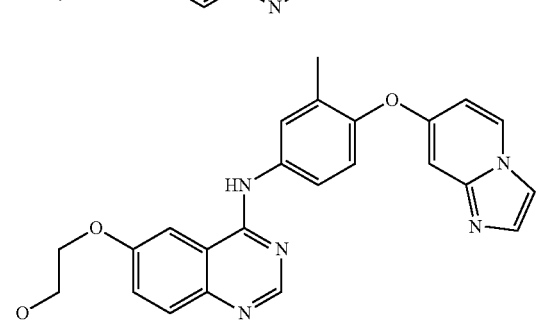
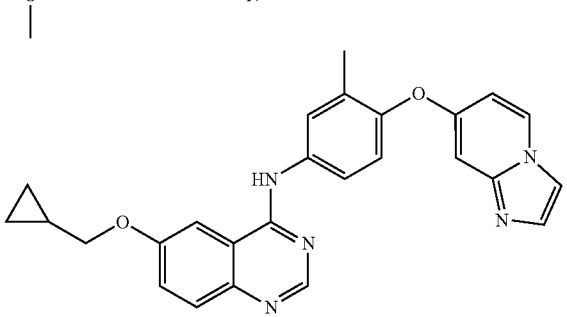

223
-continued
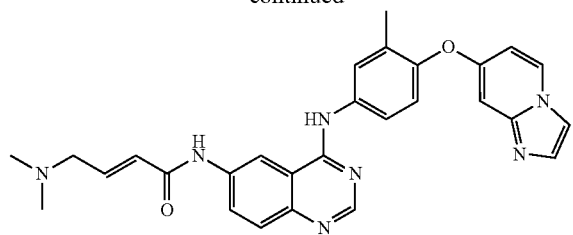
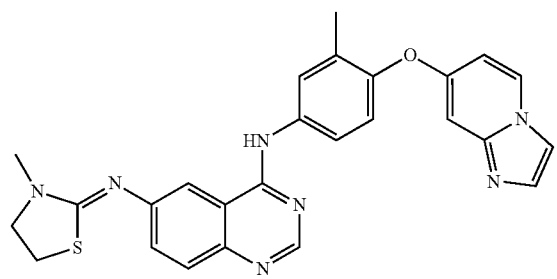
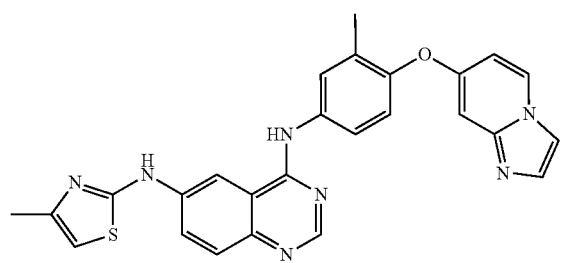
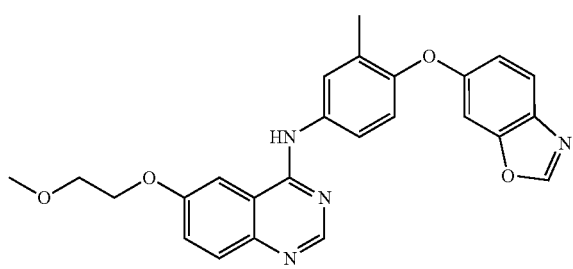
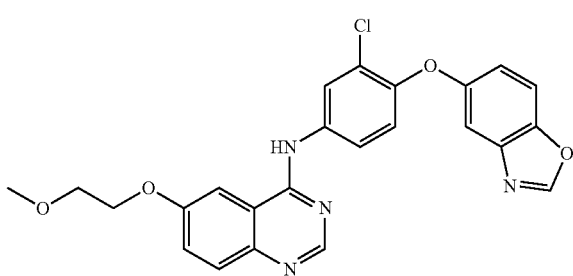
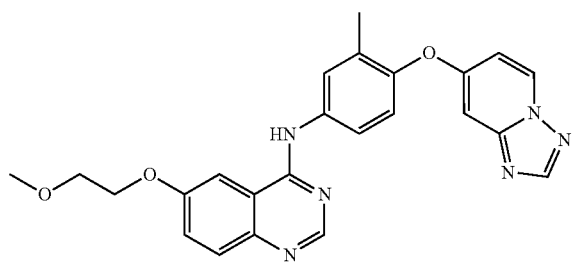
224
-continued
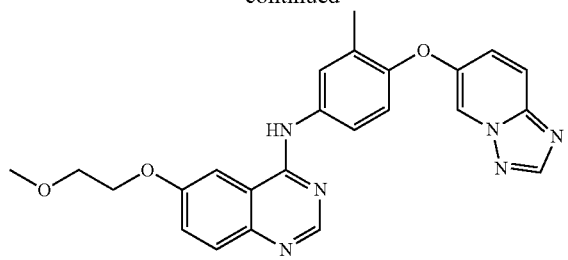
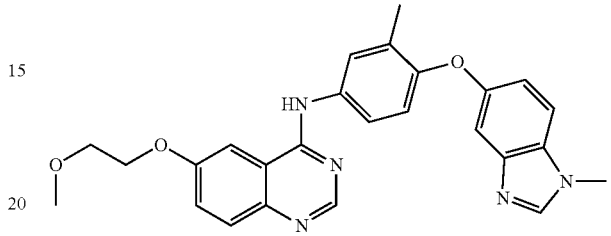
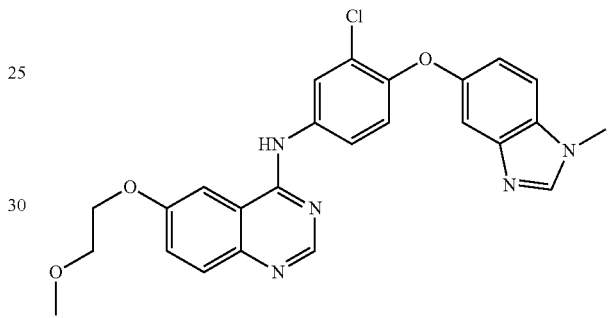
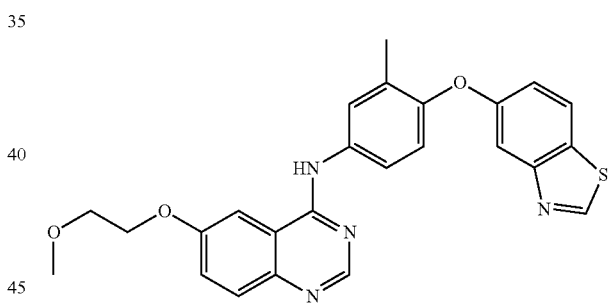
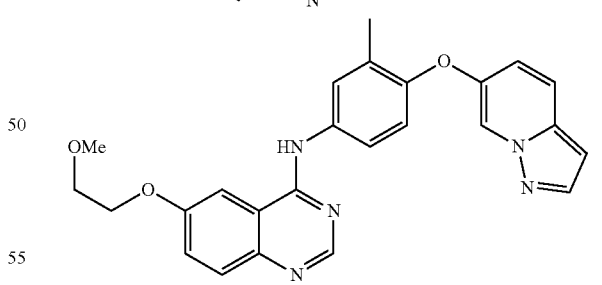
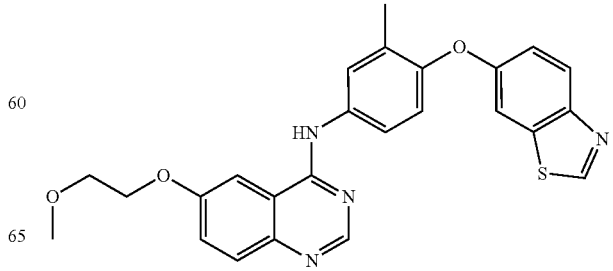

225
-continued
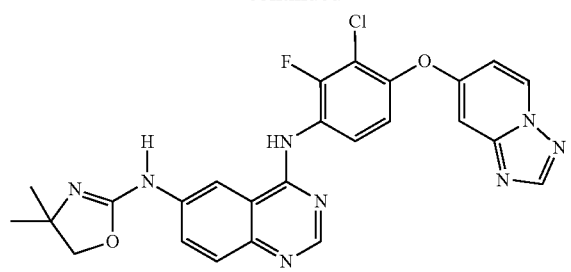
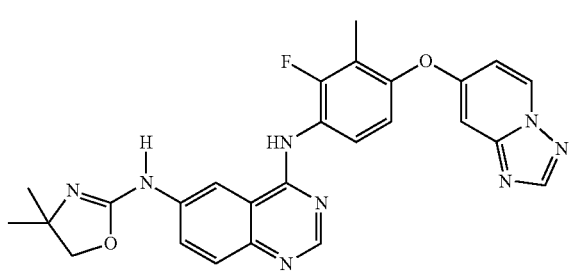
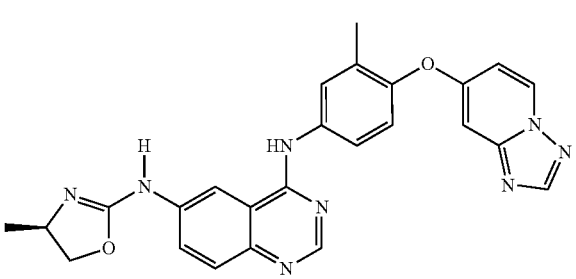
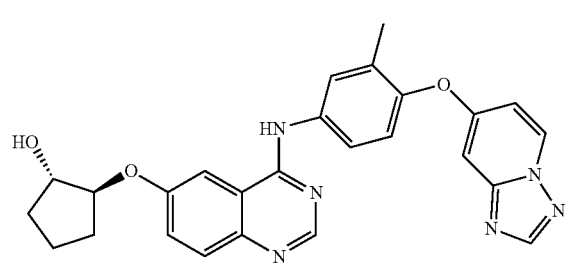
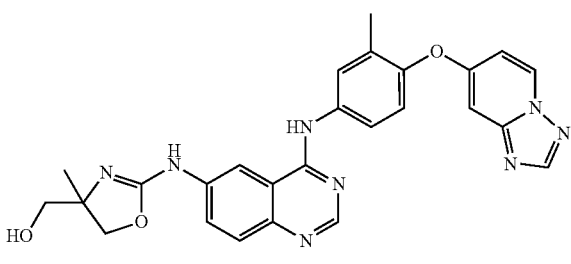
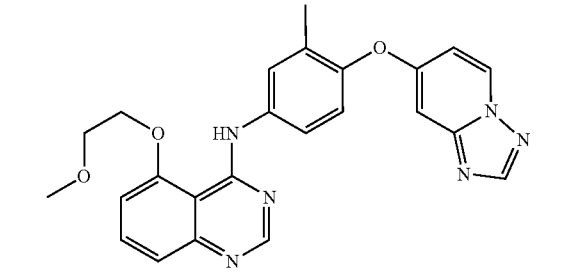
226
-continued
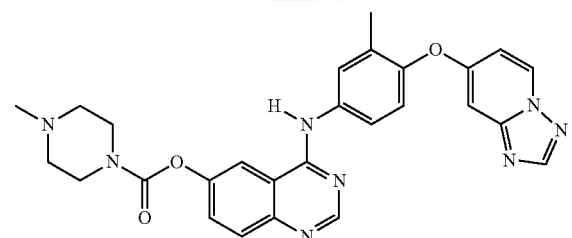
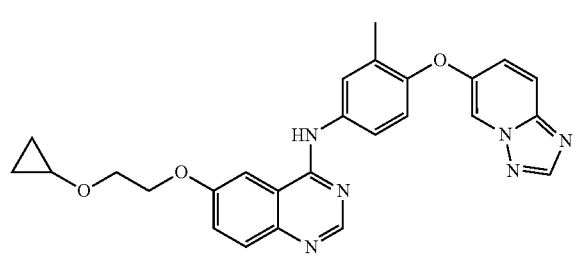
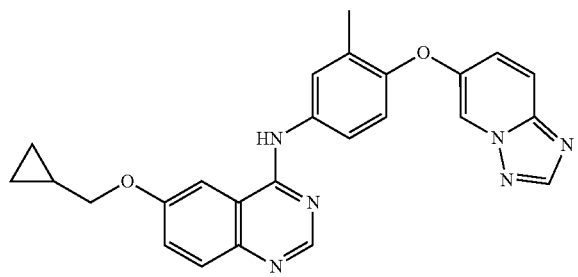
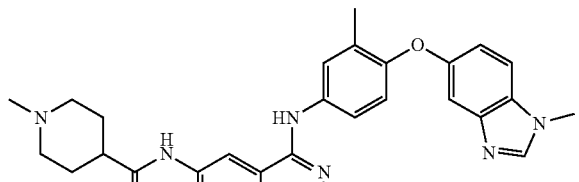
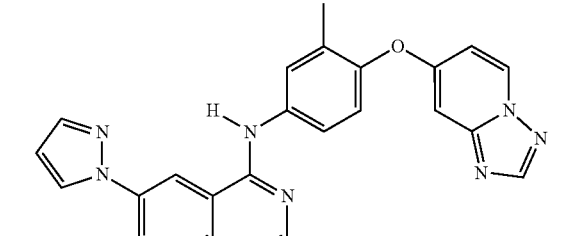
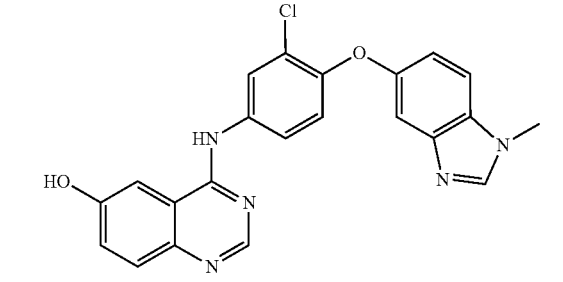

227
-continued
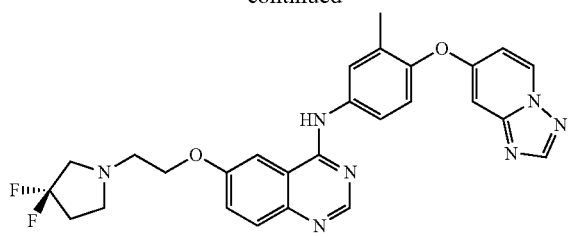
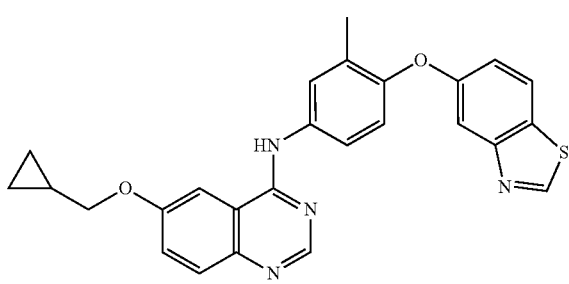
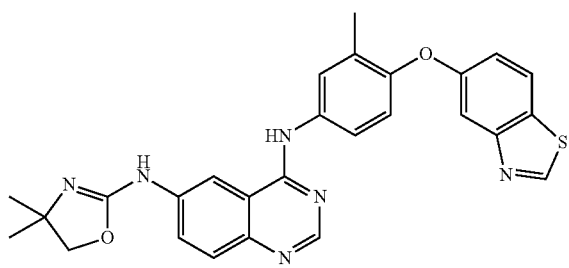
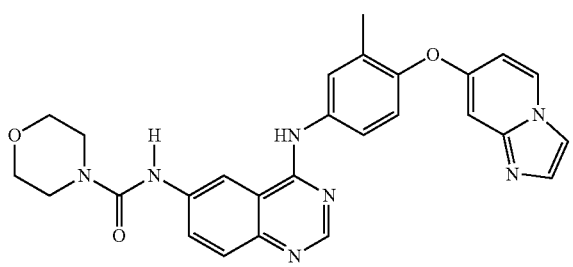
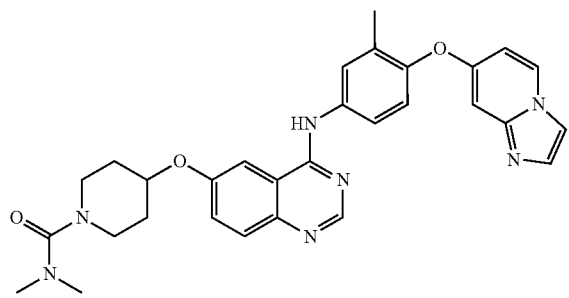
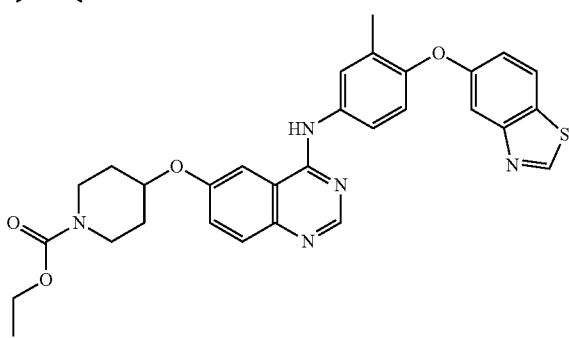
228
-continued
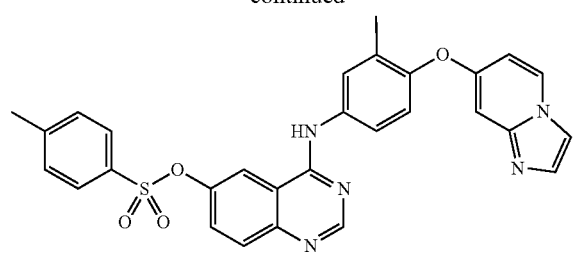
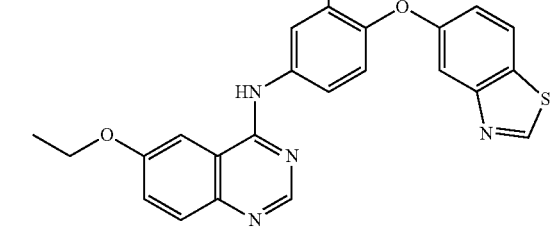
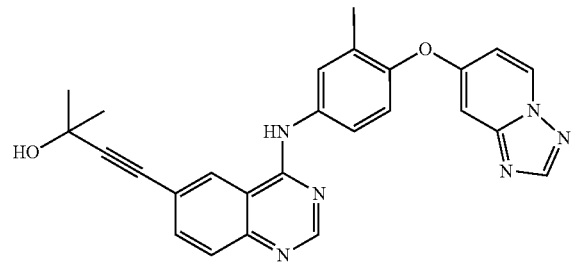
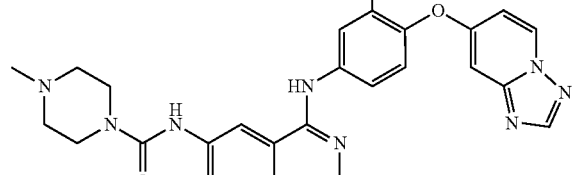
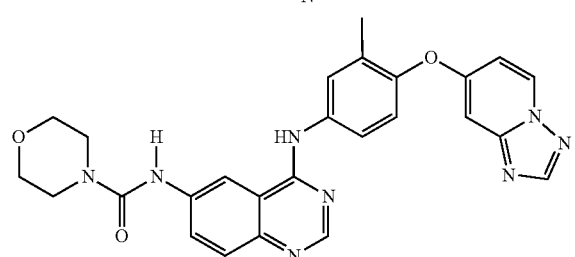

229
-continued
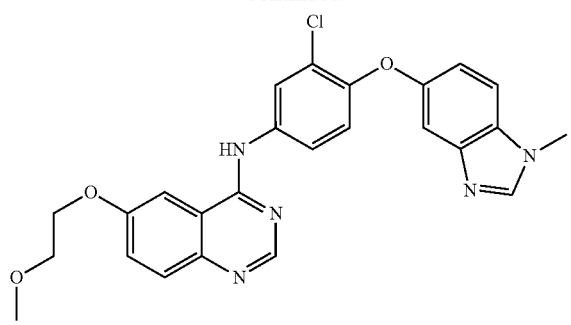
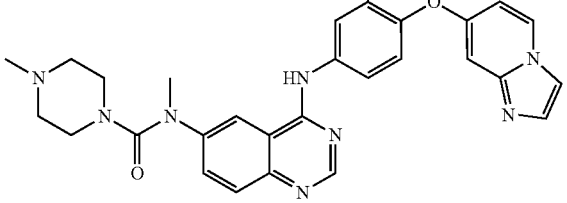
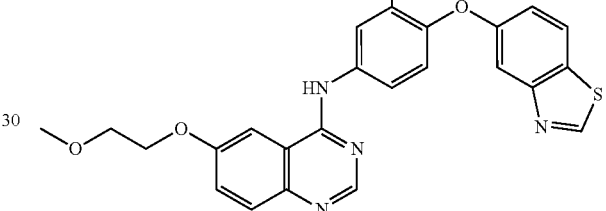
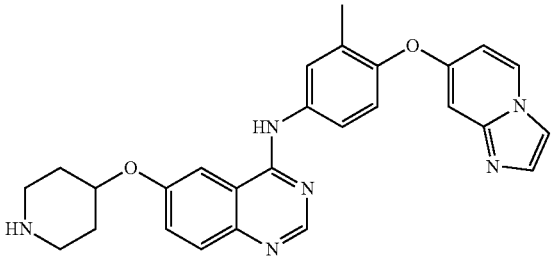
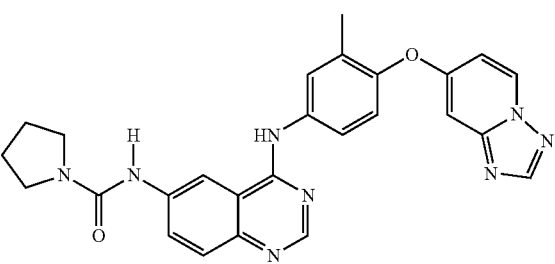
230
-continued
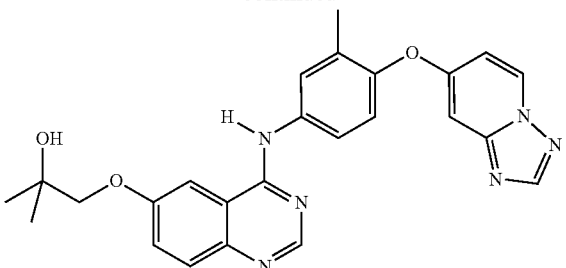
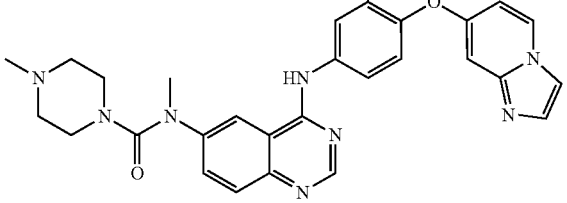
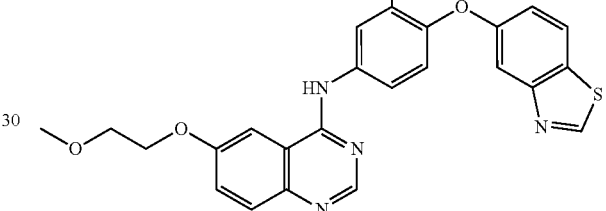
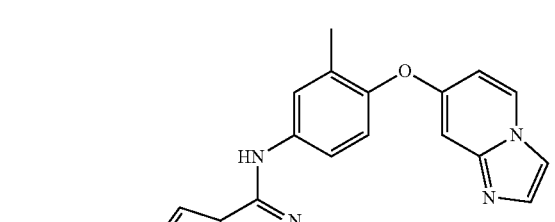
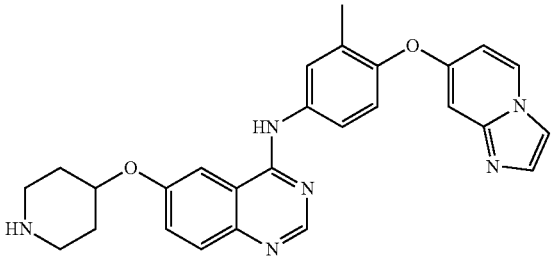

231
-continued
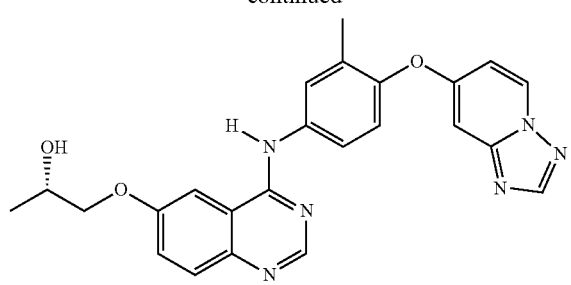
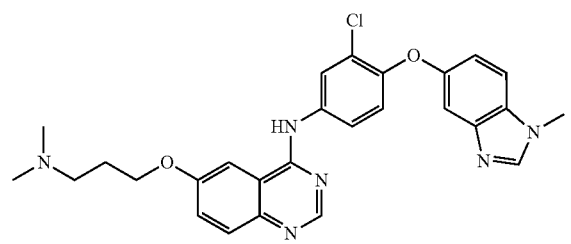
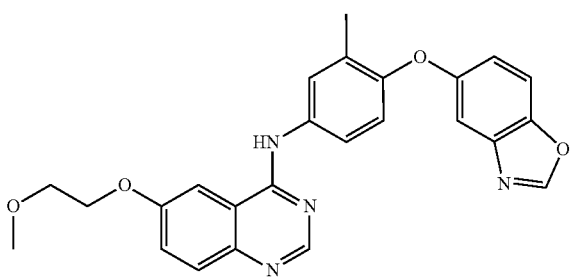
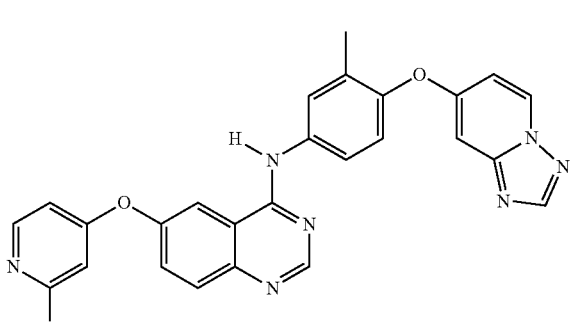
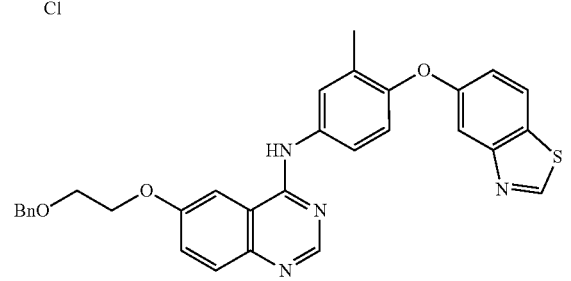
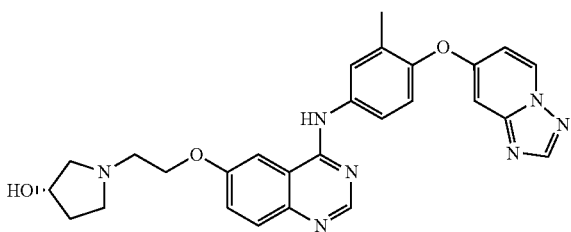
232
-continued
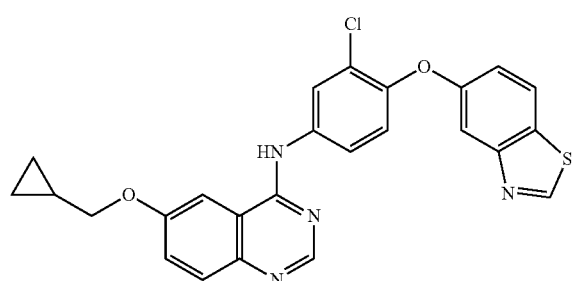
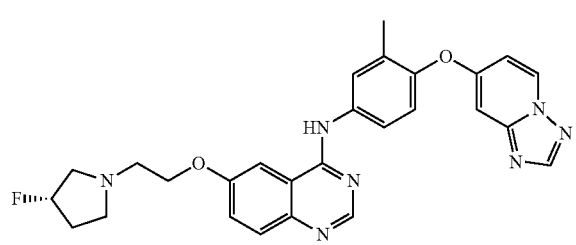
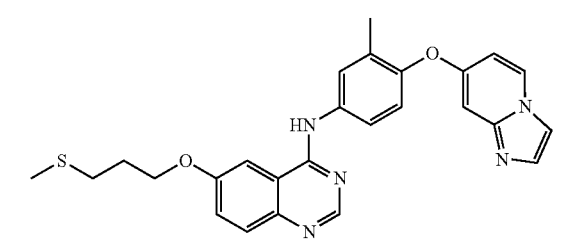
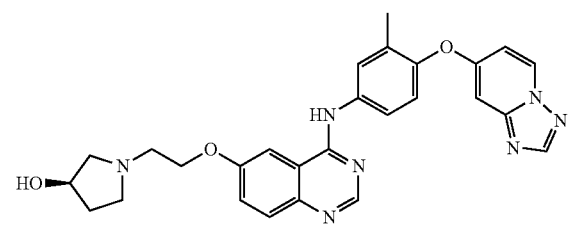
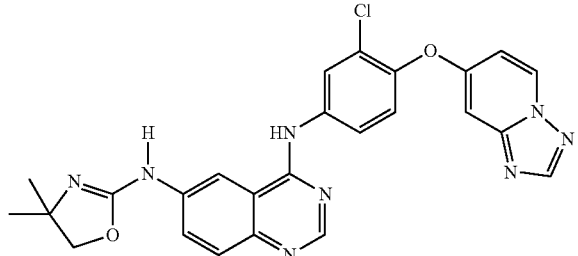
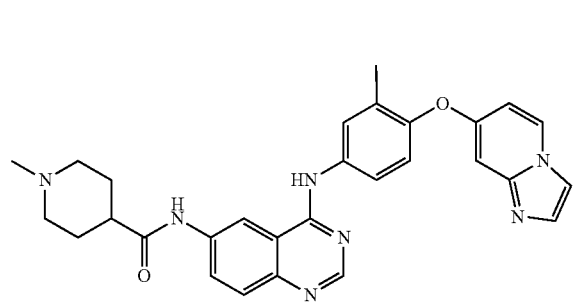

233
-continued
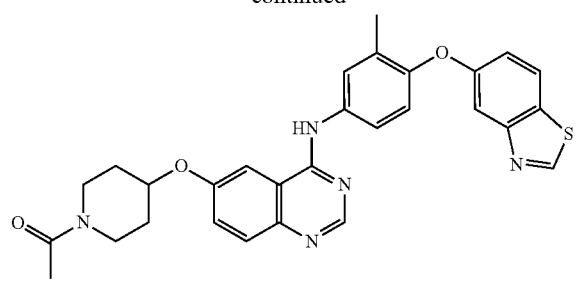
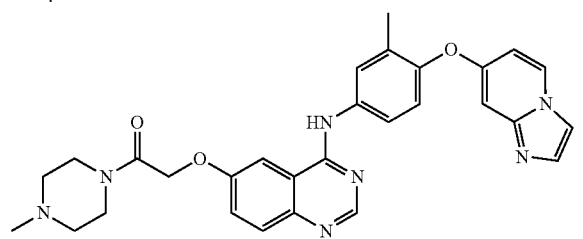
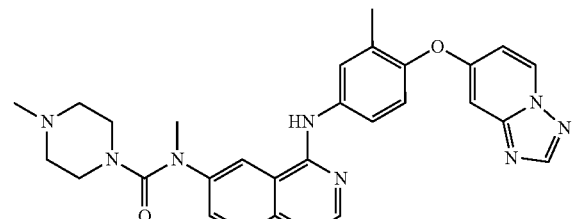
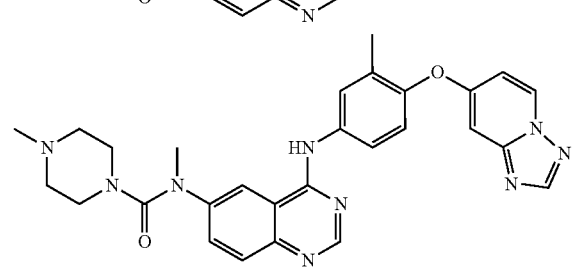
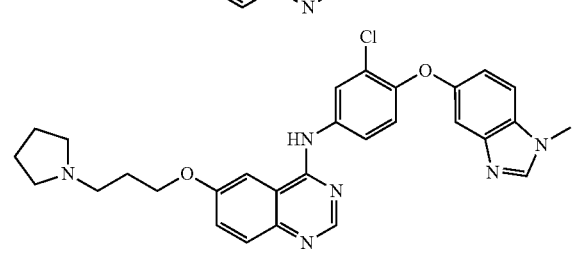
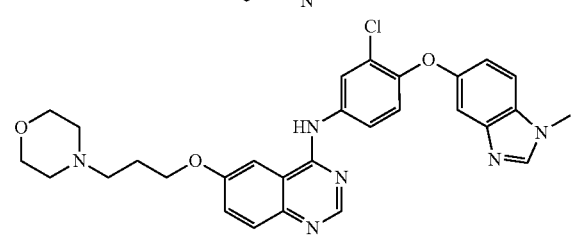
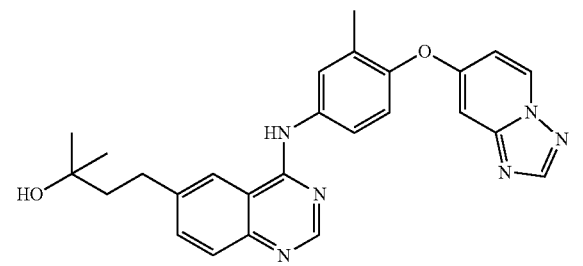
234
-continued
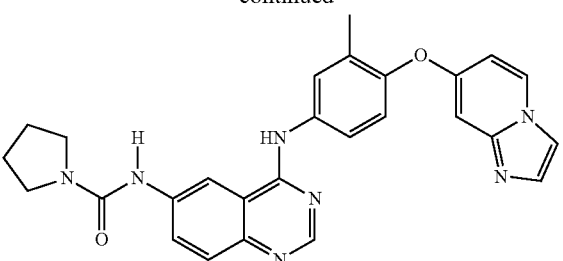
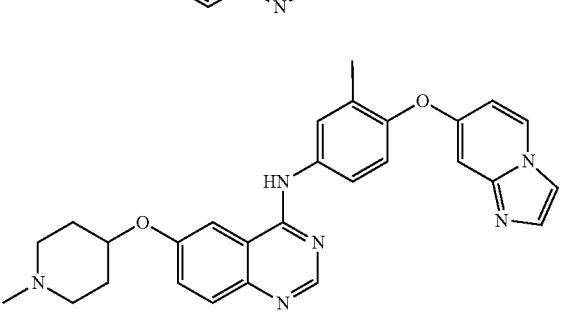
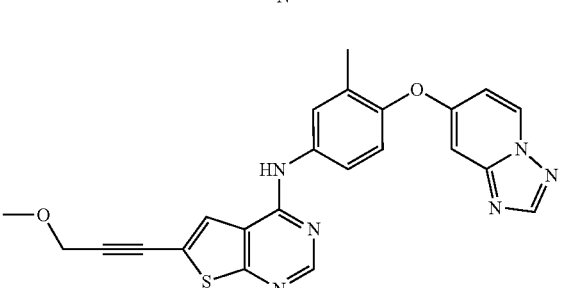
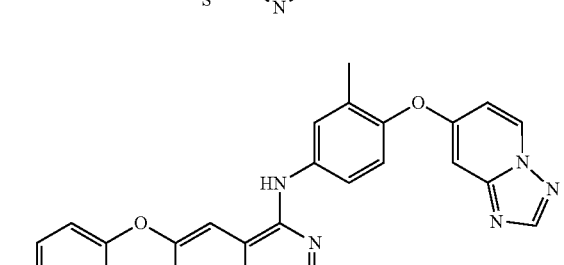
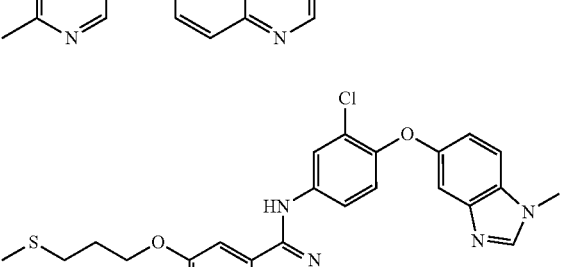
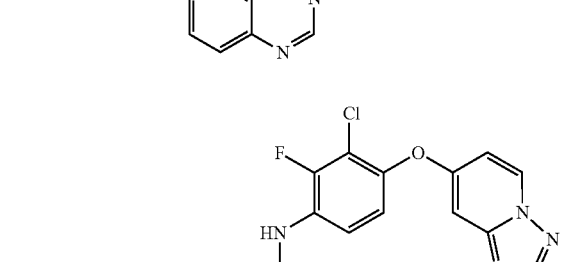
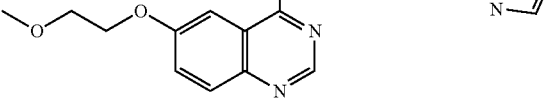

235
-continued
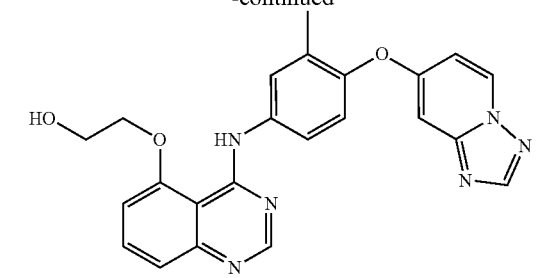
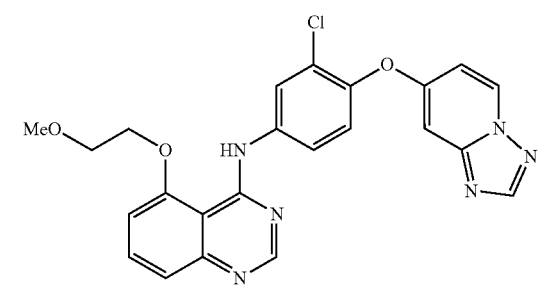
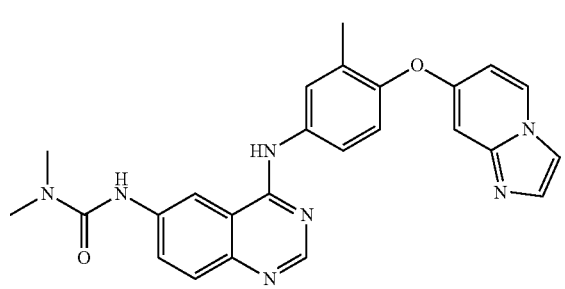
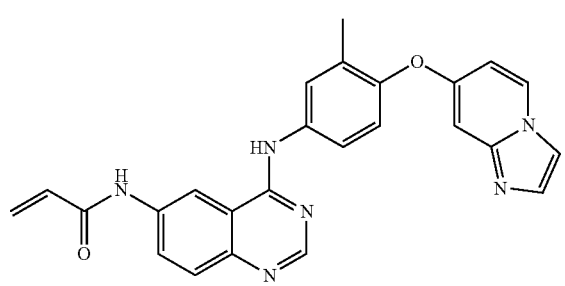
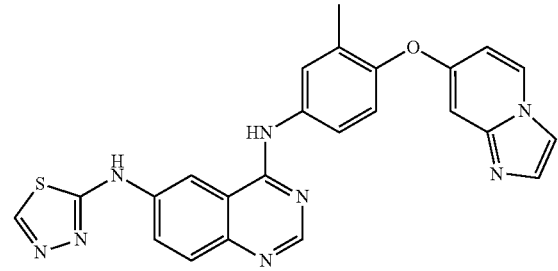
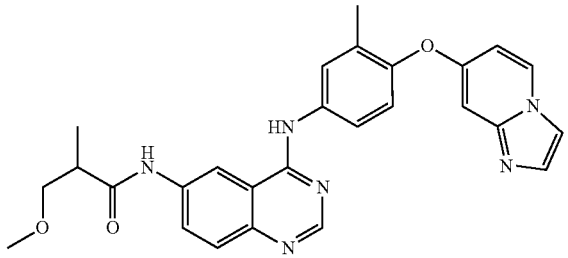
236
-continued
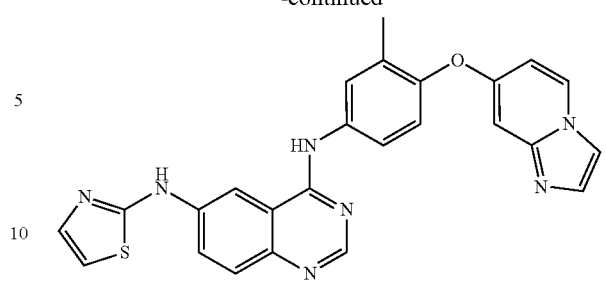
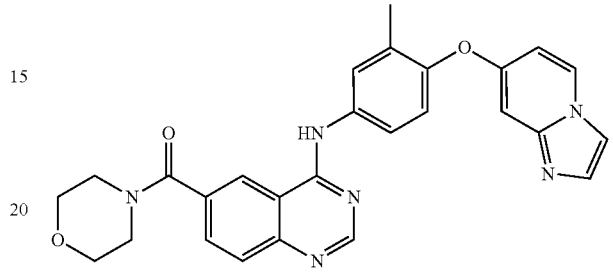
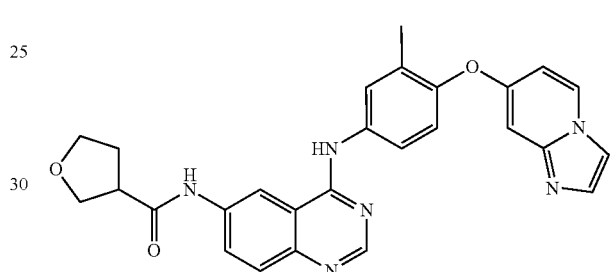
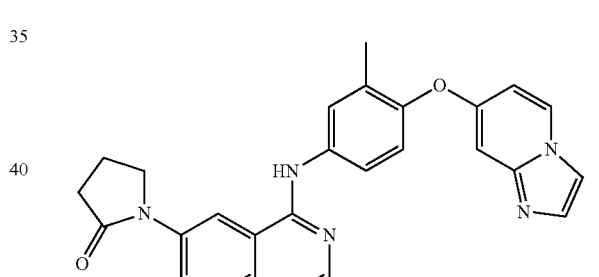
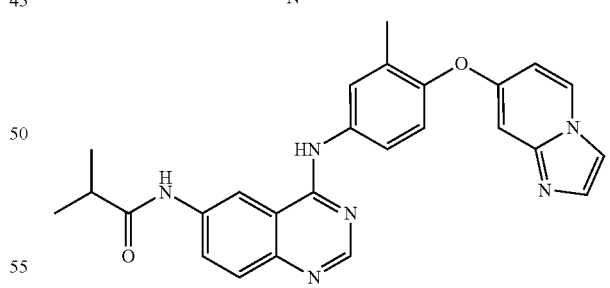
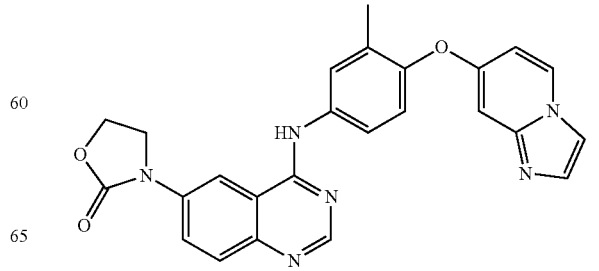

237
-continued
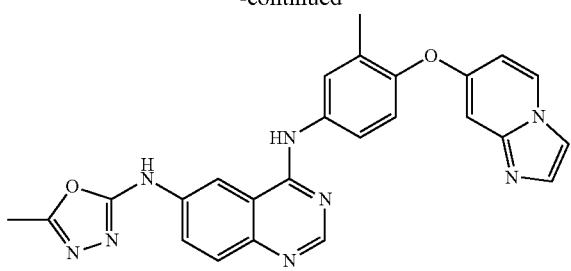
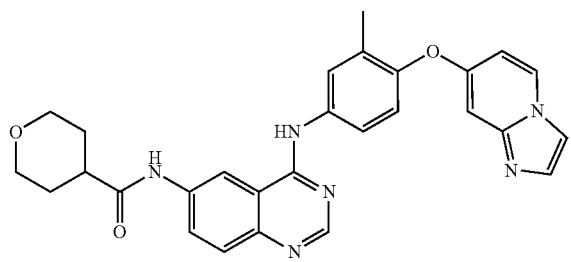
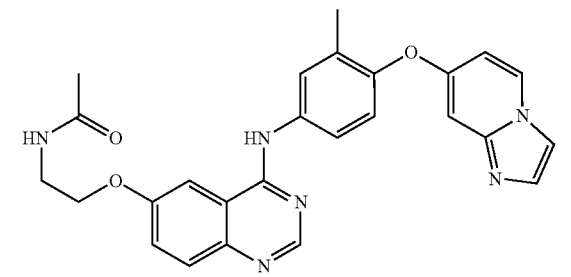
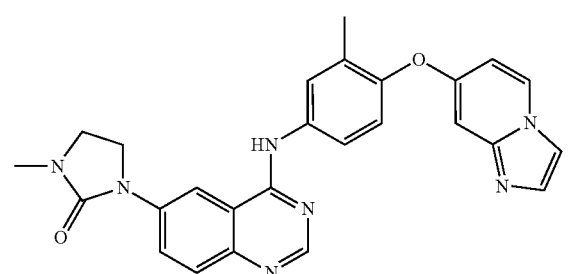
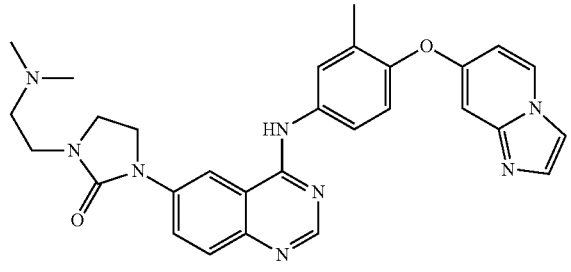
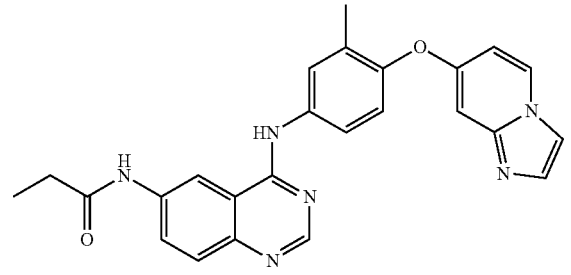
238
-continued
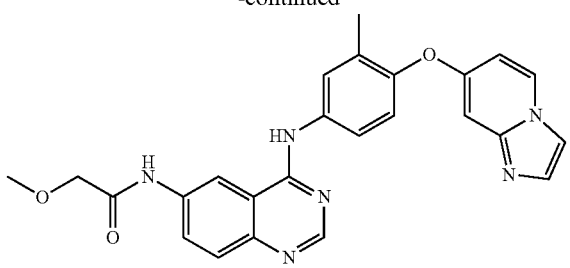

239
-continued
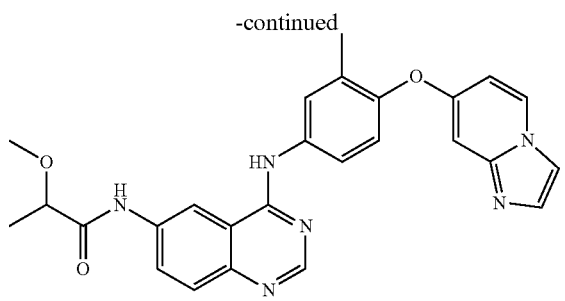
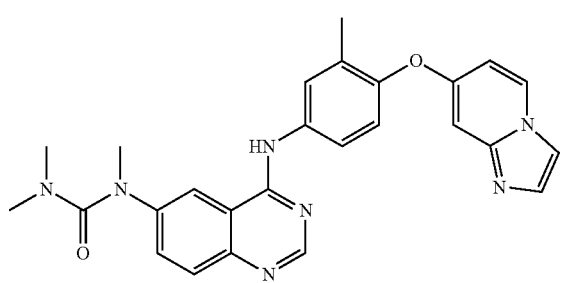
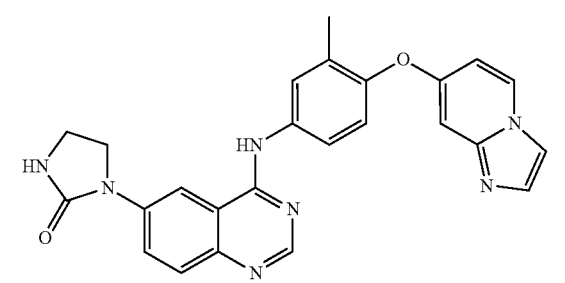
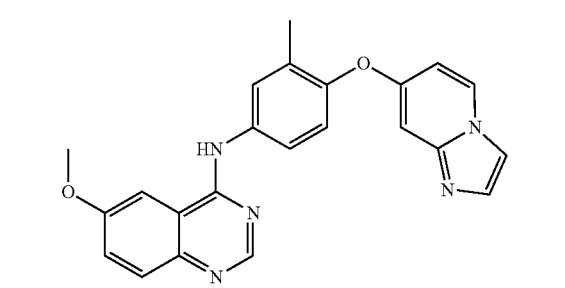
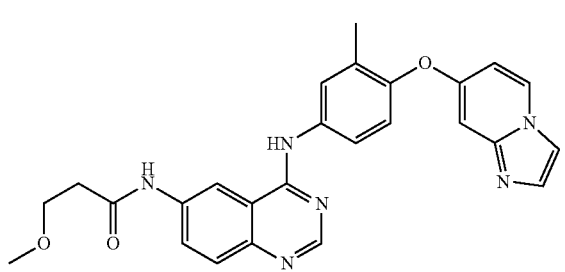
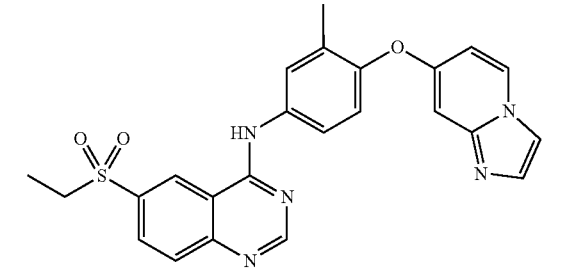
240
-continued
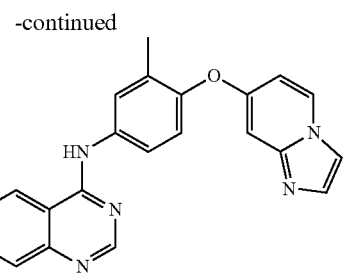
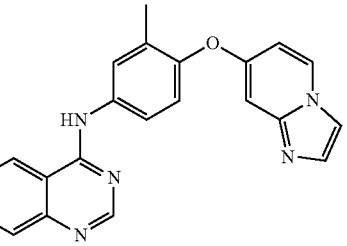
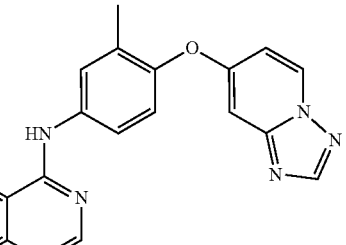
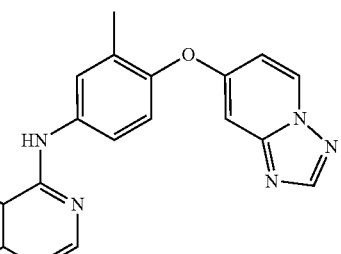
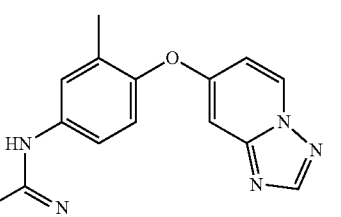
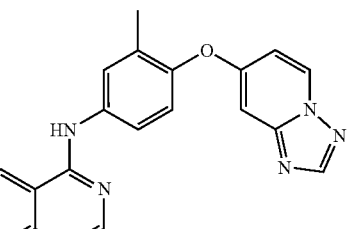

241           242
-continued    -continued

243
-continued
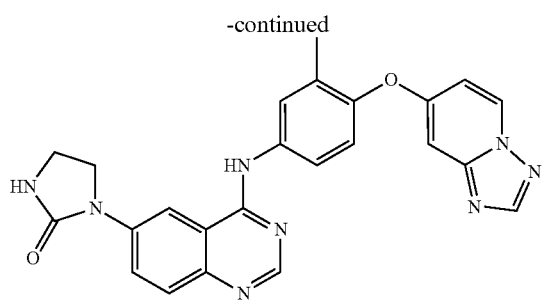
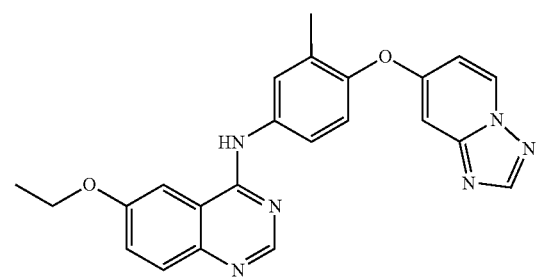
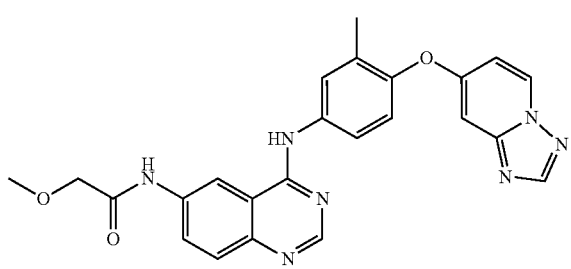
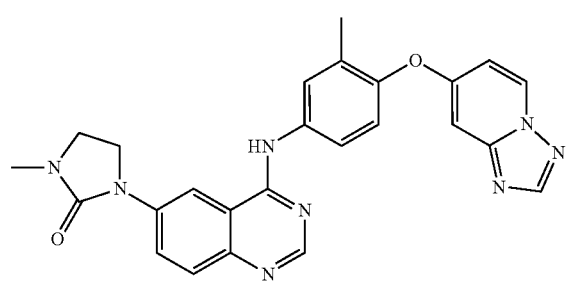
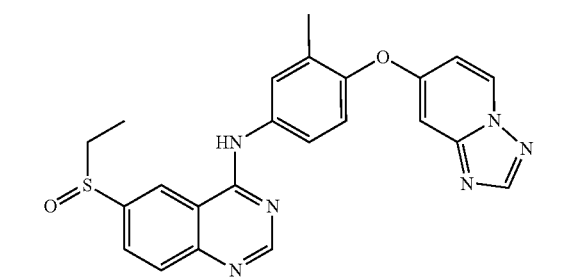
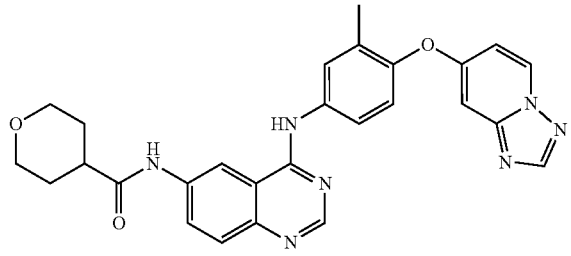
244
-continued
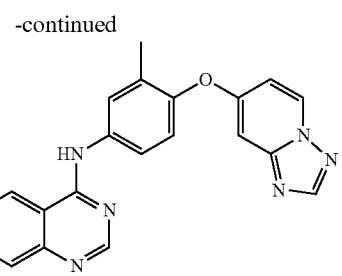
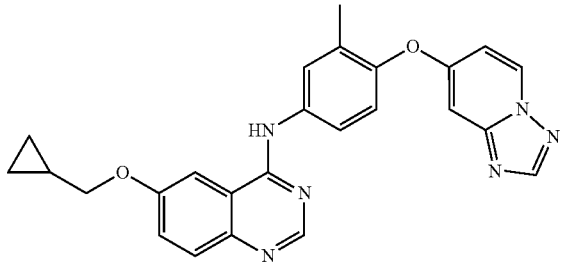
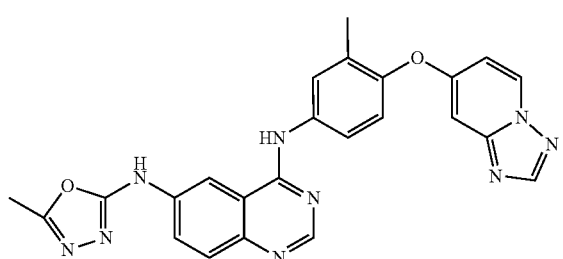
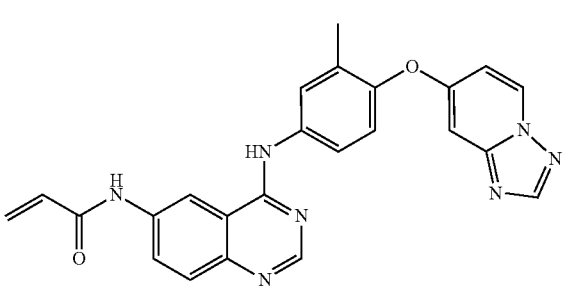
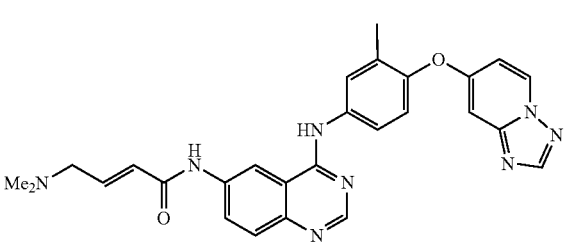
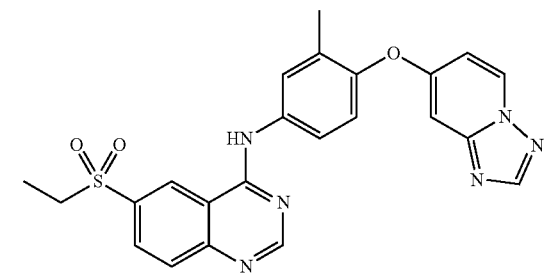

245
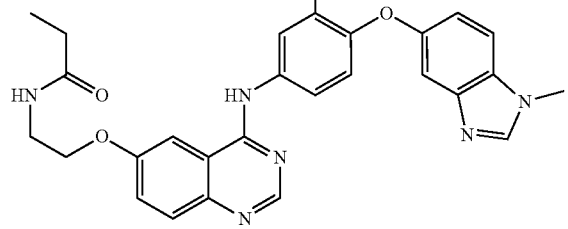
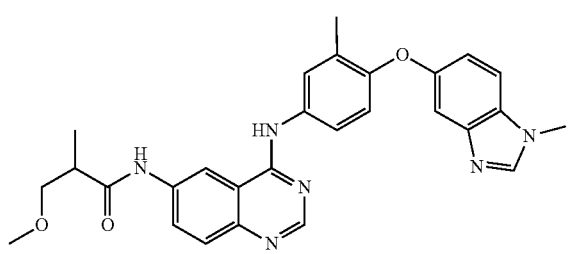
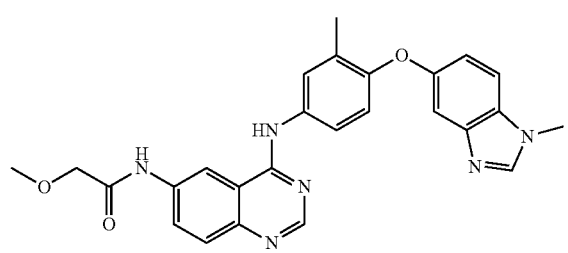
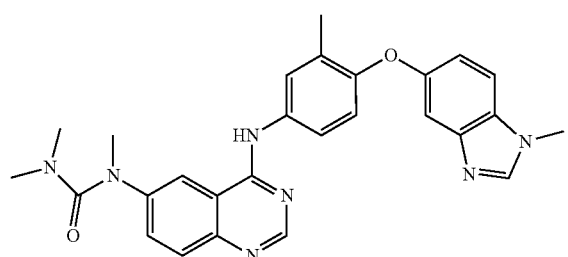
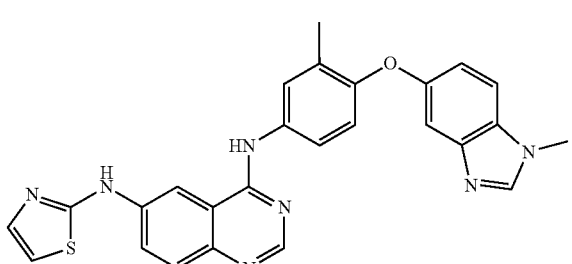
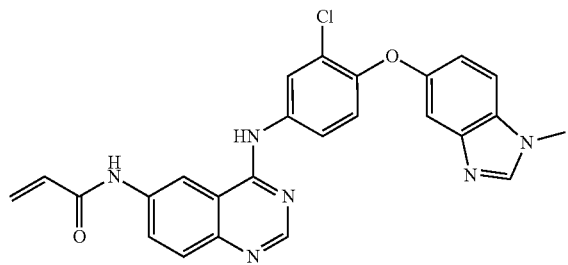
246
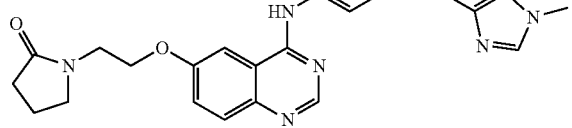
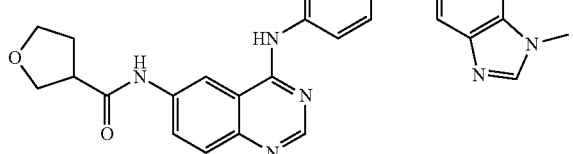
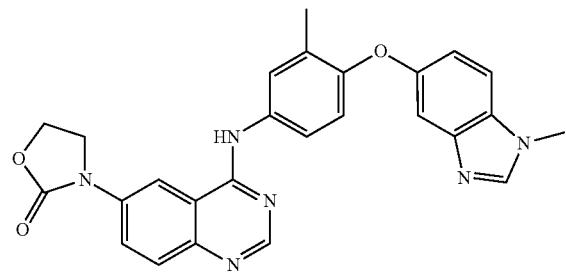
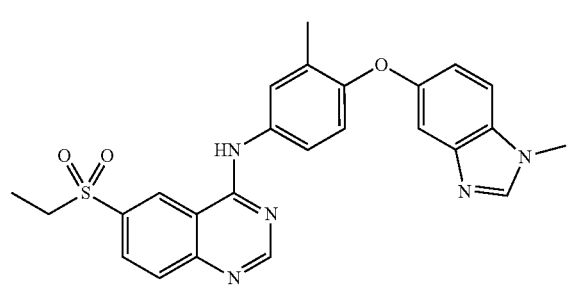
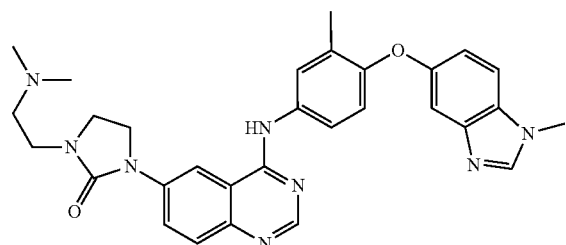
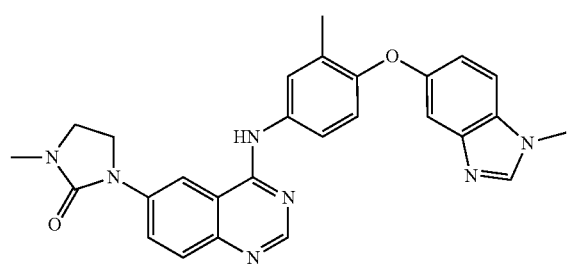

247
-continued
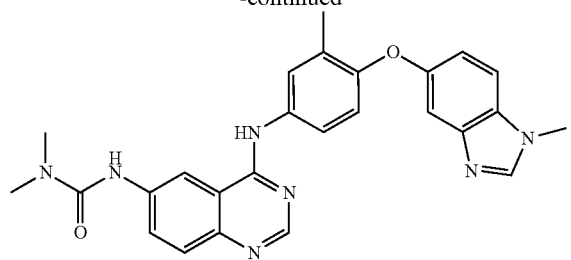
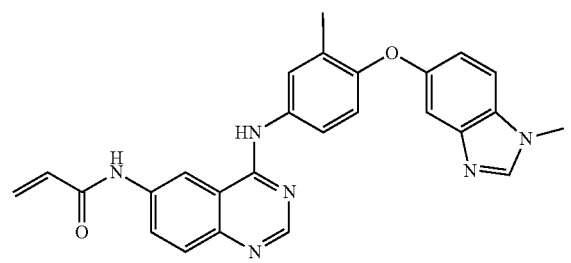
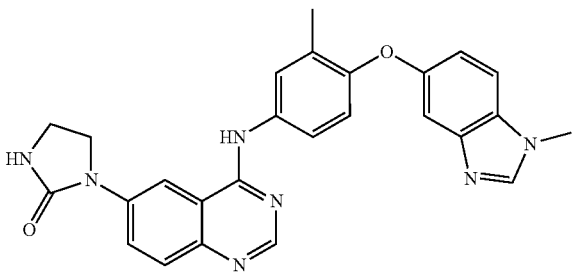
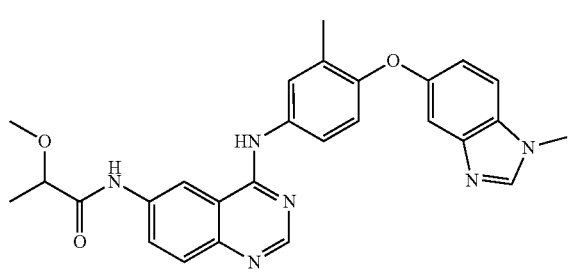
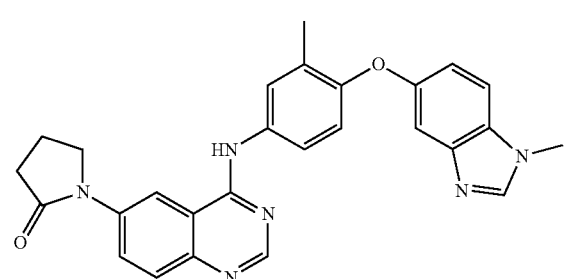
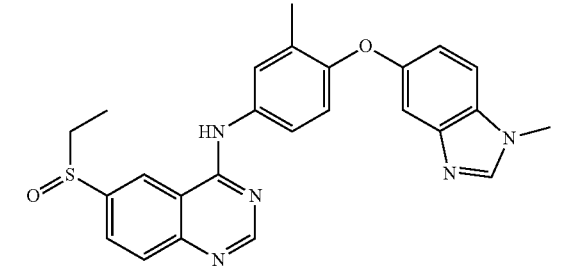
248
-continued
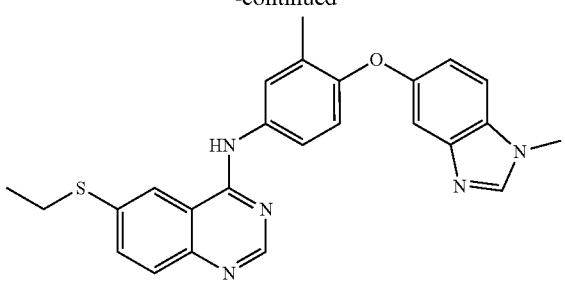
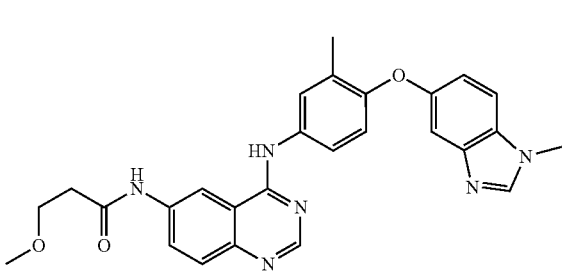
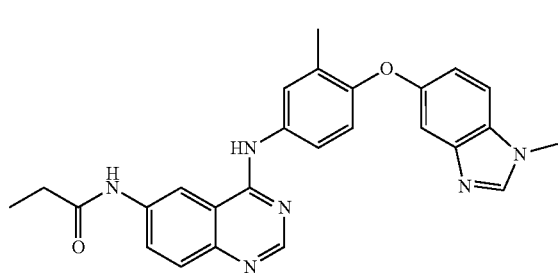
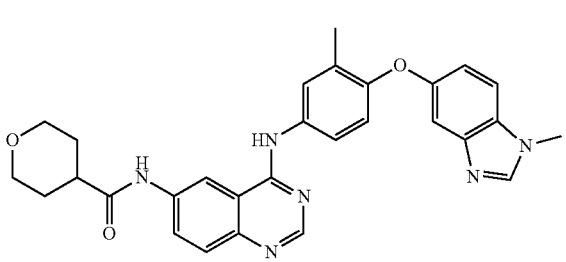
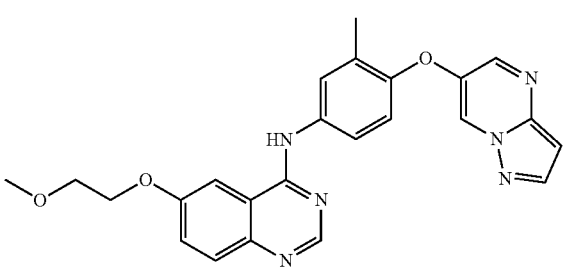
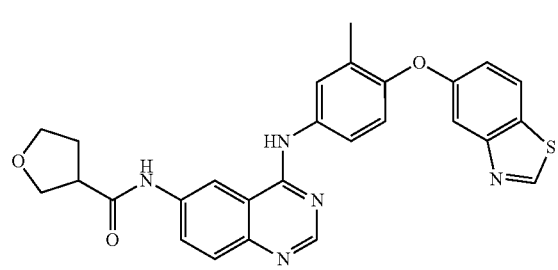

249
-continued
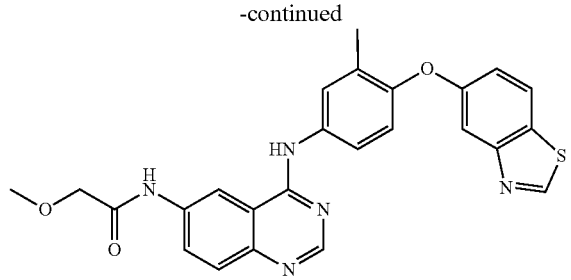
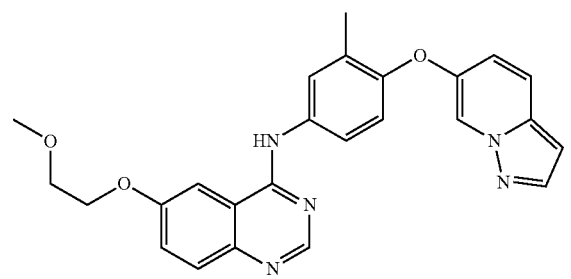
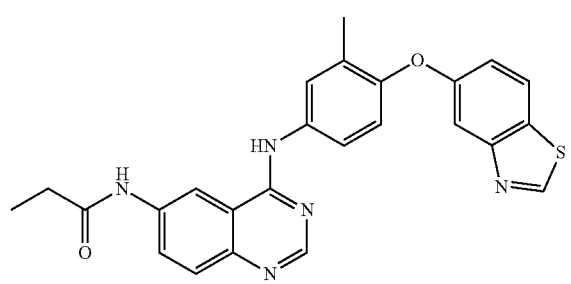
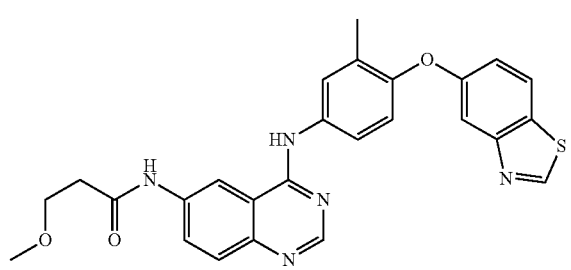
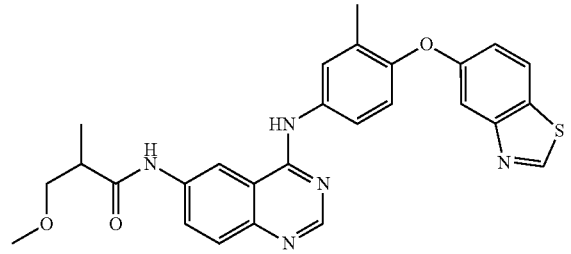
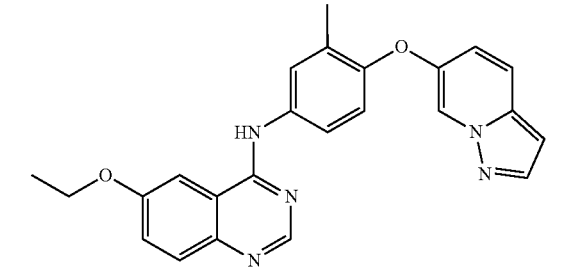
250
-continued
racemic
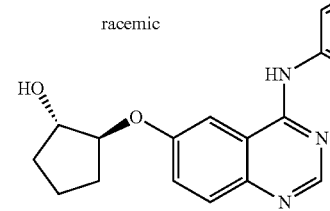
racemic
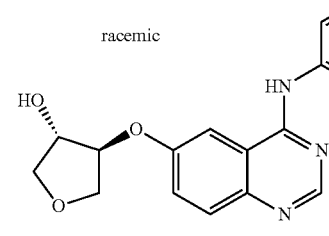
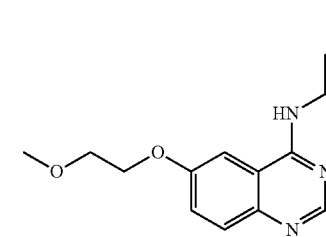
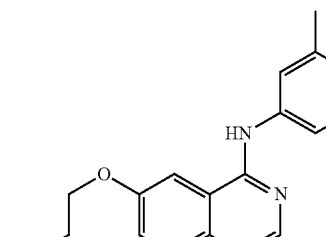
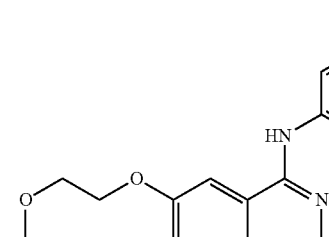
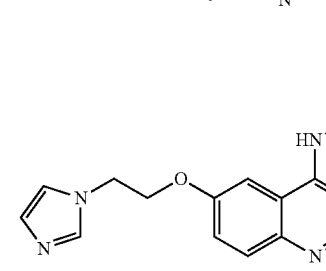

251
-continued
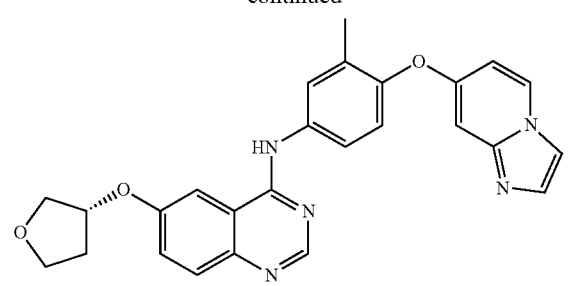
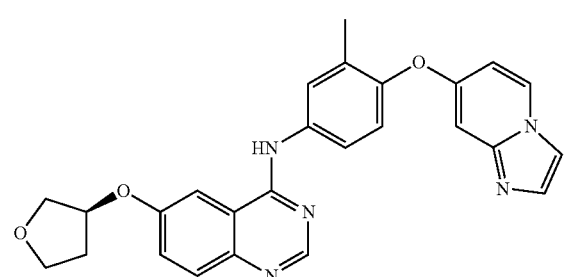
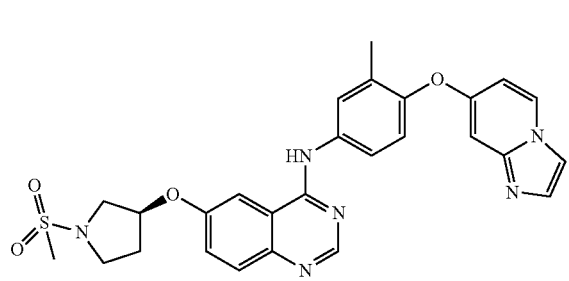
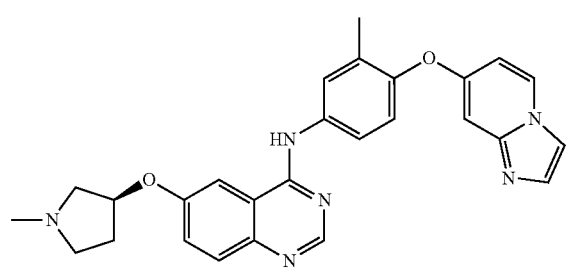
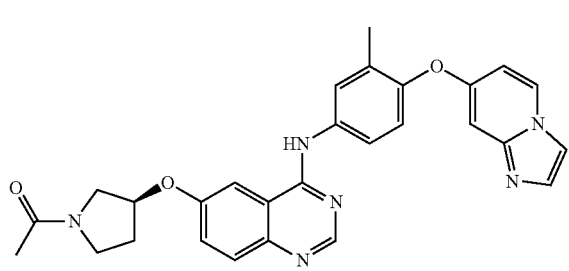
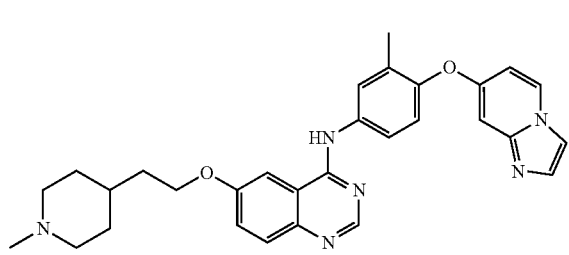
252
-continued
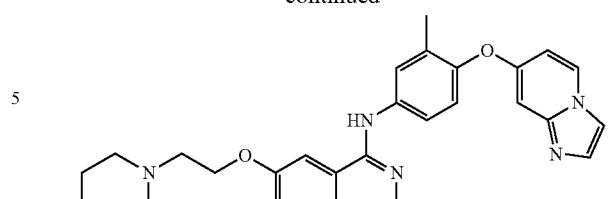
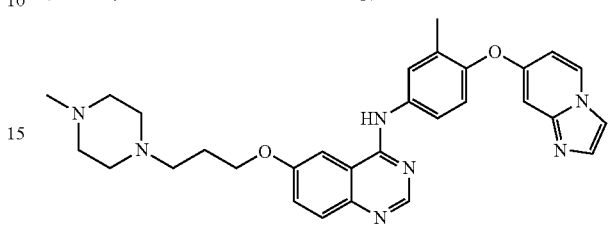
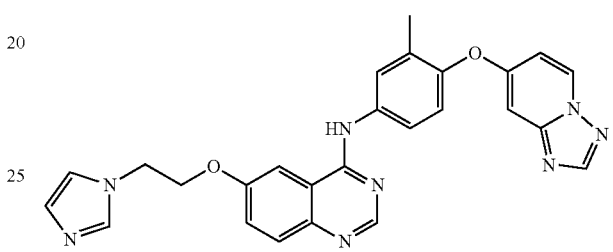
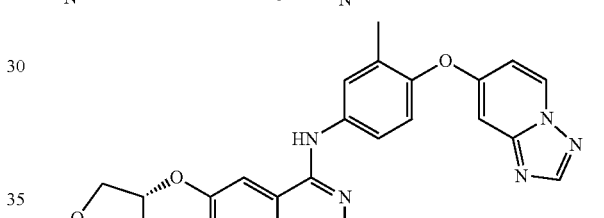
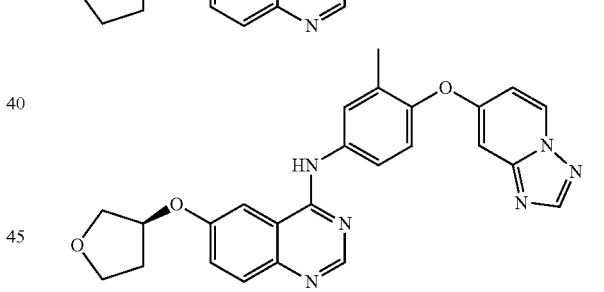
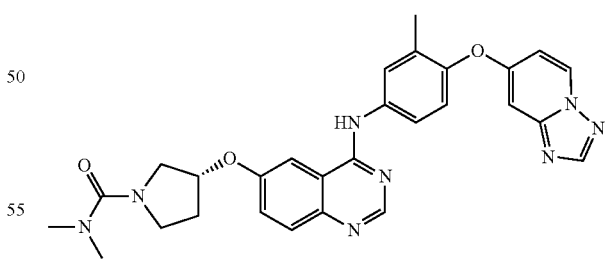
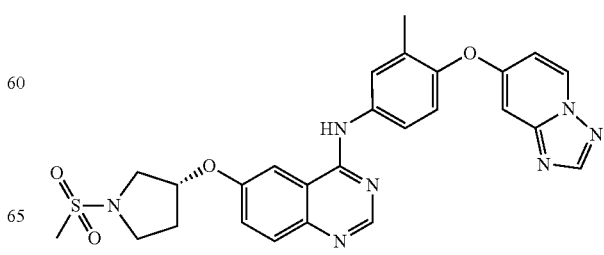

253
-continued
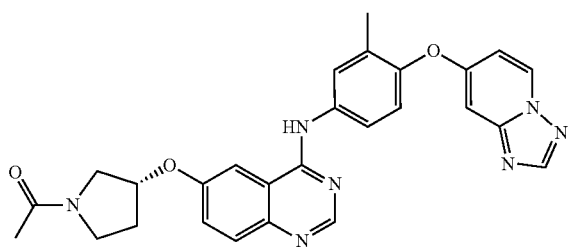
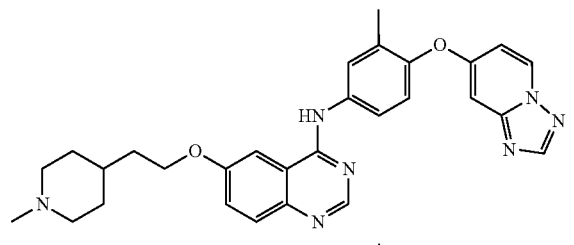
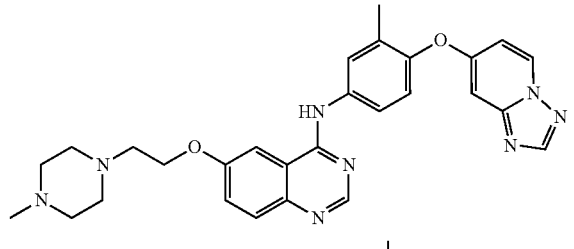
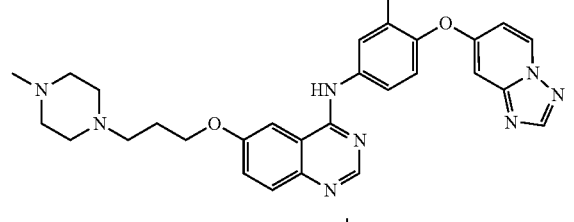
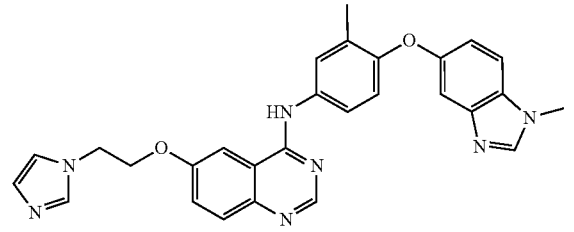
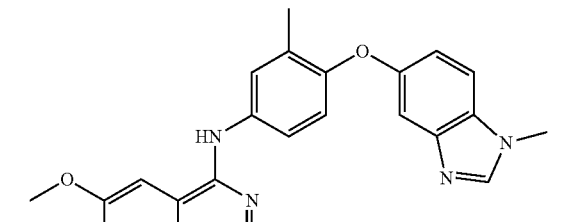
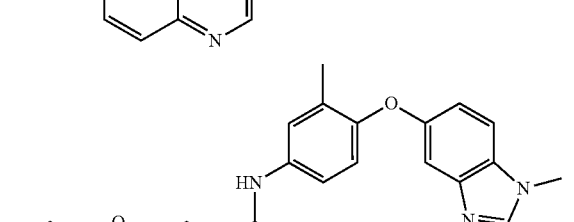
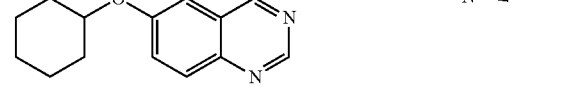
254
-continued
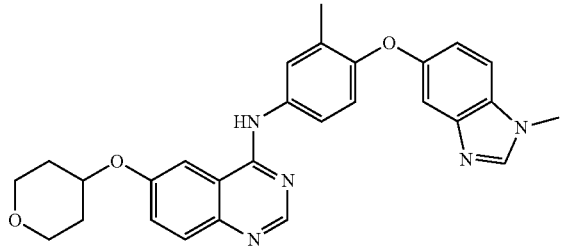
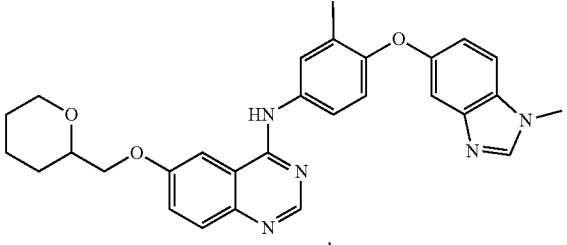
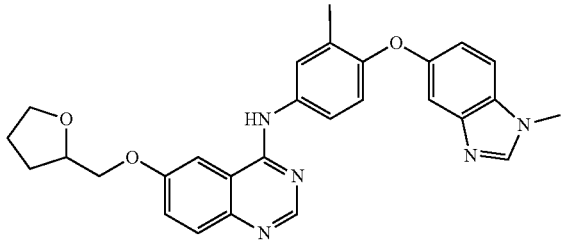
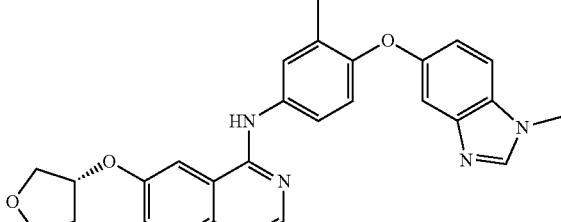
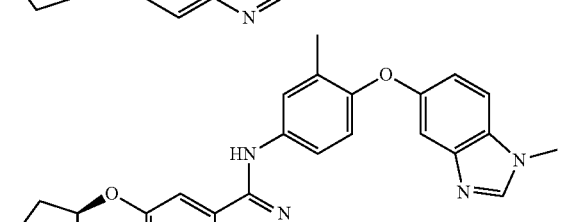
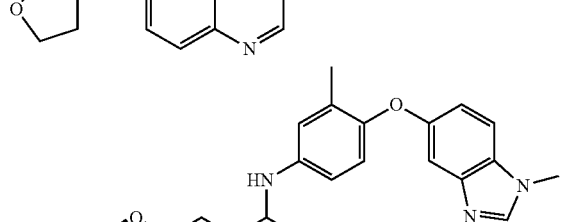
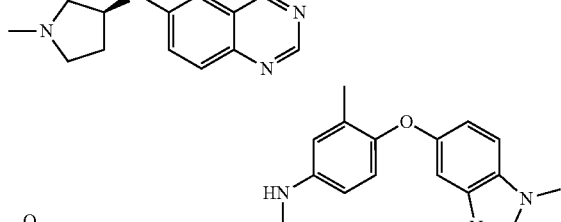
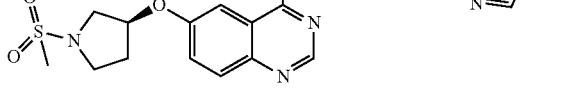

255
-continued
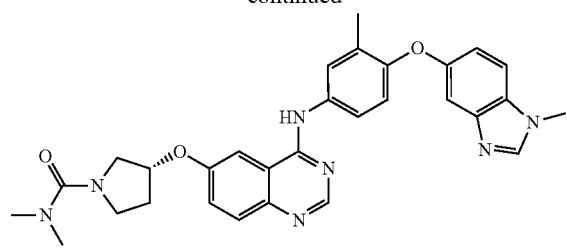
256
-continued
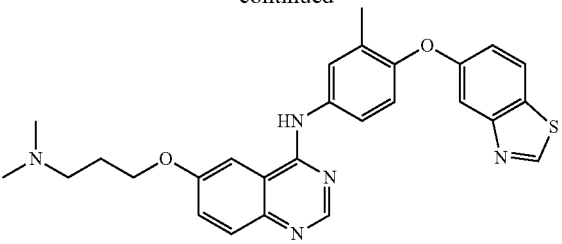
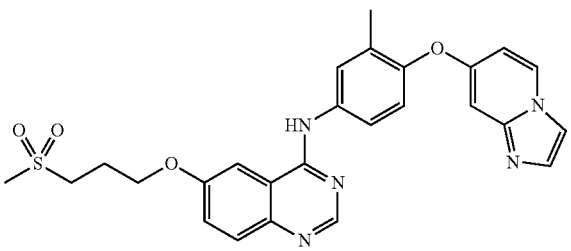
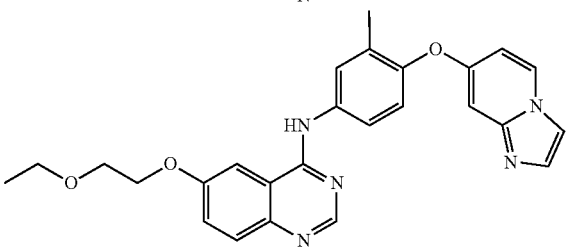
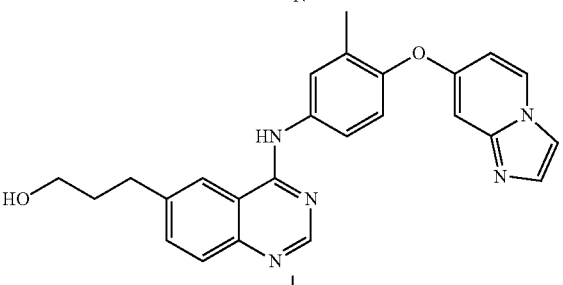
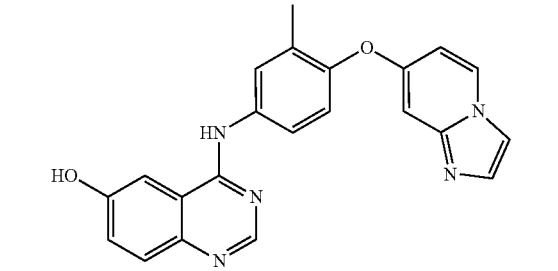
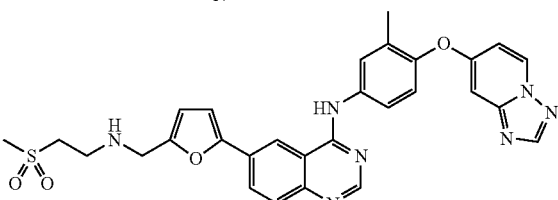
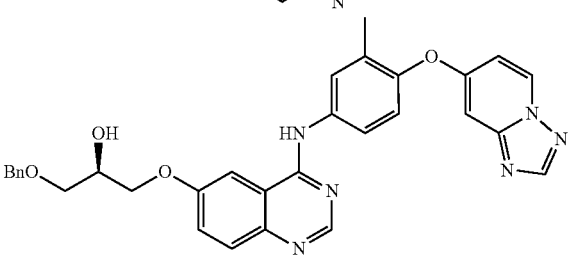

257
-continued
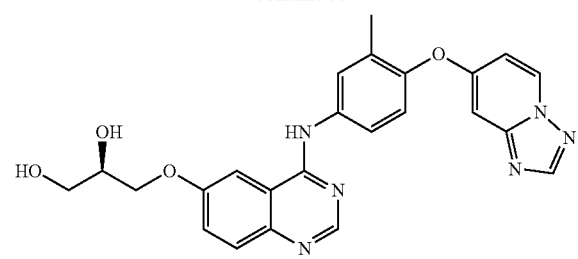
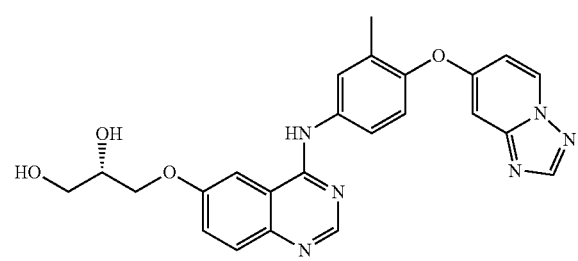
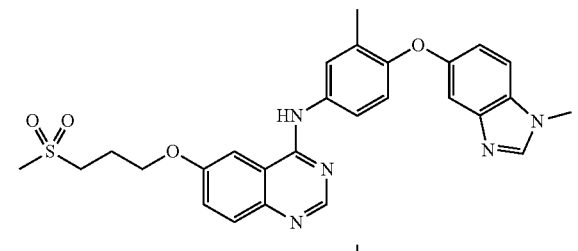
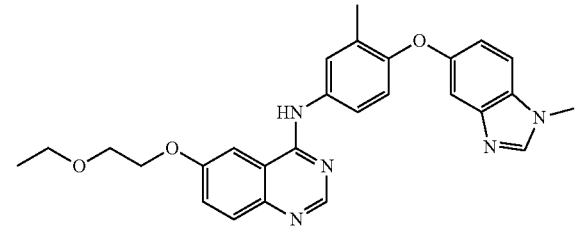
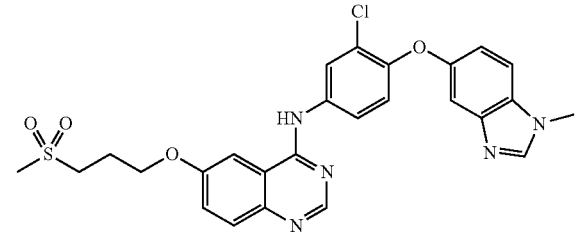
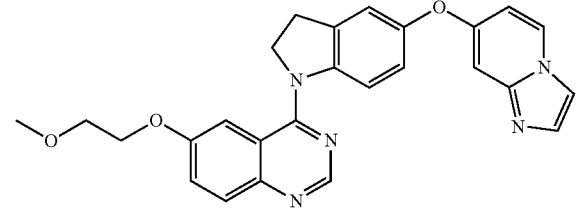
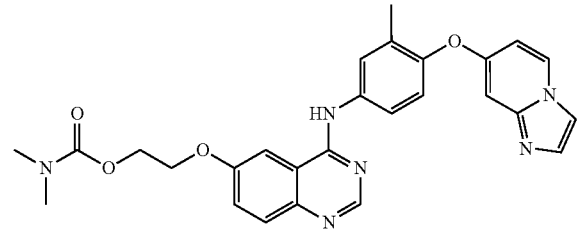
258
-continued
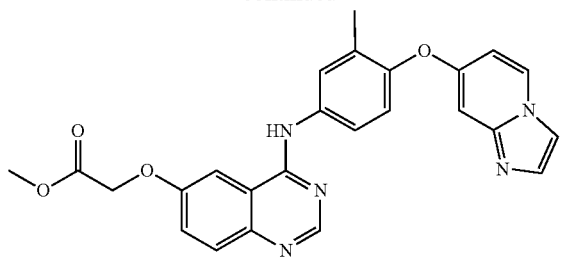
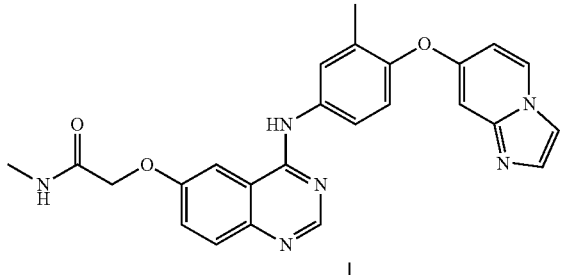
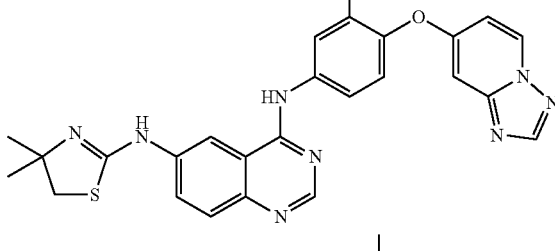
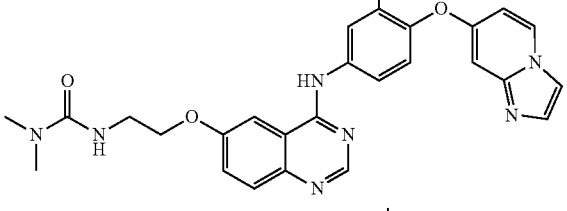
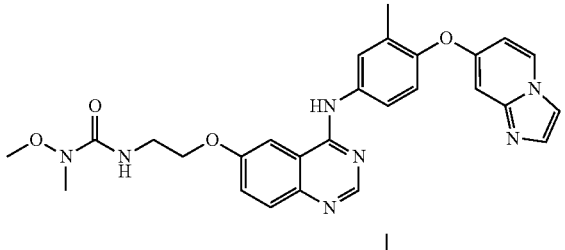
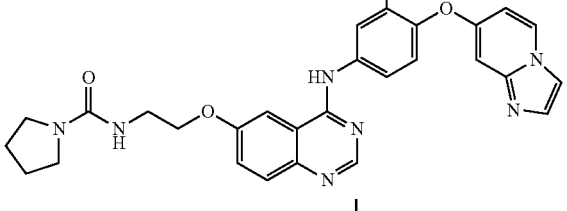
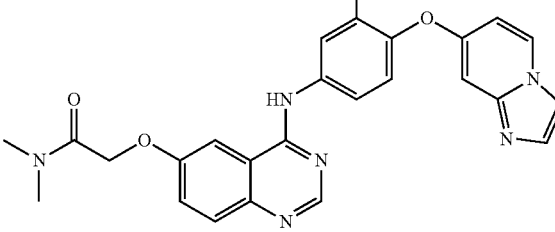

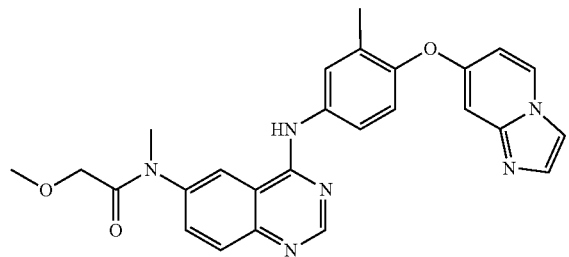
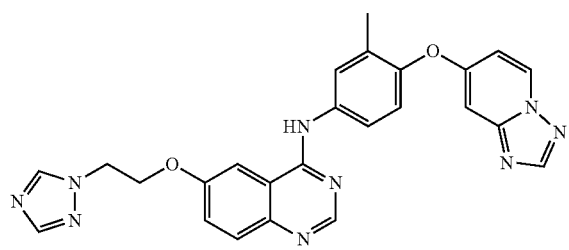
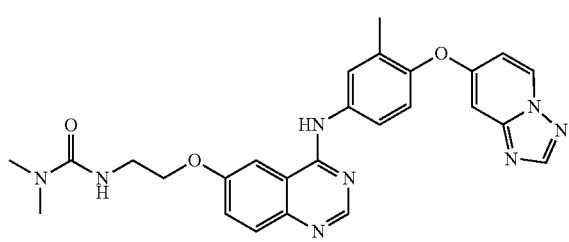
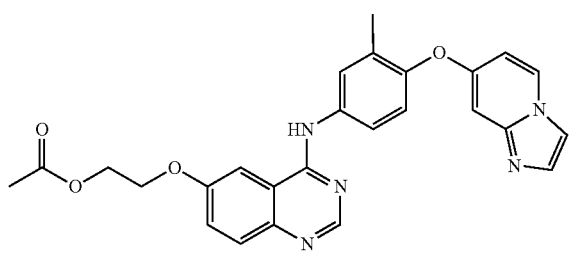
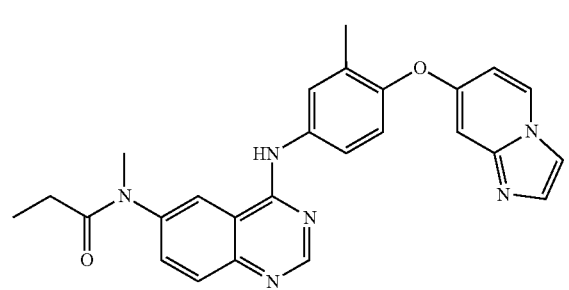
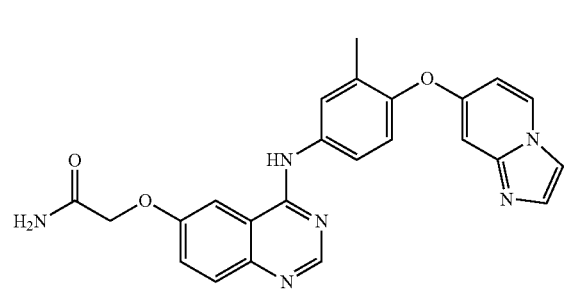
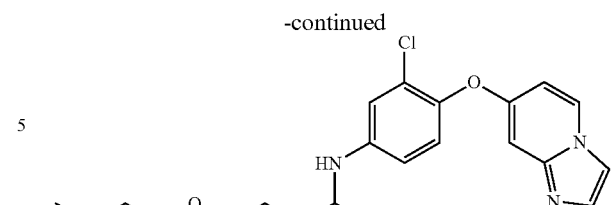
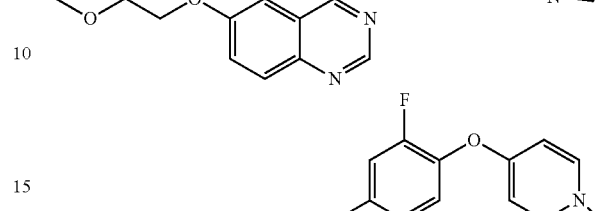
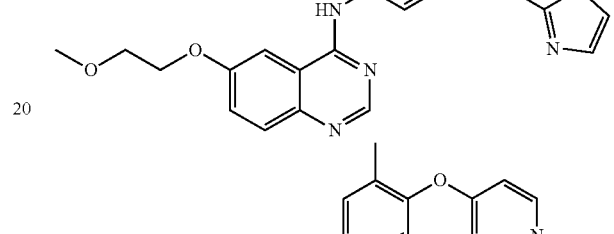
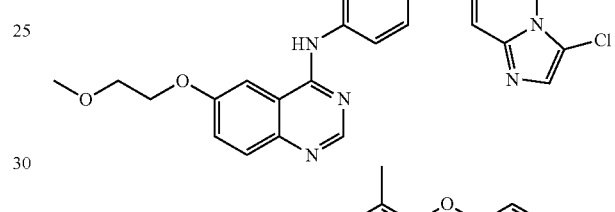
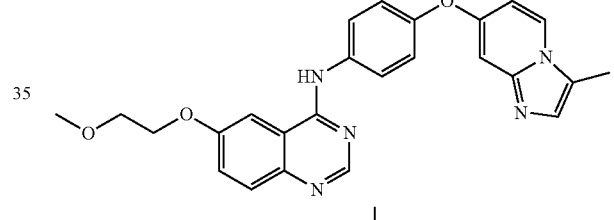
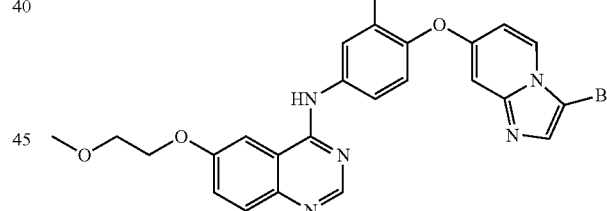
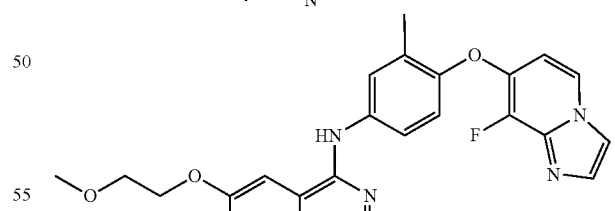
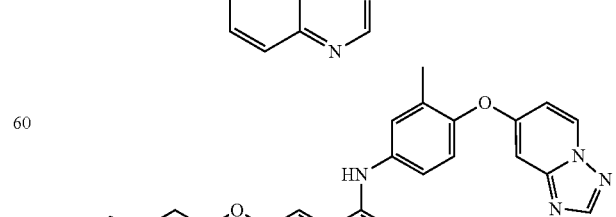

-continued
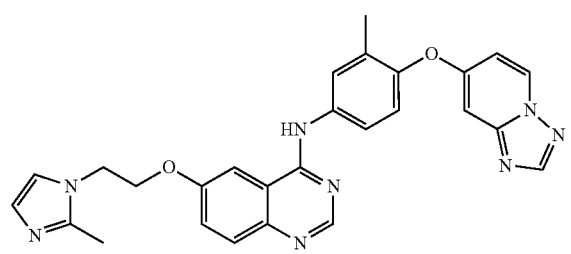
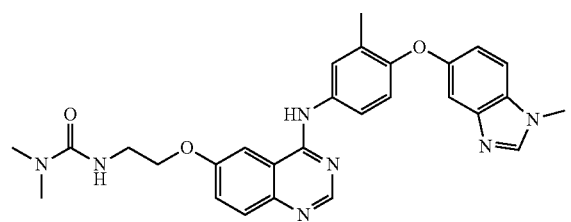
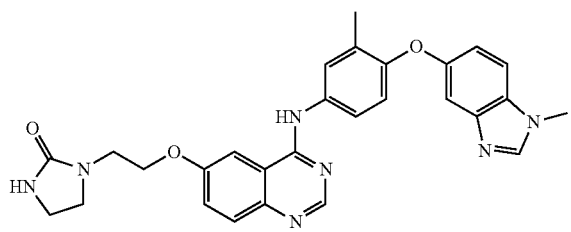
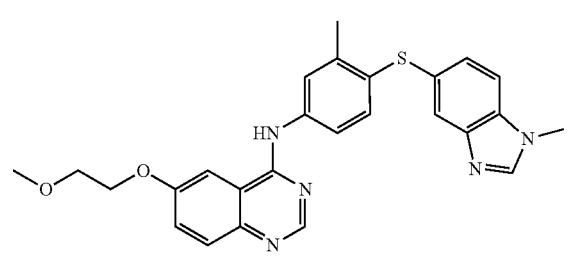
or a pharmaceutically acceptable salt thereof.
25. A compound according to claim 24, having the structure:
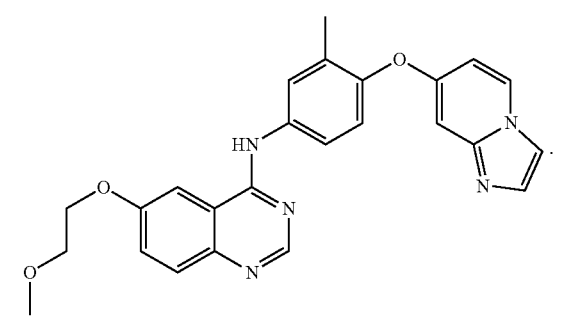 [SMILES: COCCOc1ccc2ncnc(Nc3ccc(Oc4ccn5ccnc5c4)c(C)c3)c2c1]
26. A compound according to claim 24, having the structure:
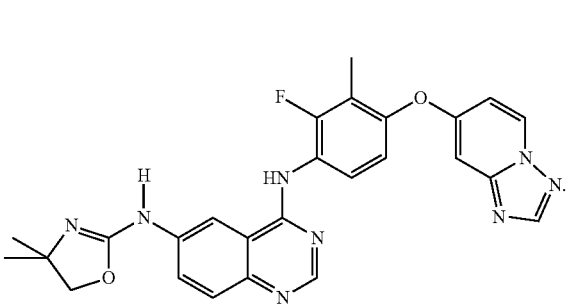 [SMILES: Cc1c(Oc2ccn3ncnc3c2)ccc(Nc2ncnc3ccc(NC4=NC(C)(C)CO4)cc23)c1F]
27. A compound according to claim 24, having the structure:
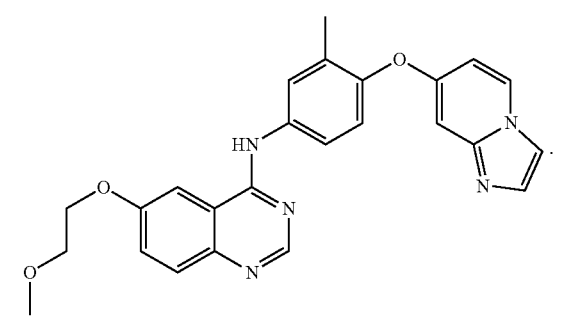 [SMILES: COCCOc1ccc2ncnc(Nc3ccc(Oc4ccn5ccnc5c4)c(C)c3)c2c1]
28. A compound according to claim 24, having the structure:
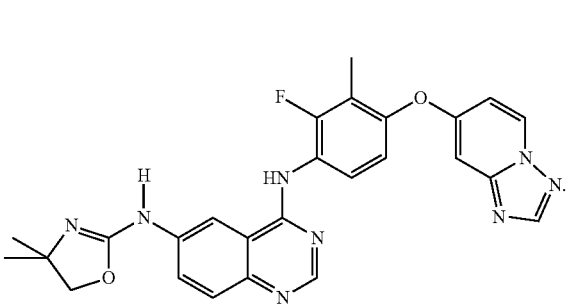 [SMILES: Cc1c(Oc2ccn3ncnc3c2)ccc(Nc2ncnc3ccc(NC4=NC(C)(C)CO4)cc23)c1F]
29. A compound according to claim 24, having the structure:
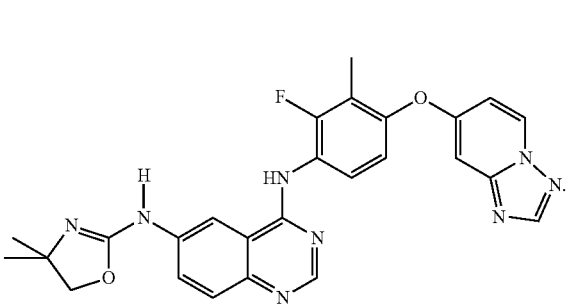 [SMILES: Cc1c(Oc2ccn3ncnc3c2)ccc(Nc2ncnc3ccc(NC4=NC(C)(C)CO4)cc23)c1F]

30. A compound according to claim 24, having the structure:

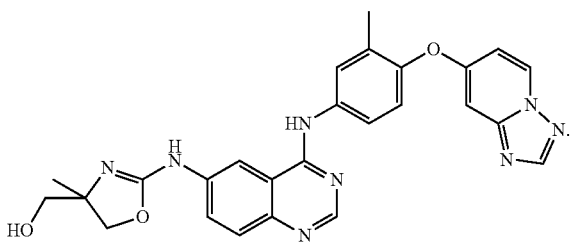 [SMILES: Cc1cc(Nc2ncnc3ccc(NC4=NC(C)(CO)CO4)cc23)ccc1Oc1ccn2ncnc2c1]

31. A compound of Formula 8:

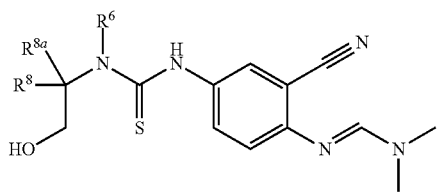

8 wherein each $R^6$, $R^8$, and $R^{8a}$ are independently hydrogen, trifluoromethyl, alkyl, saturated or partially unsaturated cycloalkyl, saturated or partially unsaturated heterocyclyl, aryl, arylalkyl, heteroaryl, heteroarylalkyl, or heterocyclylalkyl, wherein said alkyl, cycloalkyl, heterocyclyl, aryl, arylalkyl, heteroaryl, heteroarylalkyl, and heterocyclylalkyl are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, $OR^{15}$, $NR^{15}R^{16}$, $SR^{15}$, $S(=O)R^{15}$, $SO_2R^{15}$, trifluoromethyl, difluoromethyl, fluoromethyl, fluoromethoxy, difluoromethoxy, trifluoromethoxy, azido, aryl, heteroaryl, arylalkyl, heteroarylalkyl, and heterocyclylalkyl, or $R^8$ and $R^{8a}$ together with the atom to which they are attached form a 3 to 6 membered carbocyclic ring;

or $R^6$ and $R^8$ together with the atoms to which they are attached form a 3 to 10 membered saturated or partially unsaturated heterocyclyl ring optionally containing one or more additional heteroatoms selected from N, O, S, SO, $SO_2$ and $NR^6$, wherein said carbocyclic and heterocyclic rings are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^{15}$, $NR^{15}R^{16}$, $SR^{15}$, heteroaryl, arylalkyl, heteroarylalkyl, and heterocyclylalkyl;

$R^{15}$ and $R^{16}$ are independently H, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, C(=O)$R^a$, C(=O)$OR^a$, OC(=O)$R^a$, C(=O)$NR^aR^b$, $NR^aC(=O)R^b$, $NR^aC(=O)NR^bR^c$, OC(=O)$NR^aR^b$, and C(=O)CH$_2OR^a$;

or $R^{15}$ and $R^{16}$ together with the atom to which they are attached form a heterocyclic ring optionally containing one or more additional heteroatoms selected from N, O, S, SO, $SO_2$ and $NR^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^a$, $NR^aR^b$, $SR^a$, heteroaryl, arylalkyl, heteroarylalkyl, and heterocyclylalkyl; and $R^a$, $R^b$ and $R^c$ are independently H, alkyl, alkenyl, alkynyl, saturated or partially unsaturated cycloalkyl, saturated or partially unsaturated heterocyclyl, aryl, or heteroaryl, or $NR^aR^b$ forms a 5-6 membered heterocyclic ring having 1-2 ring nitrogen atoms and optionally substituted with ($C_1$-$C_3$ alkyl), or $NR^bR^c$ forms a 5-6 membered heterocyclic ring having 1-2 ring nitrogen atoms.

32. A compound of Formula 9:

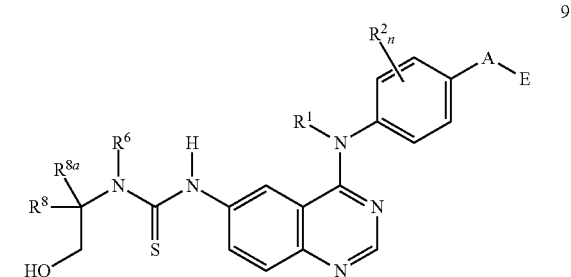

9 wherein A is O, C(=O), S, SO or $SO_2$;

E is:

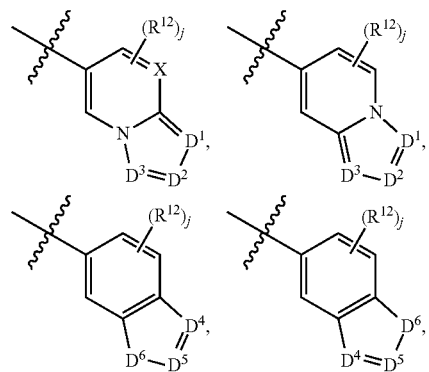

-continued

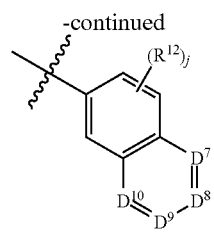

X is N or CH;

$D^1$, $D^2$ and $D^3$ are independently N or $CR^{19}$;

$D^4$ and $D^5$ are independently N or $CR^{19}$ and $D^6$ is O, S, or $NR^{20}$, wherein at least one of $D^4$ and $D^5$ is not $CR^{19}$;

$D^7$, $D^8$, $D^9$ and $D^{10}$ are independently N or $CR^{19}$, wherein at least one of $D^7$, $D^8$, $D^9$ and $D^{10}$ is N;

$R^1$ is H or alkyl;

each $R^2$ is independently halogen, cyano, nitro, trifluoromethyl, difluoromethyl, fluoromethyl, fluoromethoxy, difluoromethoxy, trifluoromethoxy, azido, —$SR^{18}$, —$OR^{15}$, —$C(O)R^{15}$, —$C(O)OR^{15}$, —$NR^{14}C(O)OR^{18}$, —$OC(O)R^{15}$, —$NR^{14}SO_2R^{18}$, —$SO_2NR^{15}R^{14}$, —$NR^{14}C(O)R^{15}$, —$C(O)NR^{15}R^{14}$, —$NR^{15}C(O)NR^{15}R^{14}$, —$NR^{13}C(NCN)NR^{15}R^{14}$, —$NR^{15}R^{14}$, alkyl, alkenyl, alkynyl, saturated or partially unsaturated cycloalkyl, cycloalkylalkyl, —$S(O)_p$(alkyl), —$S(O)_p(CR^{13}R^{14})_q$-aryl, aryl, arylalkyl, heteroaryl, heteroarylalkyl, saturated or partially unsaturated heterocyclyl, heterocyclylalkyl, —$O(CR^{13}R^{14})_q$-aryl, —$NR^{15}(CR^{13}R^{14})_q$-aryl, —$O(CR^{13}R^{14})_q$-heteroaryl, —$NR^{13}(CR^{13}R^{14})_q$-heteroaryl, —$O(CR^{13}R^{14})_q$-heterocyclyl or —$NR^{15}(CR^{13}R^{14})_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^{13}SO_2R^{18}$, —$SO_2NR^{15}R^{13}$, —$C(O)R^{15}$, —$C(O)OR^{15}$, —$OC(O)R^{15}$, —$NR^{13}C(O)OR^{18}$, —$NR^{13}C(O)R^{15}$, —$C(O)NR^{15}R^{13}$, —$NR^{15}R^{13}$, —$NR^{14}C(O)NR^{15}R^{13}$, —$NR^{14}C(NCN)NR^{15}R^{13}$, —$OR^{15}$, aryl, heteroaryl, arylalkyl, heteroarylalkyl, saturated and partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, $NR^{15}R^{13}$ and $OR^{15}$;

each $R^6$, $R^8$, and $R^{8a}$ are independently hydrogen, trifluoromethyl, alkyl, saturated or partially unsaturated cycloalkyl, saturated or partially unsaturated heterocyclyl, aryl, arylalkyl, heteroaryl, heteroarylalkyl, or heterocyclylalkyl, wherein said alkyl, cycloalkyl, heterocyclyl, aryl, arylalkyl, heteroaryl, heteroarylalkyl, and heterocyclylalkyl are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, $OR^{15}$, $NR^{15}R^{16}$, $SR^{15}$, $S(=O)R^{15}$, $SO_2R^{15}$, trifluoromethyl, difluoromethyl, fluoromethyl, fluoromethoxy, difluoromethoxy, trifluoromethoxy, azido, aryl, heteroaryl, arylalkyl, heteroarylalkyl, and heterocyclylalkyl, or $R^8$ and $R^{8a}$ together with the atom to which they are attached form a 3 to 6 membered carbocyclic ring;

or $R^6$ and $R^8$ together with the atoms to which they are attached form a 3 to 10 membered saturated or partially unsaturated heterocyclyl ring optionally containing one or more additional heteroatoms selected from N, O, S, SO, $SO_2$ and $NR^6$, wherein said carbocyclic and heterocyclic rings are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^{15}$, Nee, $SR^{15}$, heteroaryl, arylalkyl, heteroarylalkyl, and heterocyclylalkyl;

each $R^{12}$ is independently halogen, cyano, nitro, trifluoromethyl, difluoromethyl, fluoromethyl, fluoromethoxy, difluoromethoxy, trifluoromethoxy, azido, —$SR^{18}$, —$OR^{15}$, —$C(O)R^{15}$, —$C(O)OR^{15}$, —$NR^{14}C(O)OR^{18}$, —$OC(O)R^{15}$, —$NR^{14}SO_2R^{18}$, —$SO_2NR^{15}R^{14}$, —$NR^{14}C(O)R^{15}$, —$C(O)NR^{15}R^{14}$, —$NR^{13}C(O)NR^{15}R^{14}$, —$NR^{13}C(NCN)NR^{15}R^{14}$, —$NR^{15}R^{14}$, alkyl, alkenyl, alkynyl, saturated or partially unsaturated cycloalkyl, cycloalkylalkyl, —$S(O)_p$(alkyl), —$S(O)_p(CR^{13}R^{14})_q$-aryl, aryl, arylalkyl, heteroaryl, heteroarylalkyl, saturated or partially unsaturated heterocyclyl, heterocyclylalkyl, —$O(CR^{13}R^{14})_q$-aryl, —$NR^{15}(CR^{13}R^{14})_q$-aryl, —$O(CR^{13}R^{14})_q$-heteroaryl, —$NR^{13}(CR^{13}R^{14})_q$-heteroaryl, —$O(CR^{13}R^{14})_q$-heterocyclyl or —$NR^{15}(CR^{13R14})_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^{13}SO_2R^{18}$, —$SO_2NR^{15}R^{13}$, —$C(O)R^{15}$, —$C(O)OR^{15}$, —$OC(O)R^{15}$, —$NR^{13}C(O)OR^{18}$, —$NR^{13}C(O)R^{15}$, —$C(O)NR^{15}R^{13}$, —$NR^{15}R^{13}$, —$NR^{14}C(O)NR^{15}R^{13}$, —$NR^{14}C(NCN)NR^{15}R^{13}$, —$OR^{15}$, aryl, heteroaryl, arylalkyl, heteroarylalkyl, saturated and partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, $NR^{15}R^{13}$ and $OR^{15}$;

$R^{13}$ and $R^{14}$ are independently hydrogen or alkyl, or $R^{13}$ and $R^{14}$ together with the atoms to which they are attached form a saturated or partially unsaturated cycloalkyl, or saturated or partially unsaturated heterocyclyl ring, wherein said alkyl, cycloalkyl and heterocyclyl portions are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, $C(=O)R^a$, $C(=O)OR^a$, $OC(=O)R^a$, $C(=O)NR^aR^b$, $NR^aC(=O)R^b$, and $NR^aC(=O)NR^bR^c$;

$R^{15}$ and $R^{16}$ are independently H, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, $C(=O)R^a$, $C(=O)OR^a$, $OC(=O)R^a$, $C(=O)NR^aR^b$, $NR^aC(=O)R^b$, $NR^aC(=O)NR^bR^c$, $OC(=O)NR^aR^b$, and $C(=O)CH_2OR^a$;

or $R^{15}$ and $R^{16}$ together with the atom to which they are attached form a heterocyclic ring optionally containing one or more additional heteroatoms selected from N, O, S, SO, $SO_2$ and $NR^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, $OR^a$, $NR^aR^b$, $SR^a$, heteroaryl, arylalkyl, heteroarylalkyl, and heterocyclylalkyl, or $R^{13}$ and $R^{15}$ together with the atom to which they are attached form a saturated or partially unsaturated cycloalkyl or saturated or partially unsaturated heterocyclyl ring, wherein said cycloalkyl and heterocyclyl are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, $C(=O)R^a$, $C(=O)OR^a$, $OC(=O)R^a$, $C(=O)NR^aR^b$, $NR^aC(=O)R^b$, and $NR^aC(=O)NR^bR^c$;

$R^{18}$ is $CF_3$, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, saturated or partially unsaturated heterocyclyl, cycloalkylalkyl, aryl, arylalkyl, heteroaryl, heteroarylalkyl and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, $C(=O)R^a$, $C(=O)OR^a$, $OC(=O)R^a$, $C(=O)NR^aR^b$, $NR^aC(=O)R^b$, and $NR^aC(=O)NR^bR^c$, or $R^{15}$ and $R^{18}$ together with the atoms to which they are attached form a saturated or partially unsaturated cycloalkyl or saturated or partially unsaturated heterocyclyl ring, wherein said cycloalkyl and heterocyclyl are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, S—S—$R^a$, $C(=O)R^a$, $C(=O)OR^a$, $OC(=O)R^a$, $C(=O)NR^aR^b$, $NR^aC(=O)R^b$, and $NR^aC(=O)NR^bR^c$;

each $R^{19}$ is independently H, halogen, cyano, nitro, trifluoromethyl, difluoromethyl, fluoromethyl, fluoromethoxy, difluoromethoxy, trifluoromethoxy, azido, —$SR^{18}$, —$OR^{15}$, —$C(O)R^{15}$, —$C(O)OR^{15}$, —$NR^{14}C(O)OR^{18}$, —$OC(O)R^{15}$, —$NR^{14}SO_2R^{18}$, —$SO_2NR^{15}R^{14}$, —$NR^{14}C(O)R^{15}$, —$C(O)NR^{15}R^{14}$, —$NR^{13}C(O)NR^{15}R^{14}$, —$NR^{13}C(NCN)NR^{15}R^{14}$, —$NR^{15}R^{14}$, alkyl, alkenyl, alkynyl, saturated or partially unsaturated cycloalkyl, cycloalkylalkyl, —$S(O)_p$(alkyl), —$S(O)_p(CR^{13}R^{14})_q$-aryl, aryl, arylalkyl, heteroaryl, heteroarylalkyl, saturated or partially unsaturated heterocyclyl, heterocyclylalkyl, —$O(CR^{13}R^{14})_q$-aryl, —$NR^{15}(CR^{13}R^{14})_q$-aryl, —$O(CR^{13}R^{14})_q$-heteroaryl, —$NR^{13}(CR^{13}R^{14})_q$-heteroaryl, —$O(CR^{13}R^{14})_q$-heterocyclyl or —$NR^{15}(CR^{13}R^{14})_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^{13}SO_2R^{18}$, —$SO_2NR^{15}R^{13}$, —$C(O)R^{15}$, —$C(O)OR^{15}$, —$OC(O)R^{15}$, —$NR^{13}C(O)OR^{18}$, —$NR^{13}C(O)R^{15}$, —$C(O)NR^{15}R^{13}$, —$NR^{15}R^{13}$, —$NR^{14}C(O)NR^{15}R^{13}$, —$NR^{14}C(NCN)NR^{15}R^{13}$, —$OR^{15}$, aryl, heteroaryl, arylalkyl, heteroarylalkyl, saturated or partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, $NR^{15}R^{13}$ and $OR^{15}$;

each $R^{2o}$ is independently $C_1$-$C_4$ alkyl, saturated or partially unsaturated cycloalkyl, trifluoromethyl, difluoromethyl, or fluoromethyl;

$R^a$, $R^b$ and $R^c$ are independently H, alkyl, alkenyl, alkynyl, saturated or partially unsaturated cycloalkyl, saturated or partially unsaturated heterocyclyl, aryl, or heteroaryl, or $NR^aR^b$ forms a 5-6 membered heterocyclic ring having 1-2 ring nitrogen atoms and optionally substituted with ($C_1$-$C_3$ alkyl), or $NR^bR^c$ forms a 5-6 membered heterocyclic ring having 1-2 ring nitrogen atoms;

j is 0, 1, 2 or 3;

n is 0, 1, 2, 3, or 4;

q is 0, 1, 2, 3, 4, or 5; and p is 0, 1 or 2.

33. A process for preparing a compound of Formula 9:

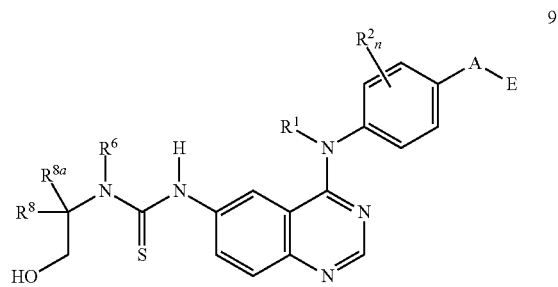

comprising condensing a compound of Formula 8:

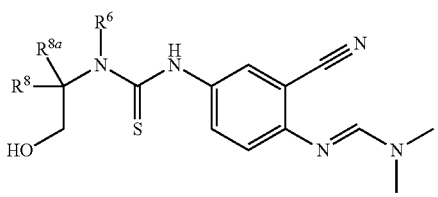

with a compound of Formula 2:

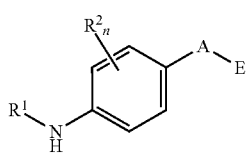

in the presence of an acid in a suitable solvent to provide a compound of Formula 9;

wherein A is O, C(=O), S, SO or SO$_2$;

E is:

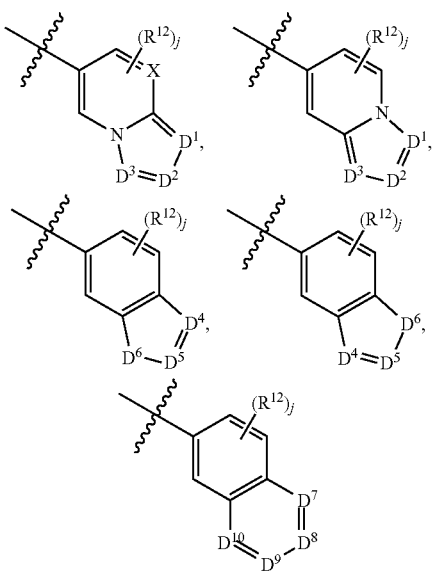

X is N or CH;

D$^1$, D$^2$ and D$^3$ are independently N or CR$^{19}$;

D$^4$ and D$^5$ are independently N or CR$^{19}$ and D$^6$ is O, S, or NR$^{20}$, wherein at least one of D$^4$ and D$^5$ is not CR$^{19}$;

D$^7$, D$^8$, D$^9$ and D$^{10}$ are independently N or CR$^{19}$, wherein at least one of D$^7$, D$^8$, D$^9$ and D$^{10}$ is N;

R$^1$ is H or alkyl;

each R$^2$ is independently halogen, cyano, nitro, trifluoromethyl, difluoromethyl, fluoromethyl, fluoromethoxy, difluoromethoxy, trifluoromethoxy, azido, —SR$^{18}$, —OR$^{15}$, —C(O)R$^{15}$, —C(O)OR$^{15}$, —NR$^{14}$C(O)OR$^{18}$, —OC(O)R$^{15}$, —NR$^{14}$SO$_2$R$^{18}$, —SO$_2$NR$^{15}$R$^{14}$, —NR$^{14}$C(O)R$^{15}$, —C(O)NR$^{15}$R$^{14}$, —NR$^{15}$C(O)NR$^{15}$R$^{14}$, —NR$^{13}$C(NCN)NR$^{15}$R$^{14}$, —NR$^{15}$R$^{14}$, alkyl, alkenyl, alkynyl, saturated or partially unsaturated cycloalkyl, cycloalkylalkyl, —S(O)$_p$(alkyl), —S(O)$_p$(CR$^{13}$R$^{14}$)$_q$-aryl, aryl, arylalkyl, heteroaryl, heteroarylalkyl, saturated or partially unsaturated heterocyclyl, heterocyclylalkyl, —O(CR$^{13}$R$^{14}$)$_q$-aryl, —NR$^{15}$(CR$^{13}$R$^{14}$)$_q$-aryl, —O(CR$^{13}$R$^{14}$)$_q$-heteroaryl, —NR$^{13}$(CR$^{13}$R$^{14}$)$_q$-heteroaryl, —O(CR$^{13}$R$^{14}$)$_q$-heterocyclyl or —NR$^{15}$(CR$^{13}$R$^{14}$)$_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR$^{13}$SO$_2$R$^{18}$, —SO$_2$NR$^{15}$R$^{13}$, —C(O)R$^{15}$, —C(O)OR$^{15}$, —OC(O)R$^{15}$, —NR$^{13}$C(O)OR$^{18}$, —NR$^{13}$C(O)R$^{15}$, —C(O)NR$^{15}$R$^{13}$, —NR$^{15}$R$^{13}$, —NR$^{14}$C(O)NR$^{15}$R$^{13}$, —NR$^{14}$C(NCN)NR$^{15}$R$^{13}$, —OR$^{15}$, aryl, heteroaryl, arylalkyl, heteroarylalkyl, saturated and partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, NR$^{15}$R$^{13}$ and OR$^{15}$;

each R$^6$, R$^8$, and R$^{8a}$ are independently hydrogen, trifluoromethyl, alkyl, saturated or partially unsaturated cycloalkyl, saturated or partially unsaturated heterocyclyl, aryl, arylalkyl, heteroaryl, heteroarylalkyl, or heterocyclylalkyl, wherein said alkyl, cycloalkyl, heterocyclyl, aryl, arylalkyl, heteroaryl, heteroarylalkyl, and heterocyclylalkyl are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, OR$^{15}$, NR$^{15}$R$^{16}$, SR$^{15}$, S(=O)R$^{15}$, SO$_2$R$^{15}$, trifluoromethyl, difluoromethyl, fluoromethyl, fluoromethoxy, difluoromethoxy, trifluoromethoxy, azido, aryl, heteroaryl, arylalkyl, heteroarylalkyl, and heterocyclylalkyl, or R$^8$ and R$^{8a}$ together with the atom to which they are attached form a 3 to 6 membered carbocyclic ring;

or R$^6$ and R$^8$ together with the atoms to which they are attached form a 3 to 10 membered saturated or partially unsaturated heterocyclyl ring optionally containing one or more additional heteroatoms selected from N, O, S, SO, SO$_2$ and NR$^6$, wherein said carbocyclic and heterocyclic rings are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, OR$^{15}$, NR$^{15}$R$^{16}$, SR$^{15}$, heteroaryl, arylalkyl, heteroarylalkyl, and heterocyclylalkyl;

each R$^{12}$ is independently halogen, cyano, nitro, trifluoromethyl, difluoromethyl, fluoromethyl, fluoromethoxy, difluoromethoxy, trifluoromethoxy, azido, —SR$^{18}$, —OR$^{15}$, —C(O)R$^{15}$, —C(O)OR$^{15}$, —NR$^{14}$C(O)OR$^{18}$, —OC(O)R$^{15}$, —NR$^{14}$SO$_2$R$^{18}$, —SO$_2$NR$^{15}$R$^{14}$, —NR$^{14}$C(O)R$^{15}$, —C(O)NR$^{15}$R$^{14}$, —NR$^{13}$C(O)NR$^{15}$R$^{14}$, —NR$^{13}$C(NCN)NR$^{15}$R$^{14}$, —NR$^{15}$R$^{14}$, alkyl, alkenyl, alkynyl, saturated or partially unsaturated cycloalkyl, cycloalkylalkyl, —S(O)$_p$(alkyl), —S(O)$_p$(CR$^{13}$R$^{14}$)$_q$-aryl, aryl, arylalkyl, heteroaryl, heteroarylalkyl, saturated or partially unsaturated heterocyclyl, heterocyclylalkyl, —O($CR^{13}R^{14}$)$_q$-aryl, —$NR^{15}$($CR^{13}R^{14}$)$_q$-aryl, —O($CR^{13}R^{14}$)$_q$-heteroaryl, —$NR^{13}$($CR^{13}R^{14}$)$_q$-heteroaryl, —O($CR^{13}R^{14}$)$_q$-heterocyclyl or —$NR^{15}R^{14}$)$_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^{13}SO_2R^{18}$, —$SO_2NR^{15}R^{13}$, —C(O)$R^{15}$, —C(O)O$R^{15}$, —OC(O)$R^{15}$, —$NR^{13}$C(O)O$R^{18}$, —$NR^{13}$C(O)$R^{15}$, —C(O)$NR^{15}R^{13}$, —$NR^{15}R^{13}$, —$NR^{14}$C(O)$NR^{15}R^{13}$, —$NR^{14}$C(NCN)$NR^{15}R^{13}$, —O$R^{15}$, aryl, heteroaryl, arylalkyl, heteroarylalkyl, saturated and partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, $NR^{15}R^{13}$ and O$R^{15}$;

$R^{13}$ and $R^{14}$ are independently hydrogen or alkyl, or $R^{13}$ and $R^{14}$ together with the atoms to which they are attached form a saturated or partially unsaturated cycloalkyl, or saturated or partially unsaturated heterocyclyl ring, wherein said alkyl, cycloalkyl and heterocyclyl portions are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, O$R^a$, $NR^aR^b$, $NR^aOR^b$, $NR^aCO_2R^b$, $NR^aCOR^b$, $SO_2NR^aR^b$, S$R^a$, SO$R^a$, $SO_2R^a$, S—S—$R^a$, C(=O)$R^a$, C(=O)O$R^a$, OC(=O)$R^a$, C(=O)$NR^aR^b$, $NR^a$C(=O)$R^b$, and $NR^a$C(=O)$NR^bR^c$;

$R^{15}$ and $R^{16}$ are independently H, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, O$R^a$, $NR^aR^b$, $NR^aOR^b$, $NR^aCO_2R^b$, $NR^aCOR^b$, $SO_2NR^aR^b$, S$R^a$, SO$R^a$, $SO_2R^a$, S—S—$R^a$, C(=O)$R^a$, C(=O)O$R^a$, OC(=O)$R^a$, C(=O)$NR^aR^b$, $NR^a$C(=O)$R^b$, $NR^a$C(=O)$NR^bR^c$, OC(=O)$NR^aR^b$, and C(=O)$CH_2OR^a$;

or $R^{15}$ and $R^{16}$ together with the atom to which they are attached form a heterocyclic ring optionally containing one or more additional heteroatoms selected from N, O, S, SO, $SO_2$ and $NR^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, O$R^a$, $NR^aR^b$, S$R^a$, heteroaryl, arylalkyl, heteroarylalkyl, and heterocyclylalkyl, or $R^{13}$ and $R^{15}$ together with the atom to which they are attached form a saturated or partially unsaturated cycloalkyl or saturated or partially unsaturated heterocyclyl ring, wherein said cycloalkyl and heterocyclyl are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, O$R^a$, $NR^aR^b$, $NR^aOR^b$, $NR^aCO_2R^b$, $NR^aCOR^b$, $SO_2NR^aR^b$, S$R^a$, SO$R^a$, $SO_2R^a$, S—S—$R^a$, C(=O)$R^a$, C(=O)O$R^a$, OC(=O)$R^a$, C(=O)$NR^aR^b$, $NR^a$C(=O)$R^b$, and $NR^a$C(=O)$NR^bR^c$;

$R^{18}$ is $CF_3$, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, saturated or partially unsaturated heterocyclyl, cycloalkylalkyl, aryl, arylalkyl, heteroaryl, heteroarylalkyl and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, O$R^a$, $NR^aR^b$, $NR^aOR^b$, $NR^aCO_2R^b$, $NR^aCOR^b$, $SO_2NR^aR^b$, S$R^a$, SO$R^a$, $SO_2R^a$, S—S—$R^a$, C(=O)$R^a$, C(=O)O$R^a$, OC(=O)$R^a$, C(=O)$NR^aR^b$, $NR^a$C(=O)$R^b$, and $NR^a$C(=O)$NR^bR^c$, or $R^{15}$ and $R^{18}$ together with the atoms to which they are attached form a saturated or partially unsaturated cycloalkyl or saturated or partially unsaturated heterocyclyl ring, wherein said cycloalkyl and heterocyclyl are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, O$R^a$, $NR^aR^b$, $NR^aOR^b$, $NR^aCO_2R^b$, $NR^aCOR^b$, $SO_2NR^aR^b$, S$R^a$, SO$R^a$, $SO_2R^a$, S—S—$R^a$, C(=O)$R^a$, C(=O)O$R^a$, OC(=O)$R^a$, C(=O)$NR^aR^b$, $NR^a$C(=O)$R^b$, and $NR^a$C(=O)$NR^bR^c$;

each $R^{19}$ is independently H, halogen, cyano, nitro, trifluoromethyl, difluoromethoxy, fluoromethyl, fluoromethoxy, difluoromethoxy, trifluoromethoxy, azido, —S$R^{18}$, —O$R^{15}$, —C(O)$R^{15}$, —C(O)O$R^{15}$, —$NR^{14}$C(O)O$R^{18}$, —OC(O)$R^{15}$, —$NR^{14}SO_2R^{18}$, —$SO_2NR^{15}R^{14}$, —$NR^{14}$C(O)$R^{15}$, —C(O)$NR^{15}R^{14}$, —$NR^{13}$C(O)$NR^{15}R^{14}$, —$NR^{13}$C(NCN)$NR^{15}R^{14}$, —$NR^{15}R^{14}$, alkyl, alkenyl, alkynyl, saturated or partially unsaturated cycloalkyl, cycloalkylalkyl, —S(O)$_p$(alkyl), —S(O)$_p$($CR^{13}R^{14}$)$_q$-aryl, aryl, arylalkyl, heteroaryl, heteroarylalkyl, saturated or partially unsaturated heterocyclyl, heterocyclylalkyl, —O($CR^{13}R^{14}$)$_q$-aryl, —$NR^{15}$($CR^{13}R^{14}$)$_q$-aryl, —O($CR^{13}R^{14}$)$_q$-heteroaryl, —$NR^{13}$($CR^{13}R^{14}$)$_q$-heteroaryl, —O($CR^{13}R^{14}$)$_q$-heterocyclyl or —$NR^{15}$($CR^{13}R^{14}$)$_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^{13}SO_2R^{18}$, $SO_2NR^{15}R^{13}$, —C(O)$R^{15}$, —C(O)O$R^{15}$, —OC(O)$^{15}$, —$NR^{13}$C(O)O$R^{18}$, —$NR^{13}$C(O)$R^{15}$, —C(O)$NR^{15}R^{13}$, $NR^{15}R^{13}$, —$NR^{14}$C(O)$NR^{15}R^{13}$, —$NR^{14}$C(NCN)$NR^{15}R^{13}$, —O$R^{15}$, aryl, heteroaryl, arylalkyl, heteroarylalkyl, saturated or partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, $NR^{15}R^{13}$ and $OR^{15}$;

each $R^{20}$ is independently $C_1$-$C_4$ alkyl, saturated or partially unsaturated cycloalkyl, trifluoromethyl, difluoromethyl, or fluoromethyl;

$R^a$, $R^b$ and $R^c$ are independently H, alkyl, alkenyl, alkynyl, saturated or partially unsaturated cycloalkyl, saturated or partially unsaturated heterocyclyl, aryl, or heteroaryl, or $NR^aR^b$ forms a 5-6 membered heterocyclic ring having 1-2 ring nitrogen atoms and optionally substituted with ($C_1$-$C_3$ alkyl),
or $NR^bR^c$ forms a 5-6 membered heterocyclic ring having 1-2 ring nitrogen atoms;

j is 0, 1, 2 or 3;
n is 0, 1, 2, 3, or 4;
q is 0, 1, 2, 3, 4, or 5; and
p is 0, 1 or 2.

34. The process of claim 33, wherein the acid is HOAc and the solvent is isopropyl acetate.

35. A process for preparing a compound of Formula 10:

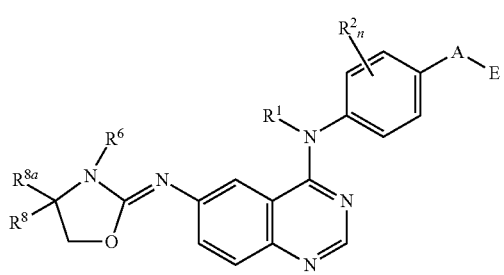

10 comprising:
(a) condensing a compound of Formula 8:

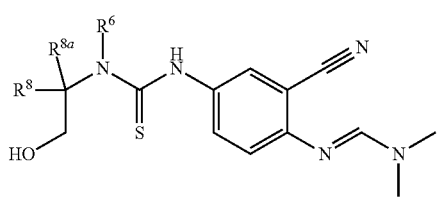

8 with a compound of Formula 2:

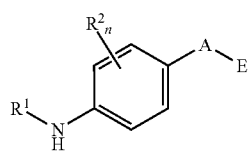

2 in the presence of an acid in a suitable solvent to provide a compound of Formula 9:

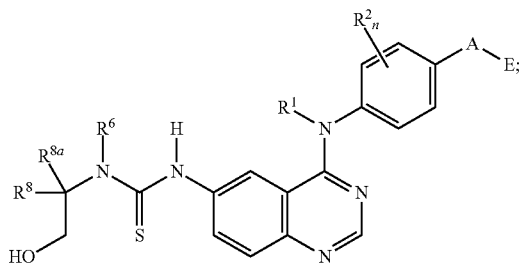

9 and
(b) cyclizing the thiourea of Formula 9 to provide a compound of Formula 10;
wherein A is O, C(=O), S, SO or $SO_2$;
E is:

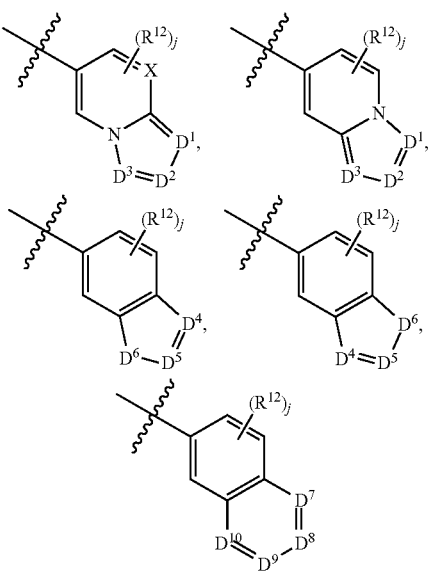

X is N or CH;
$D^1$, $D^2$ and $D^3$ are independently N or $CR^{19}$;
$D^4$ and $D^5$ are independently N or $CR^{19}$ and $D^6$ is O, S, or $NR^{20}$, wherein at least one of
$D^4$ and $D^5$ is not $CR^{19}$;
$D^7$, $D^8$, $D^9$ and $D^{10}$ are independently N or $CR^{19}$, wherein at least one of $D^7$, $D^8$, $D^9$ and $D^{10}$ is N;
$R^1$ is H or alkyl;
each $R^2$ is independently halogen, cyano, nitro, trifluoromethyl, difluoromethyl, fluoromethyl, fluoromethoxy, difluoromethoxy, trifluoromethoxy, azido, —$SR^{18}$, —$OR^{15}$, —$C(O)R^{15}$, —$C(O)OR^{15}$, —$NR^{14}C(O)OR^{18}$, —$OC(O)R^{15}$, —$NR^{14}SO_2R^{18}$, —$SO_2NR^{15}R^{14}$, —$NR^{14}C(O)R^{15}$, —$C(O)NR^{15}R^{14}$, —$NR^{15}C(O)NR^{15}R^{14}$, —$NR^{13}C(NCN)NR^{15}R^{14}$, —$NR^{15}R^{14}$, alkyl, alkenyl, alkynyl, saturated or partially unsaturated cycloalkyl, cycloalkylalkyl, —S(O)$_p$(alkyl), —S(O)$_p$(CR$^{13}$R$^{14}$)$_q$-aryl, aryl, arylalkyl, heteroaryl, heteroarylalkyl, saturated or partially unsaturated heterocyclyl, heterocyclylalkyl, —O(CR$^{13}$R$^{14}$)$_q$-aryl, —NR$^{15}$(CR$^{13}$R$^{14}$)$_q$-aryl, —O(CR$^{13}$R$^{14}$)$_q$-heteroaryl, —NR$^{13}$(CR$^{13}$R$^{14}$)$_q$-heteroaryl, —O(CR$^{13}$R$^{14}$)$_q$-heterocyclyl or —NR$^{15}$(CR$^{13}$R$^{14}$)$_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR$^{13}$SO$_2$R$^{18}$, —SO$_2$NR$^{15}$R$^{13}$, —C(O)R$^{15}$, —C(O)OR$^{15}$, —OC(O)R$^{15}$, —NR$^{13}$C(O)OR$^{18}$, —NR$^{13}$C(O)R$^{15}$, —C(O)NR$^{15}$R$^{13}$, —NR$^{15}$R$^{13}$, —NR$^{14}$C(O)NR$^{15}$R$^{13}$, —NR$^{14}$C(NCN)NR$^{15}$R$^{13}$, —OR$^{15}$, aryl, heteroaryl, arylalkyl, heteroarylalkyl, saturated and partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, NR$^{15}$R$^{13}$ and OR$^{15}$;

each R$^6$, R$^8$, and R$^{8a}$ are independently hydrogen, trifluoromethyl, alkyl, saturated or partially unsaturated cycloalkyl, saturated or partially unsaturated heterocyclyl, aryl, arylalkyl, heteroaryl, heteroarylalkyl, or heterocyclylalkyl, wherein said alkyl, cycloalkyl, heterocyclyl, aryl, arylalkyl, heteroaryl, heteroarylalkyl, and heterocyclylalkyl are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, OR$^{15}$, NR$^{15}$R$^{16}$, SR$^{15}$, S(=O)R$^{15}$, SO$_2$R$^{15}$, trifluoromethyl, difluoromethyl, fluoromethyl, fluoromethoxy, difluoromethoxy, trifluoromethoxy, azido, aryl, heteroaryl, arylalkyl, heteroarylalkyl, and heterocyclylalkyl, or R$^8$ and R$^{8a}$ together with the atom to which they are attached form a 3 to 6 membered carbocyclic ring;

or R$^6$ and R$^8$ together with the atoms to which they are attached form a 3 to 10 membered saturated or partially unsaturated heterocyclyl ring optionally containing one or more additional heteroatoms selected from N, O, S, SO, SO$_2$ and NR$^6$, wherein said carbocyclic and heterocyclic rings are optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, OR$^{15}$, NR$^{15}$R$^{16}$, SR$^{15}$, heteroaryl, arylalkyl, heteroarylalkyl, and heterocyclylalkyl;

each R$^{12}$ is independently halogen, cyano, nitro, trifluoromethyl, difluoromethyl, fluoromethyl, fluoromethoxy, difluoromethoxy, trifluoromethoxy, azido, —SR$^{18}$, —OR$^{15}$, —C(O)R$^{15}$, —C(O)OR$^{15}$, —NR$^{14}$C(O)OR$^{18}$, —OC(O)R$^{15}$, —NR$^{14}$SO$_2$R$^{18}$, —SO$_2$NR$^{15}$R$^{14}$, —NR$^{14}$C(O)R$^{15}$, —C(O)NR$^{15}$R$^{14}$, —NR$^{13}$C(O)NR$^{15}$R$^{14}$, —NR$^{13}$C(NCN)NR$^{15}$R$^{14}$, —NR$^{15}$R$^{14}$, alkyl, alkenyl, alkynyl, saturated or partially unsaturated cycloalkyl, cycloalkylalkyl, —S(O)$_p$(alkyl), —S(O)$_p$(CR$^{13}$R$^{14}$)$_q$-aryl, aryl, arylalkyl, heteroaryl, heteroarylalkyl, saturated or partially unsaturated heterocyclyl, heterocyclylalkyl, —O(CR$^{13}$R$^{14}$)$_q$-aryl, —NR$^{15}$(CR$^{13}$R$^{14}$)$_q$-aryl, —O(CR$^{13}$R$^{14}$)$_q$-heteroaryl, —NR$^{13}$(CR$^{13}$R$^{14}$)$_q$-heteroaryl, —O(CR$^{13}$R$^{14}$)$_q$-heterocyclyl or —NR$^{15}$(CR$^{13}$R$^{14}$)$_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR$^{13}$SO$_2$R$^{18}$, —SO$_2$NR$^{15}$R$^{13}$, —C(O)R$^{15}$, —C(O)OR$^{15}$, —OC(O)R$^{15}$, —NR$^{13}$C(O)OR$^{18}$, —NR$^{13}$C(O)R$^{15}$, —C(O)NR$^{15}$R$^{13}$, —NR$^{15}$R$^{13}$, —NR$^{14}$C(O)NR$^{15}$R$^{13}$, —NR$^{14}$C(NCN)NR$^{15}$R$^{13}$, —OR$^{15}$, aryl, heteroaryl, arylalkyl, heteroarylalkyl, saturated and partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, NR$^{15}$R$^{13}$ and OR$^{15}$;

R$^{13}$ and R$^{14}$ are independently hydrogen or alkyl, or R$^{13}$ and R$^{14}$ together with the atoms to which they are attached form a saturated or partially unsaturated cycloalkyl, or saturated or partially unsaturated heterocyclyl ring, wherein said alkyl, cycloalkyl and heterocyclyl portions are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, OR$^a$, NR$^a$R$^b$, NR$^a$OR$^b$, NR$^a$CO$_2$R$^b$, NR$^a$COR$^b$, SO$_2$NR$^a$R$^b$, SR$^a$, SOR$^a$, SO$_2$R$^a$, S—S—R$^a$, C(=O)R$^a$, C(=O)OR$^a$, OC(=O)R$^a$, C(=O)NR$^a$R$^b$, NR$^a$C(=O)R$^b$, and NR$^a$C(=O)NR$^b$R$^c$;

R$^{15}$ and R$^{16}$ are independently H, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, OR$^a$, NR$^a$R$^b$, NR$^a$OR$^b$, NR$^a$CO$_2$R$^b$, NR$^a$COR$^b$, SO$_2$NR$^a$R$^b$, SR$^a$, SOR$^a$, SO$_2$R$^a$, S—S—R$^a$, C(=O)R$^a$, C(=O)OR$^a$, OC(=O)R$^a$, C(=O)NR$^a$R$^b$, NR$^a$C(=O)R$^b$, NR$^a$C(=O)NR$^b$R$^c$, OC(=O)NR$^a$R$^b$, and C(=O)CH$_2$OR$^a$;

or R$^{15}$ and R$^{16}$ together with the atom to which they are attached form a heterocyclic ring optionally containing one or more additional heteroatoms selected from N, O, S, SO, SO$_2$ and NR$^6$, wherein said heterocyclic ring is optionally substituted with one or more groups independently selected from oxo, halogen, alkyl, alkenyl, alkynyl, saturated and partially unsaturated cycloalkyl, saturated and partially unsaturated heterocyclyl, cycloalkylalkyl, cyano, nitro, trifluoromethyl, difluoromethyl, fluoromethyl, fluoromethoxy, difluoromethoxy, trifluoromethoxy, azido, aryl, OR$^a$, NR$^a$R$^b$, SR$^a$, heteroaryl, arylalkyl, heteroarylalkyl, and heterocyclylalkyl, or R$^{13}$ and R$^{15}$ together with the atom to which they are attached form a saturated or partially unsaturated cycloalkyl or saturated or partially unsaturated heterocyclyl ring, wherein said cycloalkyl and heterocyclyl are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, $S-S-R^a$, $C(=O)R^a$, $C(=O)OR^a$, $OC(=O)R^a$, $C(=O)NR^aR^b$, $NR^aC(=O)R^b$, and $NR^aC(=O)NR^bR^c$;

$R^{18}$ is $CF_3$, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, saturated or partially unsaturated heterocyclyl, cycloalkylalkyl, aryl, arylalkyl, heteroaryl, heteroarylalkyl and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, heteroaryl, halogen, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, $S-S-R^a$, $C(=O)R^a$, $C(=O)OR^a$, $OC(=O)R^a$, $C(=O)NR^aR^b$, $NR^aC(=O)R^b$, and $NR^aC(=O)NR^bR^c$, or $R^{15}$ and $R^{18}$ together with the atoms to which they are attached form a saturated or partially unsaturated cycloalkyl or saturated or partially unsaturated heterocyclyl ring, wherein said cycloalkyl and heterocyclyl are optionally substituted with one or more groups independently selected from halogen, cyano, nitro, trifluoromethyl, difluoromethyl, fluoromethyl, fluoromethoxy, difluoromethoxy, trifluoromethoxy, azido, oxo, $OR^a$, $NR^aR^b$, $NR^aOR^b$, $NR^aCO_2R^b$, $NR^aCOR^b$, $SO_2NR^aR^b$, $SR^a$, $SOR^a$, $SO_2R^a$, $S-S-R^a$, $C(=O)R^a$, $C(=O)OR^a$, $OC(=O)R^a$, $C(=O)NR^aR^b$, $NR^aC(=O)R^b$, and $NR^aC(=O)NR^bR^c$;

each $R^{19}$ is independently H, halogen, cyano, nitro, trifluoromethyl, difluoromethyl, fluoromethyl, fluoromethoxy, difluoromethoxy, trifluoromethoxy, azido, $-SR^{18}$, $-OR^{15}$, $-C(O)R^{15}$, $-C(O)OR^{15}$, $-NR^{14}C(O)OR^{18}$, $-OC(O)R^{15}$, $-NR^{14}SO_2R^{18}$, $-SO_2NR^{15}R^{14}$, $-NR^{14}C(O)R^{15}$, $-C(O)NR^{15}R^{14}$, $-NR^{13}C(O)NR^{15}R^{14}$, $-NR^{13}C(NCN)NR^{15}R^{14}$, $-NR^{15}R^{14}$, alkyl, alkenyl, alkynyl, saturated or partially unsaturated cycloalkyl, cycloalkylalkyl, $-S(O)_p(alkyl)$, $-S(O)_p(CR^{13}R^{14})_q$-aryl, aryl, arylalkyl, heteroaryl, heteroarylalkyl, saturated or partially unsaturated heterocyclyl, heterocyclylalkyl, $-O(CR^{13}R^{14})_q$-aryl, $-NR^{15}(CR^{13}R^{14})_q$-aryl, $-O(CR^{13}R^{14})_q$-heteroaryl, $-NR^{13}(CR^{13}R^{14})_q$-heteroaryl, $-O(CR^{13}R^{14})_q$-heterocyclyl or $-NR^{15}(CR^{13}R^{14})_q$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, $-NR^{13}SO_2R^{18}$, $-SO_2NR^{15}R^{13}$, $-C(O)R^{15}$, $-C(O)OR^{15}$, $-OC(O)R^{15}$, $-NR^{13}C(O)OR^{18}$, $-NR^{13}C(O)R^{15}$, $-C(O)NR^{15}R^{13}$, $-NR^{15}R^{13}$, $-NR^{14}C(O)NR^{15}R^{13}$, $-NR^{14}C(NCN)NR^{15}R^{13}$, $-OR^{15}$, aryl, heteroaryl, arylalkyl, heteroarylalkyl, saturated or partially unsaturated heterocyclyl, and heterocyclylalkyl, and wherein said aryl, heteroaryl, arylalkyl, heteroarylalkyl, heterocyclyl or heterocyclylalkyl rings may be further substituted with one or more groups selected from halogen, hydroxyl, cyano, nitro, azido, fluoromethyl, difluoromethyl, trifluoromethyl, alkyl, alkenyl, alkynyl, saturated and partially unsaturated cycloalkyl, saturated and partially unsaturated heterocyclyl, $NR^{15}R^{13}$ and $OR^{15}$;

each $R^{20}$ is independently $C_1$-$C_4$ alkyl, saturated or partially unsaturated cycloalkyl, trifluoromethyl, difluoromethyl, or fluoromethyl;

$R^a$, $R^b$ and $R^c$ are independently H, alkyl, alkenyl, alkynyl, saturated or partially unsaturated cycloalkyl, saturated or partially unsaturated heterocyclyl, aryl, or heteroaryl, or $NR^aR^b$ forms a 5-6 membered heterocyclic ring having 1-2 ring nitrogen atoms and optionally substituted with ($C_1$-$C_3$ alkyl), or $NR^bR^c$ forms a 5-6 membered heterocyclic ring having 1-2 ring nitrogen atoms;

j is 0, 1, 2 or 3;

n is 0, 1, 2, 3, or 4;

q is 0, 1, 2, 3, 4, or 5; and p is 0, 1 or 2.

36. The process of claim 35, wherein the acid is HOAc and the solvent is isopropyl acetate.

37. The process of claim 35, wherein the thiourea is cyclized by treating the compound of Formula 9 with TsCl and aqueous NaOH in THF.

\* \* \* \* \*

UNITED STATES PATENT AND TRADEMARK OFFICE
CERTIFICATE OF CORRECTION

PATENT NO. : 8,648,087 B2  Page 1 of 1
APPLICATION NO. : 12/085048
DATED : February 11, 2014
INVENTOR(S) : Lyssikatos et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1609 days.

Signed and Sealed this
Twenty-ninth Day of September, 2015

Michelle K. Lee
*Director of the United States Patent and Trademark Office*